US012161634B2

(12) United States Patent
Luke et al.

(10) Patent No.: US 12,161,634 B2
(45) Date of Patent: Dec. 10, 2024

(54) PYRUVATE KINASE R (PKR) ACTIVATING COMPOSITIONS

(71) Applicant: Novo Nordisk Health Care AG, Zurich (CH)

(72) Inventors: George P. Luke, Clinton, CT (US); Sonia Rodriguez Rodriguez, Avon, CT (US); Hongwei Zhang, Watertown, MA (US); Shanming Kuang, Plainsboro, MA (US); Yuwen Xu, Jiangsu (CN)

(73) Assignee: Novo Nordisk Health Care AG, Zurich (CH)

( * ) Notice: Subject to any disclaimer, the term of this patent is extended or adjusted under 35 U.S.C. 154(b) by 267 days.

(21) Appl. No.: 17/761,788

(22) PCT Filed: Sep. 18, 2020

(86) PCT No.: PCT/US2020/051645
§ 371 (c)(1),
(2) Date: Mar. 18, 2022

(87) PCT Pub. No.: WO2021/055863
PCT Pub. Date: Mar. 25, 2021

(65) Prior Publication Data
US 2022/0378755 A1    Dec. 1, 2022

(51) Int. Cl.
*A61K 31/436* (2006.01)
*A61K 9/00* (2006.01)
*A61K 9/20* (2006.01)
*A61K 9/48* (2006.01)
*A61P 7/06* (2006.01)

(52) U.S. Cl.
CPC .......... *A61K 31/436* (2013.01); *A61K 9/0053* (2013.01); *A61K 9/2009* (2013.01); *A61K 9/2018* (2013.01); *A61K 9/2027* (2013.01); *A61K 9/2054* (2013.01); *A61K 9/4825* (2013.01); *A61P 7/06* (2018.01)

(58) Field of Classification Search
None
See application file for complete search history.

(56) References Cited

U.S. PATENT DOCUMENTS

| | | |
|---|---|---|
| 4,602,093 A | 7/1986 | Baldwin et al. |
| 4,918,073 A | 4/1990 | Ruger et al. |
| 5,030,631 A | 7/1991 | Bauer |
| 5,037,467 A | 8/1991 | Cho et al. |
| 5,059,605 A | 10/1991 | Clough et al. |
| 5,089,621 A | 2/1992 | Kim et al. |
| 5,091,384 A | 2/1992 | Kim et al. |
| 5,180,719 A | 1/1993 | White et al. |
| 5,250,544 A | 10/1993 | Lavielle et al. |
| 5,336,772 A | 8/1994 | Saiki et al. |
| 5,480,899 A | 1/1996 | Yano et al. |
| 5,672,601 A | 9/1997 | Cignarella |
| 5,714,625 A | 2/1998 | Hada et al. |
| 5,747,502 A | 5/1998 | Hanaoka et al. |
| 5,962,703 A | 10/1999 | Moszner et al. |
| 6,214,879 B1 | 4/2001 | Abraham et al. |
| 6,534,501 B2 | 3/2003 | Abraham et al. |
| 6,710,052 B2 | 3/2004 | Pease et al. |
| 6,878,715 B1 | 4/2005 | Klein et al. |
| 7,138,401 B2 | 11/2006 | Kasibhatla et al. |
| 7,160,885 B2 | 1/2007 | Currie et al. |
| 7,875,603 B2 | 1/2011 | Rathinavelu et al. |
| 8,501,953 B2 | 8/2013 | Salituro et al. |
| 8,552,050 B2 | 10/2013 | Cantley et al. |
| 8,692,001 B2 | 4/2014 | Becker et al. |
| 8,742,119 B2 | 6/2014 | Salituro et al. |
| 8,785,450 B2 | 7/2014 | Salituro et al. |
| 8,841,305 B2 | 9/2014 | Thomas et al. |
| 8,877,791 B2 | 11/2014 | Cantley et al. |
| 8,889,667 B2 | 11/2014 | Salituro et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,108,921 B2 | 8/2015 | Cianchetta et al. |
| 9,181,231 B2 | 11/2015 | Su |
| 9,221,792 B2 | 12/2015 | Salituro et al. |
| 9,248,199 B2 | 2/2016 | Metcalf |
| 9,328,077 B2 | 5/2016 | Salituro et al. |
| 9,394,257 B2 | 7/2016 | Ho et al. |
| 9,422,279 B2 | 8/2016 | Metcalf et al. |
| 9,458,132 B2 | 10/2016 | Cianchetta et al. |
| 9,458,139 B2 | 10/2016 | Xu et al. |
| 9,604,999 B2 | 3/2017 | Harris et al. |
| 9,708,267 B2 | 7/2017 | Boxer et al. |
| 9,744,145 B1 | 8/2017 | Liu et al. |

(Continued)

FOREIGN PATENT DOCUMENTS

| | | |
|---|---|---|
| CN | 101812063 A | 8/2010 |
| CN | 102206217 A | 10/2011 |

(Continued)

OTHER PUBLICATIONS

SureChMBL, "Open Patent Data", 2 pages, downloaded Oct. 31, 2023 from https://www.surechembl.org/knowledgebase/75969.

Schroeder et al., "Etavopivat, a Pyruvate Kinase Activator in Red Blood Cells, for the Treatment of Sickle Cell Disease", The Journal of Pharmacology and Experimental Therapeutics, Mar. 2022, vol. 380, pp. 210-219.

Abbady M.A., et al., Synthesis and biological activity of some new 4-(2-pyrazolin-3-yl)-, 4-(2-isoxazolin-e-yl)- and 4-(1,2,5,6-tetrahydro-2-thioxopyrimidin-4-yl)phenyl aminophenyl sulfides and sulfones., *Egyptian Journal of Pharmaceutical Sciences*, vol. 27, No. 1-4, (1986), Abstract Only.

(Continued)

*Primary Examiner* — Zinna Northington Davis
(74) *Attorney, Agent, or Firm* — Jianjie Hu

(57) ABSTRACT

The present disclosure provides crystalline solid forms, spray-dried dispersions and pharmaceutical compositions, including solid oral dosage forms, of (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one ("Compound 1"), and preparation methods thereof.

16 Claims, 51 Drawing Sheets

(56) References Cited

U.S. PATENT DOCUMENTS

| | | |
|---|---|---|
| 9,776,960 B2 | 10/2017 | Xu et al. |
| 9,802,900 B2 | 10/2017 | Li et al. |
| 9,957,250 B2 | 5/2018 | Metcalf et al. |
| 9,981,939 B2 | 5/2018 | Metcalf et al. |
| 10,004,725 B2 | 6/2018 | Dufu et al. |
| 10,017,491 B2 | 7/2018 | Metcalf et al. |
| 10,034,879 B2 | 7/2018 | Metcalf et al. |
| 10,077,249 B2 | 9/2018 | Li et al. |
| 10,100,040 B2 | 10/2018 | Li et al. |
| 10,100,043 B2 | 10/2018 | Metcalf et al. |
| 10,208,052 B1 | 2/2019 | Zheng et al. |
| 10,266,551 B2 | 4/2019 | Li et al. |
| 10,315,991 B2 | 6/2019 | Xu et al. |
| 10,377,741 B2 | 8/2019 | Metcalf et al. |
| 10,435,393 B2 | 10/2019 | Xu et al. |
| 10,450,269 B1 | 10/2019 | Xu et al. |
| 10,472,371 B2 | 11/2019 | Zheng et al. |
| 10,493,035 B2 | 12/2019 | Dalziel et al. |
| 10,577,345 B2 | 3/2020 | Li et al. |
| 10,675,274 B2 | 6/2020 | Ericsson et al. |
| 10,683,285 B2 | 6/2020 | Li |
| 10,695,330 B2 | 6/2020 | Li et al. |
| 10,836,771 B2 | 11/2020 | Zheng et al. |
| 11,014,927 B2 | 5/2021 | Ericsson et al. |
| 11,071,725 B2 | 7/2021 | Ericsson et al. |
| 11,396,513 B2 | 7/2022 | Zheng et al. |
| 11,649,242 B2 | 5/2023 | Ericsson et al. |
| 11,844,787 B2 | 12/2023 | Ericsson et al. |
| 11,980,611 B2 | 5/2024 | Ericsson et al. |
| 2004/0077648 A1 | 4/2004 | Timmer et al. |
| 2004/0102458 A1 | 5/2004 | Chiosis et al. |
| 2005/0002861 A1 | 1/2005 | Krause et al. |
| 2005/0049263 A1 | 3/2005 | Kasibhatla et al. |
| 2005/0059663 A1 | 3/2005 | Martin et al. |
| 2005/0181305 A1 | 8/2005 | Shibuya |
| 2005/0256103 A1 | 11/2005 | Suzuki et al. |
| 2006/0074121 A1 | 4/2006 | Chen et al. |
| 2006/0211737 A1 | 9/2006 | Huang et al. |
| 2007/0015752 A1 | 1/2007 | Hangauer, Jr. |
| 2007/0270433 A1 | 11/2007 | Brinkman et al. |
| 2008/0058315 A1 | 3/2008 | Cai et al. |
| 2008/0184495 A1 | 8/2008 | Brun et al. |
| 2008/0253965 A1 | 10/2008 | Chiosis et al. |
| 2008/0269234 A1 | 10/2008 | Gandhi et al. |
| 2009/0042966 A1 | 2/2009 | Coleman et al. |
| 2009/0163545 A1 | 6/2009 | Goldfarb |
| 2009/0291921 A1 | 11/2009 | Jabri et al. |
| 2010/0029575 A1 | 2/2010 | Junien et al. |
| 2010/0120863 A1 | 5/2010 | Biftu et al. |
| 2010/0144594 A1 | 6/2010 | Zoller et al. |
| 2010/0144722 A1 | 6/2010 | Alexander et al. |
| 2010/0152157 A1 | 6/2010 | Puech et al. |
| 2010/0179154 A1 | 7/2010 | Almario Garcia et al. |
| 2010/0216774 A1 | 8/2010 | Bender et al. |
| 2010/0324030 A1 | 12/2010 | Dale et al. |
| 2011/0059089 A1 | 3/2011 | Swagemakers et al. |
| 2011/0085969 A1 | 4/2011 | Rollo et al. |
| 2011/0104054 A1 | 5/2011 | Chiosis et al. |
| 2012/0134979 A1 | 5/2012 | Xia et al. |
| 2012/0252818 A1 | 10/2012 | Chiosis et al. |
| 2013/0109684 A1 | 5/2013 | Blagg et al. |
| 2013/0116430 A1 | 5/2013 | Fujiwara et al. |
| 2013/0155489 A1 | 6/2013 | Kato et al. |
| 2013/0190315 A1 | 7/2013 | Metcalf et al. |
| 2013/0190316 A1 | 7/2013 | Metcalf et al. |
| 2014/0228360 A1 | 8/2014 | Duncan et al. |
| 2014/0242602 A1 | 8/2014 | Chiosis et al. |
| 2015/0246025 A1 | 9/2015 | Desai et al. |
| 2016/0106728 A1 | 4/2016 | Shen et al. |
| 2016/0200681 A1 | 7/2016 | Yu et al. |
| 2017/0121338 A1 | 5/2017 | Zhang et al. |
| 2017/0216434 A1 | 8/2017 | Hines et al. |
| 2017/0217964 A1 | 8/2017 | Li |
| 2018/0215765 A1 | 8/2018 | Di Giorgio et al. |
| 2018/0282369 A1 | 10/2018 | Desai et al. |
| 2019/0218221 A1 | 7/2019 | Zheng et al. |
| 2020/0031839 A1 | 1/2020 | Zheng et al. |
| 2020/0069643 A1 | 3/2020 | Ericsson |
| 2020/0085798 A1 | 3/2020 | Ericsson |
| 2020/0087309 A1 | 3/2020 | Lancia, Jr. |
| 2020/0129485 A1 | 4/2020 | Ericsson et al. |
| 2020/0253939 A1 | 8/2020 | Ericsson et al. |
| 2021/0017184 A1 | 1/2021 | Zheng et al. |
| 2021/0246143 A1 | 8/2021 | Ericsson et al. |
| 2022/0031671 A1 | 2/2022 | Ericsson et al. |
| 2022/0304987 A1 | 9/2022 | Ericsson et al. |
| 2022/0378756 A1 | 12/2022 | Ericsson et al. |
| 2024/0083901 A1 | 3/2024 | Ericsson et al. |
| 2024/0131011 A1 | 4/2024 | Luke et al. |

FOREIGN PATENT DOCUMENTS

| | | |
|---|---|---|
| CN | 102952139 A | 3/2013 |
| CN | 103570722 A | 2/2014 |
| CN | 104736534 A | 6/2015 |
| CN | 105037367 A | 11/2015 |
| CN | 105085528 A | 11/2015 |
| CN | 105153119 A | 12/2015 |
| CN | 105254628 A | 1/2016 |
| CN | 105294694 A | 2/2016 |
| CN | 105348286 A | 2/2016 |
| CN | 106928222 A | 7/2017 |
| CN | 109912610 A | 6/2019 |
| DE | 102008010661 A1 | 9/2009 |
| EP | 0007529 A1 | 2/1980 |
| EP | 0036711 A2 | 9/1981 |
| EP | 0264883 A2 | 4/1988 |
| EP | 0273534 A2 | 7/1988 |
| EP | 0338372 A2 | 10/1988 |
| EP | 0363212 A2 | 4/1990 |
| EP | 0378255 A2 | 7/1990 |
| EP | 0424850 A1 | 5/1991 |
| EP | 0424851 A1 | 5/1991 |
| EP | 0424852 A1 | 5/1991 |
| EP | 0486022 A2 | 5/1992 |
| EP | 0520277 A2 | 12/1992 |
| EP | 0590415 A2 | 4/1994 |
| EP | 0737670 A1 | 10/1996 |
| EP | 1096310 A2 | 5/2001 |
| EP | 1099692 A1 | 5/2001 |
| EP | 1249233 A1 | 10/2002 |
| EP | 1952800 A2 | 8/2008 |
| EP | 3141542 A1 | 3/2017 |
| EP | 2797416 B1 | 8/2017 |
| EP | 3483164 A1 | 5/2019 |
| IN | 1809/MUM/2013 | 5/2013 |
| IN | 2013/MU01809 | 3/2015 |
| JP | S 61 200544 | 9/1986 |
| JP | 3 13040 B2 | 2/1991 |
| JP | 3 275666 | 12/1991 |
| JP | 04 054181 A | 2/1992 |
| JP | 05125050 A | 5/1993 |
| JP | 05 196976 | 8/1993 |
| JP | 7 164400 | 6/1995 |
| JP | 1 110376 | 1/1999 |
| JP | 2001261653 A | 9/2001 |
| JP | 2003514673 | 4/2003 |
| JP | 2004175674 A | 6/2004 |
| JP | 2007246885 A | 9/2007 |
| JP | 2007328090 A | 12/2007 |
| JP | 2008031064 A | 2/2008 |
| JP | 2008063256 A | 3/2008 |
| JP | 2009149707 A | 7/2009 |
| JP | 2009212473 A | 9/2009 |
| JP | 2010192782 A | 9/2010 |
| JP | 2011246649 A | 12/2011 |
| JP | 2012188474 A | 10/2012 |
| JP | 2012188475 A | 10/2012 |
| JP | 2013171968 A | 9/2013 |
| KR | 20110096442 A | 8/2011 |
| LB | 11379 | 7/2018 |
| RU | 2517693 C2 | 4/2011 |
| RU | 2472794 C1 | 11/2012 |
| WO | WO 1993/011106 | 6/1993 |

(56) References Cited

FOREIGN PATENT DOCUMENTS

| | | |
|---|---|---|
| WO | WO 1993/022298 A1 | 11/1993 |
| WO | WO 1995/019353 A1 | 7/1995 |
| WO | WO 1998/038239 | 9/1998 |
| WO | WO 1998/050364 A1 | 11/1998 |
| WO | WO 1999/001442 A1 | 1/1999 |
| WO | WO 1999/002493 A1 | 1/1999 |
| WO | WO 1999/047489 A1 | 9/1999 |
| WO | WO 1999/047516 A1 | 9/1999 |
| WO | WO 1999/048461 A2 | 9/1999 |
| WO | WO 1999/048490 A1 | 9/1999 |
| WO | WO 1999/065895 A1 | 12/1999 |
| WO | WO 1999/065901 | 12/1999 |
| WO | WO 2000/004023 A1 | 1/2000 |
| WO | WO 2000/021951 A1 | 4/2000 |
| WO | WO 2000/053591 A1 | 9/2000 |
| WO | WO 2001/010842 A2 | 2/2001 |
| WO | WO 2001/032764 | 5/2001 |
| WO | WO 2001/043744 A1 | 6/2001 |
| WO | WO 2001/053288 A2 | 7/2001 |
| WO | WO 2001/057037 A2 | 8/2001 |
| WO | WO 2001/085728 A2 | 11/2001 |
| WO | WO 2002/030358 | 4/2002 |
| WO | WO 2002/034754 A2 | 5/2002 |
| WO | WO 2002/060902 A1 | 8/2002 |
| WO | WO 2002/076989 A1 | 10/2002 |
| WO | WO 2002/095063 A1 | 11/2002 |
| WO | WO 2003/015769 A1 | 2/2003 |
| WO | WO 2003/037860 A2 | 5/2003 |
| WO | WO 2003/063794 | 8/2003 |
| WO | WO 2003/067332 A2 | 8/2003 |
| WO | WO 2003/084948 A1 | 10/2003 |
| WO | WO 2004/002490 A2 | 1/2004 |
| WO | WO 2004/007770 A2 | 1/2004 |
| WO | WO 2004/009600 A1 | 1/2004 |
| WO | WO 2004/013144 A1 | 2/2004 |
| WO | WO 2004/014374 A1 | 2/2004 |
| WO | WO 2004/014382 | 2/2004 |
| WO | WO 2004/024676 A1 | 3/2004 |
| WO | WO 2004/080457 A1 | 9/2004 |
| WO | WO 2004/089470 A2 | 10/2004 |
| WO | WO 2004/089947 A2 | 10/2004 |
| WO | WO 2004/104000 A1 | 12/2004 |
| WO | WO 2005/000098 A2 | 1/2005 |
| WO | WO 2005/002577 A1 | 1/2005 |
| WO | WO 2005/009965 A1 | 2/2005 |
| WO | WO 2005/011653 A2 | 2/2005 |
| WO | WO 2005/011656 A2 | 2/2005 |
| WO | WO 2005/016915 A1 | 2/2005 |
| WO | WO 2005/023761 A2 | 3/2005 |
| WO | WO 2005/049570 | 6/2005 |
| WO | WO 2005/058869 | 6/2005 |
| WO | WO 2005/058870 | 6/2005 |
| WO | WO 2005/058871 | 6/2005 |
| WO | WO 2005/058873 | 6/2005 |
| WO | WO 2005/058874 | 6/2005 |
| WO | WO 2005/084667 A1 | 9/2005 |
| WO | WO 2005/094251 A2 | 10/2005 |
| WO | WO 2005/094834 A1 | 10/2005 |
| WO | WO 2005/103015 A1 | 11/2005 |
| WO | WO 2006/002100 A2 | 1/2006 |
| WO | WO 2006/009886 A1 | 1/2006 |
| WO | WO 2006/018279 A2 | 2/2006 |
| WO | WO 2006/018280 A2 | 2/2006 |
| WO | WO 2006/021448 A1 | 3/2006 |
| WO | WO 2006/023608 A2 | 3/2006 |
| WO | WO 2006/034315 A2 | 3/2006 |
| WO | WO 2006/038172 A1 | 4/2006 |
| WO | WO 2006/060122 A2 | 6/2006 |
| WO | WO 2006/084030 A2 | 8/2006 |
| WO | WO 2006/086445 A2 | 8/2006 |
| WO | WO 2006/099884 A1 | 9/2006 |
| WO | WO 2006/101521 A2 | 9/2006 |
| WO | WO 2006/110390 A1 | 10/2006 |
| WO | WO 2006/123121 A1 | 11/2006 |
| WO | WO 2006/130469 A1 | 12/2006 |
| WO | WO 2006/137485 A1 | 12/2006 |
| WO | WO 2007/006926 A2 | 1/2007 |
| WO | WO 2007/007069 A1 | 1/2007 |
| WO | WO 2007/019344 A1 | 2/2007 |
| WO | WO 2007/027734 A2 | 3/2007 |
| WO | WO 2007/042325 A1 | 4/2007 |
| WO | WO 2007/083119 A2 | 7/2007 |
| WO | WO 2007/087231 A2 | 8/2007 |
| WO | WO 2007/088123 A2 | 8/2007 |
| WO | WO 2007/097931 A2 | 8/2007 |
| WO | WO 2007/098418 A1 | 8/2007 |
| WO | WO 2007/126745 A2 | 11/2007 |
| WO | WO 2007/136603 A2 | 11/2007 |
| WO | WO 2007/138351 A2 | 12/2007 |
| WO | WO 2008/005937 A2 | 1/2008 |
| WO | WO 2008/019139 A2 | 2/2008 |
| WO | WO 2008/032905 A1 | 3/2008 |
| WO | WO 2008/057608 A2 | 5/2008 |
| WO | WO 2008/083027 A1 | 7/2008 |
| WO | WO 2008/094203 A2 | 8/2008 |
| WO | WO 2008/115719 A1 | 9/2008 |
| WO | WO 2008/120003 A1 | 10/2008 |
| WO | WO 2008/135141 A1 | 11/2008 |
| WO | WO 2008/139585 A1 | 11/2008 |
| WO | WO 2009/001126 A1 | 12/2008 |
| WO | WO 2009/004356 A1 | 1/2009 |
| WO | WO 2009/025781 A1 | 2/2009 |
| WO | WO 2009/025784 A1 | 2/2009 |
| WO | WO 2009/063244 A1 | 5/2009 |
| WO | WO 2009/077527 A1 | 6/2009 |
| WO | WO 2009/093032 A1 | 7/2009 |
| WO | WO 2009/112677 | 9/2009 |
| WO | WO 2009/121623 A2 | 10/2009 |
| WO | WO 2009/136889 A1 | 11/2009 |
| WO | WO 2009/153554 A1 | 12/2009 |
| WO | WO 2010/002802 A1 | 1/2010 |
| WO | WO 2010/021717 A2 | 2/2010 |
| WO | WO 2010/028761 A1 | 3/2010 |
| WO | WO 2010/042867 A2 | 4/2010 |
| WO | WO 2010/058318 A1 | 5/2010 |
| WO | WO 2010/092181 A1 | 8/2010 |
| WO | WO 2010/105243 A1 | 9/2010 |
| WO | WO 2010/108268 A1 | 9/2010 |
| WO | WO 2010/115688 A1 | 10/2010 |
| WO | WO 2010/118063 | 10/2010 |
| WO | WO 2010/129596 | 11/2010 |
| WO | WO 2010/132599 A1 | 11/2010 |
| WO | WO 2010/135524 A1 | 11/2010 |
| WO | WO 2010/151797 | 12/2010 |
| WO | WO 2011/002816 | 1/2011 |
| WO | WO 2011/002817 | 1/2011 |
| WO | WO 2011/025690 A1 | 3/2011 |
| WO | WO 2011/037793 A1 | 3/2011 |
| WO | WO 2011/050210 | 4/2011 |
| WO | WO 2011/050211 | 4/2011 |
| WO | WO 2011/060321 A1 | 5/2011 |
| WO | WO 2011/063055 A2 | 5/2011 |
| WO | WO 2011/103256 A1 | 8/2011 |
| WO | WO 2011/116282 A2 | 9/2011 |
| WO | WO 2011/137089 A1 | 11/2011 |
| WO | WO 2011/146358 A1 | 11/2011 |
| WO | WO 2012/002577 A1 | 1/2012 |
| WO | WO 2012/007861 A1 | 1/2012 |
| WO | WO 2012/007868 A2 | 1/2012 |
| WO | WO 2012/007877 A2 | 1/2012 |
| WO | WO 2012/019426 A1 | 2/2012 |
| WO | WO 2012/019427 A1 | 2/2012 |
| WO | WO 2012/056319 A1 | 5/2012 |
| WO | WO 2012/068096 A2 | 5/2012 |
| WO | WO 2012/071519 A1 | 5/2012 |
| WO | WO 2012/071684 A1 | 6/2012 |
| WO | WO 2012/080729 A2 | 6/2012 |
| WO | WO 2012/083246 | 6/2012 |
| WO | WO 2012/088314 | 6/2012 |
| WO | WO 2012/092426 A1 | 7/2012 |
| WO | WO 2012/092442 | 7/2012 |
| WO | WO 2012/092485 A1 | 7/2012 |
| WO | WO 2012/151440 A1 | 11/2012 |
| WO | WO 2012/151448 A1 | 11/2012 |

(56) References Cited

FOREIGN PATENT DOCUMENTS

| | | |
|---|---|---|
| WO | WO 2012/151450 A1 | 11/2012 |
| WO | WO 2012/151451 A1 | 11/2012 |
| WO | WO 2012/151452 A1 | 11/2012 |
| WO | WO 2012/160392 | 11/2012 |
| WO | WO 2012/160447 A1 | 11/2012 |
| WO | WO 2012/174126 | 12/2012 |
| WO | WO 2013/003249 A1 | 1/2013 |
| WO | WO 2013/003250 A1 | 1/2013 |
| WO | WO 2013/021054 A1 | 2/2013 |
| WO | WO 2013/038390 A1 | 3/2013 |
| WO | WO 2013/056153 | 4/2013 |
| WO | WO 2013/102142 A1 | 7/2013 |
| WO | WO 2013/102826 A1 | 7/2013 |
| WO | WO 2013/118805 A1 | 8/2013 |
| WO | WO 2013/126856 A1 | 8/2013 |
| WO | WO 2013/127266 A1 | 9/2013 |
| WO | WO 2013/155223 A1 | 10/2013 |
| WO | WO 2013/177224 A1 | 11/2013 |
| WO | WO 2013/184794 A2 | 12/2013 |
| WO | WO 2014/008458 A2 | 1/2014 |
| WO | WO 2014/014050 A1 | 1/2014 |
| WO | WO 2014/018355 A1 | 1/2014 |
| WO | WO 2014/023814 A1 | 2/2014 |
| WO | WO 2014/044356 A1 | 3/2014 |
| WO | WO 2014/048865 A1 | 4/2014 |
| WO | WO 2014/061031 A1 | 4/2014 |
| WO | WO 2014/062838 A2 | 4/2014 |
| WO | WO 2014/074848 | 5/2014 |
| WO | WO 2014/102817 A1 | 7/2014 |
| WO | WO 2014/118634 A1 | 8/2014 |
| WO | WO 2014/130890 A1 | 8/2014 |
| WO | WO 2014/139144 A1 | 9/2014 |
| WO | WO 2014/139325 A1 | 9/2014 |
| WO | WO 2014/139978 A1 | 9/2014 |
| WO | WO 2014/144715 A1 | 9/2014 |
| WO | WO 2014/150276 A1 | 9/2014 |
| WO | WO 2014/152588 A1 | 9/2014 |
| WO | WO 2014/172638 A2 | 10/2014 |
| WO | WO 2015/030514 A1 | 3/2015 |
| WO | WO 2015/036078 | 3/2015 |
| WO | WO 2015/042397 A1 | 3/2015 |
| WO | WO 2015/048336 A2 | 4/2015 |
| WO | WO 2015/051230 A1 | 4/2015 |
| WO | WO 2015/054555 A1 | 4/2015 |
| WO | WO 2015/078374 A1 | 6/2015 |
| WO | WO 2015/093948 A2 | 6/2015 |
| WO | WO 2015/116061 A1 | 8/2015 |
| WO | WO 2015/130915 A1 | 9/2015 |
| WO | WO 2015/144605 A1 | 10/2015 |
| WO | WO 2015/172732 A1 | 11/2015 |
| WO | WO 2015/183173 A1 | 12/2015 |
| WO | WO 2015/192701 A1 | 12/2015 |
| WO | WO 2016/005576 A1 | 1/2016 |
| WO | WO 2016/005577 A1 | 1/2016 |
| WO | WO 2016/014324 A1 | 1/2016 |
| WO | WO 2016/014522 A1 | 1/2016 |
| WO | WO 2016/021815 | 2/2016 |
| WO | WO 2016/044604 A1 | 3/2016 |
| WO | WO 2016/044629 A1 | 3/2016 |
| WO | WO 2016/044650 A1 | 3/2016 |
| WO | WO 2016/046837 A1 | 3/2016 |
| WO | WO 2016/047592 A1 | 3/2016 |
| WO | WO 2016/168647 A1 | 10/2016 |
| WO | WO 2016/181408 A2 | 11/2016 |
| WO | WO 2016/196816 | 12/2016 |
| WO | WO 2016/201227 A1 | 12/2016 |
| WO | WO 2017/006270 | 1/2017 |
| WO | WO 2017/050791 A1 | 3/2017 |
| WO | WO 2017/050792 A1 | 3/2017 |
| WO | WO 2017/191274 A2 | 11/2017 |
| WO | WO 2017/214002 A1 | 12/2017 |
| WO | WO 2018/049263 A1 | 3/2018 |
| WO | WO 2018/109277 A1 | 6/2018 |
| WO | WO 2018/175474 A1 | 9/2018 |
| WO | WO 2019/035863 A1 | 2/2019 |
| WO | WO 2019/035864 A1 | 2/2019 |
| WO | WO 2019/035865 A1 | 2/2019 |
| WO | WO 2019/099651 A1 | 5/2019 |
| WO | WO 2019/104134 | 5/2019 |
| WO | WO 2019/113359 | 6/2019 |
| WO | WO 2020/061252 | 3/2020 |
| WO | WO 2020/061255 | 3/2020 |
| WO | WO 2020/061261 | 3/2020 |
| WO | WO 2020/061378 | 3/2020 |
| WO | 2020139916 A1 | 7/2020 |
| WO | WO 2020/191022 | 9/2020 |

OTHER PUBLICATIONS

Abraham DJ, Mehanna AS, Wireko FC, et al. "Vanillin, a potential agent for the treatment of sickle cell anemia." *Blood*. 1991;77(6):1334-41.

Adakveo [package insert]. East Hanover, New Jersey, Novartis Pharmaceuticals Corporation (Nov. 2019), 10 pgs.

Agios First Quarter 2020 Financial Results (Apr. 30, 2020), pp. 1-22.

Agrawal RK, Patel RK, Shah V, Nainiwal L, Trivedi B. "Hydroxyurea in sickle cell disease: drug review." *Indian J Hematol Blood Transfus*. Jun. 30, 2014(2):91-96.

Agrawal, R. K. et al., "Hydroxyurea in Sickle Cell Disease: Drug Review", *Indian J. Hematol Blood Transfus*, 30(2), pp. 91-96, (Apr.-Jun. 2014).

Aiuti, A. et al, Progress and prospects: gene therapy clinical trials (part 2), *Gene Ther*, 14(22):1555-1563 (2007).

Al-Hakim, A.K. et al., 14-3-3 cooperates with LKB1 to regulate the activity and localization of QSK and SIK, *Journal of Cell Science* 118 (23), pp. 5661-5673 (Aug. 2005).

Al-Hakim, A.K. et al., "Control of AMPK-related kinases by USP9X and atypical Lys29/Lys33-linked polyubiquitin chains", *Biochemical Journal*, 411 (2), pp. 249-260, (Feb. 2008).

Alves-Filho, J.C. & Palsson-Mcdermott, E.M., Pyruvate Kinase M2: A Potential Target for Regulating Inflammation, *Frontiers in Immunology*, 7(145): Article 145 (2016).

Ambrus, J. et al., Studies on the vasoocclusive crisis of sickle cell disease. III. In vitro and in vivo effect of the pyrimido-pyrimidine derivative, RA-233: studies on its mechanism of action, *J Med*, 18(3-4):165-198 (1987).

Amer, J. et al., Red blood cells, platelets and polymorphonuclear neutrophils of patients with sickle cell disease exhibit oxidative stress that can be ameliorated by antioxidants, *British Journal of Haematology*, 132(1):108-113 (2006).

Andresen, C.A. et al., "Protein Interaction Screening for the Ankyrin Repeats and Suppressor of Cytokine Signaling (SOCS) Box (ASB) Family Identify Asb11 as a Novel Endoplasmic Reticulum Resident Ubiquitin Ligase", *The Journal of Biological Chemistry*, vol. 289, No. 4, pp. 2043-2054, (Jan. 24, 2014).

Ataga KI, Kutlar A, Kanter J, Liles D, Cancado R, Friedrisch J, Guthrie TH, Knight-Madden J, Alvarez OA, Gordeuk VR, Gualandro S, Colella MP, Smith WR, Rollins SA, Stocker JW, Rother RP. "Crizanlizumab for the prevention of pain crises in sickle cell disease." *N Engl J Med*. Feb. 2, 2017, 376(5):429-439.

Atkinson, Peter J., et al., 3,4-Dihydro-2H-benzoxazinones are 5-HT1A receptor antagonists with potent 5-HT reuptake inhibitory activity, *BioOrganic & Medicinal Chemistry Letters*, 15(3), pp. 737-741 (2005).

Austin, Nigel E., et al., "Novel 2,3,4,5-tetrahydro-1H-3-benzazepines with high affinity and selectivity for the dopamine D3 receptor", *BioOrganic & Medicinal Chemistry Letters*, 10(22), pp. 2553-2555, (2000).

Bailey, S.D. et al., "Variation at the NFATC2 Locus Increases the Risk of Thiazolidinedione-Induced Edema in the Diabetes Reduction Assessment with Ramipril and rosiglitazone Medication (DREAM) Study", *Diabetes Care*, vol. 33, No. 10, pp. 2250-2254, (Oct. 2010).

Bakshi N, Sinha CB, Ross D, Khemani K, Loewenstein G, Krishnamurti L. "Proponent or collaborative: Physician perspectives and approaches to disease modifying therapies in sickle cell disease." *PLoS One*. Jul. 20, 2017 12(7):e0178413.

(56) References Cited

OTHER PUBLICATIONS

Balakin, Konstantin V. et al., Comprehensive Computational Assessment of ADME Properties using Mapping Techniques, *Current Drug Discovery Technologies*, 2(2), pp. 99-113 (2005).
Banerjee, S. et al., "Interplay between Polo kinase, LKB1-activated NUAK1 kinase, PP1β phosphatase complex and the SCFβ$^{TrCP}$ E3 ubiquitin ligase", *Biochem. J.* 461, pp. 233-245, (2014).
Banerjee, T. and Kuypers F.A., Reactive oxygen species and phosphatidylserine externalization in murine sickle red cells, *British Journal of Haematology*, 124:391-402 (2004).
Barbier AJ, Bodie S, Connor G, et al. "Safety, tolerability, pharmacokinetics and pharmacodynamics of multiple doses of AG-519, an allosteric activator of pyruvate kinase-R, in healthy subjects." *Blood*. 2016, 128:1264.
Barua, A.K., et al., Chemistry and Industry Communications to the Editor 1376 24 (Oct. 1970).
Bennett, Eric J., et al., "Dynamics of Cullin-RING Ubiquitin Ligase Network Revealed by Systematic Quantitative Proteomics", *Cell* 143, pp. 951-965, (Dec. 10, 2010).
Betz T, Lenz M, Joanny JF, Sykes C. "ATP-dependent mechanics of red blood cells." *Proc Natl Acad Sci USA*. 2009;106(36):15320-5.
Beutler, E. and Gelbart, T., "Estimating the prevalence of pyruvate kinase deficiency from the gene frequency in the general white population", *Blood*, 95(11): 3585-3588 (2000).
Bianchi, P. and Zanella, A., "Hematologically important mutations: red cell pyruvate kinase", (Third update), *Blood Cells Mol Dis.*, 26(1): 47-53 (2000).
Biftu, T. et al., "Omarigliptin (MK-3102): A Novel Long-Acting DPP-4 Inhibitor for Once-Weekly Treatment of Type 2 Diabetes", *Journal of Medicinal Chemistry*, 57, pp. 3205-3212, (2014).
Bouwmeester, T. et al., "A physical and functional map of the human TNF-α/NF-κB signal transduction pathway", *Nature Cell Biology*, vol. 6, No. 2, pp. 97-105, (Feb. 2004).
Boxer, M.B. et al., "Evaluation of Substituted N,N$^1$-Diarylsulfonamides as Activators of the Tumor Cell Specific M2 Isoform of Pyruvate Kinase", *J. Med. Chem.*, 53: pp. 1048-1055 (2010).
Brajenovic, M. et al., "Comprehensive Proteomic Analysis of Human Par Protein Complexes Reveals an Interconnected Protein Network", *The Journal of Biological Chemistry*, vol. 275, No. 13, pp. 12804-12811 (Mar. 2004).
Brehme, M. et al., "Charting the molecular network of the drug target Bcr-Abl", *PNAS*, vol. 106, No. 18, pp. 7414-7419, (May 2009).
Bridges, C.R., et al., "USP9X deubiquitylating enzyme maintains RAPTOR protein levels, mTORC1 signalling and proliferation in neural progenitors", *Scientific Reports* 7:391, pp. 1-15, (Mar. 2017).
Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," *Blood* (2020) 136 (Supplement 1):19-20, Nov. 4, 2020.
Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," ASH 2020, Dec. 7, 2020.
Budzikiewicz, Herbert et al., "Vincetene, a benzopyrroloisoquinoline alkaloid, from *Cynanchum vincetoxicum* (L.) Pers. (Asclepiadaceae)", *Liebigs Annalen Der Chemie*, (8), pp. 1212-1231 (1979).
Buontempo P, Jubin RG, Buontempo C, Real R, Kazo F, O'Brien S, Adeel F, Abuchowski A. "Pegylated carboxyhemoglobin bovine (Sanguinate) restores RBCs roundness and reduces pain during a sickle cell vaso-occlusive crisis." *Blood*. 2017, 130:969.
Cabrales, P. et al., "A look inside the mechanistic black box: Are red blood cells the critical effectors of RRx-001 cytotoxicity?", *Med Oncol.*, 33(7):63 (2016).
CAS Registry No. 1208929-16-1, Tert-Butyl 1H,2H,3H,4H,5H,6H-Pyrrolo[3,4-C]Pyrrole-2-Carboxylate Hydrochloride (Mar. 11, 2010).

Castilhos, L. et al., "Altered E-NTPDase/E-ADA activities and CD39 expression in platelets of sickle cell anemia patients", *Biomed Pharmacother.*, 79:241-246 (2016).
Castilhos, L. et al., "Increased oxidative stress alters nucleosides metabolite levels in sickle cell anemia", *Redox Rep.*, 22(6):451-459 (2017).
Castilhos, L. et al., "Sickle cell anemia induces changes in peripheral lymphocytes E-NTPDase/E-ADA activities and cytokines secretion in patients under treatment", *Biomedicine & Pharmacotherapy* 73 (2015), pp. 102-108.
Castro, O., Viability and function of stored sickle erythrocytes, *Transfusion*, 20(6):695-703 (1980).
Cazzola, M., Pyruvate kinase deficiency, Haematologica, 90(1): 1-2 (2005).
Charache, S. et al., Effect of 2,3-Diphosphateglycerate on oxygen affinity of blood in sickle, Cell Anemia, Journal of Clinical Investigation, 49(4):806-812 (1970).
Chaudhary, Neelam & Maddika, Subbareddy, "WWP2-WWP1 Ubiquitin Ligase Complex Coordinated by PPM1G Maintains the Balance Between Cellular p73 and ΔNp73 Levels", *Mol. Cell. Biol.* (Oct. 2014).
Chen, Yue et al.—Preclinical Pharmacokinetic/Pharmacodynamic Relationships for AG-348, an Investigational Small-Molecule Activator of Pyruvate Kinase, European Hematology Association, Jun. 13, 2015.
Cheung, Yiu-Yin et al., Solution-Phase Parallel Synthesis and SAR of Homopiperazinyl Analogs as Positive Allosteric Modulators of MGlu$_4$, *ACS Comb Sci.* 13(2), pp. 159-165, (Mar. 2011).
Chiosis et al., Development of a Purine-Scaffold Novel Class of Hsp90 Binders that Inhibit the Proliferation of Cancer Cells and Induce the Degradation of Her2 Tyrosine Kinase, BioOrganic & Medicinal Chemistry, vol. 10, Iss 11, (Nov. 2002), pp. 3555-3564.
Chiou WL, Barve A. "Linear correlation of the fraction of oral dose absorbed of 64 drugs between humans and rats." *Pharm Res.* Nov. 1998, 15(11):1792-5.
Chonat, S. et al.,—Improvement in Red Blood Cell Physiology in Children With Sickle Cell Anemia Receiving Voxelotor—Childrens Healthcare of Atlanta (Dec. 2019).
Choudhury, N.R., et al., "RNA-binding activity of TRIM25 is mediated by its PRY/SPRY domain and is required for ubiquitination", BMC Biology 15:105, pp. 1-20, (2017).
Christensen, R.D. et al., Siblings with Severe Pyruvate Kinase Deficiency and a Complex Genotype, American Journal of Medical Genetics, Part A, (2016), pp. 2449-2452.
Chubukov V, Johnson K, Kosinski PA, et al. "Characterization of metabolic response to AG-348, an allosteric activator of red cell pyruvate kinase, in healthy volunteers and pyruvate kinase deficiency patients." Poster presented at: 58th American Society of Hematology Annual Meeting and Exposition; Dec. 4, 2016; San Diego, California. http://investor.agios.com/staticfiles/e1e9fd70-c84b-4472-bff3-bef0ecf05482 Accessed Jul. 28, 2017.
Chung, J.Y.L. et al., "Evolution of a Manufacturing Route to Omarigliptin, A Long-Acting DPP-4 Inhibitor for the Treatment of Type 2 Diabetes", *Organic Process Research & Development*, 19, pp. 1760-1768, (2015).
Clinical Trial Study—NCT02604433—U.S. National Library of Medicine, An Efficacy and Safety Study of Luspatercept (ACE-536) Versus Placebo in Adults Who Require Regular Red Blood Cell Transfusions Due to Beta (β) Thalassemia (BELIEVE), Submitted Date: Nov. 13, 2015, 24 pgs.
ClinicalTrials.gov, NCT03815695, (v1)—U.S. National Library of Medicine, "A SAD/MAD to Assess the Safety, Pharmacokinetics and Pharmacodynamics of FT-4202 in Healthy Volunteers and Sickle Cell Disease Patients" (Jan. 22, 2019).
Clinical Trials Study, NCT03815695, (v2)—U.S. National Library of Medicine, "A SAD/MAD to Assess the Safety, Pharmacokinetics and Pharmacodynamics of FT-4202 in Healthy Volunteers and Sickle Cell Disease Patients," (Mar. 13, 2019) pp. 1-5.
ClinicalTrials.gov, NCT03815695, (v3)—U.S. National Library of Medicine, "A SAD/MAD to Assess the Safety, Pharmacokinetics and Pharmacodynamics of FT-4202 in Healthy Volunteers and Sickle Cell Disease Patients" (Sep. 16, 2019).

(56) References Cited

OTHER PUBLICATIONS

Clinical Trial Study—NCT03815695, (v4)—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Sep. 19, 2019 (v4), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Sep. 23, 2019 (v5), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Oct. 9, 2019 (v6), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Oct. 10, 2019 (v7), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Nov. 27, 2019 (v8), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Jan. 15, 2020 (v9 ), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Jan. 16, 2020 (v10), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Feb. 21, 2020 (v11), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Apr. 1, 2020, (v12), 12 pgs.
ClinicalTrials.gov, NCT03815695 (v13), "A SAD/MAD to Assess the Safety, Pharmacokinetics and Pharmacodynamics of FT-4202 in Healthy Volunteers and Sickle Cell Patients," Jun. 15, 2020.
ClinicalTrials.gov, NCT03815695 (v14), "A SAD/MAD to Assess the Safety, Pharmacokinetics and Pharmacodynamics of FT-4202 in Healthy Volunteers and Sickle Cell Patients," Jul. 17, 2020.
ClinicalTrials.gov, NCT03815695 (v15), "A SAD/MAD to Assess the Safety, Pharmacokinetics and Pharmacodynamics of FT-4202 in Healthy Volunteers and Sickle Cell Patients," Aug. 19, 2020.
ClinicalTrials.gov, NCT03815695 (v16), "A SAD/MAD to Assess the Safety, Pharmacokinetics and Pharmacodynamics of FT-4202 in Healthy Volunteers and Sickle Cell Patients," Sep. 1, 2020.
ClinicalTrials.gov, NCT03815695 (v17), "A SAD/MAD to Assess the Safety, Pharmacokinetics and Pharmacodynamics of FT-4202 in Healthy Volunteers and Sickle Cell Patients," Sep. 18, 2020.
ClinicalTrials.gov, NCT03815695 (v18), "A SAD/MAD to Assess the Safety, Pharmacokinetics and Pharmacodynamics of FT-4202 in Healthy Volunteers and Sickle Cell Patients," Oct. 15, 2020.
ClinicalTrials.gov, NCT03815695 (v19), "A SAD/MAD to Assess the Safety, Pharmacokinetics and Pharmacodynamices of FT-4202 in Healthy Volunteers and Sickle Cell Patients," Study Record Versions 19—Dec. 24, 2020.
ClinicalTrials.gov, NCT03815695 (v20), "A SAD/MAD to Assess the Safety, Pharmacokinetics and Pharmacodynamices of FT-4202 in Healthy Volunteers and Sickle Cell Patients," Study Record Versions 20, Jan. 8, 2021.
ClinicalTrials.gov, NCT04624659 (v1), "A Study of FT-4202 in Adults and Adolescents With Sickle Cell Disease," Study Record Version 1—Nov. 5, 2020.
ClinicalTrials.gov, NCT04624659 (v2), "A Study of FT-4202 in Adults and Adolescents With Sickle Cell Disease," Study Record Version 2—Nov. 10, 2020.
ClinicalTrials.gov, NCT04624659 (v3), "A Study of FT-4202 in Adults and Adolescents With Sickle Cell Disease," Study Record Versions 3—Dec. 10, 2020.
ClinicalTrials.gov, NCT04624659 (v4), "A Study of FT-4202 in Adults and Adolescents With Sickle Cell Disease," Study Record Versions 4, Dec. 28, 2020.
ClinicalTrials.gov, NCT04624659 (v5), "A Study of FT-4202 in Adults and Adolescents With Sickle Cell Disease," Study Record Versions 5, Jan. 7, 2021.
ClinicalTrials.gov, NCT04624659 (v6), "A Study of FT-4202 in Adults and Adolescents With Sickle Cell Disease," Study Record Versions 6, Jan. 14, 2021.
ClinicalTrials.gov, NCT04624659 (v7), "A Study of FT-4202 in Adults and Adolescents With Sickle Cell Disease," Study Record Versions 7, Feb. 8, 2021.
Cloutier, P. et al., "R2TP/Prefoldin-like component RUVBL1/RUVBL2 directly interacts with ZNHIT2 to regulate assembly of U5 small nuclear ribonucleoprotein", Nature Communications, pp. 1-14 (May 2017).
Cole, D.C. et al., Conformationally Constrained N1-arylsulfonyltryptamine derivatives as 5-HT6 receptor antagonists, BioOrganic & Medicinal Chemistry Letters, vol. 15, No. 21, (Nov. 1, 2005), pp. 4780-4785.
Cox, J.L., et al., "The SOX2-Interactome in Brain Cancer Cell Identifies the Requirement of MSI2 and USP9X for the Growth of Brain Tumor Cell", PLoS One, vol. 8, Issue 5, pp. 1-13, (May 2013).
Croasdell, G., European Hematology Association—20th Annual Congress (Jun. 11-14, 2015—Vienna, Austria) Meeting Report, Drugs of Today (2015), 51(7),I pp. 441-445.
Das, A. et al., "USP9X counteracts differential ubiquitination of NPHP5 by MARCH7 and BBS11 to regulate ciliogenesis", PLOS Genetics, pp. 1-24, (May 12, 2017).
Davis, Z.H., et al., "Global Mapping of Herpesvirus-Host Protein Complexes Reveals a Transcription Strategy for Late Genes", Molecular Cell 57, pp. 349-360; (Jan. 22, 2015).
De Furia, F. et al., The effects of cyanate in vitro on red blood cell metabolism and function in sickle cell anemia, J Clin Invest., 51(3):566-574 (1972).
De Jong, K. and Kuypers, F., Sulphydryl modifications alter scramblase activity in murine sickle cell disease, British Journal of Haematology, 133(4):427-432 (2006).
De Rosa MC, Carelli Alinovi C, Galtieri A, Russo A, Giardina B. "Allosteric properties of hemoglobin and the plasma membrane of the erythrocyte: New insights in gas transport and metabolic modulation." IUBMB Life. 2008, 60(2):87-93.
Diez, A. et al., Life-threatening nonspherocytic hemolytic anemia in a patient with a null mutation in the PKLR gene and no compensatory PKM gene expression, Blood, 106:1851 (2005).
Diez-Silva M, Dao M, Han J, Lim CT, Suresh S. "Shape and biomechanical characteristics of human red blood cells in health and disease." MRS Bull. May 2010, 35(5):382-8.
Drissi, R. et al., "Quantitative Proteomics Reveals Dynamic Interactions of the Mini chromosome Maintenance Complex (MCM) in the Cellular Response to Etoposide Induced DNA Damage", Molecular & Cellular Proteomics, pp. 2002-2013, (2015).
Droxia [package insert]. Princeton, New Jersey, Bristol-Myers Squibb Company, (Dec. 2017), 28 pgs.
Droxia [package insert]. Princeton, New Jersey, Bristol-Myers Squibb Company (Dec. 2019), 25 pgs.
Dupont, S. et al., "FAM/USP9x, a Deubiquitinating Enzyme Essential for TGFβ Signaling, Controls Smad4 Monoubiquitination", Cell, 136, pp. 123-135, (Jan. 9, 2009).

(56) References Cited

OTHER PUBLICATIONS

Dzandu JK, Johnson RM. "Membrane protein phosphorylation in intact normal and sickle cell erythrocytes." J Biol Chem. Jul. 10, 1980 255(13):6382-6.
El-Sharief, A.M., et al., Some halogenated sulfonamides with biological interest, Journal of the Indian Chemical Society, vol. 61, No. 6, (1984), pp. 537-543.
Emam, H.A., et al., Heterocyclization of sulfamido chalcones to pyrazoline, cyanopyridone, nicotinonitrile and hydrobenzo [1,2-c] pyrazole derivatives, Journal of the Serbian Chemical Society, vol. 62, No. 7, (1997), Abstract only.
Endari [package insert]. Torrance, California: Emmaus Medical, Inc., (Jul. 2017), 8 pgs.
Endari [package insert]. Torrance, California, Emmaus Medical, Inc., (Nov. 2019), 10 pgs.
Ernst, A. et al., "A Strategy for Modulation of Enzymes in the Ubiquitin System", Science, 339, pp. 1-15, (Feb. 2013).
Estepp, et al., Phase 1 Single (SAD) and Multiple Ascending Dose (MAD) Study of the Safety, Pharmacokinetics (PK) and Pharmacodynamics (PD) of FT-4202, a PKR-Activator, in Healthy and Sickle Cell Disease Subjects, Abstract, e-Poster, European Hematology Association Open Access Library, Presentation EHA25, (May 14, 2020), 2 pgs.
Estepp, et al., Phase 1 Single (SAD) and Multiple Ascending Dose (MAD) Study of the Safety, Phyarmacokinetics (PK) and Pharmacodynamics (PD) of FT-4202, a PKR Activator, in Healthy and Sickle Cell Disease Subjects, Poster, EP1531, (Jun. 12, 2020), 1 pg.
Estepp, J.H. et al., A clinically meaningful fetal hemoglobin threshold for children with sickle cell anemia during hydroxyurea therapy, Am J Hematol., 92:1333-1339 (2017).
Estepp, Jeremie H., et al., "Phase 1 Single (SAD) and Multiple Ascending Dose (MAD) Study of the Safety, Pharmacokinetics (PK) and Pharmacodynamics (PD) of FT-4202, a PKR Activator, in Healthy Volunteers and Patients with Sickle Cell Disease," Virtual meeting [poster EP1531] presented at the 25th Congress of the European Hematology Association; Jul. 11-21, 2020.
European Hematology Association HemaSphere Abstract Book, 15th Annual Sickle Cell & Thalassaemia & 1st EHA European Sickle Cell Conference, Oct. 26-31, 2020.
Fioravanti, R., et al., Synthesis and Biological Evaluation of N-substituted-3, 5-diphenyl-2-pyrazoline derivatives as cyclooxygenase (COX-2) inhibitors, European Journal of Medicinal Chemistry, vol. 45, No. 12, (Dec. 1, 2010), pp. 6135-6138, XP027526583.
Fitch, R. W. et al., Phantasmidine: An Epibatidine Congener from the Ecuadorian Poison Frog Epipedobates anthonyi, Journal of Natural Products (2010), vol. 73, No. 3, pp. 331-337.
Fleischhacker, W., et al., "Heterocyclic fused naphthalene systems from thebaine. 1", Liebigs Annalen Der Chemie, (5), pp. 844-851, (1983).
Fogeron, M.L. et al., "LGALS3BP regulates centriole biogenesis and centrosome hypertrophy in cancer cells", Nature Communications, 4:1531, pp. 1-14; (2013).
Forma Therapeutics, Press Release, "Forma Therapeutics Presents Clinical Proof-of-Concept Data at the 62nd Annual ASH Meeting Supporting the Potential of its Novel Investigational PKR Activator, FT-4202, to Treat Sickle Cell Disease (SCD)" (Dec. 7, 2020).
Forma Therapeutics, Inc., Press Release—"Forma Therapeutics Announces Positive FT-4202 600 mg Multiple Ascending Dose Cohort Data Supporting the Doses Being Evaluated in Phase 2/3 Registrational Trial, Called the Hibiscus Study", Mar. 30, 2021—2 pgs.
Frost, David A., et al., "Naturally occurring compounds related to phenalenone. V. Synthetic approaches to structures based on 8,9-dihydro-8,8,9-trimethylphenaleno [1,2-b] furan-7-one", Journal of the Chemical Society, Perkin Transactions 1: Organic and Bio-Organic Chemistry (1972-1999), pp 2159-2169.
Gaudet, P. et al., "Phylogenetic-based propagation of functional annotations within the Gene Ontology consortium", vol. 12, No. 5, pp. 449-462; (Aug. 2011).
Giannone, R.J., et al., "The Protein Network Surrounding the Human Telomere Repeat Binding Factors TRF1, TRF2, and POT1", PLoS One, vol. 5, Issue 8, pp. 1-10, (Aug. 2010).
Gizi, A. et al., Assessment of oxidative stress in patients with sickle cell disease: The glutathione system and the oxidant-antioxidant status, Blood Cells Mol Dis., 46(3):220-225 (2011).
Gladwin, M., Adenosine recepter crossroads in sickle cell disease, Nature Medicine, 17(1):38-40, (2011).
Glombitza, S. et al., Adenosine causes cAMP-dependent activation of chick embryo red cell carbonic anhydrase and 2,3-DPG synthesis, American Journal of Physiology, 271(4):973-81 (1996).
Gomez-Bougie, P. et al., "Noxa controls Mule-dependent Mcl-1 ubiquitination through the regulation of the Mcl-1/USP9X interaction", Biochemical and Biophysical Research Communications 413, pp. 460-464, (2011).
Goncharov, T. et al., "OTUB1 modulates c-IAP1 stability to regulate signaling pathways", The EMBO Journal 32, No. 8, pp. 1103-1114, (2013).
Grace RF, Rose C, Layton DM, Yaish HM, Barcellini W, Galactéros F, Morton DH, Ravindranath Y, Kuo KHM, van Beers EJ, Kwiatkowski JL, Silver BA, Merica E, Kung C, Cohen M, Yang H, Hixon J, Kosinski PA, Silver L, Dang L, Yuan Z, Barbier AJ, Glader B. "Effects of AG_348, a pyruvate kinase activator, on anemia and hemolysis in patients with pyruvate kinase deficiency: Data from the DRIVE PK study". Blood. 2016, 128:402.
Grace, et al., Safety and Efficacy of Mitapivat in Pyruvate Kinase Deficiency, N. Engl. J. Med. 381, 10, (Sep. 5, 2019), p. 933-944.
Grasso, D. et al., "Zymophagy, a Novel Selective Autophagy Pathway Mediated by VMP1-USP9x-p62, Prevents Pancreatic Cell Death", The Journal of Biological Chemistry, vol. 286, No. 10, pp. 8308-8324, (Mar. 2011).
Greco, T.M. et al., "Nuclear Import of Histone Deacetylase 5 by Requisite Nuclear Localization Signal Phosphorylation", Molecular & Cellular Proteomics 10: , pp. 1-15, (2011).
Grou, C.P., et al., "Identification of ubiquitin-specific protease 9X (USP9X) as a deubiquitinase acting on the ubiquitin-peroxin 5 (PEX5) thioester conjugate", J. Biol. Chem., pp. 1-24; (Feb. 27, 2012).
Habata, S. et al., "BAG3-mediated Mcl-1 stabilization contributes to drug resistance via interaction with USP9X in ovarian cancer", International Journal of Oncology 49: pp. 402-410, (2016).
Han, K.J. et al., "Ubiquitin-specific Protease 9x Deubiquitinates and Stabilizes the Spinal Muscular Atrophy Protein—Survival Motor Neuron", J. Biol. Chem., pp. 1-22, (Oct. 2012).
Hanson, D. et al., "Identifying biological pathways that underlie primordial short stature using network analysis", Journal of Molecular Endocrinology, pp. 333-344, (2014).
Harada, R. et al., "Structure of pristimerin, a quinonoid triterpene", Tetrahedron Letters, pp. 603-607, (1962).
Harayama, Takashi et al., "Novel synthesis of naphthobenzazepines from N-bromobenzylnaphthylamines by regioselective C—H activation utilizing the intramolecular coordination of an amine to Pd", Synlett, (8), pp. 1141-1144, (2003).
Hauri, S. et al., "Interaction proteome of human Hippo signaling: modular control of the co-activator YAP1", Molecular Systems Biology, 9: 713, pp. 1-16 (Nov. 2013).
Havugimana, P. et al., "A Census of Human Soluble Protein Complexes", Cell 150, pp. 1068-1081, (Aug. 2012).
Hebbel RP, Eaton JW, Balasingam M, Steinberg MH. "Spontaneous oxygen radical generation by sickle erythrocytes." J Clin Invest. 1982, 70(6):1253-9.
Hein, M.Y., et al., "A Human Interactome in Three Quantitative Dimensions Organized by Stoichiometries and Abundances", Cell 163, pp. 712-723, (Oct. 2015).
Hierso, R. et al., Effects of oxidative stress on red blood cell rheology in sickle cell patients, British Journal of Haematology, 166(4):601-606 (2014).
Homan, C.C. et al., "Mutations in USP9X Are Associated with X-linked Intellectual Disability and Disrupt Neuronal Cell Migration and Growth", The American Journal of Human Genetics 94, pp. 470-478, (Mar. 2014).
Hoppe CC, Inati AC, Brown C, et al. "Initial results from a cohort in a phase 2a study (GBT440-007) evaluating adolescents with

(56) References Cited

OTHER PUBLICATIONS sickle cell disease treated with multiple doses of GBT440, a HbS polymerization inhibitor." Blood. 2017:130(Suppl 1): 689.
Husain, M.I., et al., Synthesis of some new N-[4-(acetyl/phenyl-5-arylpyrazolin-3-yl)phenyl]arylsulfonamides as oral hypoglycemic agents, Indian Drugs, vol. 24, No. 4, (1987), Abstract only.
Huttlin, E. L., et al., "The BioPlex Network: A Systematic Exploration of the Human Interactome", Cell 162, pp. 425-440, (Jul. 2015).
Huttlin, E.L., et al., "Architecture of the human interactome defines protein communities and disease networks", Nature, pp. 1-35, (May 2017).
Hydrea [package insert]. Princeton, New Jersey, Bristol-Myers Squibb Company (Jul. 2019), 29 pgs.
Imamura K, Tanaka T. "Multimolecular forms of pyruvate kinase from rat and other mammalian tissues. I Electrophoretic studies." J Biochem. 1972, 71:1043-51.
Imamura K, Tanaka T. "Pyruvate kinase isozymes from rat." Methods Enzymol. 1982, 90:150-65.
International Search Report and Written Opinion for PCT/US2019/051831, dated Dec. 6, 2019 (Dec. 6, 2019).
International Search Report and Written Opinion for PCT/US2020/051645, dated Dec. 7, 2020 (Dec. 7, 2020).
International Search Report and Written Opinion for PCT/US2020/051579, dated Dec. 10, 2020 (Dec. 10, 2020).
International Search Report and Written Opinion for PCT/US2019/052024, dated Dec. 23, 2019 (Dec. 23, 2019).
International Search Report and Written Opinion for PCT/US2018/023405, dated Jun. 5, 2018 (Jun. 5, 2018).
Iwasaki, Tameo et al., "Novel Selective PDE IV Inhibitors as Antiasthmatic Agents. Synthesis and Biological Activities of a Series of 1-Aryl-2,3-bis (hydroxymethyl) naphthalene Lignans", Journal of Medicinal Chemistry (1996), pp. 2696-2704.
Jendralla, H. et al., Synthesis of 1,2,3,4,5,6-Hexahydropyrrolo[3,4-c]pyrrole dihydrobromide and 1,2,3,5-Tetrahydro-2-[(4-Methyl-Phenyl) Sulfonyl]Pyrrolo[3,4-c]Pyrrole, Heterocycles, 41(6): 1291-1298 (1995).
Jin, Y. et al., Effects of gamma irradiation on red cells from donors with sickle cell trait, Transfusion, 37(8): 804-808 (1997).
Johansen, L.D., et al., "IKAP localizes to membrane ruffles with filamin A and regulates actin cytoskeleton organization and cell migration", Journal of Cell Science 121, pp. 854-864, (Dec. 2007).
Jones, M.H., et al., "The *Drosophila* developmental gene fat facets has a human homologue in Xp11.4 which escapes X-inactivation and has related sequences on Yq11.2", Human Molecular Genetics, vol. 5, No. 11, pp. 1695-1701, (Aug. 1996).
Jorgensen, Eugene C., et al., "Thyroxine analogs. 20. Substituted 1- and 2-naphthyl ethers of 3,5-diiodotyrosine", Journal of Medicinal Chemistry 14(11), pp. 1023-1026, (1971).
Joshi, B., et al., Indian J. Chem., Sect. B (1983), 22B(2), Abstract only. Chemical Abstract No. 99:105146.
Joshi, P., et al., "The functional interactome landscape of the human histone deacetylase family", Molecular Systems Biology 9, 672, (2013).
Kalai, T. et al., Synthesis of Pyrroline Nitroxide Annulated Carbocycles and Heterocycles, Synthesis No. 6, pp. 831-837 (2000).
Kalfa, et al., FORMA Therapeutics, Inc., Watertown, MA, Power Pointe Presentation, Dated Nov. 6, 2019 , Phase 1 Single and Multiple Ascending Dose Study of the Safety, Tolerability, Pharmacokinetics and Pharmacodynamics of FT-4202, an Allosteric activator of Pyruvate Kinase-R, in Healthy and Sickle Cell Disease Subjects, 15 pgs.
Kalfa, T. A. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", JSCDH-D-20-0053, vol. VII, Pub. Date: Jun. 12, 2020; pp. 83-84.
Kalfa, T. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", 14th Annual Sickle Cell Disease Research and Educational Symposium/43rd National Sickle Cell Disease Scientific Meeting (Sep. 23-25, 2020).
Kalfa, T.A. et al., "616 Phase 1 Single (SAD) and Julotiple Ascending Dose (MAD) Studies of the Safety, Tolerability, Pharmacokinetics (PK) and Pharmacodynamics (PD) of FT-4202, an Allosteric Activator of Pyruvate Kinase-R, in Healthy and Sickle Cell Disease Subjects", (Nov. 2019).
Kaltenbach, L.S., et al., "Huntingtin Interacting Proteins Are Genetic Modifiers of Neurodegeneration", PLoS Genetics, vol. 3, Issue 5, pp. 689-708, (May 2007).
Kasturi, Tirumalai R., et al., "Reactions of tetrahalo-1,2-benzoquinones. III. Reaction of tetrachloro-1,2-benzoquinone withtetralones and naphthols: pathway to the condensates", Journal of the Chemical Society C: Organic, (9), pp. 1257-1259, (1970).
Katzenellenbogen, R.A., et al., "NFX1-123 and Poly(A) Binding Proteins Synergistically Augment Activation of Telomerase In Human Papillomavirus Type 16 E6-Expressing Cells", Journal of Virology, vol. 81, pp. 3786-3796, (Apr. 2007).
Khafagy, M.M., Synthesis of some pyrimidine and pyrazoline derivatives, Al-Azhar Bulletin of Science, vol. 3, No. 1, (1992), Abstract only.
Kharalkar, S.S. et al., Identification of Novel Allosteric Regulators of Human-Erythrocyte Pyruvate Kinase, Chemistry & Biodiversity, vol. 4, pp. 2603-2617 (Feb. 2007).
Kim H, Kosinski P, Kung C, Dang L, Chen Y, Yang H, Chen YS, Kramer J, Liu G. "A fit-for-purpose LC-MS/MS method for the simultaneous quantitation of ATP and 2,3-DPG in human K2EDTA whole blood." J Chromatogr B Analyt Technol Biomed Life Sci. Sep. 1, 2017 1061-1062:89-96.
Kim J, Lee H, Shin S. "Advances in the measurement of red blood cell deformability: A brief review." J Cell Biotech. 2015;1:63-79.
Kim, M., et al., "Role of Angiomotin-like 2 mono-ubiquitination on YAP inhibition", EMBO reports, vol. 17, No. 1., pp. 64-78, (Nov. 23, 2015).
Kimura, K., et al., "Diversification of transcriptional modulation: Large-scale identification and characterization of putative alternative promoters of human genes", Genome Research 16, pp. 55-65, (2006).
Kirli, K., et al., "A deep proteomics perspective on CRM1-mediated nuclear export and nucleocytoplasmic partitioning", eLife, pp. 1-28; (2015).
Knauff, E.A.H., et al., "Genome-wide association study in premature ovarian failure patients suggests ADAMTS19 as a possible candidate gene", Human Reproduction, vol. 24, No. 9, pp. 2372-2379, (2009).
Kodama, K. et al., Solvent-induced dual chirality switching in the optical resolution of tropic acid via diastereomeric salt formation with (1R,2S)-2-amino-1,2-diphenylethanol, Tetrahedron 70:7923-7928 (2014).
Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin SC Disease Irrespective of Prior Hydroxyurea Use," Blood (2020) 136 (Supplement1):23-24, Nov. 4, 2020.
Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin SC Disease Irrespective of Prior Hydroxyurea Use," Presented at the 62nd American Society of Hematology (ASH) Annual Meeting, Dec. 5, 2020.
Kristensen, A.R., Gsponer, J. and Foster, L.J., "A high-throughput approach for measuring temporal changes in the interactome", Nat Methods, 9(9), pp. 1-12, (2012).
Kuehl, G. et al., In vitro interactions of 51Cr in human red blood cells and hemolysates, Vox Sang., 40(4):260-272 (1981).
Kung C, Hixon J, Kosinski PA, et al. "AG-348 enhances pyruvate kinase activity in red blood cells from patients with pyruvate kinase deficiency." Blood. 2017;130(11):1347-1356.
Kurita, R. et al., Establishment of Immortalized Human Erythroid Progenitor Cell Lines Able to Produce Enucleated Red Blood Cells, PLoS One, vol. 8, Iss.3, pp. 1-15 (Mar. 2013).

(56) References Cited

OTHER PUBLICATIONS

Kushwaha, D., et al., "USP9X inhibition promotes radiation-induced apoptosis in non-small cell lung cancer cells expressing mid-to-high MCL1", Cancer Biology & Therapy 16:3, pp. 392-401, (Mar. 2015).
Kwasna, D., et al., "Discovery and Characterization of ZUFSP/ZUP1, a Distinct Deubiquitinase Class Important for Genome Stability", Molecular Cell 70, pp. 150-164, (2018).
Le Quesne, P.W. et al., One-Step Preparation of Tetrakis(bromomethyl)ethylene from Pinacolyl Alcohol, J. Org. Chem., 40(1): 142-143 (1975).
Le, Kha et al., Population pharmacokinetics and pharmacodynamics of AG-519, a pyruvate kinase activator for the treatment of pyruvate kinase deficiency, in human healthy volunteers, Agios Pharma—1263 Poster,—58th American Society of Hematology Annual Meeting and Exposition, Dec. 3-6, 2016—San Diego, CA.
Le, Kha et al., Population pharmacokinetics and pharmacodynamics of AG-348 in healthy human volunteers guide dose selection for the treatment of pyruvate kinase deficiency, Agios Pharma—3336 Poster,—57th American Society of Hematology Annual Meeting and Exposition, Dec. 5-8, 2015—Orlando, FL.
Lehrer-Graiwer J, Howard J, Hemmaway CJ, et al. "Long-term dosing in sickle cell disease subjects with GBT440, a novel HbS polymerization inhibitor." Blood, 2016:128(22): 2488.
Lehrer-Graiwer, Josh et al., Long-Term Dosinig in Sickle Cell Disease Subjects with GBT440, a Novel HbS Polymerization Inhibitor, blood, 114, Hemoglobinopathies, Excluding Thalassemia—Clinical Poster II, Dec. 2, 2016.
Lenihan, J.A., Saha, Orthis, and Young P.W., "Proteomic analysis reveals novel ligands and substrates for LNX1 E3 ubiquitin ligase", PLoS One, pp. 1-18; (Nov. 2017).
Li, X., et al., "Defining the protein-protein interaction network of the human protein tyrosine phosphatase family", The American Society for Biochemistry and Molecular Biology, Inc., pp. 1-54, (2016).
Litinov RI, Weisel JW. "Role of red blood cells in haemostasis and thrombosis." ISBT Sci Ser. Feb. 2017, 12(1):176-183.
Liu, X.H., et al., European Journal of Cancer, vol. 31A, No. 6, pp. 953-963, (1995).
Llauger et al., "Evaluation of 8-Arylsulfanyl, 8-Arylsulfoxyl, and 8-Arylsulfonyl Adenine Derivatives as Inhibitors of the Heat Shock Protein 90", J. Med. Chem., 48 (8), pp. 2892-2905, (Mar. 25, 2005).
Llauger et al., "Synthesis of 8-arylsulfoxyl/sulfonyl adenines", Tetrahedron Letters, vol. 45, Issue 52, (Dec. 20, 2004), pp. 9549-9552.
Lochmatter, C. et al., Integrative phosphoproteomics links IL-23R signalling with metabolic adaption in lymphocytes, Scientific Reports, 6:24491 (2016).
Lockwood, S. et al., Endothelium-derived nitric oxide production is increased by ATP released from red blood cells incubated with hydroxyurea, Nitric Oxide, 38:1-7 (2014).
Loriga G. et al., Synthesis of 3,6-diazabicyclo [3.1.1]heptanes as novel ligands for the opioid receptors, Bioorganic & Medicinal Chemistry, Pergamon, GB, vol. 14, No. 3, pp. 676-691, (Feb. 1, 2006).
Lu, L., et al., "The HECT Type Ubiquitin Ligase NEDL2 Is Degraded by Anaphase-promoting Complex/Cyclosome (APC/C)-Cdh1, and Its Tight Regulation Maintains the Metaphase to Anaphase Transition", The Journal of Biological Chemistry, vol. 288, No. 50, pp. 35637-35650; (Dec. 2013).
Lucas, et al., "Facile Synthesis of a Library of 9-Alkyl-8-benzyl-9H-purin-6-ylamine Derivatives", J. Comb. Chem., 3 (6), pp. 518-520, (Sep. 21, 2001).
MacDonald, Gregor J., et al, "Design and Synthesis of trans-3-(2-(4-((3-(3-(5-Methyl-1,2,4-oxadiazolyl))-phenyl(carboxamido)cyclohexyl)ethyl)-7-methylsulfonyl-2,3,4,5-tetrahydro-1H-3-benzazepine (SB-414796): A Potent and Selective Dopamine D3 Receptor Antagonist", Journal of Medicinal Chemistry, 46(23), pp. 4952-4964 (2003).
Macdonald, Rosemary, Red cell 2,3-diphosphoglycerate and oxygen affinity, Anaesthesia, vol. 32, pp. 544-553, (1977).
Martinez-Mayorga Karina et al, Ligand/kappa-opioid receptor interactions: Insights from the X-ray crystal structure, European Journal of Medicinal Chemistry, vol. 66, pp. 114-121 (May 30, 2013).
Mathe-Allainmat, Monique et al., "Synthesis of 2-Amido-2, 3-dihydro-1H-phanalene Derivatives as New Conformationally Restricted Ligands for Melatonin Receptors", Journal of Medicinal Chemistry, 39(16), pp. 3089-3095, (1996).
McCluskey A., et al., BioOrganic & Medicinal Chemistry Letters 10 (2000), pp. 1687-1690.
McCluskey A., et al., Bioorganic & Medicinal Chemistry Letters 11 (2001), pp. 2941-2946.
McGarry, E., et al., "The deubiquitinase USP9X maintains DNA replication fork stability and DNA damage checkpoint responses by regulating CLASPIN during S-phase", Cancerres.aacrjournals.org, pp. 1-39; (2016).
Metcalf B, Chuang C, Dufu K, et al. "Discovery of GBT440, an orally bioavailable R-state stabilizer of sickle cell hemoglobin." ACS Med Chem Lett. 2017; 8(3):321-326.
Meza, N.W. et al, In vitro and in vivo expression of human erythrocyte pyruvate kinase in erythroid cells: a gene therapy approach, Hum Gene Ther, 18(6):502-514 (2007).
Middelkoop, E. et al., Studies on sickled erythrocytes provide evidence that the asymmetric distribution of phosphatidylserine in the red cell membrane is maintained by both ATP-dependent translocation and interaction with membrane skeletal proteins, Biochimica et Biophysica Acta, 937:281-288 (1988).
Misra H. Bainbridge J, Berryman J, Abuchowski A, Galvez KM, Uribe LF, Hernandez AL, Sosa NR. "A phase 1b open label, randomized, safety study of SANGUINATE™ in patients with sickle cell anemia." Rev Bras Hematol Hemoter. Jan.-Mar. 2017, 39(1):20-7.
Miwa, S. and Fujii, H., Molecular basis of erythroenzymopathies associated with hereditary hemolytic anemia: tabulation of mutant enzymes, Am J Hematol., 51(2): 122-132 (1996).
Moehrle, H., et al., "1,2,3,4-Tetrahydroquinolines as substrates for Mannich compounds", Chemical Sciences, 53(7), pp. 742-752; (1998).
Moriyama R, Lombardo CR, Workman RF, Low PS. "Regulation of linkages between the erythrocyte membrane and its skeleton by 2,3-diphosphoglycerate." J Biol Chem. May 25, 1993 268(15):10990-6.
Mouchantaf, R., et al., "The Ubiquitin Ligase Itch Is Autoubiquitylated in Vivo and in Vitro but Is Protected from Degradation by Interacting with the Deubiquitylating Enzyme FAM/USP9X", The Journal of Biological Chemistry, vol. 281, No. 50, pp. 38738-38747, (Dec. 2006).
Murn, J. et al., "Control of a neuronal morphology program by an RNA-binding zinc finger protein, Unkempt", Genes & Development 29, pp. 501-512, (2015).
Murray, R.Z., Jolly, L.A., Wood, S.A., "The FAM Deubiquitylating Enzyme Localizes to Multiple Points of Protein Trafficking in Epithelia, where It Associates with E-cadherin and β-catenin", Molecular Biology of the Cell, vol, 15, pp. 1591-1599; (Apr. 2004).
Muzyamba, M. and Gibson, J., Effect of 1-chloro-2,4-dinitrobenzene on K+ transport in normal and sickle human red blood cells, Journal of Physiology, 547(3):903-911 (2003).
Nagai, H., et al., "Ubiquitine-like Sequence in ASK1 Plays Critical Roles in the Recognition and Stabilization by USP9X and Oxidative Stress-Induced Cell Death", Molecular Cell 36, pp. 805-818, (Dec. 2009).
Nagy, Peter I., et al., "Theoretical and Experimental Study on Ion-Pair Formation and Partitioning of Organic Salts in Octanol/Water and Dichloromethane/Water Sytems", Journal of the American Chemical Society, 122 (28), pp. 6583-6593 (2000).
Nam, Keun-Soo et al., "Synthesis of quinolone antimicrobial agents and their antibacterial activities," 5 Korean J. Med. Chem. (1995), pp. 2-5.
Narayanan, N., Wang, Z., Li, L., and Yang, Y., "Arginine methylation of USP9X promotes its interaction with TDRD3 and its anti-apoptotic activities in breast cancer cells", Cell Discovery 3, pp. 1-17, (2017).

(56) References Cited

OTHER PUBLICATIONS

Nathan, J.A., et al., "The Ubiquitin E3 Ligase MARCH7 is Differentially Regulated by the Deubiquitylating Enzymes USP7 and USP9X", Traffic, 9, pp. 1130-1145, (2008).
Neto, E.D. et al., "Shotgun sequencing of the human transcriptome with ORF expressed sequence tags", PNAS, vol. 97, No. 7, pp. 3491-3496, (Mar. 2000).
Noma, T., et al., "Stage- and sex-dependent expressions of Usp9x, an X-linked mouse ortholog of Drosophila Fat facets, during gonadal development and oogenesis in mice", Gene Expression Patters 2, pp. 87-91, (2002).
O'Connor, H.F., et al., "Ubiquitin-Activated Interaction Traps (UBAITs) identify E3 ligase binding partners", EMBO reports, vol. 16, No. 12., (2015).
Obach RS. "Prediction of human clearance of twenty-nine drugs from hepatic microsomal intrinsic clearance data: An examination of in vitro half-life approach and nonspecific binding to microsomes." Drug Metab Dispos. Nov. 1999, 27(11):1350-9.
Oksenberg D, Dufu K, Patel MP, Chuang C, Li Z, Xu Q, Silva-Garcia A, Zhou C, Hutchaleelaha A, Patskovska L, Patskovsky Y, Almo SC, Sinha U, Metcalf BW, Archer DR. "GBT440 increases haemoglobin oxygen affinity, reduces sickling and prolongs RBC half-life in a murine model of sickle cell disease." Br J Haematol. Oct. 2016, 175(1):141-53.
Oliviero, G., et al., "The variant Polycomb Repressor Complex 1 component PCGF1 interacts with a pluripotency sub-network that includes DPPA4, a regulator of embryogenesis", pp. 1-11, (2015).
Olsen, J.V., et al., "Global, In Vivo, and Site-Specific Phosphorylation Dynamics in Signaling Networks", Cell 127, pp. 635-648, (Nov. 2006).
Oski, M.D., Frank A., "The Role of Organic Phosphates in Erythrocytes on the Oxygen Dissociation of Hemoglobin," Annals of Clinical Laboratory Science, vol. 1, No. 2 (Nov. 1970), pp. 162-176.
Ould Amar, A.K. et al., Assessment of qualitative functional parameters of stored red blood cells from donors with sickle cell trait (AS) or with heterozygote (AC) status, Transfus Clin Biol., 3(4):225-233 (1996).
Ouyang, W., et al., "β-catenin is regulated by USP9x and mediates resistance to TRAIL-induced apoptosis in breast cancer", Oncology Reports 35, pp. 717-724, (2016).
Oxbryta [package insert]. San Francisco, California, Global Blood Therapeutics, Inc. (Nov. 2019), 15 pgs.
Oxbryta Slide Show—Jan. 2020.
Paemka, L., et al., "Seizures Are Regulated by Ubiquitin-specific Peptidase 9 X-linked (USP9X), a De-Ubiquitinase", PLoS Genetics, 11(3): pp. 1-16, (Mar. 2015).
Palsson-Mcdermott, EM et al., Pyruvate kinase M2 regulates Hif-1a activity and IL-1β induction and is a critical determinant of the Warburg Effect in LPS-activated macrophages, Cell Metabolism, 21:65-80 (2015).
Papp, S.J., et al., "DNA damage shifts circadian clock time via Hausp-dependent Cry1 stabilization", eLIFE, p.p. 1-19, (2015).
Park, Yoon, Jin, Hyung-seung, and Liu, Yun-Cai, "Regulation of T cell function by the ubiquitin-specific protease USP9X via modulating the Carma 1-Bcl10-Malt1 complex", PNAS, vol. 110, No. 23, pp. 9433-9438, (Jun. 2013).
Pászty C. "Transgenic and gene knock-out mouse models of sickle cell anemia and the thalassemias." Curr Opin Hematol. 1997, 4(2): 88-93.
Patel, P., et al., Synthesis of some novel pyrazoline and cyanopyridine derivatives as antimicrobial agents, Il Farmaco, vol. 51, No. 1, (1996), Abstract only.
Pavagadhi, T.H., et al., 3-(3'-phenoxyphenylmethyl)-5-aryl-1-acetylpyrazolines, Journal of the Institution of Chemists (India), vol. 73, No. 3, (2001), Abstract only.
Peddaboina, C. et al., "The downregulation of Mcl-1 via USP9X inhibition sensitizes solid tumors to Bcl-xl inhibition", BMC Cancer, 12:541, pp. 1-12, (2012).
Perez-Mancera, P.A., et al., "The deubiquitinase USP9X suppresses pancreatic ductal adenocarcinoma", Nature, 486(7402): pp. 266-270; (Dec. 2012).
Platt OS. "Hydroxyurea for the treatment of sickle cell anemia." N Engl J Med. 2008;358(13):1362-9.
Poillon W., & Kim, B., 2,3-Diphosphoglycerate and intracellular pH as interdependent determinants of the physiologic solubility of deoxyhemoglobin S, Blood, 76:1028-1036 (1990).
Poillon, W. et al., Antisickling effects of 2,3-Diphosphoglycerate Depletion, Blood, 85(11):3289-3296 (1995).
Poillon, W. et al., Intracellular hemoglobin S polymerization and the clinical severity of sickle cell anemia, Blood, 91:1777-1783 (1998).
Poillon, W. et al., The Effect of 2,3-Diphosphoglycerate on the Solubility of Deoxyhemoglobin S1, Archives of Biochemistry and Biophysics, vol. 249, No. 2, pp. 301-305, (Sep. 1986).
Press Release—"Agios Announces New Data from AG-348 and AG-519 Demonstrating Potential for First Disease-modifying Treatment for Patients with PK Deficiency" Dec. 4, 2016—Globe Newswire.
Press Release—"Agios Presents Updated Data from DRIVE PK Study Demonstrating AG-348 is Well-Tolerated and Results in Clinically Relevant, Rapid and Sustained Hemoglobin Increases in Patients with Pyruvate Kinase Deficiency" Dec. 10, 2017—Globe Newswire.
PubChem SID: 440235168, modify date Feb. 25, 2021 (Feb. 25, 2021), Version 2, p. 1-7, Structure.
PubChem SID: 440235168, date Feb. 18, 2021 (Feb. 18, 2021), Version 1 of 2, p. 1-7, Structure.
PubChem CID: 135338361, create date: Dec. 15, 2018 (Dec. 15, 2018), p. 1, formula.
PubChem CID: 135338378, create date: Dec. 15, 2018 (Dec. 15, 2018), p. 1, formula.
PubChem CID: 69203074, create date: Nov. 30, 2012 (Nov. 30, 2012), pp. 1-20, compound summary.
PubChem CID: 69203505, create date: Nov. 30, 2012 (Nov. 30, 2012), pp. 1-20, compound summary.
Rab, et al., AG-348 (Mitapivat), an allosteric activator of red blood cell pyruvate kinase, increases enzymatic activity, protein stability, and ATP levels over a broad range of PKLR genotypes, Haematologica, 105:xxx, (Jan. 23, 2020).
Rab, M.A.E. et al., Rapid and reproducible characterization of sickling during automated deoxygenation in sickle cell disease patients, Am. J. Hematol. (2019; 94; pp. 575-584.
Rabai M, Detterich JA, Wenby RB, et al. "Deformability analysis of sickle blood using ektacytometry." Biorheology. 2014;51(2-3):159-70.
Ramdani, G. and Langsley, G., ATP, an Extracellular Signaling Molecule in Red Blood Cells: A Messenger for Malaria?, Biomed Journal, 37(5):284-292 (2014).
Raththagala, M. et al., Hydroxyurea stimulates the release of ATP from rabbit erythrocytes through an increase in calcium and nitric oxide production, European Journal of Pharmacology, 645(1-3):32-38 (2010).
Reblozyl [package insert]. Cambridge, Massachusetts, Acceleron Pharma, Inc. (2020), 27 pgs.
Reblozyl [package insert]. Summit, New Jersey, Celgene Corporation (Nov. 2019), 16 pgs.
Rice-Evans C, Omorphos SC, Baysal E. "Cell membranes and oxidative damage." Biochem J. Jul. 1, 1986 237(1):265-9.
Rosa, M. et al., Allosteric properties of hemoglobin and the plasma membrane of the erythrocyte: New insights in gas transport and metabolic modulation, Life, 60(2):87-93 (2008).
Ross, M.T., et al., "The DNA sequence of the human X chromosome", Nature, 434, pp. 325-337; (Mar. 2005).
Rott, Ruth, et al., "α-Synuclein fate is determined by USP9X-regulated monoubiquitination", PNAS, (2011).
Roy, R., et al., "hnRNPA1 couples nuclear export and translation of specific mRNAs downstream of FGF-2/S6K2 signalling", Nucleic Acids Research, vol. 42, No. 20, pp. 12483-12497, (Oct. 2014).
Rush, J., et al., "Immunoaffinity profiling of tyrosine phosphorylation in cancer cells", Nature Biotechnology, vol. 23, No. 1, pp. 94-101, (2005).

(56) References Cited

OTHER PUBLICATIONS

Sampson M, Archibong AE, Powell A, et al. "Perturbation of the developmental potential of preimplantation mouse embryos by hydroxyurea." Int J Environ Res Public Health. 2010;7(5):2033-44.
Sato, Y., et al., "Ubiquitin-specific protease 9X in host cells interacts with herpes simplex virus 1 ICP0", J. Vet. Med. Sci. 78(3), pp. 405-410; (2016).
Savio et al., "USP9X Controls EGFR Fate by Deubiquitinating the Endocytic Adaptor Eps15", Current Biology 26, pp. 173-183, (Jan. 2016).
Schwartz, R. et al., Two distinct pathways mediate the formation of intermediate density cells and hyperdense cells from normal density sickle red blood cells, Blood, 92(12):4844-4855 (1998).
Schwickart, M., et al., "Deubiquitinase USP9X stabilizes MCL1 and promotes tumour cell survival", Nature vol. 463, pp. 103-108; (Jan. 2010).
Sega, M. et al., Fluorescence assay of the interaction between hemoglobin and the cytoplasmic domain of erythrocyte membrane band 3, Blood Cells Mol Dis., 55(3):266-271 (2015).
Shen, G., et al., "MicroRNA-26b inhibits epithelial-mesenchymal transition in hepatocellular carcinoma by targeting USP9X," BMC Cancer 14:393, pp. 1-11, (2014).
Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Blood (2020) 136 (Supplement 1):21-22, Nov. 4, 2020.
Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Presented at the 62nd American Society of Hematology (ASH) Annual Meeting, Dec. 5, 2020.
Siklos [package insert]. Lannoy, France, Delpharm Lille, (May 2019), 24 pgs.
Siklos [package insert]. Paris, France, Addmedica, (Dec. 2017), 25 pgs.
Siklos [package insert]. Paris, France, Addmedica, (May 2018), 23 pgs.
Smidrkal, Jan., "Synthesis of fagaronine", Collection of Czechoslovak Chemical Communications, 53(12), pp. 3184-3192, (1988).
Sorathiya, S.D., et al., Preparation and antimicrobial activity of 3-(p-(2',5'-dibromobenzenesulfonamido)phenyl)-5-aryl-1H/acetyl/phenyl-2-pyrazolines, Indian Journal of Chemistry, Section B: Organic, Incl. Medicinal Chemistry, vol. 36B, No. 7, (1997), Abstract only.
Soupene, E. and Kuypers, F., Identification of an erythroid ATP-dependent aminophospholipid transporter, British Journal of Haematology, 133(4):436-438 (2006).
Space SL, Lane PA, Pickett CK, Weil JV. "Nitric oxide attenuates normal and sickle red blood cell adherence to pulmonary endothelium." Am J Hematol. Apr. 2000, 63(4):200-4.
Spinella, J.F., et al., "Genomic characterization of pediatric T-cell acute lymphoblastic leukemia reveals novel recurrent driver mutations", Oncotarget, vol. 7, No. 40, pp. 65485-65503, (Sep. 2016).
Stasiuk, M. et al., Transformations of erythrocytes shape and its regulation, Postepy Biochem., 55(4):425-33 (2009). English Abstract.
St-Denis, N., et al., "Phenotypic and Interaction Profiling of the Human Phosphatases Identifies Diverse Mitotic Regulators", Cell Reports 17, pp. 2488-2501, (Nov. 2016).
Stebbins et al., Crystal Structure of an Hsp90-Geldanamycin Complex: Targeting of a Protein Chaperone by an Antitumor Agent, Cell, (Apr. 1997), 89, p. 241.
Steinberg, Martin H., Pathophysiologically based drug treatment of sickle cell disease, Trends in Pharmacological Sciences, vol. 27, No. 4, (Apr. 2006).
Strausberg, R.L., et al., "Generation and initial analysis of more than 15,000 fulllength human and mouse cDNA sequences", PNAS vol. 99, No. 26, pp. 16899-16903, (Dec. 2002).
Sun, H., et al., "Bcr-Abl ubiquitination and Usp9x inhibition block kinase signaling and promote CML cell apoptosis", Blood, (Jan. 2011).
Sundd, Prithu et al., Pathophysiology of Sickle Cell Disease, Annual Review of Pathology: Mechanisms of Disease, (Oct. 9, 2018), pp. 261-290.
Swanson, Devin M. et al., "Identification and biological evaluation of 4-(3-trifluoromethylpyridine-2-yl) piperazine-1-c arboxylic acid (5-trifluoromethylpyridin-2-yl) amide, a high affinity TRPV1 (VR1) vanilloid receptor antagonist", Journal of Medicinal Chemistry, 48(6), pp. 1857-1872 (2005).
Taipale, M., et al., "A Quantitative Chaperone Interaction Network Reveals the Architecture of Cellular Protein Homeostasis Pathways", Cell 158, pp. 434-448, (Jul. 2014).
Takenaka, M. et al, Isolation and characterization of the human pyruvate kinase M gene, Eur J Biochem, 198(1):101-106 (1991).
Talmud, P.J., et al., "Gene-centric Association Signals for Lipids and Apolipoproteins Identified via the Human CVD Bead Chip", The American Journal of Human Genetics 85, pp. 628-642, (Nov. 2009).
Tanpaichitr, V.S. et al, Successful bone marrow transplantation in a child with red blood cell pyruvate kinase deficiency, Bone Marrow Transplant, 26(6):689-690 (2000).
Taya, S., et al., "The deubiquitinating enzyme Fam interacts with and stabilizes β-catenin", Genes to Cells 4, pp. 757-767, (1999).
Taya, S., et al., "The Ras Target AF-6 is a Substrate of the Fam Deubiquitinating Enzyme", The Journal of Cell Biology, vol. 142, No. 4, pp. 1053-1062, (Aug. 1998).
Telen, Marilyn, Malik, Punam, and Vercellotti, Gregory M., Therapeutic strategies for sickle cell disease: towards a multi-agent approach, Nature Reviews/Drug Discovery; (Dec. 4, 2018).
Terao, Y., et al., "Trifluoroacetic Acid-Catalyzed 1,3-Cycloaddition of the Simplest Iminium Ylide Leading to 3- or 3,4-Substituted Pyrrolidines and 2,5-Dihydropyrroles", Chem. Pharm. Bull., 33(7), pp. 2762-2766, (1985).
Théard, D., et al., "USP9x-mediated deubiquitination of EFA6 regulates de novo tight junction assembly", The EMBO Journal, vol. 29, No. 9, pp. 1499-1509, (2010).
Thein, Swee Lay, The Molecular Basis of β-Thalassemia, Cold Spring Harb Perspect Med. (2013).
Thompson, Alexis, M.D., M.P.H., "A Targeted Agent for Sickle Cell Disease—Changing the Protein but Not the Gene," The New England Journal of Medicine, (Jun. 14, 2019).
Tian, S., et al., Yaoxue Xueba (1993), 28(11), pp. 870-875. Chemical Abstract No. 120:299229.
Toloczko, A., et al., "Deubiquitinating Enzyme USP9X Suppresses Tumor Growth via LATS kinase and Core Components of the Hippo pathway", Cancer Research, pp. 1-37, (Jul. 2017).
Tripathi, Ashutoshi and Safo, Martin K., In Silico-Screening Approaches for Lead Generation: Identification of Novel Allosteric Modulators of Human-Erythrocyte Pyruvate Kinase, Allostery: Methods and Protocols, Methods in Molecular Biology, Chpt. 19, vol, 796, pp. 351-367 (2012).
Trivigno, D., et al., "Deubiquitinase USP9x Confers Radioresistance through Stabilization of Mcl-1 1,2", NEO Plasia, vol. 14, No. 10, pp. 893-904, (Oct. 2012).
Tsai, Y.C., et al., "Functional Proteomics Establishes the Interaction of SIRT7 with Chromatin Remodeling Complexes and Expands Its Role in Regulation of RNA Polymerase I Transcription", Molecular & Cellular Proteomics 11.5, pp. 60-76, (2012).
Tsutsumi H, Tani K, Fujii H, Miwa S. "Expression of L- and M-type pyruvate kinase in human tissues. Genomics." 1988, 2(1):86-9.
United States Securities and Exchange Commission, Form S-1 Registration Statement, Forma Therapeutics Holdings, Inc., dated Dec. 8, 2020, 374 pages.
United States Securities and Exchange Commission, Form S-1, Registration Statement—Forma Therapeutics Holdings, Inc., May 29, 2020.
Upadhyay J., et al., Studies on pyrazolines. Part III. Preparation and antimicrobial activity of 3-(4-phenylsulfonamidophenyl)-5-aryl-1-ace tyl/phenyl -4,5-dihydropyrazoles, Journal of the Indian Chemical Society, vol. 68, No. 7, (1991), pp. 413-414.
Van Zweiten, R. et al., Inborn defects in the antioxidant systems of human red blood cells, Free Radio Biol Med., 67:377-386 (2014).

(56) References Cited

OTHER PUBLICATIONS

Vanderah et al, Novel d-amino acid tetrapeptides produce potent antinociception by selectively acting at peripheral kappa-opioid receptors, European Journal of Pharmacology, Elsevier Science, vol. 583, No. 1, pp. 62-72 (Jan. 24, 2008).
Varjosalo, M., et al., The Protein Interaction Landscape of the Human CMGC Kinase Group, Cell Reports 3, pp. 1306-1320, (Apr. 2013).
Verma, S.K. et al., Imidazole-Catalyzed Monoacylation of Symmetrical Diamines, Organic Letters, 12(19): 4232-4235, (2010).
Vichinsky, E. et al., "A Phase 3 Randomized Trial of Voxelotor in Sickle Cell Disease," N Engl J Med. DOI: 10.1056/NEJMoa1903212 (Jun. 2019).
Vichinsky, E. et al., Protocol to A Phase 3 Randomized Trial of Voxelotor in Sickle Cell Disease, (Jun. 14, 2019).
Vichinsky, E. et al., Supplementary Appendix to A Phase 3 Randomized Trial of Voxelotor in Sickle Cell Disease, (Jun. 14, 2019).
Vong, Q. P., et al., "Chromosome Alignment and Segregation Regulated by Ubiquitination of Survivin", Science, vol. 310, pp. 1499-1504, (Dec. 2, 2005).
Voskou S, Aslan M, Fanis P, Phylactides M, Kleanthous M. "Oxidative stress in β-thalassaemia and sickle cell disease." Redox Biol. Dec. 2015, 6:226-39.
Wagner, G. et al., Red cell vesiculation—a common membrane physiologic event, J Lab Clin., 108(4):315-324 (1986).
Wan, C., et al., "Panorama of ancient metazoan macromolecular complexes", Nature 525(7569), pp. 339-344, (Sep. 2015).
Wang, G.S., et al., Journal of Ethnopharmacology, 26 (1989), pp. 147-162.
Wang, H. et al., JMJD5 regulates PKM2 nuclear translocation and reprograms HIF-1a-mediated glucose metabolism, PNAS, 111(1):279-284 (2014).
Wang, J., et al, "TopBP1 Controls BLM Protein Level to Maintain Genome Stability", Molecular Cell 52, pp. 667-678, (Dec. 2013).
Wang, Q., et al., "The X-linked Deubiquitinase USP9X Is an Integral Component of Centrosome", The American Society for Biochemistry and Molecular Biology, Inc., pp. 1-33, (2017).
Wang, S. et al., "Ablation of the oncogenic transcription factor ERG by deubiquitinase inhibition in prostate cancer", PNAS, vol. 111, No. 11, pp. 4251-4256, (Mar. 2014).
Wang, S., et al., "The ubiquitin ligase TRIM25 targets ERG for degradation in prostate cancer", Oncotarget, vol. 7, No. 40, pp. 64921-64931, (2016).
Wang, X, et al., "Hsp90 Cochaperone Aha1 Downregulation Rescues Misfolding of CFTR in Cystic Fibrosis", Cell 127, pp. 803-815, (Nov. 2006).
Waza et al., Nature, 11, No. 10, (Oct. 2005), pp. 1088-1095.
Weatherall, D., The inherited diseases of hemoglobin are an emerging global health burden, Blood, 115(22):4331-43336 (2010).
Wei, Wan-Guo et al., "A practical procedure for multisubstituted .beta.-naphthols and their derivatives", Tetrahedron, 59(34), pp. 6621-6625, (2003).
Willcocks, J. et al., Simultaneous determination of low free Mg2+ and pH in human sickle cells using P NMR spectroscopy, The Journal of Biological Chemistry, 277(51):49911-49920 (2002).
Wood BL, Gibson DF, Tait JF. "Increased erythrocyte phosphatidylserine exposure in sickle cell disease: flow-cytometric measurement and clinical associations." Blood., 88(5):1873-80 (Sep. 1, 1996).
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease (PRAISE)," Blood (2020) 136 (Supplement 1):19-20, Nov. 4, 2020.
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease," Presented at the 62nd American Society of Hematology (ASH) Annual Meeting, Dec. 7, 2020.
Woods, N.T., et al., "Charting the Landscape of Tandem BRCT Domain-Mediated Protein Interactions", Sci Signal, 5(242), pp. 1-35, (2014).

Wright, S.W. et al., A Convenient Preparation of Heteroaryl Sulfonamides and Sulfonyl Fluorides from Heteroaryl Thiols, J. Org. Chem., 71: 1080-1084 (2006).
Wu, Y., et al., "Aberrant phosphorylation of SMAD4 Thr277-mediated USP9x-SMAD4 interaction by free fatty acids promotes breast cancer matastasis", Cancer Research, pp. 1-34, (2017).
Wu, Z., et al., "Targeted Ubiquitination and Degradation of G-Protein-Coupled Receptor Kinase 5 by the DDB1-CUL4 Ubiquitin Ligase Complex", PLoS One, vol. 7, Issue 8, pp. 1-11, (Aug. 2012).
Xie, Y., et al., "Deubiquitinase FAM/USP9X Interacts with the E3 Ubiquitin Ligase SMURF1 Protein and Protects It from Ligase Activity-dependent Self-degradation", The Journal of Biological Chemistry., vol. 288, No. 5, pp. 2976-2985, (Feb. 2013).
Xu, Z., et al., "Identification of a Deubiquitinating Enzyme as a Novel AGS3-Interacting Protein", PLoS One, vol. 5, Issue 3, pp. 1-12, (Mar. 2010).
Yan, J., et al., "Usp9x- and Noxa-mediated Mcl-1 downregulation contributes to pemetrexed-induced apoptosis in human non-small-cell lung cancer cells", Cell Death and Disease 5, pp. 1-7, (2014).
Yang H, Merica E, Chen Y, Cohen M, Goldwater R, Hill C, et al. "Phase I single (SAD) and multiple ascending dose (MAD) studies of the safety, tolerability, pharmacokinetics (PK) and pharmacodynamics (PD) of AG-348, a first-in-class allosteric activator of pyruvate kinase-R, in healthy subjects." Blood. 2014, 124:4007.
Yang H, Merica E, Chen Y, et al. "Phase 1 Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers." Clin Pharmacol Drug Dev. Aug. 9, 2018.
Yang, H. et al., Phase 1 Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers, 8 Clin. Pharmacol. Drug Dev. 246-259 (2019).
Yi, S., et al., Leukemia Research, vol. 15(10), (1991), pp. 883-886.
You, J. and Pickart, C.M., "A HECT Domain E3 Enzyme Assembles Novel Polyubiquitin Chains", vol. 276, No. 23, pp. 19871-19878, (2001).
Yu, W., et al., "Large-Scale Concatenation cDNA Sequencing", Genome Research 7, pp. 353-358, (1997).
Zanella A, Fermo E, Bianchi P, Chiarelli LR, Valentini G. "Pyruvate kinase deficiency: The genotype-phenotype association." Blood Rev. 2007, 23:217-31.
Zanella A, Fermo E, Bianchi P, Valentini G. "Red cell pyruvate kinase deficiency: molecular and clinical aspects." Br J Haematol. 2005;130(1):11-25.
Zhang, C., et al., "Synergistic anti-tumor activity of gemcitabine and ABT-737 in vitro and in vivo through disrupting the interaction of USP9X and Mcl-1", Molecular Cancer Therapeutics, (May 12, 2011).
Zhang, C., et al., "USP9X destabilizes pVHL and promotes cell proliferation", Oncotarget, vol. 7, No. 37, pp. 60519-60534, (2016).
Zhang, Y & Xia, Y., Adenosine signaling in normal and sickle erythrocytes and beyond, Microbes Infect., 14(10) (2012).
Zhang, Y. et al., Detrimental effects of adenosine signaling in sickle cell disease, Nature Medicine, 17(1):79-87 (2011).
Zhang, Yongmin et al., "Organic reactions in chiral micelles. 7. The structural effects on the asymmetric oxidation of prochiral sulfides in chiral micelles", Chinese Journal of Chemistry, (1990), pp. 89-96.
Zhao, Y., et al., "Noncanonical regulation of alkylation damage resistance by the OTUD4 deubiquitinase", EMBO Journal, vol. 34, No. 12, pp. 1687-1703, (2015).
Zhi et al., Hybrid Antibacterals. DNA Polymerase—Topoisomerase Inhibitors. J. Med. Chem., published on Web Jan. 25, 2006., vol. 49, pp. 1455-1465, especially p. 1456. Scheme 3, compound 4; p. 1457, Scheme 4, compound 13, p. 1462.
Zhou, L., et al., "The Scaffold Protein KSR1, a Novel Therapeutic Target for the Treatment of Merlin-Deficient Tumors", Oncogene 35(26), pp. 3443-3453, (Jun. 2016).
Zhou, ZH et al., Phosphorus, Sulfur and Silicon and the Related Elements (1999), 152, pp.45-52. Chemical Abstract No. 132: 180853.

(56) References Cited

OTHER PUBLICATIONS

Zhu, Tong et al., Polymer-Supported Synthesis of Pyridone-Focused Libraries as Inhibitors of Anaplastic Lymphoma Kinase, Journal of Combinatorial Chemistry, 8(3), pp. 401-409, (2006).

Qian et al., "Drug-polymer solubility and miscibility: Stability consideration and practical challenges in amorphous solid dispersion development", J. Pharm. Sci., Jul. 2010, vol. 99, No. 7, pp. 2941-2947.

Clinical Trial Study—NCT04000165 "A Dose-Finding Study of AG-348 in Sickle Cell Disease", ClinicalTrials.gov, Jun. 27, 2019, 9 pages.

Kalfa, T.A. et al., "Phase 1 Single (SAD) and Multiple Ascending Dose (MAD) Studies of the Safety, Tolerability, Pharmacokinetics (PK) and Pharmacodynamics (PD) of FT-4202, an Allosteric Activator of Pyruvate Kinase-R, in Healthy and Sickle Cell Disease Subjects", Blood, American Society of Hematology, Nov. 13, 2019, pp. 3, vol. 134.

National Center for Biotechnology Information. PubChem Substance Record for SID 377251214, SCHEMBL20511283, Source: SureChEMBL. https://pubchem.ncbi.nlm.nih.gov/substance/377251214. Accessed Nov. 3, 2020. Available Dec. 15, 2018. (Year: 2018).

Supplemental European Search Report for EP Application 20 86 4351, Aug. 2, 2023, 10 pages.

U.S. Appl. No. 16/576,720, filed Sep. 19, 2019, 47 pages.

PYRUVATE KINASE R (PKR) ACTIVATING COMPOSITIONS

CROSS-REFERENCE TO RELATED APPLICATIONS

This application claims the benefit of and priority to U.S. patent application Ser. No. 16/576,720, filed Sep. 19, 2019; U.S. patent application Ser. No. 16/576,360, filed Sep. 19, 2019; U.S. Patent Application No. 62/902,887, filed Sep. 19, 2019; U.S. Patent Application No. 62/906,437, filed Sep. 26, 2019; International Application No. PCT/US2019/052024, filed Sep. 19, 2019; U.S. Patent Application No. 63/024,432, filed May 13, 2020; U.S. Patent Application No. 63/024,441, filed May 13, 2020; U.S. Patent Application No. 62/704,785, filed May 28, 2020; and U.S. Patent Application No. 62/705,106, filed Jun. 11, 2020; each of which is incorporated by reference in its entirety.

TECHNICAL FIELD

The present disclosure is directed to solid forms, dispersions and pharmaceutical compositions of a pyruvate kinase R (PKR) activating compound. More specifically, the present disclosure is directed to crystalline solid forms, spray-dried dispersions and pharmaceutical compositions of (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one, and preparation methods thereof.

BACKGROUND

Chemical compounds can form one or more different pharmaceutically acceptable solid forms, including amorphous and crystalline forms. Amorphous solid forms include dispersions, such as spray-dried dispersions, of amorphous and crystalline chemical compounds. Individual solid forms of bioactive chemical compounds can have different properties. There is a need for the identification and selection of appropriate solid forms of bioactive chemical compounds (including appropriate crystalline forms, where applicable) for the development of pharmaceutically acceptable dosage forms for the treatment of various diseases or conditions.

The compound (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one ("Compound 1"),

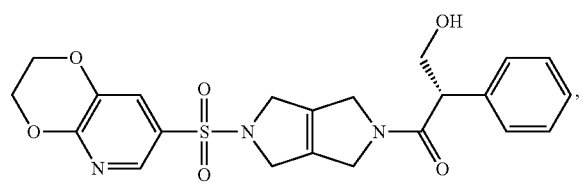

is a small molecule PKR activator which modulates pyruvate kinase activity. Compound 1 is described in International Publication No. WO 2018/175474 as one of many compounds suitable as small molecule modulators of pyruvate kinase activity. There remains a need for identifying solid forms of Compound 1 useful for various therapeutic applications.

SUMMARY

One aspect of the disclosure relates to solid oral dosage forms comprising a stabilized amorphous pharmaceutical composition of the compound (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (also referred to as "stabilized amorphous Compound 1"). As used herein, the term "stabilized amorphous Compound 1" refers to an amorphous solid form of Compound 1 that is stabilized (e.g., by combination with certain stabilizing polymers and/or other manufacturing processes) to prevent the formation of crystalline forms of Compound 1 or solid phase separation of Compound 1 under certain storage conditions described herein (e.g., stabilized amorphous pharmaceutical compositions comprising Compound 1 and one or more additional components that do not show crystalline diffraction peaks by XRPD analysis (Method D) after 2 weeks of storage at 60° C./75% RH (exposed), and/or show a single glass transition temperature ($T_G$) with no melt endotherm by DSC analysis (Method B) after 2 weeks of storage at 60° C./75% RH (exposed)).

In some embodiments, the stabilized amorphous Compound 1 is obtained by spray drying a solution of Compound 1 with a stabilizing polymer. The inventors discovered that amorphous Compound 1 has higher oral bioavailability than certain crystalline forms of Compound 1, including crystalline form Type A. Accordingly, in some embodiments, solid oral dosage forms comprising stabilized amorphous Compound 1 advantageously provide superior oral bioavailability of Compound 1 in comparison to solid oral dosage forms comprising certain crystalline forms of Compound 1.

Also disclosed herein are an amorphous spray-dried dispersion (SDD) of Compound 1, preparation methods thereof, and pharmaceutical compositions containing the same. The present disclosure provides various solid forms of Compound 1, including one or more pharmaceutically acceptable crystalline and amorphous forms for Compound 1, useful for the therapeutic oral administration of Compound 1. The various solid forms of Compound 1 can be identified by certain characteristic properties. For example, certain crystalline forms of Compound 1 have distinct characteristic XRPD peaks.

Another aspect of the disclosure relates to solid forms of Compound 1. Solid forms of Compound 1 disclosed herein include various crystalline forms (including Type A, Type B, Type C, Type D, Type E, Type F, Type G, Type H, Type I, Type J, Type K, Type L, and Type M) of Compound 1, preparation methods thereof, and pharmaceutical compositions containing the same.

One aspect of the present disclosure relates to novel crystalline solid forms of Compound 1:

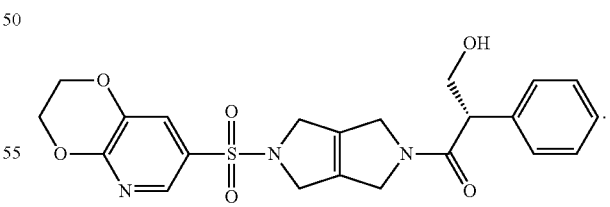

A novel Compound 1 crystalline form Type A can be identified by X-ray Powder Diffraction (XRPD) pattern having one or more characteristic diffractions at angles (2 theta±0.2) of 4.61, 15.66, 23.19, and 24.76. A novel Compound 1 crystalline form Type A can be identified by X-ray Powder Diffraction (XRPD) pattern having one or more characteristic diffractions at angles (2 theta±0.2) of 4.6, 15.7, 23.2, and 24.8. A novel Compound 1 crystalline form Type A can be identified by X-ray Powder Diffraction (XRPD)

pattern having one or more characteristic diffractions at angles (2 theta±0.2) of 4.6, 7.2, 15.7, 21.3, 23.2, and 24.8.

A novel Compound 1 crystalline form Type B can be identified by X-ray Powder Diffraction (XRPD) pattern having one or more characteristic diffractions at angles (2 theta±0.2) of 4.52, 15.57, 22.89, 23.34, and 25.13. A novel Compound 1 crystalline form Type B can be identified by X-ray Powder Diffraction (XRPD) pattern having one or more characteristic diffractions at angles (2 theta±0.2) of 4.5, 15.6, 22.9, 23.3, and 25.1. A novel Compound 1 crystalline form Type B can be identified by X-ray Powder Diffraction (XRPD) pattern having one or more characteristic diffractions at angles (2 theta±0.2) of 4.5, 15.6, 22.2, 22.9, 23.3, and 25.1.

A novel Compound 1 crystalline form Type C can be identified by X-ray Powder Diffraction (XRPD) pattern having one or more characteristic diffractions at angles (2 theta±0.2) of 4.55, 18.85, 23.02, and 24.65. A novel Compound 1 crystalline form Type C can be identified by X-ray Powder Diffraction (XRPD) pattern having one or more characteristic diffractions at angles (2 theta±0.2) of 4.5, 18.9, 23.0, and 24.7. A novel Compound 1 crystalline form Type C can be identified by X-ray Powder Diffraction (XRPD) pattern having one or more characteristic diffractions at angles (2 theta±0.2) of 4.5, 7.3, 11.2, 18.9, 23.0, and 24.7.

A novel Compound 1 crystalline form Type D can be identified by X-ray Powder Diffraction (XRPD) pattern having one or more characteristic diffractions at angles (2 theta±0.2) of 9.72, 13.08, 15.74, 21.90, and 23.59. A novel Compound 1 crystalline form Type D can be identified by X-ray Powder Diffraction (XRPD) pattern having one or more characteristic diffractions at angles (2 theta±0.2) of 9.7, 13.1, 15.7, 21.9, and 23.6. A novel Compound 1 crystalline form Type D can be identified by X-ray Powder Diffraction (XRPD) pattern having one or more characteristic diffractions at angles (2 theta±0.2) of 6.2, 9.7, 13.1, 15.7, 21.9, and 23.6 and not having a diffraction at an angle (2 theta±0.2) of 23.3.

A novel Compound 1 crystalline form Type E can be identified by X-ray Powder Diffraction (XRPD) pattern having one or more characteristic diffractions at angles (2 theta±0.2) of 15.12, 15.75, 17.48, 20.05, 21.93, and 26.72. A novel Compound 1 crystalline form Type E can be identified by X-ray Powder Diffraction (XRPD) pattern having one or more characteristic diffractions at angles (2 theta±0.2) of 15.1, 15.8, 17.5, 20.1, 21.9, and 26.7. A novel Compound 1 crystalline form Type E can be identified by X-ray Powder Diffraction (XRPD) pattern having one or more characteristic diffractions at angles (2 theta±0.2) of 15.1, 15.8, 17.5, 20.1, 21.9, and 26.7.

A novel Compound 1 crystalline form Type F can be identified by X-ray Powder Diffraction (XRPD) pattern having one or more characteristic diffractions at angles (2 theta±0.2) of 5.45, 14.66, 16.00, 16.79, 20.01, 21.36, and 22.45. A novel Compound 1 crystalline form Type F can be identified by X-ray Powder Diffraction (XRPD) pattern having one or more characteristic diffractions at angles (2 theta±0.2) of 5.4, 14.7, 16.0, 16.8, 20.0, 21.4, and 22.5. A novel Compound 1 crystalline form Type F can be identified by X-ray Powder Diffraction (XRPD) pattern having one or more characteristic diffractions at angles (2 theta±0.2) of 5.4, 14.7, 16.0, 16.8, and 21.4.

A novel Compound 1 crystalline form Type G can be identified by X-ray Powder Diffraction (XRPD) pattern having one or more characteristic diffractions at angles (2 theta±0.2) of 5.36, 14.34, 16.58, and 21.35. A novel Compound 1 crystalline form Type G can be identified by X-ray Powder Diffraction (XRPD) pattern having one or more characteristic diffractions at angles (2 theta±0.2) of 5.4, 14.3, 16.6, and 21.4. A novel Compound 1 crystalline form Type G can be identified by X-ray Powder Diffraction (XRPD) pattern having one or more characteristic diffractions at angles (2 theta±0.2) of 5.4, 14.3, 16.6, 21.3, and 22.3.

A novel Compound 1 crystalline form Type H can be identified by X-ray Powder Diffraction (XRPD) pattern having one or more characteristic diffractions at angles (2 theta±0.2) of 5.8, 14.7, 16.6, 20.0, 21.3, and 25.4.

A novel Compound 1 crystalline form Type I can be identified by X-ray Powder Diffraction (XRPD) pattern having one or more characteristic diffractions at angles (2 theta±0.2) of 5.2, 14.6, 15.5, 20.2, and 21.1.

A novel Compound 1 crystalline form Type J can be identified by X-ray Powder Diffraction (XRPD) pattern having one or more characteristic diffractions at angles (2 theta±0.2) of 4.5, 5.7, 22.8, 23.1, and 24.5.

A novel Compound 1 crystalline form Type K can be identified by X-ray Powder Diffraction (XRPD) pattern having one or more characteristic diffractions at angles (2 theta±0.2) of 4.6, 15.4, 15.6, 16.1, 23.2, and 27.4.

A novel Compound 1 crystalline form Type L can be identified by X-ray Powder Diffraction (XRPD) pattern having one or more characteristic diffractions at angles (2 theta±0.2) of 5.9, 11.9, 17.8, 21.6, 23.9, and 36.1.

A novel Compound 1 crystalline form Type M can be identified by X-ray Powder Diffraction (XRPD) pattern having one or more characteristic diffractions at angles (2 theta±0.2) of 4.5, 5.8, 9.7, 15.6, 21.9, and 26.7.

Another aspect of the present disclosure relates to a pharmaceutical composition comprising a therapeutically effective amount of any of the crystalline solid forms of Compound 1 described above, and one or more pharmaceutically acceptable excipients.

Yet another aspect of the present disclosure relates to a novel amorphous solid dispersion of Compound 1. The novel amorphous solid form of Compound 1 can be prepared by spray-drying a mixture comprising Compound 1 and a polymer.

Still another aspect of the present disclosure relates to a pharmaceutical composition comprising the novel amorphous solid form of Compound 1 described above. The pharmaceutical composition may be in an oral dosage form, such as tablets.

Another aspect of the present disclosure relates to tablet dosage forms comprising Compound 1.

DETAILED DESCRIPTION

Figure 1:
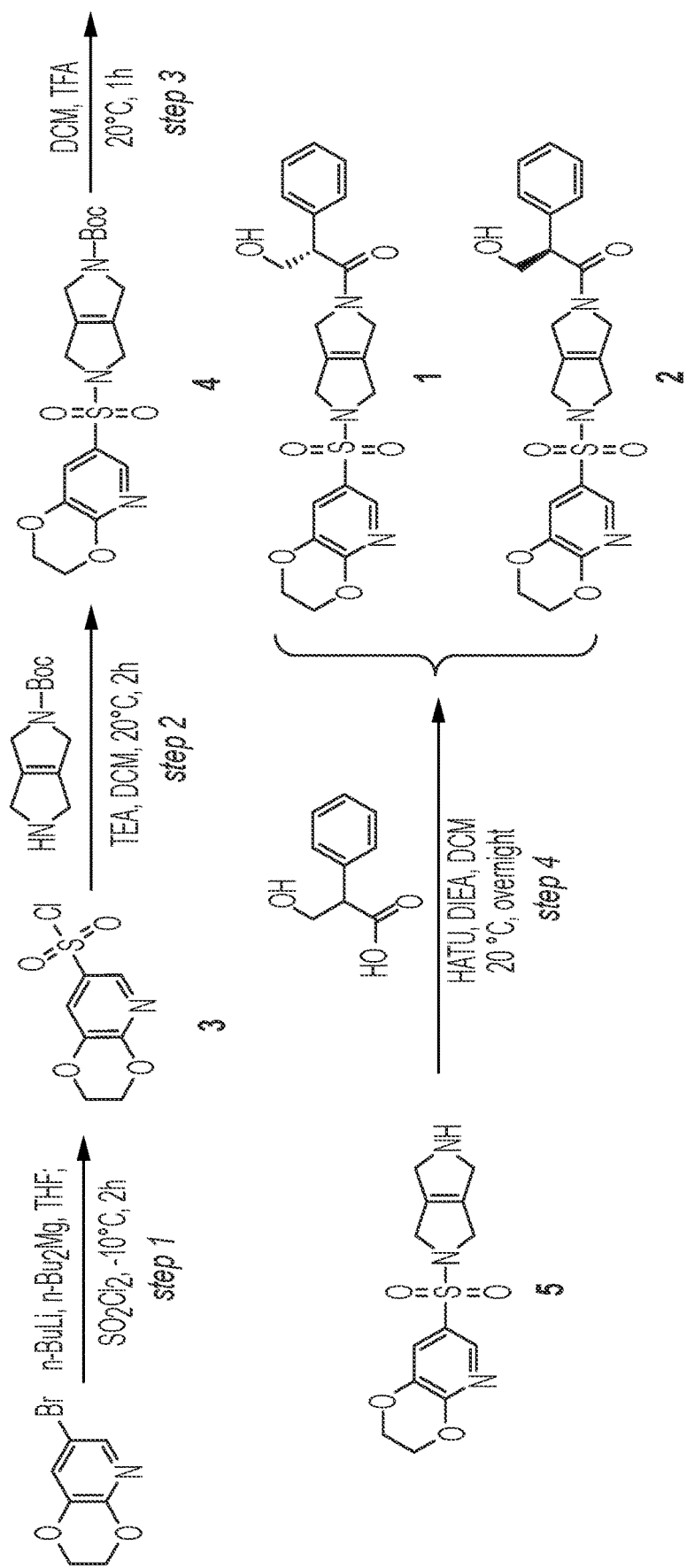
FIG. 1 depicts a reaction scheme to prepare Compound 1.

The chemical compound (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one ("Compound 1"),

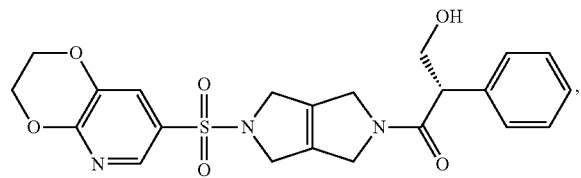 [SMILES: O=C([C@H](CO)c1ccccc1)N1CC2=C(C1)CN(S(=O)(=O)c1cnc3c(c1)OCCO3)C2]

is a small molecule modulator of pyruvate kinase. The present disclosure provides various solid forms of Compound 1, pharmaceutical compositions thereof, and methods of preparing those novel solid forms of Compound 1. The solid forms described herein (e.g., crystalline solid forms and amorphous solid forms) are associated with favorable characteristics such as favorable or improved solubility, dissolution, bioavailability, stability, and ease of formulation relative to other forms of Compound 1. For example, certain amorphous solid dispersions described herein advantageously have high drug loads (e.g., ≥25%, ≥40%, ≥50%, etc.), are free or substantially free of crystalline Compound 1, are physically stable (i.e., remain free or substantially free of crystalline Compound 1 over time in accelerated stability studies), are highly soluble, and/or do not require extensive drying to remove residual solvents. Further, certain tablet dosage forms described herein advantageously have high drug loads (e.g., ≥10 weight % of the tablet core, ≥15 weight % of the tablet core, ≥30 weight % of the tablet core), small tablet sizes (e.g., tablet core weight≤1200 mg, ≤1000 mg, ≤800 mg, ≤700 mg, etc. per tablet), are free or substantially free of crystalline Compound 1, and/or are physically stable (i.e., remain free or substantially free of crystalline Compound 1 over time in accelerated stability studies).

In some embodiments, Compound 1 is in a crystalline solid form (e.g., Type A, Type B, Type C, Type D, Type E, Type F, or Type G). In some embodiments, Compound 1 is in a crystalline solid form (e.g., Type A, Type B, Type C, Type D, Type E, Type F, Type G, Type H, Type I, Type J, Type K, Type L, or Type M). In some embodiments, the crystalline solid form is Type A. In some embodiments, the crystalline solid form is Type B. In some embodiments, the crystalline solid form is Type C. In some embodiments, the crystalline solid form is Type D. In some embodiments, the crystalline solid form is Type E. In some embodiments, the crystalline solid form is Type F. In some embodiments, the crystalline solid form is Type G. In some embodiments, the crystalline solid form is Type H. In some embodiments, the crystalline solid form is Type I. In some embodiments, the crystalline solid form is Type J. In some embodiments, the crystalline solid form is Type K. In some embodiments, the crystalline solid form is Type L. In some embodiments, the crystalline solid form is Type M.

In some embodiments, Compound 1 is in amorphous form (e.g., an amorphous solid dispersion). In some embodiments, the amorphous solid dispersion comprises Compound 1 and a polymer.

Compound 1 Crystalline Form Type A

A novel Compound 1 crystalline form Type A can be identified by an X-ray Powder Diffraction (XRPD) pattern having one or more characteristic diffractions at angles (2 theta±0.2) of 4.61, 15.66, 23.19, and 24.76. A novel Compound 1 crystalline form Type A can be identified by an X-ray Powder Diffraction (XRPD) pattern having one or more characteristic diffractions at angles (2 theta±0.2) of 4.6, 15.7, 23.2, and 24.8. In some embodiments, Compound 1 crystalline form Type A can be identified by X-ray Powder Diffraction (XRPD), having one or more characteristic diffractions at angles (2 theta±0.2) of 4.61, 15.66, 23.19, and 24.76, corresponding to d-spacing (angstroms±0.2) of 19.19, 5.66, 3.84, and 3.60, respectively. In some embodiments, Compound 1 crystalline form Type A can be identified by X-ray Powder Diffraction (XRPD), having one or more characteristic diffractions at angles (2 theta±0.2) of 4.6, 15.7, 23.2, and 24.8, corresponding to d-spacing (angstroms±0.2) of 19.2, 5.7, 3.8, and 3.6, respectively.

In some embodiments, Compound 1 crystalline form Type A can be identified by an XRPD pattern having one or more characteristic diffractions at angles (2 theta±0.2) of 4.6, 7.2, 15.7, 21.3, 23.2, and 24.8. In some embodiments, Compound 1 crystalline form Type A can be identified by XRPD, having one or more characteristic diffractions at angles (2 theta±0.2) of 4.6, 7.2, 15.7, 21.3, 23.2, and 24.8, corresponding to d-spacing (angstroms±0.2) of 19.2, 12.3, 5.7, 4.2, 3.8, and 3.6, respectively.

In some embodiments, Compound 1 crystalline form Type A can be identified by an XRPD pattern having one or more characteristic diffractions at angles (2 theta±0.2) of 4.61, 7.22, 15.66, 20.48, 21.35, 21.66, 22.47, 23.19, 24.76, and 26.73. In some embodiments, Compound 1 crystalline form Type A can be identified by an XRPD pattern having one or more characteristic diffractions at angles (2 theta±0.2) of 4.6, 7.2, 15.7, 20.5, 21.4, 21.7, 22.5, 23.2, 24.8, and 26.7. In some embodiments, Compound 1 crystalline form Type A can be identified by XRPD, having one or more characteristic diffractions at angles (2 theta±0.2) of 4.61, 7.22, 15.66, 20.48, 21.35, 21.66, 22.47, 23.19, 24.76, and 26.73, corresponding to d-spacing (angstroms±0.2) of 19.19, 12.25, 5.66, 4.34, 4.16, 4.10, 3.96, 3.84, 3.60, and 3.34, respectively. In some embodiments, Compound 1 crystalline form Type A can be identified by XRPD, having one or more characteristic diffractions at angles (2 theta±0.2) of 4.6, 7.2, 15.7, 20.5, 21.4, 21.7, 22.5, 23.2, 24.8, and 26.7, corresponding to d-spacing (angstroms±0.2) of 19.2, 12.2, 5.7, 4.3, 4.2, 4.1, 4.0, 3.8, 3.6, and 3.3, respectively.

In some embodiments, Compound 1 crystalline form Type A is characterized by an X-ray Power Diffraction having one or more characteristic diffractions at angles (2 theta±0.2) of:
4.61
5.80
7.22
7.68
11.21
12.31
14.44
15.66
16.95
18.02
19.20
20.48
21.35
21.66
22.47
23.19
24.76
26.73
28.01
28.49
29.35
30.25
32.14
34.12
36.46

In some embodiments, Compound 1 crystalline form Type A is characterized by an X-ray Power Diffraction having one or more characteristic diffractions at angles (2 theta±0.2) of:
4.6
5.8
7.2
7.7
11.2
12.3
14.4
15.7
16.9
18.0
19.2
20.5
21.3
21.7
22.5
23.2
24.8
26.7
28.0
28.5
29.4
30.3
32.1
34.1
36.5

In some embodiments, Compound 1 crystalline form Type A is characterized by an X-ray Power Diffraction pattern having one or more characteristic diffractions at angles (2 theta±0.2) and corresponding d-spacing (angstroms±0.2) of:

| 2 theta | d-spacing |
|---------|-----------|
| 4.61    | 19.19     |
| 5.80    | 15.24     |
| 7.22    | 12.25     |
| 7.68    | 11.50     |
| 11.21   | 7.89      |
| 12.31   | 7.19      |
| 14.44   | 6.13      |
| 15.66   | 5.66      |
| 16.95   | 5.23      |
| 18.02   | 4.92      |
| 19.20   | 4.62      |
| 20.48   | 4.34      |
| 21.35   | 4.16      |
| 21.66   | 4.10      |
| 22.47   | 3.96      |
| 23.19   | 3.84      |
| 24.76   | 3.60      |
| 26.73   | 3.34      |
| 28.01   | 3.19      |
| 28.49   | 3.13      |
| 29.35   | 3.04      |
| 30.25   | 2.95      |
| 32.14   | 2.79      |
| 34.12   | 2.63      |
| 36.46   | 2.46      |

In some embodiments, Compound 1 crystalline form Type A is characterized by an X-ray Power Diffraction pattern having one or more characteristic diffractions at angles (2 theta±0.2) and corresponding d-spacing (angstroms±0.2) of:

| 2 theta | d-spacing |
|---------|-----------|
| 4.6     | 19.2      |
| 5.8     | 15.2      |
| 7.2     | 12.2      |
| 7.7     | 11.5      |
| 11.2    | 7.9       |
| 12.3    | 7.2       |
| 14.4    | 6.1       |
| 15.7    | 5.7       |
| 16.9    | 5.2       |
| 18.0    | 4.9       |
| 19.2    | 4.6       |
| 20.5    | 4.3       |
| 21.3    | 4.2       |
| 21.7    | 4.1       |
| 22.5    | 4.0       |
| 23.2    | 3.8       |
| 24.8    | 3.6       |
| 26.7    | 3.3       |
| 28.0    | 3.2       |
| 28.5    | 3.1       |
| 29.4    | 3.0       |
| 30.3    | 3.0       |
| 32.1    | 2.8       |
| 34.1    | 2.6       |
| 36.5    | 2.5       |

In some embodiments, Compound 1 crystalline form Type A is characterized by a thermogravimetric analysis (TGA) thermogram with a weight loss of about 1.9% up to 100° C. In some embodiments, Compound 1 crystalline form Type A is characterized by a differential scanning calorimetry (DSC) endotherm having a peak temperature of about 85.9° C. and an onset temperature of about 146.0° C. In some embodiments, Compound 1 crystalline form Type A is characterized by a dynamic vapor sorption (DVS) of about 3.4% water uptake by weight up to 40% relative humidity. In some embodiments, Compound 1 crystalline form Type A is characterized by a dynamic vapor sorption (DVS) of about 1.0% water uptake by weight from 40% to 80% relative humidity.

Compound 1 Crystalline Form Type B

A novel Compound 1 crystalline form Type B can be identified by an X-ray Powder Diffraction (XRPD) pattern having one or more characteristic diffractions at angles (2 theta±0.2) of 4.52, 15.57, 22.89, 23.34, and 25.13. A novel Compound 1 crystalline form Type B can be identified by an X-ray Powder Diffraction (XRPD) pattern having one or more characteristic diffractions at angles (2 theta±0.2) of 4.5, 15.6, 22.9, 23.3, and 25.1. In some embodiments, Compound 1 crystalline form Type B can be identified by X-ray Powder Diffraction (XRPD), having one or more characteristic diffractions at angles (2 theta±0.2) of 4.52, 15.57, 22.89, 23.34, and 25.13, corresponding to d-spacing (angstroms±0.2) of 19.53, 5.69, 3.89, 3.81, and 3.54, respectively. In some embodiments, Compound 1 crystalline form Type B can be identified by X-ray Powder Diffraction (XRPD), having one or more characteristic diffractions at angles (2 theta±0.2) of 4.5, 15.6, 22.9, 23.3, and 25.1, corresponding to d-spacing (angstroms±0.2) of 19.5, 5.7, 3.9, 3.8, and 3.5, respectively.

In some embodiments, Compound 1 crystalline form Type B can be identified by an XRPD pattern having one or more characteristic diffractions at angles (2 theta±0.2) of 4.5, 15.6, 22.2, 22.9, 23.3, and 25.1. In some embodiments, Compound 1 crystalline form Type B can be identified by XRPD, having one or more characteristic diffractions at angles (2 theta±0.2) of 4.5, 15.6, 22.2, 22.9, 23.3, and 25.1, corresponding to d-spacing (angstroms±0.2) of 19.5, 5.7, 4.0, 3.9, 3.8, and 3.5, respectively.

In some embodiments, Compound 1 crystalline form Type B can be identified by an XRPD pattern having one or more characteristic diffractions at angles (2 theta±0.2) of 4.52, 9.86, 15.57, 19.93, 22.19, 22.89, 23.34, 25.13, and 28.30. In some embodiments, Compound 1 crystalline form Type B can be identified by an XRPD pattern having one or more characteristic diffractions at angles (2 theta±0.2) of 4.5, 9.9, 15.6, 19.9, 22.2, 22.9, 23.3, 25.1, and 28.3. In some embodiments, Compound 1 crystalline form Type B can be identified by XRPD, having one or more characteristic diffractions at angles (2 theta±0.2) of 4.52, 9.86, 15.57, 19.93, 22.19, 22.89, 23.34, 25.13, and 28.30, corresponding to d-spacing (angstroms±0.2) of 19.53, 8.97, 5.69, 4.45, 4.00, 3.89, 3.81, 3.54, and 3.15, respectively. In some embodiments, Compound 1 crystalline form Type B can be identified by XRPD, having one or more characteristic diffractions at angles (2 theta±0.2) of 4.5, 9.9, 15.6, 19.9, 22.2, 22.9, 23.3, 25.1, and 28.3, corresponding to d-spacing (angstroms±0.2) of 19.5, 9.0, 5.7, 4.5, 4.0, 3.9, 3.8, 3.5, and 3.2, respectively.

In some embodiments, Compound 1 crystalline form Type B is characterized by an X-ray Power Diffraction having one or more characteristic diffractions at angles (2 theta±0.2) of:
4.52
8.98
9.86
12.37
13.18
15.57
16.86
18.21
19.11
19.93
20.92
22.19
22.89
23.34
25.13
25.80
26.71
28.30
29.39

In some embodiments, Compound 1 crystalline form Type B is characterized by an X-ray Power Diffraction having one or more characteristic diffractions at angles (2 theta±0.2) of:
4.5
9.0
9.9
12.4
13.2
15.6
16.9
18.2
19.1
19.9
20.9
22.2
22.9
23.3
25.1
25.8
26.7
28.3
29.4

In some embodiments, Compound 1 crystalline form Type B is characterized by an X-ray Power Diffraction pattern having one or more characteristic diffractions at angles (2 theta±0.2) and corresponding d-spacing (angstroms±0.2) of:

| 2 theta | d-spacing |
|---|---|
| 4.52 | 19.53 |
| 8.98 | 9.85 |
| 9.86 | 8.97 |
| 12.37 | 7.15 |
| 13.18 | 6.72 |
| 15.57 | 5.69 |
| 16.86 | 5.26 |
| 18.21 | 4.87 |
| 19.11 | 4.64 |
| 19.93 | 4.45 |
| 20.92 | 4.25 |
| 22.19 | 4.00 |
| 22.89 | 3.89 |
| 23.34 | 3.81 |
| 25.13 | 3.54 |
| 25.80 | 3.45 |
| 26.71 | 3.34 |
| 28.30 | 3.15 |
| 29.39 | 3.04 |

In some embodiments, Compound 1 crystalline form Type B is characterized by an X-ray Power Diffraction pattern having one or more characteristic diffractions at angles (2 theta±0.2) and corresponding d-spacing (angstroms±0.2) of:

| 2 theta | d-spacing |
|---|---|
| 4.5 | 19.5 |
| 9.0 | 9.9 |
| 9.9 | 9.0 |
| 12.4 | 7.2 |
| 13.2 | 6.7 |
| 15.6 | 5.7 |
| 16.9 | 5.3 |
| 18.2 | 4.9 |
| 19.1 | 4.6 |
| 19.9 | 4.5 |
| 20.9 | 4.2 |

-continued

| 2 theta | d-spacing |
|---------|-----------|
| 22.2 | 4.0 |
| 22.9 | 3.9 |
| 23.3 | 3.8 |
| 25.1 | 3.5 |
| 25.8 | 3.5 |
| 26.7 | 3.3 |
| 28.3 | 3.2 |
| 29.4 | 3.0 |

In some embodiments, Compound 1 crystalline form B is characterized by a thermogravimetric analysis (TGA) thermogram with a weight loss of about 1.8% up to 100° C., and/or a thermogravimetric analysis (TGA) thermogram with a weight loss of about 2.3% up to 120° C. In some embodiments, Compound 1 crystalline form Type B is characterized by a differential scanning calorimetry (DSC) endotherm having an onset temperature of about 138.2-139.2° C. In some embodiments, Compound 1 crystalline form Type B is characterized by a dynamic vapor sorption (DVS) of about 2.9% water uptake by weight up to 60% relative humidity, and a dynamic vapor sorption (DVS) of about 0.4% water uptake by weight from 60% to 80% relative humidity.

Compound 1 Crystalline Form Type C

A novel Compound 1 crystalline form Type C can be identified by an X-ray Powder Diffraction (XRPD) pattern having one or more characteristic diffractions at angles (2 theta±0.2) of 4.55, 18.85, 23.02, and 24.65. A novel Compound 1 crystalline form Type C can be identified by an X-ray Powder Diffraction (XRPD) pattern having one or more characteristic diffractions at angles (2 theta±0.2) of 4.5, 18.9, 23.0, and 24.7. In some embodiments, Compound 1 crystalline form Type C can be identified by X-ray Powder Diffraction (XRPD), having one or more characteristic diffractions at angles (2 theta±0.2) of 4.55, 18.85, 23.02, and 24.65, corresponding to d-spacing (angstroms±0.2) of 19.43, 4.71, 3.86, and 3.61, respectively. In some embodiments, Compound 1 crystalline form Type C can be identified by X-ray Powder Diffraction (XRPD), having one or more characteristic diffractions at angles (2 theta±0.2) of 4.5, 18.9, 23.0, and 24.7, corresponding to d-spacing (angstroms±0.2) of 19.4, 4.7, 3.9, and 3.6, respectively.

In some embodiments, Compound 1 crystalline form Type C can be identified by an XRPD pattern having one or more characteristic diffractions at angles (2 theta±0.2) of 4.5, 7.3, 11.2, 18.9, 23.0, and 24.7. In some embodiments, Compound 1 crystalline form Type C can be identified by XRPD, having one or more characteristic diffractions at angles (2 theta±0.2) of 4.5, 7.3, 11.2, 18.9, 23.0, and 24.7, corresponding to d-spacing (angstroms±0.2) of 19.4, 12.0, 7.9, 4.7, 3.9, and 3.6, respectively.

In some embodiments, Compound 1 crystalline form Type C can be identified by an XRPD pattern having one or more characteristic diffractions at angles (2 theta±0.2) of 4.55, 7.34, 9.07, 11.17, 18.34, 18.85, 19.57, 21.66, 23.02, and 24.65. In some embodiments, Compound 1 crystalline form Type C can be identified by an XRPD pattern having one or more characteristic diffractions at angles (2 theta±0.2) of 4.5, 7.3, 9.1, 11.2, 18.34, 18.9, 19.6, 21.7, 23.0, and 24.7. In some embodiments, Compound 1 crystalline form Type C can be identified by XRPD, having one or more characteristic diffractions at angles (2 theta±0.2) of 4.55, 7.34, 9.07, 11.17, 18.34, 18.85, 19.57, 21.66, 23.02, and 24.65, corresponding to d-spacing (angstroms±0.2) of 19.43, 12.05, 9.75, 7.92, 4.84, 4.71, 4.54, 4.10, 3.86, and 3.61, respectively. In some embodiments, Compound 1 crystalline form Type C can be identified by XRPD, having one or more characteristic diffractions at angles (2 theta±0.2) of 4.5, 7.3, 9.1, 11.2, 18.3, 18.9, 19.6, 21.7, 23.0, and 24.7, corresponding to d-spacing (angstroms±0.2) of 19.4, 12.0, 9.8, 7.9, 4.8, 4.7, 4.5, 4.1, 3.9, and 3.6, respectively.

In some embodiments, Compound 1 crystalline form Type C is characterized by an X-ray Power Diffraction having one or more characteristic diffractions at angles (2 theta±0.2) of:
4.55
7.34
9.07
11.17
12.29
14.51
15.66
18.34
18.85
19.57
20.38
21.66
23.02
24.65
26.39
28.28
30.09
32.31
33.91
37.19

In some embodiments, Compound 1 crystalline form Type C is characterized by an X-ray Power Diffraction having one or more characteristic diffractions at angles (2 theta±0.2) of:
4.5
7.3
9.1
11.2
12.3
14.5
15.7
18.3
18.9
19.6
20.4
21.7
23.0
24.7
26.4
28.3
30.1
32.3
33.9
37.2

In some embodiments, Compound 1 crystalline form Type C is characterized by an X-ray Power Diffraction pattern having one or more characteristic diffractions at angles (2 theta±0.2) and corresponding d-spacing (angstroms±0.2) of:

| 2 theta | d-spacing |
|---------|-----------|
| 4.55 | 19.43 |
| 7.34 | 12.05 |
| 9.07 | 9.75 |
| 11.17 | 7.92 |
| 12.29 | 7.20 |
| 14.51 | 6.11 |

| 2 theta | d-spacing |
| --- | --- |
| 15.66 | 5.66 |
| 18.34 | 4.84 |
| 18.85 | 4.71 |
| 19.57 | 4.54 |
| 20.38 | 4.36 |
| 21.66 | 4.10 |
| 23.02 | 3.86 |
| 24.65 | 3.61 |
| 26.39 | 3.38 |
| 28.28 | 3.16 |
| 30.09 | 2.97 |
| 32.31 | 2.77 |
| 33.91 | 2.64 |
| 37.19 | 2.42 |

In some embodiments, Compound 1 crystalline form Type C is characterized by an X-ray Power Diffraction pattern having one or more characteristic diffractions at angles (2 theta±0.2) and corresponding d-spacing (angstroms±0.2) of:

| 2 theta | d-spacing |
| --- | --- |
| 4.5 | 19.4 |
| 7.3 | 12.0 |
| 9.1 | 9.8 |
| 11.2 | 7.9 |
| 12.3 | 7.2 |
| 14.5 | 6.1 |
| 15.7 | 5.7 |
| 18.3 | 4.8 |
| 18.9 | 4.7 |
| 19.6 | 4.5 |
| 20.4 | 4.4 |
| 21.7 | 4.1 |
| 23.0 | 3.9 |
| 24.7 | 3.6 |
| 26.4 | 3.4 |
| 28.3 | 3.2 |
| 30.1 | 3.0 |
| 32.3 | 2.8 |
| 33.9 | 2.6 |
| 37.2 | 2.4 |

In some embodiments, Compound 1 crystalline form Type C is characterized by a thermogravimetric analysis (TGA) thermogram with a weight loss of about 1.0% up to 100° C., and/or a thermogravimetric analysis (TGA) thermogram with a weight loss of about 2.3% up to 130° C. In some embodiments, Compound 1 crystalline form Type C is characterized by a differential scanning calorimetry (DSC) endotherm having an onset temperature of about 152.2-154.2° C. In some embodiments, Compound 1 crystalline form Type C is characterized by a dynamic vapor sorption (DVS) of about 1.8% water uptake by weight up to 60% relative humidity, and a dynamic vapor sorption (DVS) of about 0.5% water uptake by weight from 60% to 80% relative humidity.

Compound 1 Crystalline Form Type D

A novel Compound 1 crystalline form Type D can be identified by an X-ray Powder Diffraction (XRPD) pattern having one or more characteristic diffractions at angles (2 theta±0.2) of 9.72, 13.08, 15.74, 21.90, and 23.59. A novel Compound 1 crystalline form Type D can be identified by an X-ray Powder Diffraction (XRPD) pattern having one or more characteristic diffractions at angles (2 theta±0.2) of 9.7, 13.1, 15.7, 21.9, and 23.6. In some embodiments, Compound 1 crystalline form Type D can be identified by X-ray Powder Diffraction (XRPD), having one or more characteristic diffractions at angles (2 theta±0.2) of 9.72, 13.08, 15.74, 21.90, and 23.59, corresponding to d-spacing (angstroms±0.2) of 9.10, 6.77, 5.63, 4.06 and 3.77, respectively. In some embodiments, Compound 1 crystalline form Type D can be identified by X-ray Powder Diffraction (XRPD), having one or more characteristic diffractions at angles (2 theta±0.2) of 9.7, 13.1, 15.7, 21.9, and 23.6, corresponding to d-spacing (angstroms±0.2) of 9.1, 6.8, 5.6, 4.1 and 3.8, respectively.

In some embodiments, Compound 1 crystalline form Type D can be identified by an XRPD pattern having one or more characteristic diffractions at angles (2 theta±0.2) of 6.2, 9.7, 13.1, 15.7, 21.9, and 23.6 and not having a diffraction at an angle (2 theta±0.2) of 23.3. In some embodiments, Compound 1 crystalline form Type D can be identified by XRPD, having one or more characteristic diffractions at angles (2 theta±0.2) of 6.2, 9.7, 13.1, 15.7, 21.9, and 23.6, corresponding to d-spacing (angstroms±0.2) of 14.4, 9.1, 6.8, 5.6, 4.1 and 3.8, respectively, and not having a diffraction at an angle (2 theta±0.2) of 23.3.

In some embodiments, Compound 1 crystalline form Type D can be identified by an XRPD pattern having one or more characteristic diffractions at angles (2 theta±0.2) of 4.27, 6.15, 8.71, 9.72, 12.31, 13.08, 13.76, 15.74, 18.02, 21.90, 23.59, and 26.71. In some embodiments, Compound 1 crystalline form Type D can be identified by an XRPD pattern having one or more characteristic diffractions at angles (2 theta±0.2) of 4.3, 6.2, 8.7, 9.7, 12.3, 13.1, 13.8, 15.7, 18.0, 21.9, 23.6, and 26.7. In some embodiments, Compound 1 crystalline form Type D can be identified by XRPD, having one or more characteristic diffractions at angles (2 theta±0.2) of 4.27, 6.15, 8.71, 9.72, 12.31, 13.08, 13.76, 15.74, 18.02, 21.90, 23.59, and 26.71, corresponding to d-spacing (angstroms±0.2) of 20.68, 14.36, 10.16, 9.10, 7.19, 6.77, 6.44, 5.63, 4.92, 4.06, 3.77, and 3.34, respectively. In some embodiments, Compound 1 crystalline form Type D can be identified by XRPD, having one or more characteristic diffractions at angles (2 theta±0.2) of 4.3, 6.2, 8.7, 9.7, 12.3, 13.1, 13.8, 15.7, 18.0, 21.9, 23.6, and 26.7, corresponding to d-spacing (angstroms±0.2) of 20.7, 14.4, 10.2, 9.1, 7.2, 6.8, 6.4, 5.6, 4.9, 4.1, 3.8, and 3.3, respectively.

In some embodiments, Compound 1 crystalline form Type D is characterized by an X-ray Power Diffraction having one or more characteristic diffractions at angles (2 theta±0.2) of:
4.27
6.15
8.71
9.72
12.31
13.08
13.76
15.74
18.02
19.55
21.90
23.59
24.79
26.71
29.50
30.82
31.74
35.40
37.84
38.61

In some embodiments, Compound 1 crystalline form Type D is characterized by an X-ray Power Diffraction having one or more characteristic diffractions at angles (2 theta±0.2) of:
4.3
6.2
8.7
9.7
12.3
13.1
13.8
15.7
18.0
19.5
21.9
23.6
24.8
26.7
29.5
30.8
31.7
35.4
37.8
38.6

In some embodiments, Compound 1 crystalline form Type D is characterized by an X-ray Power Diffraction pattern having one or more characteristic diffractions at angles (2 theta±0.2) and corresponding d-spacing (angstroms±0.2) of:

| 2 theta | d-spacing |
|---|---|
| 4.27 | 20.68 |
| 6.15 | 14.36 |
| 8.71 | 10.16 |
| 9.72 | 9.10 |
| 12.31 | 7.19 |
| 13.08 | 6.77 |
| 13.76 | 6.44 |
| 15.74 | 5.63 |
| 18.02 | 4.92 |
| 19.55 | 4.54 |
| 21.90 | 4.06 |
| 23.59 | 3.77 |
| 24.79 | 3.59 |
| 26.71 | 3.34 |
| 29.50 | 3.03 |
| 30.82 | 2.90 |
| 31.74 | 2.82 |
| 35.40 | 2.54 |
| 37.84 | 2.38 |
| 38.61 | 2.33 |

In some embodiments, Compound 1 crystalline form Type D is characterized by an X-ray Power Diffraction pattern having one or more characteristic diffractions at angles (2 theta±0.2) and corresponding d-spacing (angstroms±0.2) of:

| 2 theta | d-spacing |
|---|---|
| 4.3 | 20.7 |
| 6.2 | 14.4 |
| 8.7 | 10.2 |
| 9.7 | 9.1 |
| 12.3 | 7.2 |
| 13.1 | 6.8 |
| 13.8 | 6.4 |
| 15.7 | 5.6 |
| 18.0 | 4.9 |
| 19.5 | 4.5 |
| 21.9 | 4.1 |
| 23.6 | 3.8 |
| 24.8 | 3.6 |
| 26.7 | 3.3 |
| 29.5 | 3.0 |
| 30.8 | 2.9 |
| 31.7 | 2.8 |
| 35.4 | 2.5 |
| 37.8 | 2.4 |
| 38.6 | 2.3 |

In some embodiments, Compound 1 crystalline form Type D is characterized by a thermogravimetric analysis (TGA) thermogram with a weight loss of about 9.6% up to 130° C. In some embodiments, Compound 1 crystalline form Type D is characterized by a differential scanning calorimetry (DSC) endotherm having an onset temperature of about 91.9° C.

Compound 1 Crystalline Form Type E

A novel Compound 1 crystalline form Type E can be identified by an X-ray Powder Diffraction (XRPD) pattern having one or more characteristic diffractions at angles (2 theta±0.2) of 15.12, 15.75, 17.48, 20.05, 21.93, and 26.72. A novel Compound 1 crystalline form Type E can be identified by an X-ray Powder Diffraction (XRPD) pattern having one or more characteristic diffractions at angles (2 theta±0.2) of 15.1, 15.8, 17.5, 20.1, 21.9, and 26.7. In some embodiments, Compound 1 crystalline form Type E can be identified by X-ray Powder Diffraction (XRPD), having one or more characteristic diffractions at angles (2 theta±0.2) of 15.12, 15.75, 17.48, 20.05, 21.93, and 26.72, corresponding to d-spacing (angstroms±0.2) of 5.86, 5.63, 5.07, 4.43, 4.05, and 3.34, respectively. In some embodiments, Compound 1 crystalline form Type E can be identified by X-ray Powder Diffraction (XRPD), having one or more characteristic diffractions at angles (2 theta±0.2) of 15.1, 15.8, 17.5, 20.1, 21.9, and 26.7, corresponding to d-spacing (angstroms±0.2) of 5.9, 5.6, 5.1, 4.4, 4.1, and 3.3, respectively.

In some embodiments, Compound 1 crystalline form Type E can be identified by an XRPD pattern having one or more characteristic diffractions at angles (2 theta±0.2) of 15.1, 15.8, 17.5, 20.1, 21.9, and 26.7. In some embodiments, Compound 1 crystalline form Type E can be identified by XRPD, having one or more characteristic diffractions at angles (2 theta±0.2) of 15.1, 15.8, 17.5, 19.0, 20.1, 21.9, and 26.7, corresponding to d-spacing (angstroms±0.2) of 5.9, 5.6, 5.1, 4.7, 4.4, 4.1, and 3.3, respectively.

In some embodiments, Compound 1 crystalline form Type E can be identified by an XRPD pattern having one or more characteristic diffractions at angles (2 theta±0.2) of 4.59, 15.12, 15.75, 17.48, 20.05, 21.93, 23.18, 23.70, and 26.72. In some embodiments, Compound 1 crystalline form Type E can be identified by an XRPD pattern having one or more characteristic diffractions at angles (2 theta±0.2) of 4.6, 15.1, 15.8, 17.5, 20.1, 21.9, 23.2, 23.7, and 26.7. In some embodiments, Compound 1 crystalline form Type E can be identified by XRPD, having one or more characteristic diffractions at angles (2 theta±0.2) of 4.59, 15.12, 15.75, 17.48, 20.05, 21.93, 23.18, 23.70, and 26.72, corresponding to d-spacing (angstroms±0.2) of 19.27, 5.86, 5.63, 5.07, 4.43, 4.05, 3.84, 3.75, and 3.34, respectively. In some embodiments, Compound 1 crystalline form Type E can be identified by XRPD, having one or more characteristic diffractions at angles (2 theta±0.2) of 4.6, 15.1, 15.8, 17.5, 20.1, 21.9, 23.2, 23.7, and 26.7, corresponding to d-spacing (angstroms±0.2) of 19.3, 5.9, 5.6, 5.1, 4.4, 4.1, 3.8, 3.8, and 3.3, respectively.

In some embodiments, Compound 1 crystalline form Type E can be identified by an XRPD pattern having one or more characteristic diffractions at angles (2 theta±0.2) of 4.59, 9.76, 12.36, 13.12, 15.12, 15.75, 16.84, 17.48, 18.06, 19.02, 20.05, 21.93, 23.18, 23.70, 26.72, and 27.81. In some embodiments, Compound 1 crystalline form Type E can be identified by an XRPD pattern having one or more characteristic diffractions at angles (2 theta±0.2) of 4.6, 9.8, 12.4, 13.1, 15.1, 15.8, 16.8, 17.5, 18.1, 19.0, 20.1, 21.9, 23.2, 23.7, 26.7, and 27.8. In some embodiments, Compound 1 crystalline form Type E can be identified by XRPD, having one or more characteristic diffractions at angles (2 theta±0.2) of 4.59, 9.76, 12.36, 13.12, 15.12, 15.75, 16.84, 17.48, 18.06, 19.02, 20.05, 21.93, 23.18, 23.70, 26.72, and 27.81, corresponding to d-spacing (angstroms±0.2) of 19.27, 9.06, 7.16, 6.75, 5.86, 5.63, 5.27, 5.07, 4.91, 4.67, 4.43, 4.05, 3.84, 3.75, 3.34, and 3.21, respectively. In some embodiments, Compound 1 crystalline form Type E can be identified by XRPD, having one or more characteristic diffractions at angles (2 theta±0.2) of 4.6, 9.8, 12.4, 13.1, 15.1, 15.8, 16.8, 17.5, 18.1, 19.0, 20.1, 21.9, 23.2, 23.7, 26.7, and 27.8, corresponding to d-spacing (angstroms±0.2) of 19.3, 9.1, 7.2, 6.7, 5.9, 5.6, 5.3, 5.1, 4.9, 4.7, 4.4, 4.1, 3.8, 3.8, 3.3, and 3.2, respectively.

In some embodiments, Compound 1 crystalline form Type E is characterized by an X-ray Power Diffraction having one or more characteristic diffractions at angles (2 theta±0.2) of:
4.59
8.76
9.76
13.12
13.83
15.12
15.75
16.84
17.48
18.06
19.02
20.05
21.93
23.18
23.70
24.82
26.72
27.81
29.51
30.76
31.74
33.03
34.52
35.39
36.72
37.77
38.66

In some embodiments, Compound 1 crystalline form Type E is characterized by an X-ray Power Diffraction having one or more characteristic diffractions at angles (2 theta±0.2) of:
4.6
8.8
9.8
12.4
13.1
13.8
15.1
15.8
16.8
17.5
18.1
19.0
20.1
21.9
23.2
23.7
24.8
26.7
27.8
29.5
30.8
31.7
33.0
34.5
35.4
36.7
37.8
38.7

In some embodiments, Compound 1 crystalline form Type E is characterized by an X-ray Power Diffraction pattern having one or more characteristic diffractions at angles (2 theta±0.2) and corresponding d-spacing (angstroms±0.2) of:

| 2 theta | d-spacing |
|---|---|
| 4.59 | 19.27 |
| 8.76 | 10.09 |
| 9.76 | 9.06 |
| 12.36 | 7.16 |
| 13.12 | 6.75 |
| 13.83 | 6.40 |
| 15.12 | 5.86 |
| 15.75 | 5.63 |
| 16.84 | 5.27 |
| 17.48 | 5.07 |
| 18.06 | 4.91 |
| 19.02 | 4.67 |
| 20.05 | 4.43 |
| 21.93 | 4.05 |
| 23.18 | 3.84 |
| 23.70 | 3.75 |
| 24.82 | 3.59 |
| 26.72 | 3.34 |
| 27.81 | 3.21 |
| 29.51 | 3.03 |
| 30.76 | 2.91 |
| 31.74 | 2.82 |
| 33.03 | 2.71 |
| 34.52 | 2.60 |
| 35.39 | 2.54 |
| 36.72 | 2.45 |
| 37.77 | 2.38 |
| 38.66 | 2.33 |

In some embodiments, Compound 1 crystalline form Type E is characterized by an X-ray Power Diffraction pattern having one or more characteristic diffractions at angles (2 theta±0.2) and corresponding d-spacing (angstroms±0.2) of:

| 2 theta | d-spacing |
|---|---|
| 4.6 | 19.3 |
| 8.8 | 10.1 |
| 9.8 | 9.1 |
| 12.4 | 7.2 |
| 13.1 | 6.7 |
| 13.8 | 6.4 |
| 15.1 | 5.9 |
| 15.8 | 5.6 |
| 16.8 | 5.3 |
| 17.5 | 5.1 |
| 18.1 | 4.9 |
| 19.0 | 4.7 |
| 20.1 | 4.4 |
| 21.9 | 4.1 |
| 23.2 | 3.8 |

-continued

| 2 theta | d-spacing |
| --- | --- |
| 23.7 | 3.8 |
| 24.8 | 3.6 |
| 26.7 | 3.3 |
| 27.8 | 3.2 |
| 29.5 | 3.0 |
| 30.8 | 2.9 |
| 31.7 | 2.8 |
| 33.0 | 2.7 |
| 34.5 | 2.6 |
| 35.4 | 2.5 |
| 36.7 | 2.4 |
| 37.8 | 2.4 |
| 38.7 | 2.3 |

Compound 1 Crystalline Form Type F

A novel Compound 1 crystalline form Type F can be identified by an X-ray Powder Diffraction (XRPD) pattern having one or more characteristic diffractions at angles (2 theta±0.2) of 5.45, 14.66, 16.00, 16.79, 20.01, 21.36, and 22.45. A novel Compound 1 crystalline form Type F can be identified by an X-ray Powder Diffraction (XRPD) pattern having one or more characteristic diffractions at angles (2 theta±0.2) of 5.4, 14.7, 16.0, 16.8, 20.0, 21.4, and 22.5. In some embodiments, Compound 1 crystalline form Type F can be identified by X-ray Powder Diffraction (XRPD), having one or more characteristic diffractions at angles (2 theta±0.2) of 5.45, 14.66, 16.00, 16.79, 20.01, 21.36, and 22.45, corresponding to d-spacing (angstroms±0.2) of 16.23, 6.04, 5.54, 5.28, 4.44, 4.16, and 3.96, respectively. In some embodiments, Compound 1 crystalline form Type F can be identified by X-ray Powder Diffraction (XRPD), having one or more characteristic diffractions at angles (2 theta±0.2) of 5.4, 14.7, 16.0, 16.8, 20.0, 21.4, and 22.5, corresponding to d-spacing (angstroms±0.2) of 16.2, 6.0, 5.5, 5.3, 4.4, 4.2, and 4.0, respectively.

In some embodiments, Compound 1 crystalline form Type F can be identified by an XRPD pattern having one or more characteristic diffractions at angles (2 theta±0.2) of 5.4, 14.7, 16.0, 16.8, and 21.4. In some embodiments, Compound 1 crystalline form Type F can be identified by XRPD, having one or more characteristic diffractions at angles (2 theta±0.2) of 5.4, 14.7, 16.0, 16.8, and 21.4, corresponding to d-spacing (angstroms±0.2) of 16.2, 6.0, 5.5, 5.3, and 4.2, respectively.

In some embodiments, Compound 1 crystalline form Type F can be identified by an XRPD pattern having one or more characteristic diffractions at angles (2 theta±0.2) of 5.45, 14.66, 16.00, 16.79, 18.99, 20.01, 21.36, 22.45, 23.25, and 25.32. In some embodiments, Compound 1 crystalline form Type F can be identified by an XRPD pattern having one or more characteristic diffractions at angles (2 theta±0.2) of 5.4, 14.7, 16.0, 16.8, 19.0, 20.0, 21.4, 22.5, 23.2, and 25.3. In some embodiments, Compound 1 crystalline form Type F can be identified by XRPD, having one or more characteristic diffractions at angles (2 theta±0.2) of 5.45, 14.66, 16.00, 16.79, 18.99, 20.01, 21.36, 22.45, 23.25, and 25.32, corresponding to d-spacing (angstroms±0.2) of 16.23, 6.04, 5.54, 5.28, 4.67, 4.44, 4.16, 3.96, 3.83, and 3.52, respectively. In some embodiments, Compound 1 crystalline form Type F can be identified by XRPD, having one or more characteristic diffractions at angles (2 theta±0.2) of 5.4, 14.7, 16.0, 16.8, 19.0, 20.0, 21.4, 22.5, 23.2, and 25.3, corresponding to d-spacing (angstroms±0.2) of 16.2, 6.0, 5.5, 5.3, 4.7, 4.4, 4.2, 4.0, 3.8, and 3.5, respectively.

In some embodiments, Compound 1 crystalline form Type F can be identified by an XRPD pattern having one or more characteristic diffractions at angles (2 theta±0.2) of 5.45, 12.87, 14.66, 16.00, 16.79, 17.36, 18.99, 20.01, 20.57, 21.36, 22.45, 23.25, 25.32, 26.57, 27.25, 27.97, and 30.02. In some embodiments, Compound 1 crystalline form Type F can be identified by an XRPD pattern having one or more characteristic diffractions at angles (2 theta±0.2) of 5.4, 12.9, 14.7, 16.0, 16.8, 17.4, 19.0, 20.0, 20.6, 21.4, 22.5, 23.2, 25.3, 26.6, 27.2, 28.0, and 30.0. In some embodiments, Compound 1 crystalline form Type F can be identified by XRPD, having one or more characteristic diffractions at angles (2 theta±0.2) of 5.45, 12.87, 14.66, 16.00, 16.79, 17.36, 18.99, 20.01, 20.57, 21.36, 22.45, 23.25, 25.32, 26.57, 27.25, 27.97, and 30.02, corresponding to d-spacing (angstroms±0.2) of 16.23, 6.88, 6.04, 5.54, 5.28, 5.11, 4.67, 4.44, 4.32, 4.16, 3.96, 3.83, 3.52, 3.35, 3.27, 3.19, and 2.98, respectively. In some embodiments, Compound 1 crystalline form Type F can be identified by XRPD, having one or more characteristic diffractions at angles (2 theta±0.2) of 5.4, 12.9, 14.7, 16.0, 16.8, 17.4, 19.0, 20.0, 20.6, 21.4, 22.5, 23.2, 25.3, 26.6, 27.2, 28.0, and 30.0, corresponding to d-spacing (angstroms±0.2) of 16.2, 6.9, 6.0, 5.5, 5.3, 5.1, 4.7, 4.4, 4.3, 4.2, 4.0, 3.8, 3.5, 3.4, 3.3, 3.2, and 3.0, respectively.

In some embodiments, Compound 1 crystalline form Type F is characterized by an X-ray Power Diffraction having one or more characteristic diffractions at angles (2 theta±0.2) of:
5.45
10.92
12.87
14.66
16.00
16.79
17.36
18.99
20.01
20.57
21.36
22.45
23.25
25.32
26.57
27.25
27.97
30.02
31.98
32.89
38.29
39.09

In some embodiments, Compound 1 crystalline form Type F is characterized by an X-ray Power Diffraction having one or more characteristic diffractions at angles (2 theta±0.2) of:
5.4
10.9
12.9
14.7
16.0
16.8
17.4
19.0
20.0
20.6
21.4
22.5
23.2
25.3
26.6
27.2
28.0

30.0
32.0
32.9
38.3
39.1

In some embodiments, Compound 1 crystalline form Type F is characterized by an X-ray Power Diffraction pattern having one or more characteristic diffractions at angles (2 theta±0.2) and corresponding d-spacing (angstroms±0.2) of:

| 2 theta | d-spacing |
|---|---|
| 5.45 | 16.23 |
| 10.92 | 8.10 |
| 12.87 | 6.88 |
| 14.66 | 6.04 |
| 16.00 | 5.54 |
| 16.79 | 5.28 |
| 17.36 | 5.11 |
| 18.99 | 4.67 |
| 20.01 | 4.44 |
| 20.57 | 4.32 |
| 21.36 | 4.16 |
| 22.45 | 3.96 |
| 23.25 | 3.83 |
| 25.32 | 3.52 |
| 26.57 | 3.35 |
| 27.25 | 3.27 |
| 27.97 | 3.19 |
| 30.02 | 2.98 |
| 31.98 | 2.80 |
| 32.89 | 2.72 |
| 38.29 | 2.35 |
| 39.09 | 2.30 |

In some embodiments, Compound 1 crystalline form Type F is characterized by an X-ray Power Diffraction pattern having one or more characteristic diffractions at angles (2 theta±0.2) and corresponding d-spacing (angstroms±0.2) of:

| 2 theta | d-spacing |
|---|---|
| 5.4 | 16.2 |
| 10.9 | 8.1 |
| 12.9 | 6.9 |
| 14.7 | 6.0 |
| 16.0 | 5.5 |
| 16.8 | 5.3 |
| 17.4 | 5.1 |
| 19.0 | 4.7 |
| 20.0 | 4.4 |
| 20.6 | 4.3 |
| 21.4 | 4.2 |
| 22.5 | 4.0 |
| 23.2 | 3.8 |
| 25.3 | 3.5 |
| 26.6 | 3.4 |
| 27.2 | 3.3 |
| 28.0 | 3.2 |
| 30.0 | 3.0 |
| 32.0 | 2.8 |
| 32.9 | 2.7 |
| 38.3 | 2.4 |
| 39.1 | 2.3 |

In some embodiments, Compound 1 crystalline form Type F is characterized by a thermogravimetric analysis (TGA) thermogram with a weight loss of about 6.2% up to 120° C. In some embodiments, Compound 1 crystalline form Type F is characterized by a differential scanning calorimetry (DSC) endotherm having a peak temperature of about 100.4° C. and an onset temperature of 125.9° C.

Compound 1 Crystalline Form Type G

A novel Compound 1 crystalline form Type G can be identified by an X-ray Powder Diffraction (XRPD) pattern having one or more characteristic diffractions at angles (2 theta±0.2) of 5.36, 14.34, 16.58, and 21.35. A novel Compound 1 crystalline form Type G can be identified by an X-ray Powder Diffraction (XRPD) pattern having one or more characteristic diffractions at angles (2 theta±0.2) of 5.4, 14.3, 16.6, and 21.4. In some embodiments, Compound 1 crystalline form Type G can be identified by X-ray Powder Diffraction (XRPD), having one or more characteristic diffractions at angles (2 theta±0.2) of 5.36, 14.34, 16.58, and 21.35, corresponding to d-spacing (angstroms±0.2) of 16.48, 6.18, 5.35, and 4.16, respectively. In some embodiments, Compound 1 crystalline form Type G can be identified by X-ray Powder Diffraction (XRPD), having one or more characteristic diffractions at angles (2 theta±0.2) of 5.4, 14.3, 16.6, and 21.4, corresponding to d-spacing (angstroms±0.2) of 16.5, 6.2, 5.3, and 4.2, respectively.

In some embodiments, Compound 1 crystalline form Type G can be identified by an XRPD pattern having one or more characteristic diffractions at angles (2 theta±0.2) of 5.4, 14.3, 16.6, 21.3, and 22.3. In some embodiments, Compound 1 crystalline form Type G can be identified by XRPD, having one or more characteristic diffractions at angles (2 theta±0.2) of 5.4, 14.3, 16.6, 21.3, and 22.3, corresponding to d-spacing (angstroms±0.2) of 16.5, 6.2, 5.3, 4.2, and 4.0, respectively.

In some embodiments, Compound 1 crystalline form Type G can be identified by an XRPD pattern having one or more characteristic diffractions at angles (2 theta±0.2) of 5.36, 12.83, 14.34, 15.00, 16.58, 19.78, 21.35, 22.35, 25.33, and 26.43. In some embodiments, Compound 1 crystalline form Type G can be identified by an XRPD pattern having one or more characteristic diffractions at angles (2 theta±0.2) of 5.4, 12.8, 14.3, 15.0, 16.6, 19.8, 21.3, 22.3, 25.3, and 26.4. In some embodiments, Compound 1 crystalline form Type G can be identified by XRPD, having one or more characteristic diffractions at angles (2 theta±0.2) of 5.36, 12.83, 14.34, 15.00, 16.58, 19.78, 21.35, 22.35, 25.33, and 26.43, corresponding to d-spacing (angstroms±0.2) of 16.48, 6.90, 6.18, 5.91, 5.35, 4.49, 4.16, 3.98, 3.52, and 3.37, respectively. In some embodiments, Compound 1 crystalline form Type G can be identified by XRPD, having one or more characteristic diffractions at angles (2 theta±0.2) of 5.4, 12.8, 14.3, 15.0, 16.6, 19.8, 21.3, 22.3, 25.3, and 26.4, corresponding to d-spacing (angstroms±0.2) of 16.5, 6.9, 6.2, 5.9, 5.3, 4.5, 4.2, 4.0, 3.5, and 3.4, respectively.

In some embodiments, Compound 1 crystalline form Type G can be identified by an XRPD pattern having one or more characteristic diffractions at angles (2 theta±0.2) of 5.36, 12.83, 14.34, 15.00, 15.79, 16.58, 19.78, 21.35, 22.35, 25.33, 26.43, 27.35, and 30.21. In some embodiments, Compound 1 crystalline form Type G can be identified by an XRPD pattern having one or more characteristic diffractions at angles (2 theta±0.2) of 5.34 12.8, 14.3, 15.0, 15.8, 16.6, 19.8, 21.3, 22.3, 25.3, 26.4, 27.4, and 30.2. In some embodiments, Compound 1 crystalline form Type G can be identified by XRPD, having one or more characteristic diffractions at angles (2 theta±0.2) of 5.36, 12.83, 14.34, 15.00, 15.79, 16.58, 19.78, 21.35, 22.35, 25.33, 26.43, 27.35, and 30.21, corresponding to d-spacing (angstroms±0.2) of 16.48, 6.90, 6.18, 5.91, 5.61, 5.35, 4.49, 4.16, 3.98, 3.52, 3.37, 3.26, and 2.96, respectively. In some embodiments, Compound 1 crystalline form Type G can be identified by XRPD, having one or more characteristic diffractions at angles (2 theta±0.2) of 5.4, 12.8, 14.3, 15.0, 15.8, 16.6, 19.8, 21.3, 22.3, 25.3, 26.4, 27.4, and 30.2, corresponding to d-spacing (angstroms±0.2) of 16.5, 6.9, 6.2, 5.9, 5.6, 5.3, 4.5, 4.2, 4.0, 3.5, 3.4, 3.3, and 3.0, respectively.

In some embodiments, Compound 1 crystalline form Type G is characterized by an X-ray Power Diffraction having one or more characteristic diffractions at angles (2 theta±0.2) of:
5.36
8.73
12.83
14.34
15.00
15.79
16.58
18.54
19.78
21.35
22.35
23.38
25.33
26.43
27.35
30.21
32.32
38.04

In some embodiments, Compound 1 crystalline form Type G is characterized by an X-ray Power Diffraction having one or more characteristic diffractions at angles (2 theta±0.2) of:
5.4
8.7
12.8
14.3
15.0
15.8
16.6
18.5
19.8
21.3
22.3
23.4
25.3
26.4
27.4
30.2
32.3
38.0

In some embodiments, Compound 1 crystalline form Type G is characterized by an X-ray Power Diffraction pattern having one or more characteristic diffractions at angles (2 theta±0.2) and corresponding d-spacing (angstroms±0.2) of:

| 2 theta | d-spacing |
| --- | --- |
| 5.36 | 16.48 |
| 8.73 | 10.13 |
| 12.83 | 6.90 |
| 14.34 | 6.18 |
| 15.00 | 5.91 |
| 15.79 | 5.61 |
| 16.58 | 5.35 |
| 18.54 | 4.79 |
| 19.78 | 4.49 |
| 21.35 | 4.16 |
| 22.35 | 3.98 |
| 23.38 | 3.80 |
| 25.33 | 3.52 |
| 26.43 | 3.37 |
| 27.35 | 3.26 |
| 30.21 | 2.96 |
| 32.32 | 2.77 |
| 38.04 | 2.37 |

In some embodiments, Compound 1 crystalline form Type G is characterized by an X-ray Power Diffraction pattern having one or more characteristic diffractions at angles (2 theta±0.2) and corresponding d-spacing (angstroms±0.2) of:

| 2 theta | d-spacing |
| --- | --- |
| 5.4 | 16.5 |
| 8.7 | 10.1 |
| 12.8 | 6.9 |
| 14.3 | 6.2 |
| 15.0 | 5.9 |
| 15.8 | 5.6 |
| 16.6 | 5.3 |
| 18.6 | 4.8 |
| 19.8 | 4.5 |
| 21.3 | 4.2 |
| 22.3 | 4.0 |
| 23.4 | 3.8 |
| 25.3 | 3.5 |
| 26.4 | 3.4 |
| 27.4 | 3.3 |
| 30.2 | 3.0 |
| 32.3 | 2.8 |
| 38.0 | 2.4 |

Compound 1 Crystalline Form Type H

A novel Compound 1 crystalline form Type H can be identified by an X-ray Powder Diffraction (XRPD) pattern having one or more characteristic diffractions at angles (2 theta±0.2) of 5.8, 14.7, 16.6, 20.0, 21.3, and 25.4. In some embodiments, Compound 1 crystalline form Type H can be identified by X-ray Powder Diffraction (XRPD), having one or more characteristic diffractions at angles (2 theta±0.2) of 5.8, 14.7, 16.6, 20.0, 21.3, and 25.4, corresponding to d-spacing (angstroms±0.2) of 15.3, 6.0, 5.4, 4.4, 4.2, and 3.5, respectively.

In some embodiments, Compound 1 crystalline form Type H is characterized by an X-ray Power Diffraction having one or more characteristic diffractions at angles (2 theta±0.2) of:
5.8
8.4
11.5
12.4
13.1
13.7
14.7
14.9
16.0
16.2
16.6
16.9
17.3
17.7
18.3
19.5
20.0
21.3
21.9
23.1
23.6
23.9
24.4
24.9
25.1
25.4
26.2
27.4
28.1

28.4
29.3
29.7
30.4
31.0
32.7
33.4
34.1
34.8
35.5
35.8
36.4
37.1
38.5

In some embodiments, Compound 1 crystalline form Type H is characterized by an X-ray Power Diffraction pattern having one or more characteristic diffractions at angles (2 theta±0.2) and corresponding d-spacing (angstroms±0.2) of:

| Pos. [°2Th.] | d-spacing [Å] |
| --- | --- |
| 5.8 | 15.3 |
| 8.4 | 10.5 |
| 11.5 | 7.7 |
| 12.4 | 7.2 |
| 13.1 | 6.8 |
| 13.7 | 6.5 |
| 14.7 | 6.0 |
| 14.9 | 5.9 |
| 16.0 | 5.6 |
| 16.2 | 5.5 |
| 16.6 | 5.4 |
| 16.9 | 5.3 |
| 17.3 | 5.1 |
| 17.7 | 5.0 |
| 18.3 | 4.8 |
| 19.5 | 4.6 |
| 20.0 | 4.4 |
| 21.3 | 4.2 |
| 21.9 | 4.1 |
| 23.1 | 3.9 |
| 23.6 | 3.8 |
| 23.9 | 3.7 |
| 24.4 | 3.7 |
| 24.9 | 3.6 |
| 25.1 | 3.5 |
| 25.4 | 3.5 |
| 26.2 | 3.4 |
| 27.4 | 3.3 |
| 28.1 | 3.2 |
| 28.4 | 3.1 |
| 29.3 | 3.0 |
| 29.7 | 3.0 |
| 30.4 | 2.9 |
| 31.0 | 2.9 |
| 32.7 | 2.7 |
| 33.4 | 2.7 |
| 34.1 | 2.6 |
| 34.8 | 2.6 |
| 35.5 | 2.5 |
| 35.8 | 2.5 |
| 36.4 | 2.5 |
| 37.1 | 2.4 |
| 38.5 | 2.3 |

Compound 1 Crystalline Form Type I

A novel Compound 1 crystalline form Type I can be identified by an X-ray Powder Diffraction (XRPD) pattern having one or more characteristic diffractions at angles (2 theta±0.2) of 5.2, 14.6, 15.5, 20.2, and 21.1. In some embodiments, Compound 1 crystalline form Type I can be identified by X-ray Powder Diffraction (XRPD), having one or more characteristic diffractions at angles (2 theta±0.2) of 5.2, 14.6, 15.5, 20.2, and 21.1, corresponding to d-spacing (angstroms±0.2) of 17.1, 6.1, 5.7, 4.4, and 4.2, respectively.

In some embodiments, Compound 1 crystalline form Type I is characterized by an X-ray Power Diffraction having one or more characteristic diffractions at angles (2 theta±0.2) of:

5.2
8.8
10.3
12.6
14.6
15.5
16.1
16.3
16.6
17.1
17.6
18.7
18.9
20.2
20.5
20.7
21.1
21.5
22.0
22.3
23.7
24.8
25.2
26.0
26.3
26.5
26.8
27.0
27.5
27.7
28.1
29.6
30.0
30.4
31.3
32.0
32.5
33.2
34.0
34.6
36.9
38.2
38.9
39.5

In some embodiments, Compound 1 crystalline form Type I is characterized by an X-ray Power Diffraction pattern having one or more characteristic diffractions at angles (2 theta±0.2) and corresponding d-spacing (angstroms±0.2) of:

| Pos. [°2Th.] | d-spacing [Å] |
| --- | --- |
| 5.2 | 17.1 |
| 8.8 | 10.1 |
| 10.3 | 8.6 |
| 12.6 | 7.0 |
| 14.6 | 6.1 |
| 15.5 | 5.7 |
| 16.1 | 5.5 |
| 16.3 | 5.4 |
| 16.6 | 5.3 |
| 17.1 | 5.2 |
| 17.6 | 5.0 |
| 18.7 | 4.7 |
| 18.9 | 4.7 |
| 20.2 | 4.4 |

-continued

| Pos. [°2Th.] | d-spacing [Å] |
|---|---|
| 20.5 | 4.3 |
| 20.7 | 4.3 |
| 21.1 | 4.2 |
| 21.5 | 4.1 |
| 22.0 | 4.0 |
| 22.3 | 4.0 |
| 23.7 | 3.8 |
| 24.8 | 3.6 |
| 25.2 | 3.5 |
| 26.0 | 3.4 |
| 26.3 | 3.4 |
| 26.5 | 3.4 |
| 26.8 | 3.3 |
| 27.0 | 3.3 |
| 27.5 | 3.2 |
| 27.7 | 3.2 |
| 28.1 | 3.2 |
| 29.6 | 3.0 |
| 30.0 | 3.0 |
| 30.4 | 2.9 |
| 31.3 | 2.9 |
| 32.0 | 2.8 |
| 32.5 | 2.8 |
| 33.2 | 2.7 |
| 34.0 | 2.6 |
| 34.6 | 2.6 |
| 36.9 | 2.4 |
| 38.2 | 2.4 |
| 38.9 | 2.3 |
| 39.5 | 2.3 |

Compound 1 Crystalline Form Type J

A novel Compound 1 crystalline form Type J can be identified by an X-ray Powder Diffraction (XRPD) pattern having one or more characteristic diffractions at angles (2 theta±0.2) of 4.5, 5.7, 22.8, 23.1, and 24.5. In some embodiments, Compound 1 crystalline form Type J can be identified by X-ray Powder Diffraction (XRPD), having one or more characteristic diffractions at angles (2 theta±0.2) of 4.5, 5.7, 22.8, 23.1, and 24.5, corresponding to d-spacing (angstroms±0.2) of 19.5, 15.4, 3.9, 3.8, and 3.6, respectively.

In some embodiments, Compound 1 crystalline form Type J is characterized by an X-ray Power Diffraction having one or more characteristic diffractions at angles (2 theta±0.2) of:
4.5
5.7
7.1
7.7
9.1
10.5
11.2
11.7
12.3
12.9
14.3
14.5
15.4
15.7
16.3
17.3
18.3
18.7
19.3
19.6
20.5
21.2
21.5
22.8
23.1
23.6
24.1
24.5
25.2
25.9
26.4
27.8
29.3
36.2
37.0

In some embodiments, Compound 1 crystalline form Type J is characterized by an X-ray Power Diffraction pattern having one or more characteristic diffractions at angles (2 theta±0.2) and corresponding d-spacing (angstroms±0.2) of:

| Pos. [°2Th.] | d-spacing [Å] |
|---|---|
| 4.5 | 19.5 |
| 5.7 | 15.4 |
| 7.1 | 12.7 |
| 7.7 | 11.5 |
| 9.1 | 9.7 |
| 10.5 | 8.4 |
| 11.2 | 7.9 |
| 11.7 | 7.5 |
| 12.3 | 7.2 |
| 12.9 | 6.8 |
| 14.3 | 6.2 |
| 14.5 | 6.1 |
| 15.4 | 5.8 |
| 15.7 | 5.7 |
| 16.3 | 5.4 |
| 17.3 | 5.1 |
| 18.3 | 4.9 |
| 18.7 | 4.7 |
| 19.3 | 4.6 |
| 19.6 | 4.5 |
| 20.5 | 4.3 |
| 21.2 | 4.2 |
| 21.5 | 4.1 |
| 22.8 | 3.9 |
| 23.1 | 3.8 |
| 23.6 | 3.8 |
| 24.1 | 3.7 |
| 24.5 | 3.6 |
| 25.2 | 3.5 |
| 25.9 | 3.4 |
| 26.4 | 3.4 |
| 27.8 | 3.2 |
| 29.3 | 3.0 |
| 36.2 | 2.5 |
| 37.0 | 2.4 |

Compound 1 Crystalline Form Type K

A novel Compound 1 crystalline form Type K can be identified by an X-ray Powder Diffraction (XRPD) pattern having one or more characteristic diffractions at angles (2 theta±0.2) of 4.6, 15.4, 15.6, 16.1, 23.2, and 27.4. In some embodiments, Compound 1 crystalline form Type K can be identified by X-ray Powder Diffraction (XRPD), having one or more characteristic diffractions at angles (2 theta±0.2) of 4.6, 15.4, 15.6, 16.1, 23.2, and 27.4, corresponding to d-spacing (angstroms±0.2) of 19.2, 5.7, 5.7, 5.5, 3.8, and 3.3, respectively.

In some embodiments, Compound 1 crystalline form Type K is characterized by an X-ray Power Diffraction having one or more characteristic diffractions at angles (2 theta±0.2) of:
4.6
9.3
10.1
12.9
13.9

14.7
15.4
15.6
16.1
17.8
18.3
18.6
19.3
20.0
20.7
21.6
21.9
22.9
23.2
24.4
25.0
25.5
26.0
27.4
28.8
29.2
30.7
31.1
32.7
36.3

In some embodiments, Compound 1 crystalline form Type K is characterized by an X-ray Power Diffraction pattern having one or more characteristic diffractions at angles (2 theta±0.2) and corresponding d-spacing (angstroms±0.2) of:

| Pos. [°2Th.] | d-spacing [Å] |
|---|---|
| 4.6 | 19.2 |
| 9.3 | 9.5 |
| 10.1 | 8.7 |
| 12.9 | 6.8 |
| 13.9 | 6.4 |
| 14.7 | 6.0 |
| 15.4 | 5.7 |
| 15.6 | 5.7 |
| 16.1 | 5.5 |
| 17.8 | 5.0 |
| 18.3 | 4.9 |
| 18.6 | 4.8 |
| 19.3 | 4.6 |
| 20.0 | 4.4 |
| 20.7 | 4.3 |
| 21.6 | 4.1 |
| 21.9 | 4.1 |
| 22.9 | 3.9 |
| 23.2 | 3.8 |
| 24.4 | 3.6 |
| 25.0 | 3.6 |
| 25.5 | 3.5 |
| 26.0 | 3.4 |
| 27.4 | 3.3 |
| 28.8 | 3.1 |
| 29.2 | 3.1 |
| 30.7 | 2.9 |
| 31.1 | 2.9 |
| 32.7 | 2.7 |
| 36.3 | 2.5 |

Compound 1 Crystalline Form Type L

A novel Compound 1 crystalline form Type L can be identified by an X-ray Powder Diffraction (XRPD) pattern having one or more characteristic diffractions at angles (2 theta±0.2) of 5.9, 11.9, 17.8, 21.6, 23.9, and 36.1. In some embodiments, Compound 1 crystalline form Type L can be identified by X-ray Powder Diffraction (XRPD), having one or more characteristic diffractions at angles (2 theta±0.2) of 5.9, 11.9, 17.8, 21.6, 23.9, and 36.1, corresponding to d-spacing (angstroms±0.2) of 14.9, 7.5, 5.0, 4.1, 3.7, and 2.5, respectively.

In some embodiments, Compound 1 crystalline form Type L is characterized by an X-ray Power Diffraction having one or more characteristic diffractions at angles (2 theta±0.2) of:

5.9
8.4
11.9
13.3
14.7
15.0
16.2
16.7
16.9
17.8
18.9
20.4
21.2
21.6
22.2
23.9
24.6
25.5
25.7
26.1
26.8
28.1
28.8
29.9
30.6
31.9
32.4
33.6
34.2
35.6
36.1
38.2

In some embodiments, Compound 1 crystalline form Type L is characterized by an X-ray Power Diffraction pattern having one or more characteristic diffractions at angles (2 theta±0.2) and corresponding d-spacing (angstroms±0.2) of:

| Pos. [°2Th.] | d-spacing [Å] |
|---|---|
| 5.9 | 14.9 |
| 8.4 | 10.5 |
| 11.9 | 7.5 |
| 13.3 | 6.6 |
| 14.7 | 6.0 |
| 15.0 | 5.9 |
| 16.2 | 5.5 |
| 16.7 | 5.3 |
| 16.9 | 5.2 |
| 17.8 | 5.0 |
| 18.9 | 4.7 |
| 20.4 | 4.4 |
| 21.2 | 4.2 |
| 21.6 | 4.1 |
| 22.2 | 4.0 |
| 23.9 | 3.7 |
| 24.6 | 3.6 |
| 25.5 | 3.5 |
| 25.7 | 3.5 |
| 26.1 | 3.4 |
| 26.8 | 3.3 |
| 28.1 | 3.2 |
| 28.8 | 3.1 |
| 29.9 | 3.0 |
| 30.6 | 2.9 |

-continued

| Pos. [°2Th.] | d-spacing [Å] |
|---|---|
| 31.9 | 2.8 |
| 32.4 | 2.8 |
| 33.6 | 2.7 |
| 34.2 | 2.6 |
| 35.6 | 2.5 |
| 36.1 | 2.5 |
| 38.2 | 2.4 |

Compound 1 Crystalline Form Type M

A novel Compound 1 crystalline form Type M can be identified by an X-ray Powder Diffraction (XRPD) pattern having one or more characteristic diffractions at angles (2 theta±0.2) of 4.5, 5.8, 9.7, 15.6, 21.9, and 26.7. In some embodiments, Compound 1 crystalline form Type M can be identified by X-ray Powder Diffraction (XRPD), having one or more characteristic diffractions at angles (2 theta±0.2) of 4.5, 5.8, 9.7, 15.6, 21.9, and 26.7, corresponding to d-spacing (angstroms±0.2) of 19.5, 15.3, 9.1, 5.7, 4.1, and 3.3, respectively.

In some embodiments, Compound 1 crystalline form Type M is characterized by an X-ray Power Diffraction having one or more characteristic diffractions at angles (2 theta±0.2) of:

4.5
5.8
6.1
8.7
9.0
9.7
12.3
13.1
13.7
14.5
15.1
15.6
16.8
17.4
18.0
18.5
19.5
20.0
21.4
21.9
22.3
22.9
23.3
23.5
24.1
25.0
25.8
26.3
26.7
27.8
28.1
29.4
30.8
31.7
33.0
35.3
37.8
38.6

In some embodiments, Compound 1 crystalline form Type M is characterized by an X-ray Power Diffraction pattern having one or more characteristic diffractions at angles (2 theta±0.2) and corresponding d-spacing (angstroms±0.2) of:

| Pos. [°2Th.] | d-spacing [Å] |
|---|---|
| 4.5 | 19.5 |
| 5.8 | 15.3 |
| 6.1 | 14.4 |
| 8.7 | 10.2 |
| 9.0 | 9.9 |
| 9.7 | 9.1 |
| 12.3 | 7.2 |
| 13.1 | 6.8 |
| 13.7 | 6.4 |
| 14.5 | 6.1 |
| 15.1 | 5.9 |
| 15.6 | 5.7 |
| 16.8 | 5.3 |
| 17.4 | 5.1 |
| 18.0 | 4.9 |
| 18.5 | 4.8 |
| 19.5 | 4.5 |
| 20.0 | 4.4 |
| 21.4 | 4.1 |
| 21.9 | 4.1 |
| 22.3 | 4.0 |
| 22.9 | 3.9 |
| 23.3 | 3.8 |
| 23.5 | 3.8 |
| 24.1 | 3.7 |
| 25.0 | 3.6 |
| 25.8 | 3.5 |
| 26.3 | 3.4 |
| 26.7 | 3.3 |
| 27.8 | 3.2 |
| 28.1 | 3.2 |
| 29.4 | 3.0 |
| 30.8 | 2.9 |
| 31.7 | 2.8 |
| 33.0 | 2.7 |
| 35.3 | 2.5 |
| 37.8 | 2.4 |
| 38.6 | 2.3 |

Pharmaceutical Compositions Comprising Compound 1 Crystalline Form

In some embodiments, the present disclosure provides a pharmaceutical composition comprising a therapeutically effective amount of any crystalline solid form (Type A, Type B, Type C, Type D, Type E, Type F, or Type G) of Compound 1 as discussed above, and one or more pharmaceutically acceptable excipients. In some embodiments, the present disclosure provides a pharmaceutical composition comprising a therapeutically effective amount of any crystalline solid form (Type A, Type B, Type C, Type D, Type E, Type F, Type G, Type H, Type I, Type J, Type K, Type L, or Type M) of Compound 1 as discussed above, and one or more pharmaceutically acceptable excipients. In some embodiments, the present disclosure provides a pharmaceutical composition comprising any crystalline solid form (Type A, Type B, Type C, Type D, Type E, Type F, or Type G) of Compound 1 as discussed above, and one or more pharmaceutically acceptable excipients. In some embodiments, the present disclosure provides a pharmaceutical composition comprising any crystalline solid form (Type A, Type B, Type C, Type D, Type E, Type F, Type G, Type H, Type I, Type J, Type K, Type L, or Type M) of Compound 1 as discussed above, and one or more pharmaceutically acceptable excipients. In some embodiments, the pharmaceutical composition is for oral administration.

In some embodiments, the present disclosure provides a pharmaceutical composition comprising any crystalline solid form (Type A, Type B, Type C, Type D, Type E, Type F, or Type G) of Compound 1 as discussed above, and having a water content of about 0.5-5.0 weight %, preferably about 1.0-4.5 weight %, more preferably about 1.5-4.0 weight %, even more preferably about 2.0-3.5 weight %, still more preferably about 2.5-3.0 weight % relative to the weight of the pharmaceutical composition. In some embodiments, the present disclosure provides a pharmaceutical composition comprising any crystalline solid form (Type A, Type B, Type C, Type D, Type E, Type F, Type G, Type H, Type I, Type J, Type K, Type L, or Type M) of Compound 1 as discussed above, and having a water content of about 0.5-5.0 weight %, preferably about 1.0-4.5 weight %, more preferably about 1.5-4.0 weight %, even more preferably about 2.0-3.5 weight %, still more preferably about 2.5-3.0 weight % relative to the weight of the pharmaceutical composition. In some embodiments, the present disclosure provides a pharmaceutical composition comprising any crystalline solid form (Type A, Type B, Type C, Type D, Type E, Type F, or Type G) of Compound 1 as discussed above, and having a water content in an amount selected from the following ranges: about 0.5-1.0 weight %, about 1.0-1.5 weight %, about 1.5-2.0 weight %, about 2.5-3.0 weight %, about 3.0-3.5 weight %, about 3.5-4.0 weight %, about 4.0-4.5 weight %, and about 4.5-5.0 weight % relative to the weight of the pharmaceutical composition. In some embodiments, the present disclosure provides a pharmaceutical composition comprising any crystalline solid form (Type A, Type B, Type C, Type D, Type E, Type F, Type G, Type H, Type I, Type J, Type K, Type L, or Type M) of Compound 1 as discussed above, and having a water content in an amount selected from the following ranges: about 0.5-1.0 weight %, about 1.0-1.5 weight %, about 1.5-2.0 weight %, about 2.5-3.0 weight %, about 3.0-3.5 weight %, about 3.5-4.0 weight %, about 4.0-4.5 weight %, and about 4.5-5.0 weight % relative to the weight of the pharmaceutical composition. In some embodiments, the present disclosure provides a pharmaceutical composition comprising any crystalline solid form (Type A, Type B, Type C, Type D, Type E, Type F, or Type G) of Compound 1 as discussed above, and having a water content in an amount selected from the weight percentage: about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, and about 5.0 weight % relative to the weight of the pharmaceutical composition. In some embodiments, the present disclosure provides a pharmaceutical composition comprising any crystalline solid form (Type A, Type B, Type C, Type D, Type E, Type F, Type G, Type H, Type I, Type J, Type K, Type L, or Type M) of Compound 1 as discussed above, and having a water content in an amount selected from the weight percentage: about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, and about 5.0 weight % relative to the weight of the pharmaceutical composition.

In some embodiments, the present disclosure provides a pharmaceutical composition comprising a therapeutically effective amount of Compound 1 crystalline form Type A, and one or more pharmaceutically acceptable excipients. In some embodiments, the present disclosure provides a pharmaceutical composition comprising Compound 1 crystalline form Type A, and one or more pharmaceutically acceptable excipients. In some embodiments, the pharmaceutical composition is for oral administration. In some embodiments, the pharmaceutical composition is substantially free of other crystalline forms of Compound 1. In some embodiments, the pharmaceutical composition is substantially free of amorphous Compound 1.

In some embodiments, the present disclosure provides a pharmaceutical composition comprising a therapeutically effective amount of Compound 1 crystalline form Type B, and one or more pharmaceutically acceptable excipients. In some embodiments, the present disclosure provides a pharmaceutical composition comprising Compound 1 crystalline form Type B, and one or more pharmaceutically acceptable excipients. In some embodiments, the pharmaceutical composition is for oral administration. In some embodiments, the pharmaceutical composition is substantially free of other crystalline forms of Compound 1. In some embodiments, the pharmaceutical composition is substantially free of amorphous Compound 1.

In some embodiments, the present disclosure provides a pharmaceutical composition comprising a therapeutically effective amount of Compound 1 crystalline form Type C, and one or more pharmaceutically acceptable excipients. In some embodiments, the present disclosure provides a pharmaceutical composition comprising Compound 1 crystalline form Type C, and one or more pharmaceutically acceptable excipients. In some embodiments, the pharmaceutical composition is for oral administration. In some embodiments, the pharmaceutical composition is substantially free of other crystalline forms of Compound 1. In some embodiments, the pharmaceutical composition is substantially free of amorphous Compound 1.

In some embodiments, the present disclosure provides a pharmaceutical composition comprising a therapeutically effective amount of Compound 1 crystalline form Type D, and one or more pharmaceutically acceptable excipients. In some embodiments, the present disclosure provides a pharmaceutical composition comprising Compound 1 crystalline form Type D, and one or more pharmaceutically acceptable excipients. In some embodiments, the pharmaceutical composition is for oral administration. In some embodiments, the pharmaceutical composition is substantially free of other crystalline forms of Compound 1. In some embodiments, the pharmaceutical composition is substantially free of amorphous Compound 1.

In some embodiments, the present disclosure provides a pharmaceutical composition comprising a therapeutically effective amount of Compound 1 crystalline form Type E, and one or more pharmaceutically acceptable excipients. In some embodiments, the present disclosure provides a pharmaceutical composition comprising Compound 1 crystalline form Type E, and one or more pharmaceutically acceptable excipients. In some embodiments, the pharmaceutical composition is for oral administration. In some embodiments, the pharmaceutical composition is substantially free of other crystalline forms of Compound 1. In some embodiments, the pharmaceutical composition is substantially free of amorphous Compound 1.

In some embodiments, the present disclosure provides a pharmaceutical composition comprising a therapeutically effective amount of Compound 1 crystalline form Type F, and one or more pharmaceutically acceptable excipients. In some embodiments, the present disclosure provides a pharmaceutical composition comprising Compound 1 crystalline form Type F, and one or more pharmaceutically acceptable excipients. In some embodiments, the pharmaceutical composition is for oral administration. In some embodiments, the pharmaceutical composition is substantially free of other crystalline forms of Compound 1. In some embodiments, the pharmaceutical composition is substantially free of amorphous Compound 1.

In some embodiments, the present disclosure provides a pharmaceutical composition comprising a therapeutically effective amount of Compound 1 crystalline form Type G, and one or more pharmaceutically acceptable excipients. In some embodiments, the present disclosure provides a pharmaceutical composition comprising Compound 1 crystalline form Type G, and one or more pharmaceutically acceptable excipients. In some embodiments, the pharmaceutical composition is for oral administration. In some embodiments, the pharmaceutical composition is substantially free of other crystalline forms of Compound 1. In some embodiments, the pharmaceutical composition is substantially free of amorphous Compound 1.

In some embodiments, the present disclosure provides a pharmaceutical composition comprising a crystalline form of Compound 1. In some embodiments, a pharmaceutical composition comprises a crystalline form of Compound 1 and an amorphous form of Compound 1, wherein the amorphous form of Compound 1 is present in an amount selected from the following ranges: about 90 to about 99%, about 80 to about 89%, about 70 to about 79%, about 60 to about 69%, about 50 to about 59%, about 40 to about 49%, about 30 to about 39%, about 20 to about 29%, about 10 to about 19%, about 1 to about 9% and about 0 to about 0.99%. In some embodiments, a pharmaceutical composition comprising a crystalline form of Compound 1 is substantially free of amorphous Compound 1.

In some embodiments, the present disclosure provides a pharmaceutical composition comprising Compound 1 and its enantiomer ("Compound 2"). In some embodiments, a pharmaceutical composition comprises Compound 1 and its enantiomer Compound 2, wherein Compound 1 has an enantiomeric excess selected from the following ranges: at least about 99%, at least about 95%, at least about 90%, at least about 80%, about 90 to about 99%, about 80 to about 89%, about 70 to about 79%, about 60 to about 69%, about 50 to about 59%, about 40 to about 49%, about 30 to about 39%, about 20 to about 29%, about 10 to about 19%, about 1 to about 9% and about 0 to about 0.99%. In some embodiments, a pharmaceutical composition comprises Compound 1 and its enantiomer Compound 2, wherein the weight percentage of Compound 1 relative to the total weight of Compound 1 and Compound 2 is in a percentage selected from the following ranges: about 90 to about 99%, about 80 to about 89%, about 70 to about 79%, about 60 to about 69%, about 50 to about 59%, about 40 to about 49%, about 30 to about 39%, about 20 to about 29%, about 10 to about 19%, about 1 to about 9% and about 0 to about 0.99%.

Pharmaceutical compositions described herein can comprise a pharmaceutically acceptable carrier or one or more excipients. In some embodiments, pharmaceutical compositions described herein can be provided in a unit dosage form container (e.g., in a vial or bag, or the like). In some embodiments, pharmaceutical compositions described herein can be provided in an oral dosage form. In some embodiments, an oral dosage form is a tablet.

Amorphous Solid Dispersion Comprising Compound 1

The present disclosure also provides an amorphous solid dispersion comprising Compound 1:

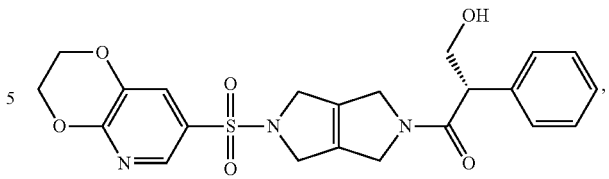

and a polymer. In some embodiments, the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof. In some embodiments, the polymer is hydroxypropylmethyl cellulose (HPMC) or hydroxypropylmethyl cellulose acetate succinate (HPMC AS). In some embodiments, the polymer is hydroxypropylmethyl cellulose acetate succinate (HPMC AS), including any grade thereof (e.g., HPMC AS MG).

Various amounts of Compound 1 and the polymer can be used in the amorphous solid dispersion. In some embodiments, the weight ratio of Compound 1 to the polymer in the amorphous solid dispersion can be selected from the following ranges: about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, and about 1:10. In some embodiments, the weight ratio of Compound 1 to the polymer in the amorphous solid dispersion is in a range of about 3:1 to about 1:3. In some embodiments, the weight ratio of Compound 1 to the polymer in the amorphous solid dispersion is in a range of about 2:1 to about 1:3. In some embodiments, the weight ratio of Compound 1 to the polymer in the amorphous solid dispersion is about 1:3. In some embodiments, the weight ratio of Compound 1 to the polymer in the amorphous solid dispersion is about 1:1. In some embodiments, the weight ratio of Compound 1 to the polymer in the amorphous solid dispersion is about 1:3, about 2:3, about 1:1, about 1.5:1, about 2:1, or about 3:1. In some embodiments, the weight ratio of Compound 1 to the polymer in the amorphous solid dispersion is about 1:3, about 2:3, about 1:1, about 1.5:1, or about 2:1.

In some embodiments, the amorphous solid dispersion is free or substantially free of crystalline Compound 1. In some embodiments, crystalline diffraction peaks are not observable by XRPD analysis (Method D) of the amorphous solid dispersion. In some embodiments, crystalline diffraction peaks are not observable by XRPD analysis (Method D) of the amorphous solid dispersion. In some embodiments, a single glass transition temperature ($T_G$) and no melt endotherm is observable by DSC analysis (Method B) of the amorphous solid dispersion.

In some embodiments, the amorphous solid dispersion is physically stable in that it remains free or substantially free of crystalline Compound 1 over time in accelerated stability studies. In some embodiments, crystalline diffraction peaks are not observable by XRPD analysis (Method D) of the amorphous solid dispersion after storage in a container as described in Example 20 for 5 months at 2-8° C. and ambient relative humidity, 5 months at 25° C. and 60% relative humidity, 1 month at 2-8° C. and ambient relative humidity, 1 month at 25° C. and 60% relative humidity, or 1 month at 40° C. and 75% relative humidity. In some embodiments, a single glass transition temperature ($T_G$) and no melt endotherm is observable by DSC analysis (Method B) of the amorphous solid dispersion after storage in a container as described in Example 20 for 5 months at 2-8° C. and ambient relative humidity, 5 months at 25° C. and 60% relative humidity, 1 month at 2-8° C. and ambient relative humidity, 1 month at 25° C. and 60% relative humidity, or 1 month at 40° C. and 75% relative humidity. In some embodiments, crystalline diffraction peaks are not observable by XRPD analysis (Method D) of the amorphous solid dispersion after storage in a sealed vial for 1 week at 60° C., storage in a sealed vial for 2 weeks at 60° C., storage in an unsealed vial for 1 week at 25° C. and 60% relative humidity, storage in an unsealed vial for 2 weeks at 25° C. and 60% relative humidity, storage in an unsealed vial for 1 week at 40° C. and 75% relative humidity, storage in an unsealed vial for 2 weeks at 40° C. and 75% relative humidity, storage in an unsealed vial for 1 week at 60° C. and 75% relative humidity, or storage in an unsealed vial for 2 weeks at 60° C. and 75% relative humidity. In some embodiments, a single glass transition temperature ($T_G$) and no melt endotherm is observable by DSC analysis (Method B) of the amorphous solid dispersion after storage in a sealed vial for 1 week at 60° C., storage in a sealed vial for 2 weeks at 60° C., storage in an unsealed vial for 1 week at 25° C. and 60% relative humidity, storage in an unsealed vial for 2 weeks at 25° C. and 60% relative humidity, storage in an unsealed vial for 1 week at 40° C. and 75% relative humidity, storage in an unsealed vial for 2 weeks at 40° C. and 75% relative humidity, storage in an unsealed vial for 1 week at 60° C. and 75% relative humidity, or storage in an unsealed vial for 2 weeks at 60° C. and 75% relative humidity.

In some embodiments, the amorphous solid dispersion is highly soluble, e.g., Compound 1 dissolves quickly and readily in biorelevant media. In some embodiments, Compound 1 has a concentration of at least 150 µg/mL, at least 200 µg/mL, at least 250 µg/mL, at least 300 µg/mL, or at least 350 µg/mL after 30 minutes in the kinetic solubility experiment described in Example 23. In some embodiments, Compound 1 has a Cmax of at least 300 µg/mL, at least 350 µg/mL, at least 400 µg/mL, at least 450 µg/mL, at least 500 µg/mL, at least 550 µg/mL, at least 600 µg/mL, at least 650 µg/mL, or at least 700 µg/mL in the kinetic solubility experiment described in Example 23. In some embodiments, Compound 1 has a concentration of at least 200 µg/mL, at least 250 µg/mL, at least 300 µg/mL, at least 350 µg/mL, at least 400 µg/mL, at least 450 µg/mL, at least 500 µg/mL, at least 550 µg/mL, or at least 600 µg/mL after 4 hours in the kinetic solubility experiment described in Example 23. In some embodiments, Compound 1 has a concentration of at least 150 µg/mL, at least 200 µg/mL, at least 250 µg/mL, or at least 300 µg/mL after 16 hours in the kinetic solubility experiment described in Example 23.

Pharmaceutical Compositions Comprising Compound 1 Amorphous Solid Dispersion

The present disclosure further provides a pharmaceutical composition comprising a therapeutically effective amount of an amorphous solid dispersion comprising Compound 1, and one or more pharmaceutically acceptable excipients. In some embodiments, the pharmaceutical composition is for oral administration.

In some embodiments, the present disclosure provides a pharmaceutical composition comprising an amorphous solid dispersion comprising Compound 1, and having a water content of about 0.5-5.0 weight %, preferably about 1.0-4.5 weight %, more preferably about 1.5-4.0 weight %, even more preferably about 2.0-3.5 weight %, still more preferably about 2.5-3.0 weight % relative to the weight of the pharmaceutical composition. In some embodiments, the present disclosure provides a pharmaceutical composition comprising an amorphous solid dispersion comprising Compound 1, and having a water content in an amount selected from the following ranges: about 0.5-1.0 weight %, about 1.0-1.5 weight %, about 1.5-2.0 weight %, about 2.5-3.0 weight %, about 3.0-3.5 weight %, about 3.5-4.0 weight %, about 4.0-4.5 weight %, and about 4.5-5.0 weight % relative to the weight of the pharmaceutical composition. In some embodiments, the present disclosure provides a pharmaceutical composition comprising an amorphous solid dispersion comprising Compound 1, and having a water content in an amount selected from the weight percentage: about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, and about 5.0 weight % relative to the weight of the pharmaceutical composition.

In some embodiments, the pharmaceutical composition comprises about 10 mg, about 25 mg, about 50 mg, about 100 mg, about 200 mg, or about 300 mg of Compound 1. In some embodiments, the pharmaceutical composition comprises about 25 mg of Compound 1. In some embodiments, the pharmaceutical composition comprises about 100 mg of Compound 1. In some embodiments, the pharmaceutical composition comprises about 200 mg of Compound 1.

Pharmaceutical compositions described herein can comprise a pharmaceutically acceptable carrier or one or more excipients. In some embodiments, pharmaceutical compositions described herein can be provided in a unit dosage form container (e.g., in a vial or bag, or the like). In some embodiments, pharmaceutical compositions described herein can be provided in an oral dosage form. In some embodiments, an oral dosage form is a tablet.

In some embodiments, the pharmaceutical composition comprises one or more pharmaceutically acceptable excipients which comprise one or more of a filler, a dry binder, a glidant, a lubricant, a disintegrant, and a film coating agent. In some embodiments, the one or more pharmaceutically acceptable excipients comprise a filler, and the filler comprises microcrystalline cellulose. In some embodiments, the one or more pharmaceutically acceptable excipients comprise a filler, and the filler comprises lactose monohydrate. In some embodiments, the one or more pharmaceutically acceptable excipients comprise a dry binder, and the dry binder comprises crospovidone. In some embodiments, the one or more pharmaceutically acceptable excipients comprise a glidant, and the glidant comprises colloidal silicon dioxide. In some embodiments, the one or more pharmaceutically acceptable excipients comprise a lubricant, and the lubricant comprises magnesium stearate. In some embodiments, the one or more pharmaceutically acceptable excipients comprise a disintegrant, and the disintegrant comprises croscarmellose sodium. In some embodiments, the one or more pharmaceutically acceptable excipients comprise a lubricant, and the lubricant comprises magnesium stearate.

In some embodiments, a pharmaceutical composition comprises a tablet core. In some embodiments, the tablet core comprises an intra granular portion comprising the amorphous solid dispersion, and an extra granular portion blended with the intra granular portion. In some embodiments, a pharmaceutical composition further comprises a coating disposed on the tablet core.

Various amounts of Compound 1 relative to the tablet core can be used in a pharmaceutical composition comprising an amorphous solid dispersion comprising Compound 1. In some embodiments, the amorphous solid dispersion comprising Compound 1 can be about 10 weight %, about 20 weight %, about 30 weight %, about 40 weight %, about 50 weight %, about 60 weight %, about 70 weight %, about 80 weight %, or about 90 weight % of the tablet core. In some embodiments, the amorphous solid dispersion comprising Compound 1 is at least about 30 weight % of the tablet core. In some embodiments, the amorphous solid dispersion comprising Compound 1 is at least about 50 weight % of the tablet core. In some embodiments, the amorphous solid dispersion comprising Compound 1 is at least about 60 weight % of the tablet core. In some embodiments, the amorphous solid dispersion comprising Compound 1 is about 50 weight % of the tablet core. In some embodiments, the amorphous solid dispersion comprising Compound 1 is about 50 to about 70 weight % of the tablet core. In some embodiments, the amorphous solid dispersion comprising Compound 1 is about 60 to about 65 weight % of the tablet core.

In some embodiments, the intra granular portion further comprises one or more of a filler, a dry binder, a glidant, and a lubricant. In some embodiments, the extra granular portion further comprises one or more of a filler, a disintegrant, and a lubricant.

In some embodiments, the tablet core has the following components:

| Function | % Formulation (weight) | Exemplary Component |
|---|---|---|
| API | 30-70% | Amorphous Solid Dispersion of Compound 1 |
| Filler | 15-40% | Microcrystalline Cellulose |
| Dry binder | 2-10% | Crospovidone |
| Glidant | 0.25-1.25% | Colloidal Silicon Dioxide |
| Lubricant | 0.25-1.00% | Magnesium Stearate |

In some embodiments, the tablet core has the following components:

| Function | % Formulation (weight) | Exemplary Component |
|---|---|---|
| API | 30-70% | Amorphous Solid Dispersion of Compound 1 |
| Filler | 15-50% | Microcrystalline Cellulose, Lactose Monohydrate |
| Dry binder | 2-10% | Crospovidone |
| Glidant | 0.25-1.25% | Colloidal Silicon Dioxide |
| Disintegrant | 2-3% | Croscarmellose Sodium |
| Lubricant | 0.25-1.00% | Magnesium Stearate |

In some embodiments, the tablet core has the following components:

| Component | Function | Range |
|---|---|---|
| SDD (1:1 drug:polymer w/w) | Active | 50-75% |
| Microcrystalline Cellulose | Filler | 15-30% |
| Lactose Monohydrate | Filler | 0-20% |
| Crosslinked polyvinylpyrrolidone | Dry Binder | 2-10% |
| Colloidal Silicon Dioxide | Glidant | <2% |
| Croscarmellose Sodium | Disintegrant | 2-10% |
| Magnesium Stearate | Lubricant | <2% |

In some embodiments, the tablet core has the following components:

| Component | Function | Range |
|---|---|---|
| SDD (1.5:1 drug:polymer w/w) | Active | 50-75% |
| Microcrystalline Cellulose | Filler | 15-30% |
| Lactose Monohydrate | Filler | 0-20% |
| Crosslinked polyvinylpyrrolidone | Dry Binder | 2-10% |
| Colloidal Silicon Dioxide | Glidant | <2% |
| Croscarmellose Sodium | Disintegrant | 2-10% |
| Magnesium Stearate | Lubricant | <2% |

In some embodiments, the Compound 1 oral unit dosage form can be a tablet comprising a total of about 10-35% by weight of Compound 1, with a total dose of about 100 mg or 200 mg, and a total weight of less than about 800 mg. In one embodiment, a tablet having a composition described in a table above comprises about 50% of an API formed as an amorphous solid dispersion of Compound 1 obtained from a 1:3 SDD process described in the examples below (e.g., about 12.5% of Compound 1 in the tablet). In one embodiment, a tablet having a composition described in a table above comprises about 30% of an API formed as an amorphous solid dispersion of Compound 1 obtained from a 1:1 SDD process described in the examples below (e.g., about 15% of Compound 1 in the tablet, with a total of about 100 mg Compound 1 in the tablet). In one embodiment, a tablet having a composition described in a table above comprises about 62% of an API formed as an amorphous solid dispersion of Compound 1 obtained from a 1:1 SDD process described in the examples below (e.g., about 31% of Compound 1 in the tablet, with a total of about 200 mg of Compound 1 in the tablet)

Methods for Preparing Amorphous Solid Dispersions of Compound 1

The present disclosure also provides a method for preparing an amorphous solid dispersion comprising Compound 1:

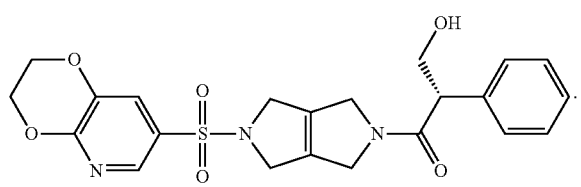 [SMILES: O=C([C@H](CO)c1ccccc1)N1CC2=C(C1)CN(S(=O)(=O)c1cnc3c(c1)OCCO3)C2]

In some embodiments, the method comprises mixing Compound 1, a polymer, and a solvent to afford a mixture, and spray-drying the mixture to afford an amorphous solid dispersion comprising Compound 1.

In some embodiments, the polymer used in the method is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof. In some embodiments, the polymer is hydroxypropylmethyl cellulose (HPMC) or hydroxypropylmethyl cellulose acetate succinate (HPMC AS). In some embodiments, the polymer is hydroxypropylmethyl cellulose acetate succinate (HPMC AS), including any grade thereof (e.g., HPMC AS MG).

Various amounts of Compound 1 and the polymer can be used in the method to prepare the amorphous solid dispersion. In some embodiments, the weight ratio of Compound 1 to the polymer used in the method to prepare the amorphous solid dispersion can be selected from the following ranges: about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, and about 1:10. In some embodiments, the weight ratio of Compound 1 to the polymer used in the method to prepare the amorphous solid dispersion is in a range of about 3:1 to about 1:3. In some embodiments, the weight ratio of Compound 1 to the polymer used in the method to prepare the amorphous solid dispersion is in a range of about 2:1 to about 1:3. In some embodiments, the weight ratio of Compound 1 to the polymer used in the method to prepare the amorphous solid dispersion is about 1:3. In some embodiments, the weight ratio of Compound 1 to the polymer used in the method to prepare the amorphous solid dispersion is about 1:1. In some embodiments, the weight ratio of Compound 1 to the polymer used in the method to prepare the amorphous solid dispersion is about 1:3, about 2:3, about 1:1, about 1.5:1, about 2:1, or about 3:1. In some embodiments, the weight ratio of Compound 1 to the polymer used in the method to prepare the amorphous solid dispersion is about 1:3, about 2:3, about 1:1, about 1.5:1, or about 2:1.

Various solvents can be used in the method to prepare the amorphous solid dispersion. In some embodiments, the solvent is dichloromethane and methanol.

The present disclosure further provides a product prepared by a process comprising mixing Compound 1, a polymer, and a solvent to afford a mixture, and spray-drying the mixture to afford an amorphous solid dispersion comprising Compound 1

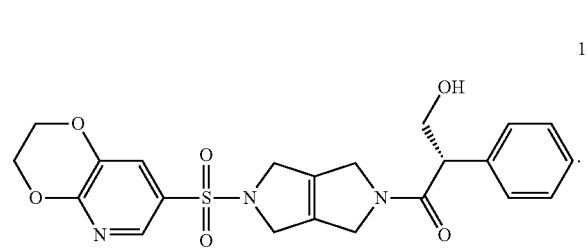 [SMILES: O=C([C@H](CO)c1ccccc1)N1CC2=C(C1)CN(S(=O)(=O)c1cnc3c(c1)OCCO3)C2]

In some embodiments, the polymer used in the process is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof. In some embodiments, the polymer is hydroxypropylmethyl cellulose (HPMC) or hydroxypropylmethyl cellulose acetate succinate (HPMC AS). In some embodiments, the polymer is hydroxypropylmethyl cellulose acetate succinate (HPMC AS), including any grade thereof (e.g., HPMC AS MG).

Various amounts of Compound 1 and the polymer can be used in the process to prepare the amorphous solid dispersion. In some embodiments, the weight ratio of Compound 1 to the polymer used in the process to prepare the amorphous solid dispersion can be selected from the following ranges: about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, and about 1:10. In some embodiments, the weight ratio of Compound 1 to the polymer used in the process to prepare the amorphous solid dispersion is in a range of about 3:1 to about 1:3. In some embodiments, the weight ratio of Compound 1 to the polymer used in the process to prepare the amorphous solid dispersion is in a range of about 2:1 to about 1:3. In some embodiments, the weight ratio of Compound 1 to the polymer used in the process to prepare the amorphous solid dispersion is about 1:3. In some embodiments, the weight ratio of Compound 1 to the polymer used in the method to prepare the amorphous solid dispersion is about 1:1. In some embodiments, the weight ratio of Compound 1 to the polymer used in the method to prepare the amorphous solid dispersion is about 1:3, about 2:3, about 1:1, about 1.5:1, about 2:1, or about 3:1. In some embodiments, the weight ratio of Compound 1 to the polymer used in the method to prepare the amorphous solid dispersion is about 1:3, about 2:3, about 1:1, about 1.5:1, or about 2:1.

Various solvents can be used in the process to prepare the amorphous solid dispersion. In some embodiments, the solvent is dichloromethane and methanol.

Pharmaceutical Compositions Comprising Compound 1

The present disclosure provides a pharmaceutical composition comprising Compound 1:

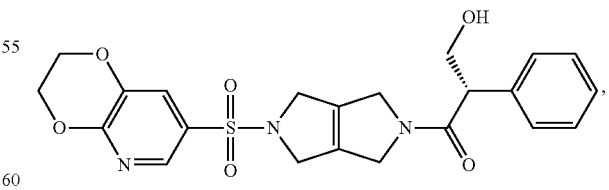

obtained by a process comprising mixing Compound 1 in a solid form, a polymer, and a solvent to afford a mixture, and spray-drying the mixture to afford an amorphous solid dispersion comprising Compound 1.

In some embodiments, the solid form is Type A of Compound 1. In some embodiments, the solid form is Type B of Compound 1. In some embodiments, the solid form is Type C of Compound 1. In some embodiments, the solid form is Type D of Compound 1. In some embodiments, the solid form is Type E of Compound 1. In some embodiments, the solid form is Type F of Compound 1. In some embodiments, the solid form is Type G of Compound 1. In some embodiments, the solid form is Type H of Compound 1. In some embodiments, the solid form is Type I of Compound 1. In some embodiments, the solid form is Type J of Compound 1. In some embodiments, the solid form is Type K of Compound 1. In some embodiments, the solid form is Type L of Compound 1. In some embodiments, the solid form is Type M of Compound 1. In some embodiments, the solid form is selected from the group consisting of Type A, Type B, Type C, Type D, Type E, Type F, Type G, Type H, Type I, Type J, Type K, Type L, and Type M of Compound 1. In some embodiments, the solid form is amorphous form of Compound 1.

In some embodiments, the pharmaceutical composition obtained by the process has a water content of about 0.5-5.0 weight %, preferably about 1.0-4.5 weight %, more preferably about 1.5-4.0 weight %, even more preferably about 2.0-3.5 weight %, still more preferably about 2.5-3.0 weight % relative to the weight of the pharmaceutical composition. In some embodiments, the pharmaceutical composition obtained by the process has a water content in an amount selected from the following ranges: about 0.5-1.0 weight %, about 1.0-1.5 weight %, about 1.5-2.0 weight %, about 2.5-3.0 weight %, about 3.0-3.5 weight %, about 3.5-4.0 weight %, about 4.0-4.5 weight %, and about 4.5-5.0 weight % relative to the weight of the pharmaceutical composition. In some embodiments, the pharmaceutical composition obtained by the process has a water content in an amount selected from the weight percentage: about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, and about 5.0 weight % relative to the weight of the pharmaceutical composition.

In some embodiments, the polymer used in the process is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof. In some embodiments, the polymer is hydroxypropylmethyl cellulose (HPMC) or hydroxypropylmethyl cellulose acetate succinate (HPMC AS). In some embodiments, the polymer is hydroxypropylmethyl cellulose acetate succinate (HPMC AS), including any grade thereof (e.g., HPMC AS MG).

Various amounts of Compound 1 and the polymer can be used in the process to prepare the amorphous solid dispersion. In some embodiments, the weight ratio of Compound 1 to the polymer used in the process to prepare the amorphous solid dispersion can be selected from the following ranges: about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, and about 1:10. In some embodiments, the weight ratio of Compound 1 to the polymer used in the process to prepare the amorphous solid dispersion is in a range of about 3:1 to about 1:3. In some embodiments, the weight ratio of Compound 1 to the polymer used in the process to prepare the amorphous solid dispersion is in a range of about 2:1 to about 1:3. In some embodiments, the weight ratio of Compound 1 to the polymer used in the process to prepare the amorphous solid dispersion is about 1:3. In some embodiments, the weight ratio of Compound 1 to the polymer used in the method to prepare the amorphous solid dispersion is about 1:1. In some embodiments, the weight ratio of Compound 1 to the polymer used in the method to prepare the amorphous solid dispersion is about 1:3, about 2:3, about 1:1, about 1.5:1, about 2:1, or about 3:1. In some embodiments, the weight ratio of Compound 1 to the polymer used in the method to prepare the amorphous solid dispersion is about 1:3, about 2:3, about 1:1, about 1.5:1, or about 2:1.

Various solvents can be used in the process to prepare the amorphous solid dispersion. In some embodiments, the solvent is dichloromethane and methanol.

Solid Oral Dosage Forms of Compound 1

The disclosure also provides solid oral dosage forms of Compound 1, such as tablets and capsules. In some embodiments, the solid oral dosage form comprises a stabilized amorphous compound (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one, wherein the stabilized amorphous compound does not show crystallinity by PXRD (Method D) after 2 weeks of storage at 60° C./75% RH (exposed). In some embodiments, the stabilized amorphous compound shows a single glass transition temperature ($T_G$) and no melt endotherm by DSC (Method B) after 2 weeks of storage at 60° C./75% RH (exposed).

In some embodiments, the solid oral dosage form contains a total of about 100 mg or about 200 mg of (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one. In some embodiments, the solid dosage form has a total weight of not more than 700 mg, 800 mg, 900 mg, 1000 mg or 1200 mg. In some embodiments, the solid oral dosage form is a tablet or capsule.

In some embodiments, the stabilized amorphous compound in the solid oral dosage form is in a spray dried dispersion with a polymer. In some embodiments, the polymer is selected from the group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof. In some embodiments, the polymer is HPMC AS. In some embodiments, the (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one is spray dried with HPMC AS in a weight ratio of 1:3 to 2:1. In some embodiments, the (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one is spray dried with HPMC AS in a weight ratio of 1:1.

The disclosure also relates to a (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one active pharmaceutical ingredient (API) composition comprising 0.05-5.0% by HPLC of (R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one.

The disclosure also relates to a tablet comprising about 100 mg or about 200 mg of stabilized amorphous compound (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one as the active pharmaceutical ingredient (API), wherein the stabilized amorphous compound does not show crystallinity by PXRD (Method D) after 2 weeks of storage of the tablet at 60° C./75% RH (exposed). In some embodiments, the API comprises less than 5.0% by HPLC of (R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one. In some embodiments, the API comprises less than 0.05% by HPLC of (R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one. In some embodiments, the tablet has a total weight of less than 700 mg, 800 mg, 900 mg, 1000 mg or 1200 mg.

Tablet Dosage Forms of Compound 1

The disclosure also provides tablet dosage forms of Compound 1. In some embodiments, the tablet dosage form comprises a tablet core, the tablet core comprising at least 10 weight % of Compound 1 in amorphous form:

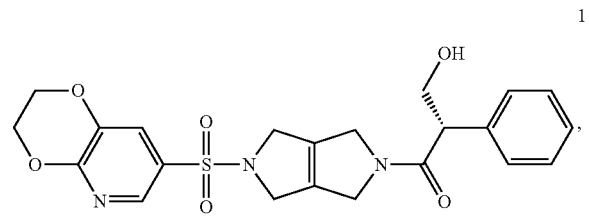 [SMILES: O=C([C@H](CO)c1ccccc1)N1CC2=C(C1)CN(S(=O)(=O)c1cnc3c(c1)OCCO3)C2]

1 wherein crystalline Compound 1 (Type A) is not observable by XRPD analysis (Method D) of the tablet core. In some embodiments, wherein the tablet core comprises at least 15 weight %, at least 20 weight %, at least 25 weight % or at least 30 weight % of Compound 1 in amorphous form. In some embodiments, the tablet core comprises about 200 mg of Compound 1 per tablet and has a total weight of no more than about 1200 mg, about 1100 mg, about 1000 mg, about 900 mg, about 800 mg, or about 700 mg per tablet per tablet.

In some embodiments, the tablet dosage form comprises a tablet core, the tablet core having a total weight of no more than about 1000 mg and comprising about 200 mg of Compound 1 in amorphous form per tablet, wherein crystalline Compound 1 (Type A) is not observable by XRPD analysis (Method D) of the tablet core. In some embodiments, the tablet core has a total weight of no more than about 800 mg per tablet.

In some embodiments, the tablet core comprises Compound 1 in highly enantiopure form. In some embodiments, the tablet core comprises 0.05-5.0% of Compound 2:

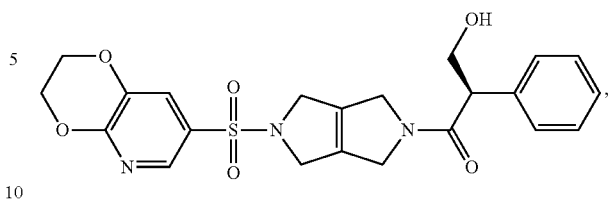

2 based on the total amount of Compound 1 and Compound 2. In some embodiments, the tablet core comprises 0.05-3.0% of Compound 2, based on the total amount of Compound 1 and Compound 2. In some embodiments, the tablet core comprises 0.05-2.0% of Compound 2, based on the total amount of Compound 1 and Compound 2. In some embodiments, the tablet core comprises 0.05-1.0% of Compound 2, based on the total amount of Compound 1 and Compound 2.

In some embodiments, the tablet dosage form is physically stable in that it remains free or substantially free of crystalline Compound 1 over time in accelerated stability studies. In some embodiments, crystalline Compound 1 (Type A) is not observable by XRPD analysis (Method D) of the tablet core after storage in a sealed container as described in Example 29 for 1 month at 25° C. and 60% relative humidity, storage in a sealed container as described in Example 29 for 2 months at 25° C. and 60% relative humidity, storage in a sealed container as described in Example 29 for 3 months at 25° C. and 60% relative humidity, storage in a sealed container as described in Example 29 for 1 month at 40° C. and 75% relative humidity, storage in a sealed container as described in Example 29 for 2 months at 40° C. and 75% relative humidity, storage in a sealed container as described in Example 29 for 3 months at 40° C. and 75% relative humidity.

In some embodiments, Compound 1 is present in an amorphous solid dispersion comprising Compound 1 and a polymer. In some embodiments, the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof. In some embodiments, the polymer is hydroxypropylmethyl cellulose (HPMC) or hydroxypropylmethyl cellulose acetate succinate (HPMC AS). In some embodiments, the polymer is hydroxypropylmethyl cellulose acetate succinate (HPMC AS), including any grade thereof (e.g., HPMC AS MG).

In some embodiments, the weight ratio of Compound 1 to the polymer is in a range of about 3:1 to about 1:3. In some embodiments, the weight ratio of Compound 1 to the polymer is in a range of about 2:1 to about 1:3. In some embodiments, the weight ratio of Compound 1 to the polymer is about 1:3. In some embodiments, the weight ratio of Compound 1 to the polymer is about 1:1. In some embodiments, the weight ratio of Compound 1 to the polymer is about 1:3, about 2:3, about 1:1, about 1.5:1, about 2:1, or about 3:1. In some embodiments, the weight ratio of Compound 1 to the polymer is about 1:3, about 2:3, about 1:1, about 1.5:1, or about 2:1.

In some embodiments, the tablet core of the tablet dosage form further comprises one or more pharmaceutically acceptable excipients. In some embodiments, the one or more pharmaceutically acceptable excipients comprise one or more of a filler, a dry binder, a glidant, a lubricant, a disintegrant, and a film coating agent.

In some embodiments, the tablet core comprises an intra granular portion comprising Compound 1; and an extra granular portion blended with the intra granular portion. In some embodiments, the intragranular portion comprises an amorphous solid dispersion comprising Compound 1 and a polymer and one or more of a filler, a dry binder, a glidant, and a lubricant, and the extragranular portion comprises one or more of a filler, a disintegrant, and a lubricant. In some embodiments, the intragranular portion comprises:
  an amorphous solid dispersion of Compound 1 in an amount of 30-70 weight % of the tablet core;
  one or more fillers in an amount of 15-50 weight % of the tablet core;
  one or more dry binders in an amount of 2.50-10 weight % of the tablet core;
  one or more glidants in an amount of 0.50-1.50 weight % of the tablet core; and
  one or more lubricants in an amount of 0.25-1 weight % of the tablet core; and
the extragranular portion comprises:
  one or more fillers in an amount of 5-15 weight % of the tablet core;
  one or more disintegrants in an amount of 1.25-5 weight % of the tablet core; and
  one or more lubricants in an amount of 0.25-1 weight % of the tablet core.

In some embodiments, the tablet dosage form comprises:
  an amorphous solid dispersion of Compound 1 in an amount of 50-75 weight % of the tablet core;
  one or more fillers in an amount of 15-50 weight % of the tablet core;
  one or more dry binders in an amount of 2-10 weight % of the tablet core;
  one or more glidants in an amount of <2 weight % of the tablet core;
  one or more disintegrants in an amount of 2-10 weight % of the tablet core; and
  one or more lubricants in an amount of <2 weight % of the tablet core.

In some embodiments, the amorphous solid dispersion comprises Compound 1 and a polymer (as described in any of the embodiments set forth herein). In some embodiments, the one or more fillers comprise microcrystalline cellulose or lactose monohydrate. In some embodiments, the one or more dry binders comprise crospovidone or crosslinked polyvinylpyrrolidone. In some embodiments, the one or more glidants comprise colloidal silicon dioxide or fumed silica. In some embodiments, the one or more lubricants comprise magnesium stearate. In some embodiments, the one or more disintegrants comprise crocarmellose sodium.

Medical Uses of the Solid Forms and Pharmaceutical Compositions

In some embodiments, the disclosure relates to a method of treating a disease associated with decreased activity of PKR in a subject in need thereof which comprises administering to the subject an effective amount of a compound of Formula I in any of the forms described herein, including any embodiment thereof.

EMBODIMENTS

In some embodiments, the disclosure relates to one or more of the following enumerated embodiments:
1. A crystalline solid form of Compound 1:

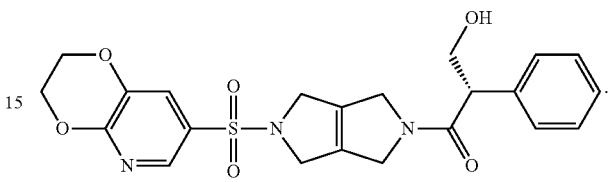

2. The crystalline solid form of embodiment 1, wherein the crystalline solid form is Type A of (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one ("Compound 1").
3. The crystalline solid form of embodiment 1 or 2, wherein Type A of Compound 1 is characterized by an X-ray powder diffraction (XRPD) pattern having diffractions at angles (2 theta±0.2) of 4.61, 15.66, 23.19, and 24.76.
4. The crystalline solid form of any one of embodiments 1-3, wherein Type A of Compound 1 is characterized by an XRPD pattern having diffractions at angles (2 theta±0.2) of 4.61, 15.66, 23.19, and 24.76, corresponding to d-spacing (angstroms±0.2) of 19.19, 5.66, 3.84, and 3.60, respectively.
5. The crystalline solid form of any one of embodiments 1-4, wherein Type A of Compound 1 is characterized by an XRPD pattern having diffractions at angles (2 theta±0.2) of 4.61, 7.22, 15.66, 20.48, 21.35, 21.66, 22.47, 23.19, 24.76, and 26.73.
6. The crystalline solid form of any one of embodiments 1-5, wherein Type A of Compound 1 is characterized by an XRPD pattern having diffractions at angles (2 theta±0.2) of 4.61, 7.22, 15.66, 20.48, 21.35, 21.66, 22.47, 23.19, 24.76, and 26.73, corresponding to d-spacing (angstroms±0.2) of 19.19, 12.25, 5.66, 4.34, 4.16, 4.10, 3.96, 3.84, 3.60, and 3.34, respectively.
7. The crystalline solid form of any one of embodiments 1-6, wherein Type A of Compound 1 is characterized by an XRPD pattern having diffractions at angles (2 theta±0.2) of:
4.61
5.80
7.22
7.68
11.21
12.31
14.44
15.66
16.95
18.02
19.20
20.48
21.35
21.66
22.47
23.19

24.76
26.73
28.01
28.49
29.35
30.25
32.14
34.12
36.46

8. The crystalline solid form of any one of embodiments 1-7, wherein Type A of Compound 1 is characterized by an XRPD pattern having diffractions at angles (2 theta±0.2) corresponding to d-spacing (angstroms±0.2) of:

| 2 theta | d-spacing |
|---|---|
| 4.61 | 19.19 |
| 5.80 | 15.24 |
| 7.22 | 12.25 |
| 7.68 | 11.50 |
| 11.21 | 7.89 |
| 12.31 | 7.19 |
| 14.44 | 6.13 |
| 15.66 | 5.66 |
| 16.95 | 5.23 |
| 18.02 | 4.92 |
| 19.20 | 4.62 |
| 20.48 | 4.34 |
| 21.35 | 4.16 |
| 21.66 | 4.10 |
| 22.47 | 3.96 |
| 23.19 | 3.84 |
| 24.76 | 3.60 |
| 26.73 | 3.34 |
| 28.01 | 3.19 |
| 28.49 | 3.13 |
| 29.35 | 3.04 |
| 30.25 | 2.95 |
| 32.14 | 2.79 |
| 34.12 | 2.63 |
| 36.46 | 2.46 |

9. The crystalline solid form of any one of embodiments 1-8, wherein Type A of Compound 1 is characterized by a thermogravimetric analysis (TGA) thermogram with a weight loss of about 1.9% up to 100° C.
10. The crystalline solid form of any one of embodiments 1-9, wherein Type A of Compound 1 is characterized by a differential scanning calorimetry (DSC) endotherm having a peak temperature of about 85.9° C. and an onset temperature of about 146.0° C.
11. The crystalline solid form of any one of embodiments 1-10, wherein Type A of Compound 1 is characterized by a dynamic vapor sorption (DVS) of about 3.4% water uptake by weight up to 40% relative humidity.
12. The crystalline solid form of any one of embodiments 1-11, wherein Type A of Compound 1 is characterized by a dynamic vapor sorption (DVS) of about 1.0% water uptake by weight from 40% to 80% relative humidity.
13. The crystalline solid form of embodiment 1, wherein the crystalline solid form is Type B of Compound 1.
14. The crystalline solid form of embodiment 1 or 13, wherein Type B of Compound 1 is characterized by an X-ray powder diffraction (XRPD) pattern having diffractions at angles (2 theta±0.2) of 4.52, 15.57, 22.89, 23.34, and 25.13.
15. The crystalline solid form of any one of embodiments 1 and 13-14, wherein Type B of Compound 1 is characterized by an XRPD pattern having diffractions at angles (2 theta±0.2) of 4.52, 15.57, 22.89, 23.34, and 25.13, corresponding to d-spacing (angstroms±0.2) of 19.53, 5.69, 3.89, 3.81, and 3.54, respectively.
16. The crystalline solid form of any one of embodiments 1 and 13-15, wherein Type B of Compound 1 is characterized by an X-ray powder diffraction (XRPD) pattern having diffractions at angles (2 theta±0.2) of 4.52, 9.86, 15.57, 19.93, 22.19, 22.89, 23.34, 25.13, and 28.30.
17. The crystalline solid form of any one of embodiments 1 and 13-16, wherein Type B of Compound 1 is characterized by an XRPD pattern having diffractions at angles (2 theta±0.2) of 4.52, 9.86, 15.57, 19.93, 22.19, 22.89, 23.34, 25.13, and 28.30, corresponding to d-spacing (angstroms±0.2) of 19.53, 8.97, 5.69, 4.45, 4.00, 3.89, 3.81, 3.54, and 3.15, respectively.
18. The crystalline solid form of any one of embodiments 1 and 13-17, wherein Type B of Compound 1 is characterized by an XRPD pattern having diffractions at angles (2 theta±0.2) of:

4.52
8.98
9.86
12.37
13.18
15.57
16.86
18.21
19.11
19.93
20.92
22.19
22.89
23.34
25.13
25.80
26.71
28.30
29.39

19. The crystalline solid form of any one of embodiments 1 and 13-18, wherein Type B of Compound 1 is characterized by an XRPD pattern having diffractions at angles (2 theta±0.2) corresponding to d-spacing (angstroms±0.2) of:

| 2 theta | d-spacing |
|---|---|
| 4.52 | 19.53 |
| 8.98 | 9.85 |
| 9.86 | 8.97 |
| 12.37 | 7.15 |
| 13.18 | 6.72 |
| 15.57 | 5.69 |
| 16.86 | 5.26 |
| 18.21 | 4.87 |
| 19.11 | 4.64 |
| 19.93 | 4.45 |
| 20.92 | 4.25 |
| 22.19 | 4.00 |
| 22.89 | 3.89 |
| 23.34 | 3.81 |
| 25.13 | 3.54 |
| 25.80 | 3.45 |
| 26.71 | 3.34 |
| 28.30 | 3.15 |
| 29.39 | 3.04 |

20. The crystalline solid form of any one of embodiments 1 and 13-19, wherein Type B of Compound 1 is characterized by a thermogravimetric analysis (TGA) thermogram with a weight loss of about 1.8% up to 100° C.

21. The crystalline solid form of any one of embodiments 1 and 13-20, wherein Type B of Compound 1 is characterized by a thermogravimetric analysis (TGA) thermogram with a weight loss of about 2.3% up to 120° C.

22. The crystalline solid form of any one of embodiments 1 and 13-21, wherein Type B of Compound 1 is characterized by a differential scanning calorimetry (DSC) endotherm having an onset temperature of about 138.2-139.2° C.

23. The crystalline solid form of any one of embodiments 1 and 13-22, wherein Type B of Compound 1 is characterized by a dynamic vapor sorption (DVS) of about 2.9% water uptake by weight up to 60% relative humidity.

24. The crystalline solid form of any one of embodiments 1 and 13-23, wherein Type B of Compound 1 is characterized by a dynamic vapor sorption (DVS) of about 0.4% water uptake by weight from 60% to 80% relative humidity.

25. The crystalline solid form of embodiment 1, wherein the crystalline solid form is Type C of Compound 1.

26. The crystalline solid form of embodiment 1 or 25, wherein Type C of Compound 1 is characterized by an X-ray powder diffraction (XRPD) pattern having diffractions at angles (2 theta±0.2) of 4.55, 18.85, 23.02, and 24.65.

27. The crystalline solid form of any one of embodiments 1 and 25-26, wherein Type C of Compound 1 is characterized by an XRPD pattern having diffractions at angles (2 theta±0.2) of 4.55, 18.85, 23.02, and 24.65, corresponding to d-spacing (angstroms±0.2) of 19.43, 4.71, 3.86, and 3.61, respectively.

28. The crystalline solid form of any one of embodiments 1 and 25-27, wherein Type C of Compound 1 is characterized by an X-ray powder diffraction (XRPD) pattern having diffractions at angles (2 theta±0.2) of 4.55, 7.34, 9.07, 11.17, 18.34, 18.85, 19.57, 21.66, 23.02, and 24.65.

29. The crystalline solid form of any one of embodiments 1 and 25-28, wherein Type C of Compound 1 is characterized by an XRPD pattern having diffractions at angles (2 theta±0.2) of 4.55, 7.34, 9.07, 11.17, 18.34, 18.85, 19.57, 21.66, 23.02, and 24.65, corresponding to d-spacing (angstroms±0.2) of 19.43, 12.05, 9.75, 7.92, 4.84, 4.71, 4.54, 4.10, 3.86, and 3.61, respectively.

30. The crystalline solid form of any one of embodiments 1 and 25-29, wherein Type C of Compound 1 is characterized by an XRPD pattern having diffractions at angles (2 theta±0.2) of:
4.55
7.34
9.07
11.17
12.29
14.51
15.66
18.34
18.85
19.57
20.38
21.66
23.02
24.65
26.39
28.28
30.09
32.31
33.91
37.19

31. The crystalline solid form of any one of embodiments 1 and 25-30, wherein Type C of Compound 1 is characterized by an XRPD pattern having diffractions at angles (2 theta±0.2) corresponding to d-spacing (angstroms±0.2) of:

| 2 theta | d-spacing |
|---|---|
| 4.55 | 19.43 |
| 7.34 | 12.05 |
| 9.07 | 9.75 |
| 11.17 | 7.92 |
| 12.29 | 7.20 |
| 14.51 | 6.11 |
| 15.66 | 5.66 |
| 18.34 | 4.84 |
| 18.85 | 4.71 |
| 19.57 | 4.54 |
| 20.38 | 4.36 |
| 21.66 | 4.10 |
| 23.02 | 3.86 |
| 24.65 | 3.61 |
| 26.39 | 3.38 |
| 28.28 | 3.16 |
| 30.09 | 2.97 |
| 32.31 | 2.77 |
| 33.91 | 2.64 |
| 37.19 | 2.42 |

32. The crystalline solid form of any one of embodiments 1 and 25-31, wherein Type C of Compound 1 is characterized by a thermogravimetric analysis (TGA) thermogram with a weight loss of about 1.0% up to 100° C.

33. The crystalline solid form of any one of embodiments 1 and 25-32, wherein Type C of Compound 1 is characterized by a thermogravimetric analysis (TGA) thermogram with a weight loss of about 2.3% up to 130° C.

34. The crystalline solid form of any one of embodiments 1 and 25-33, wherein Type C of Compound 1 is characterized by a differential scanning calorimetry (DSC) endotherm having an onset temperature of about 152.2-154.2° C.

35. The crystalline solid form of any one of embodiments 1 and 25-34, wherein Type C of Compound 1 is characterized by a dynamic vapor sorption (DVS) of about 1.8% water uptake by weight up to 60% relative humidity.

36. The crystalline solid form of any one of embodiments 1 and 25-35, wherein Type C of Compound 1 is characterized by a dynamic vapor sorption (DVS) of about 0.5% water uptake by weight from 60% to 80% relative humidity.

37. The crystalline solid form of embodiment 1, wherein the crystalline solid form is Type D of Compound 1.

38. The crystalline solid form of embodiment 1 or 37, wherein Type D of Compound 1 is characterized by an X-ray powder diffraction (XRPD) pattern having diffractions at angles (2 theta±0.2) of 9.72, 13.08, 15.74, 21.90, and 23.59.

39. The crystalline solid form of any one of embodiments 1 and 37-38, wherein Type D of Compound 1 is characterized by an XRPD pattern having diffractions at angles (2 theta±0.2) of 9.72, 13.08, 15.74, 21.90, and 23.59, corresponding to d-spacing (angstroms±0.2) of 9.10, 6.77, 5.63, 4.06 and 3.77, respectively.
40. The crystalline solid form of any one of embodiments 1 and 37-39, wherein Type D of Compound 1 is characterized by an X-ray powder diffraction (XRPD) pattern having diffractions at angles (2 theta±0.2) of 4.27, 6.15, 8.71, 9.72, 12.31, 13.08, 13.76, 15.74, 18.02, 21.90, 23.59, and 26.71.
41. The crystalline solid form of any one of embodiments 1 and 37-40, wherein Type D of Compound 1 is characterized by an XRPD pattern having diffractions at angles (2 theta±0.2) of 4.27, 6.15, 8.71, 9.72, 12.31, 13.08, 13.76, 15.74, 18.02, 21.90, 23.59, and 26.71, corresponding to d-spacing (angstroms±0.2) of 20.68, 14.36, 10.16, 9.10, 7.19, 6.77, 6.44, 5.63, 4.92, 4.06, 3.77, and 3.34, respectively.
42. The crystalline solid form of any one of embodiments 1 and 37-41, wherein Type D of Compound 1 is characterized by an XRPD pattern having diffractions at angles (2 theta±0.2) of:
4.27
6.15
8.71
9.72
12.31
13.08
13.76
15.74
18.02
19.55
21.90
23.59
24.79
26.71
29.50
30.82
31.74
35.40
37.84
38.61
43. The crystalline solid form of any one of embodiments 1 and 37-42, wherein Type D of Compound 1 is characterized by an XRPD pattern having diffractions at angles (2 theta±0.2) corresponding to d-spacing (angstroms±0.2) of:

| 2 theta | d-spacing |
| --- | --- |
| 4.27 | 20.68 |
| 6.15 | 14.36 |
| 8.71 | 10.16 |
| 9.72 | 9.10 |
| 12.31 | 7.19 |
| 13.08 | 6.77 |
| 13.76 | 6.44 |
| 15.74 | 5.63 |
| 18.02 | 4.92 |
| 19.55 | 4.54 |
| 21.90 | 4.06 |
| 23.59 | 3.77 |
| 24.79 | 3.59 |
| 26.71 | 3.34 |
| 29.50 | 3.03 |
| 30.82 | 2.90 |
| 31.74 | 2.82 |
| 35.40 | 2.54 |
| 37.84 | 2.38 |
| 38.61 | 2.33 |

44. The crystalline solid form of any one of embodiments 1 and 37-43, wherein Type D of Compound 1 is characterized by a thermogravimetric analysis (TGA) thermogram with a weight loss of about 9.6% up to 130° C.
45. The crystalline solid form of any one of embodiments 1 and 37-44, wherein Type D of Compound 1 is characterized by a differential scanning calorimetry (DSC) endotherm having an onset temperature of about 91.9° C.
46. The crystalline solid form of embodiment 1, wherein the crystalline solid form is Type E of Compound 1.
47. The crystalline solid form of embodiment 1 or 46, wherein Type E of Compound 1 is characterized by an X-ray powder diffraction (XRPD) pattern having diffractions at angles (2 theta±0.2) of 15.12, 15.75, 17.48, 20.05, 21.93, and 26.72.
48. The crystalline solid form of any one of embodiments 1 and 46-47, wherein Type E of Compound 1 is characterized by an XRPD pattern having diffractions at angles (2 theta±0.2) of 15.12, 15.75, 17.48, 20.05, 21.93, and 26.72, corresponding to d-spacing (angstroms±0.2) of 5.86, 5.63, 5.07, 4.43, 4.05, and 3.34, respectively.
49. The crystalline solid form of any one of embodiments 1 and 46-48, wherein Type E of Compound 1 is characterized by an X-ray powder diffraction (XRPD) pattern having diffractions at angles (2 theta±0.2) of 4.59, 15.12, 15.75, 17.48, 20.05, 21.93, 23.18, 23.70, and 26.72.
50. The crystalline solid form of any one of embodiments 1 and 46-49, wherein Type E of Compound 1 is characterized by an XRPD pattern having diffractions at angles (2 theta±0.2) of 4.59, 15.12, 15.75, 17.48, 20.05, 21.93, 23.18, 23.70, and 26.72, corresponding to d-spacing (angstroms±0.2) of 19.27, 5.86, 5.63, 5.07, 4.43, 4.05, 3.84, 3.75, and 3.34, respectively.
51. The crystalline solid form of any one of embodiments 1 and 46-50, wherein Type E of Compound 1 is characterized by an X-ray powder diffraction (XRPD) pattern having diffractions at angles (2 theta±0.2) of 4.59, 9.76, 12.36, 13.12, 15.12, 15.75, 16.84, 17.48, 18.06, 19.02, 20.05, 21.93, 23.18, 23.70, 26.72, and 27.81.
52. The crystalline solid form of any one of embodiments 1 and 46-51, wherein Type E of Compound 1 is characterized by an XRPD pattern having diffractions at angles (2 theta±0.2) of 4.59, 9.76, 12.36, 13.12, 15.12, 15.75, 16.84, 17.48, 18.06, 19.02, 20.05, 21.93, 23.18, 23.70, 26.72, and 27.81, corresponding to d-spacing (angstroms±0.2) of 19.27, 9.06, 7.16, 6.75, 5.86, 5.63, 5.27, 5.07, 4.91, 4.67, 4.43, 4.05, 3.84, 3.75, 3.34, and 3.21, respectively.
53. The crystalline solid form of any one of embodiments 1 and 46-52, wherein Type E of Compound 1 is characterized by an XRPD pattern having diffractions at angles (2 theta±0.2) of:
4.59
8.76
9.76
12.36
13.12
13.83
15.12
15.75
16.84
17.48

18.06
19.02
20.05
21.93
23.18
23.70
24.82
26.72
27.81
29.51
30.76
31.74
33.03
34.52
35.39
36.72
37.77
38.66

54. The crystalline solid form of any one of embodiments 1 and 46-53, wherein Type E of Compound 1 is characterized by an XRPD pattern having diffractions at angles (2 theta±0.2) corresponding to d-spacing (angstroms±0.2) of:

| 2 theta | d-spacing |
|---|---|
| 4.59 | 19.27 |
| 8.76 | 10.09 |
| 9.76 | 9.06 |
| 12.36 | 7.16 |
| 13.12 | 6.75 |
| 13.83 | 6.40 |
| 15.12 | 5.86 |
| 15.75 | 5.63 |
| 16.84 | 5.27 |
| 17.48 | 5.07 |
| 18.06 | 4.91 |
| 19.02 | 4.67 |
| 20.05 | 4.43 |
| 21.93 | 4.05 |
| 23.18 | 3.84 |
| 23.70 | 3.75 |
| 24.82 | 3.59 |
| 26.72 | 3.34 |
| 27.81 | 3.21 |
| 29.51 | 3.03 |
| 30.76 | 2.91 |
| 31.74 | 2.82 |
| 33.03 | 2.71 |
| 34.52 | 2.60 |
| 35.39 | 2.54 |
| 36.72 | 2.45 |
| 37.77 | 2.38 |
| 38.66 | 2.33 |

55. The crystalline solid form of embodiment 1, wherein the crystalline solid form is Type F of Compound 1.
56. The crystalline solid form of embodiment 1 or 55, wherein Type F of Compound 1 is characterized by an X-ray powder diffraction (XRPD) pattern having diffractions at angles (2 theta±0.2) of 5.45, 14.66, 16.00, 16.79, 20.01, 21.36, and 22.45.
57. The crystalline solid form of any one of embodiments 1 and 55-56, wherein Type F of Compound 1 is characterized by an XRPD pattern having diffractions at angles (2 theta±0.2) of 5.45, 14.66, 16.00, 16.79, 20.01, 21.36, and 22.45, corresponding to d-spacing (angstroms±0.2) of 16.23, 6.04, 5.54, 5.28, 4.44, 4.16, and 3.96, respectively.
58. The crystalline solid form of any one of embodiments 1 and 55-57, wherein Type F of Compound 1 is characterized by an X-ray powder diffraction (XRPD) pattern having diffractions at angles (2 theta±0.2) of 5.45, 14.66, 16.00, 16.79, 18.99, 20.01, 21.36, 22.45, 23.25, and 25.32.
59. The crystalline solid form of any one of embodiments 1 and 55-58, wherein Type F of Compound 1 is characterized by an XRPD pattern having diffractions at angles (2 theta±0.2) of 5.45, 14.66, 16.00, 16.79, 18.99, 20.01, 21.36, 22.45, 23.25, and 25.32, corresponding to d-spacing (angstroms±0.2) of 16.23, 6.04, 5.54, 5.28, 4.67, 4.44, 4.16, 3.96, 3.83, and 3.52, respectively.
60. The crystalline solid form of any one of embodiments 1 and 55-59, wherein Type F of Compound 1 is characterized by an X-ray powder diffraction (XRPD) pattern having diffractions at angles (2 theta±0.2) of 5.45, 12.87, 14.66, 16.00, 16.79, 17.36, 18.99, 20.01, 20.57, 21.36, 22.45, 23.25, 25.32, 26.57, 27.25, 27.97, and 30.02.
61. The crystalline solid form of any one of embodiments 1 and 55-60, wherein Type F of Compound 1 is characterized by an XRPD pattern having diffractions at angles (2 theta±0.2) of 5.45, 12.87, 14.66, 16.00, 16.79, 17.36, 18.99, 20.01, 20.57, 21.36, 22.45, 23.25, 25.32, 26.57, 27.25, 27.97, and 30.02, corresponding to d-spacing (angstroms±0.2) of 16.23, 6.88, 6.04, 5.54, 5.28, 5.11, 4.67, 4.44, 4.32, 4.16, 3.96, 3.83, 3.52, 3.35, 3.27, 3.19, and 2.98, respectively.
62. The crystalline solid form of any one of embodiments 1 and 55-61, wherein Type F of Compound 1 is characterized by an XRPD pattern having diffractions at angles (2 theta±0.2) of:
5.45
10.92
12.87
14.66
16.00
16.79
17.36
18.99
20.01
20.57
21.36
22.45
23.25
25.32
26.57
27.25
27.97
30.02
31.98
32.89
38.29
39.09

63. The crystalline solid form of any one of embodiments 1 and 55-62, wherein Type F of Compound 1 is characterized by an XRPD pattern having diffractions at angles (2 theta±0.2) corresponding to d-spacing (angstroms±0.2) of:

| 2 theta | d-spacing |
|---|---|
| 5.45 | 16.23 |
| 10.92 | 8.10 |
| 12.87 | 6.88 |
| 14.66 | 6.04 |

-continued

| 2 theta | d-spacing |
|---|---|
| 16.00 | 5.54 |
| 16.79 | 5.28 |
| 17.36 | 5.11 |
| 18.99 | 4.67 |
| 20.01 | 4.44 |
| 20.57 | 4.32 |
| 21.36 | 4.16 |
| 22.45 | 3.96 |
| 23.25 | 3.83 |
| 25.32 | 3.52 |
| 26.57 | 3.35 |
| 27.25 | 3.27 |
| 27.97 | 3.19 |
| 30.02 | 2.98 |
| 31.98 | 2.80 |
| 32.89 | 2.72 |
| 38.29 | 2.35 |
| 39.09 | 2.30 |

64. The crystalline solid form of any one of embodiments 1 and 55-63, wherein Type F of Compound 1 is characterized by a thermogravimetric analysis (TGA) thermogram with a weight loss of about 6.2% up to 120° C.

65. The crystalline solid form of any one of embodiments 1 and 55-64, wherein Type F of Compound 1 is characterized by a differential scanning calorimetry (DSC) endotherm having a peak temperature of about 100.4° C. and an onset temperature of 125.9° C.

66. The crystalline solid form of embodiment 1, wherein the crystalline solid form is Type G of Compound 1.

67. The crystalline solid form of embodiment 1 or 66, wherein Type G of Compound 1 is characterized by an X-ray powder diffraction (XRPD) pattern having diffractions at angles (2 theta±0.2) of 5.36, 14.34, 16.58, and 21.35.

68. The crystalline solid form of any one of embodiments 1 and 66-67, wherein Type G of Compound 1 is characterized by an XRPD pattern having diffractions at angles (2 theta±0.2) of 5.36, 14.34, 16.58, and 21.35, corresponding to d-spacing (angstroms±0.2) of 16.48, 6.18, 5.35, and 4.16, respectively.

69. The crystalline solid form of any one of embodiments 1 and 66-68, wherein Type G of Compound 1 is characterized by an X-ray powder diffraction (XRPD) pattern having diffractions at angles (2 theta±0.2) of 5.36, 12.83, 14.34, 15.00, 16.58, 19.78, 21.35, 22.35, 25.33, and 26.43.

70. The crystalline solid form of any one of embodiments 1 and 66-69, wherein Type G of Compound 1 is characterized by an XRPD pattern having diffractions at angles (2 theta±0.2) of 5.36, 12.83, 14.34, 15.00, 16.58, 19.78, 21.35, 22.35, 25.33, and 26.43, corresponding to d-spacing (angstroms±0.2) of 16.48, 6.90, 6.18, 5.91, 5.35, 4.49, 4.16, 3.98, 3.52, and 3.37, respectively.

71. The crystalline solid form of any one of embodiments 1 and 66-70, wherein Type G of Compound 1 is characterized by an X-ray powder diffraction (XRPD) pattern having diffractions at angles (2 theta±0.2) of 5.36, 12.83, 14.34, 15.00, 15.79, 16.58, 19.78, 21.35, 22.35, 25.33, 26.43, 27.35, and 30.21.

72. The crystalline solid form of any one of embodiments 1 and 66-71, wherein Type G of Compound 1 is characterized by an XRPD pattern having diffractions at angles (2 theta±0.2) of 5.36, 12.83, 14.34, 15.00, 15.79, 16.58, 19.78, 21.35, 22.35, 25.33, 26.43, 27.35, and 30.21, corresponding to d-spacing (angstroms±0.2) of 16.48, 6.90, 6.18, 5.91, 5.61, 5.35, 4.49, 4.16, 3.98, 3.52, 3.37, 3.26, and 2.96, respectively.

73. The crystalline solid form of any one of embodiments 1 and 66-72, wherein Type G of Compound 1 is characterized by an XRPD pattern having diffractions at angles (2 theta±0.2) of:
5.36
8.73
12.83
14.34
15.00
15.79
16.58
18.54
19.78
21.35
22.35
23.38
25.33
26.43
27.35
30.21
32.32
38.04

74. The crystalline solid form of any one of embodiments 1 and 66-73, wherein Type G of Compound 1 is characterized by an XRPD pattern having diffractions at angles (2 theta±0.2) corresponding to d-spacing (angstroms±0.2) of:

| 2 theta | d-spacing |
|---|---|
| 5.36 | 16.48 |
| 8.73 | 10.13 |
| 12.83 | 6.90 |
| 14.34 | 6.18 |
| 15.00 | 5.91 |
| 15.79 | 5.61 |
| 16.58 | 5.35 |
| 18.54 | 4.79 |
| 19.78 | 4.49 |
| 21.35 | 4.16 |
| 22.35 | 3.98 |
| 23.38 | 3.80 |
| 25.33 | 3.52 |
| 26.43 | 3.37 |
| 27.35 | 3.26 |
| 30.21 | 2.96 |
| 32.32 | 2.77 |
| 38.04 | 2.37 |

75. A pharmaceutical composition comprising a therapeutically effective amount of the crystalline solid form of any one of embodiments 1-74, and one or more pharmaceutically acceptable excipients.

76. The pharmaceutical composition of embodiment 75, wherein the pharmaceutical composition is for oral administration.

77. The pharmaceutical composition of embodiment 75 or 76, wherein the pharmaceutical composition has a water content of about 0.5-5.0 weight %.

78. The pharmaceutical composition of any one of embodiments 75-77, wherein the pharmaceutical composition has a water content of about 1.5-4.0 weight %.

79. The pharmaceutical composition of any one of embodiments 75-78, wherein the pharmaceutical composition has a water content of about 2.5-3.0 weight %.

80. An amorphous solid dispersion comprising Compound 1:

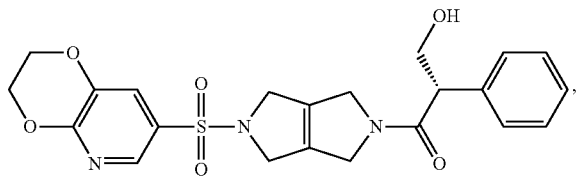 [SMILES: O=C([C@H](CO)c1ccccc1)N1CC2=C(C1)CN(S(=O)(=O)c1cnc3c(c1)OCCO3)C2]

and a polymer.
81. The amorphous solid dispersion of embodiment 80, wherein the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.
82. The amorphous solid dispersion of embodiment 80 or 81, wherein the polymer is hydroxypropylmethyl cellulose (HPMC) or hydroxypropylmethyl cellulose acetate succinate (HPMC AS).
83. The amorphous solid dispersion of any one of embodiments 80-82, wherein the weight ratio of Compound 1 to the polymer is in a range of about 3:1 to about 1:3.
84. The amorphous solid dispersion of any one of embodiments 80-83, wherein the weight ratio of Compound 1 to the polymer is about 1:3.
85. A pharmaceutical composition comprising a therapeutically effective amount of the amorphous solid dispersion of any one of embodiments 80-84, and one or more pharmaceutically acceptable excipients.
86. The pharmaceutical composition of embodiment 85, wherein the pharmaceutical composition is for oral administration.
87. The pharmaceutical composition of embodiment 85 or 86, wherein the pharmaceutical composition is in a tablet dosage form.
88. The pharmaceutical composition of any one of embodiments 85-87, wherein the pharmaceutical composition has a water content of about 0.5-5.0 weight %.
89. The pharmaceutical composition of any one of embodiments 85-88, wherein the pharmaceutical composition has a water content of about 1.5-4.0 weight %.
90. The pharmaceutical composition of any one of embodiments 85-89, wherein the pharmaceutical composition has a water content of about 2.5-3.0 weight %.
91. The pharmaceutical composition of any one of embodiments 85-90, wherein the pharmaceutical composition comprises about 10 mg, about 25 mg, about 50 mg, about 100 mg, about 200 mg, or about 300 mg of Compound 1.
92. The pharmaceutical composition of any one of embodiments 85-91, wherein the pharmaceutical composition comprises about 25 mg of Compound 1.
93. The pharmaceutical composition of any one of embodiments 85-91, wherein the pharmaceutical composition comprises about 100 mg of Compound 1.
94. The pharmaceutical composition of any one of embodiments 85-93, wherein the one or more pharmaceutically acceptable excipients comprise one or more of a filler, a dry binder, a glidant, a lubricant, a disintegrant, and a film coating agent.
95. The pharmaceutical composition of any one of embodiments 85-94, wherein the one or more pharmaceutically acceptable excipients comprise a filler, and the filler comprises microcrystalline cellulose.
96. The pharmaceutical composition of any one of embodiments 85-95, wherein the one or more pharmaceutically acceptable excipients comprise a dry binder, and the dry binder comprises crospovidone.
97. The pharmaceutical composition of any one of embodiments 85-96, wherein the one or more pharmaceutically acceptable excipients comprise a glidant, and the glidant comprises colloidal silicon dioxide.
98. The pharmaceutical composition of any one of embodiments 85-97, wherein the one or more pharmaceutically acceptable excipients comprise a lubricant, and the lubricant comprises magnesium stearate.
99. The pharmaceutical composition of any one of embodiments 85-98, wherein the one or more pharmaceutically acceptable excipients comprise a disintegrant, and the disintegrant comprises croscarmellose sodium.
100. The pharmaceutical composition of any one of embodiments 85-99, wherein the one or more pharmaceutically acceptable excipients comprise a lubricant, and the lubricant comprises magnesium stearate.
101. The pharmaceutical composition of any one of embodiments 85-100, comprising a tablet core, the tablet core comprising:
an intra granular portion comprising the amorphous solid dispersion; and
an extra granular portion blended with the intra granular portion.
102. The pharmaceutical composition of embodiment 101, further comprising a coating disposed on the tablet core.
103. The pharmaceutical composition of embodiment 101 or 102, wherein the amorphous solid dispersion is about 50 weight % of the tablet core.
104. The pharmaceutical composition of any one of embodiments 101-103, wherein the intra granular portion further comprises one or more of a filler, a dry binder, a glidant, and a lubricant.
105. The pharmaceutical composition of any one of embodiments 101-104, wherein the extra granular portion further comprises one or more of a filler, a disintegrant, and a lubricant.
106. A method for preparing an amorphous solid dispersion comprising Compound 1:

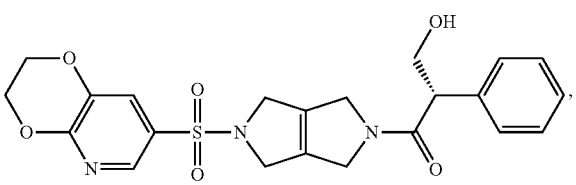 [SMILES: O=C([C@H](CO)c1ccccc1)N1CC2=C(C1)CN(S(=O)(=O)c1cnc3c(c1)OCCO3)C2]

comprising:
mixing Compound 1, a polymer, and a solvent to afford a mixture; and
spray-drying the mixture to afford an amorphous solid dispersion comprising Compound 1.
107. The method of embodiment 106, wherein the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.

108. The method of embodiment 106 or 107, wherein the polymer is hydroxypropylmethyl cellulose (HPMC) or hydroxypropylmethyl cellulose acetate succinate (HPMC AS).

109. The method of any one of embodiments 106-108, wherein the weight ratio of Compound 1 to the polymer is in a range of about 3:1 to about 1:3.

110. The method of any one of embodiments 106-109, wherein the weight ratio of Compound 1 to the polymer is about 1:3.

111. The method of any one of embodiments 106-110, wherein the solvent is dichloromethane and methanol.

112. A product prepared by a process comprising:
mixing Compound 1, a polymer, and a solvent to afford a mixture; and
spray-drying the mixture to afford an amorphous solid dispersion comprising Compound 1:

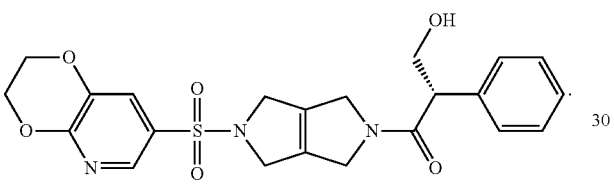

113. The product of embodiment 112, wherein the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.

114. The product of embodiment 112 or 113, wherein the polymer is hydroxypropylmethyl cellulose (HPMC) or hydroxypropylmethyl cellulose acetate succinate (HPMC AS).

115. The product of any one of embodiments 112-114, wherein the weight ratio of Compound 1 to the polymer is in a range of about 3:1 to about 1:3.

116. The product of any one of embodiments 112-115, wherein the weight ratio of Compound 1 to the polymer is about 1:3.

117. The product of any one of embodiments 112-116, wherein the solvent is dichloromethane and methanol.

118. A pharmaceutical composition comprising Compound 1:

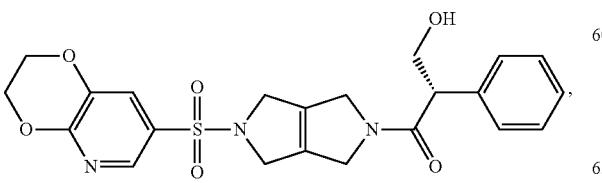

obtained by a process comprising:
mixing Compound 1 in a solid form, a polymer, and a solvent to afford a mixture; and
spray-drying the mixture to afford an amorphous solid dispersion comprising Compound 1.

119. The pharmaceutical composition of embodiment 118, wherein the solid form is Type A of Compound 1.

120. The pharmaceutical composition of embodiment 118, wherein the solid form is Type B of Compound 1.

121. The pharmaceutical composition of embodiment 118, wherein the solid form is Type C of Compound 1.

122. The pharmaceutical composition of embodiment 118, wherein the solid form is Type D of Compound 1.

123. The pharmaceutical composition of embodiment 118, wherein the solid form is Type E of Compound 1.

124. The pharmaceutical composition of embodiment 118, wherein the solid form is Type F of Compound 1.

125. The pharmaceutical composition of embodiment 118, wherein the solid form is Type G of Compound 1.

126. The pharmaceutical composition of embodiment 118, wherein the solid form is amorphous form of Compound 1.

127. The pharmaceutical composition of any one of embodiments 118-126, wherein the pharmaceutical composition has a water content of about 0.5-5.0 weight %.

128. The pharmaceutical composition of any one of embodiments 118-127, wherein the pharmaceutical composition has a water content of about 1.5-4.0 weight %.

129. The pharmaceutical composition of any one of embodiments 118-128, wherein the pharmaceutical composition has a water content of about 2.5-3.0 weight %.

130. The pharmaceutical composition of any one of embodiments 118-129, wherein the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.

131. The pharmaceutical composition of any one of embodiments 118-130, wherein the polymer is hydroxypropylmethyl cellulose (HPMC) or hydroxypropylmethyl cellulose acetate succinate (HPMC AS).

132. The pharmaceutical composition of any one of embodiments 118-131, wherein the weight ratio of Compound 1 to the polymer is in a range of about 3:1 to about 1:3.

133. The pharmaceutical composition of any one of embodiments 118-132, wherein the weight ratio of Compound 1 to the polymer is about 1:3.

134. The pharmaceutical composition of any one of embodiments 118-133, wherein the solvent is dichloromethane and methanol.

In some embodiments, the disclosure relates to one or more of the following enumerated embodiments:
1. A crystalline solid form of Compound 1:

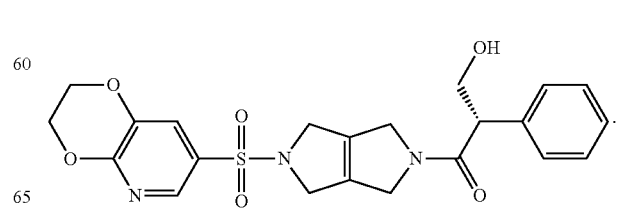

2. The crystalline solid form of embodiment 1, wherein the crystalline solid form is Type A of (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one ("Compound 1").

3. The crystalline solid form of embodiment 2, wherein Type A of Compound 1 is characterized by an X-ray powder diffraction (XRPD) pattern having diffractions at angles (2 theta±0.2) of 4.6, 15.7, 23.2, and 24.8.

4. The crystalline solid form of embodiment 2 or 3, wherein Type A of Compound 1 is characterized by an XRPD pattern having diffractions at angles (2 theta±0.2) of 4.6, 15.7, 23.2, and 24.8, corresponding to d-spacing (angstroms±0.2) of 19.2, 5.7, 3.8, and 3.6, respectively.

5. The crystalline solid form of any one of embodiments 2-4, wherein Type A of Compound 1 is characterized by an X-ray powder diffraction (XRPD) pattern having diffractions at angles (2 theta±0.2) of 4.6, 7.2, 15.7, 21.3, 23.2, and 24.8.

6. The crystalline solid form of any one of embodiments 2-5, wherein Type A of Compound 1 is characterized by an XRPD pattern having diffractions at angles (2 theta±0.2) of 4.6, 7.2, 15.7, 21.3, 23.2, and 24.8, corresponding to d-spacing (angstroms±0.2) of 19.2, 12.3, 5.7, 4.2, 3.8, and 3.6, respectively.

7. The crystalline solid form of any one of embodiment 2-6, wherein Type A of Compound 1 is characterized by an XRPD pattern having diffractions at angles (2 theta±0.2) of 4.6, 7.2, 15.7, 20.5, 21.3, 21.7, 22.5, 23.2, 24.8, and 26.7.

8. The crystalline solid form of any one of embodiment 2-7, wherein Type A of Compound 1 is characterized by an XRPD pattern having diffractions at angles (2 theta±0.2) of 4.6, 7.2, 15.7, 20.5, 21.3, 21.7, 22.5, 23.2, 24.8, and 26.7, corresponding to d-spacing (angstroms±0.2) of 19.2, 12.2, 5.7, 4.3, 4.2, 4.1, 4.0, 3.8, 3.6, and 3.3, respectively.

9. The crystalline solid form of any one of embodiments 2-8, wherein Type A of Compound 1 is characterized by an XRPD pattern having diffractions at angles (2 theta±0.2) of:
4.6
5.8
7.2
7.7
11.2
12.3
14.4
15.7
16.9
18.0
19.2
20.5
21.3
21.7
22.5
23.2
24.8
26.7
28.0
28.5
29.4
30.3
32.1
34.1
36.5.

10. The crystalline solid form of any one of embodiments 2-9, wherein Type A of Compound 1 is characterized by an XRPD pattern having diffractions at angles (2 theta±0.2) corresponding to d-spacing (angstroms±0.2) of:

| 2 theta | d-spacing |
|---------|-----------|
| 4.6 | 19.2 |
| 5.8 | 15.2 |
| 7.2 | 12.2 |
| 7.7 | 11.5 |
| 11.2 | 7.9 |
| 12.3 | 7.2 |
| 14.4 | 6.1 |
| 15.7 | 5.7 |
| 16.9 | 5.2 |
| 18.0 | 4.9 |
| 19.2 | 4.6 |
| 20.5 | 4.3 |
| 21.3 | 4.2 |
| 21.7 | 4.1 |
| 22.5 | 4.0 |
| 23.2 | 3.8 |
| 24.8 | 3.6 |
| 26.7 | 3.3 |
| 28.0 | 3.2 |
| 28.5 | 3.1 |
| 29.4 | 3.0 |
| 30.3 | 3.0 |
| 32.1 | 2.8 |
| 34.1 | 2.6 |
| 36.5 | 2.5. |

11. The crystalline solid form of any one of embodiments 2-10, wherein Type A of Compound 1 is characterized by a thermogravimetric analysis (TGA) thermogram with a weight loss of about 1.9% up to 100° C.

12. The crystalline solid form of any one of embodiments 2-11, wherein Type A of Compound 1 is characterized by a differential scanning calorimetry (DSC) endotherm having a peak temperature of about 85.9° C. and an onset temperature of about 146.0° C.

13. The crystalline solid form of any one of embodiments 2-12, wherein Type A of Compound 1 is characterized by a dynamic vapor sorption (DVS) of about 3.4% water uptake by weight up to 40% relative humidity.

14. The crystalline solid form of any one of embodiments 2-13, wherein Type A of Compound 1 is characterized by a dynamic vapor sorption (DVS) of about 1.0% water uptake by weight from 40% to 80% relative humidity.

15. The crystalline solid form of embodiment 1, wherein the crystalline solid form is Type B of Compound 1.

16. The crystalline solid form of embodiment 15, wherein Type B of Compound 1 is characterized by an X-ray powder diffraction (XRPD) pattern having diffractions at angles (2 theta±0.2) of 4.5, 15.6, 22.9, 23.3, and 25.1.

17. The crystalline solid form of embodiment 15 or 16, wherein Type B of Compound 1 is characterized by an XRPD pattern having diffractions at angles (2 theta±0.2) of 4.5, 15.6, 22.9, 23.3, and 25.1, corresponding to d-spacing (angstroms±0.2) of 19.5, 5.7, 3.9, 3.8, and 3.5, respectively.

18. The crystalline solid form of any one of embodiments 15-17, wherein Type B of Compound 1 is characterized by an X-ray powder diffraction (XRPD) pattern having diffractions at angles (2 theta±0.2) of 4.5, 15.6, 22.2, 22.9, 23.3, and 25.1.

19. The crystalline solid form of any one of embodiments 15-18, wherein Type B of Compound 1 is characterized by an XRPD pattern having diffractions at angles (2 theta±0.2) of 4.5, 15.6, 22.2, 22.9, 23.3, and 25.1, corresponding to d-spacing (angstroms±0.2) of 19.5, 5.7, 4.0, 3.9, 3.8, and 3.5, respectively.

20. The crystalline solid form of any one of embodiments 15-19, wherein Type B of Compound 1 is characterized by an X-ray powder diffraction (XRPD) pattern having diffractions at angles (2 theta±0.2) of 4.5, 9.9, 15.6, 19.9, 22.2, 22.9, 23.3, 25.1, and 28.3.

21. The crystalline solid form of any one of embodiments 15-20, wherein Type B of Compound 1 is characterized by an XRPD pattern having diffractions at angles (2 theta±0.2) of 4.5, 9.9, 15.6, 19.9, 22.2, 22.9, 23.3, 25.1, and 28.3, corresponding to d-spacing (angstroms±0.2) of 19.5, 9.0, 5.7, 4.5, 4.0, 3.9, 3.8, 3.5, and 3.2, respectively.

22. The crystalline solid form of any one of embodiments 15-21, wherein Type B of Compound 1 is characterized by an XRPD pattern having diffractions at angles (2 theta±0.2) of:
4.5
9.0
9.9
12.4
13.2
15.6
16.9
18.2
19.1
19.9
20.9
22.2
22.9
23.3
25.1
25.8
26.7
28.3
29.4.

23. The crystalline solid form of any one of embodiments 15-22, wherein Type B of Compound 1 is characterized by an XRPD pattern having diffractions at angles (2 theta±0.2) corresponding to d-spacing (angstroms±0.2) of:

| 2 theta | d-spacing |
|---|---|
| 4.5 | 19.5 |
| 9.0 | 9.9 |
| 9.9 | 9.0 |
| 12.4 | 7.2 |
| 13.2 | 6.7 |
| 15.6 | 5.7 |
| 16.9 | 5.3 |
| 18.2 | 4.9 |
| 19.1 | 4.6 |
| 19.9 | 4.5 |
| 20.9 | 4.2 |
| 22.2 | 4.0 |
| 22.9 | 3.9 |
| 23.3 | 3.8 |
| 25.1 | 3.5 |
| 25.8 | 3.5 |
| 26.7 | 3.3 |
| 28.3 | 3.2 |
| 29.4 | 3.0. |

24. The crystalline solid form of any one of embodiments 15-23, wherein Type B of Compound 1 is characterized by a thermogravimetric analysis (TGA) thermogram with a weight loss of about 1.8% up to 100° C.

25. The crystalline solid form of any one of embodiments 15-24, wherein Type B of Compound 1 is characterized by a thermogravimetric analysis (TGA) thermogram with a weight loss of about 2.3% up to 120° C.

26. The crystalline solid form of any one of embodiments 15-25, wherein Type B of Compound 1 is characterized by a differential scanning calorimetry (DSC) endotherm having an onset temperature of about 138.2-139.2° C.

27. The crystalline solid form of any one of embodiments 15-26, wherein Type B of Compound 1 is characterized by a dynamic vapor sorption (DVS) of about 2.9% water uptake by weight up to 60% relative humidity.

28. The crystalline solid form of any one of embodiments 15-27, wherein Type B of Compound 1 is characterized by a dynamic vapor sorption (DVS) of about 0.4% water uptake by weight from 60% to 80% relative humidity.

29. The crystalline solid form of embodiment 1, wherein the crystalline solid form is Type C of Compound 1.

30. The crystalline solid form of embodiment 29, wherein Type C of Compound 1 is characterized by an X-ray powder diffraction (XRPD) pattern having diffractions at angles (2 theta±0.2) of 4.5, 18.9, 23.0, and 24.7.

31. The crystalline solid form of embodiment 29 or 30, wherein Type C of Compound 1 is characterized by an XRPD pattern having diffractions at angles (2 theta±0.2) of 4.5, 18.9, 23.0, and 24.7, corresponding to d-spacing (angstroms±0.2) of 19.4, 4.7, 3.9, and 3.6, respectively.

32. The crystalline solid form of any one of embodiments 29-31, wherein Type C of Compound 1 is characterized by an X-ray powder diffraction (XRPD) pattern having diffractions at angles (2 theta±0.2) of 4.5, 7.3, 11.2, 18.9, 23.0, and 24.7.

33. The crystalline solid form of any one of embodiments 29-32, wherein Type C of Compound 1 is characterized by an XRPD pattern having diffractions at angles (2 theta±0.2) of 4.5, 7.3, 11.2, 18.9, 23.0, and 24.7, corresponding to d-spacing (angstroms±0.2) of 19.4, 12.0, 7.9, 4.7, 3.9, and 3.6, respectively.

34. The crystalline solid form of any one of embodiments 29-33, wherein Type C of Compound 1 is characterized by an X-ray powder diffraction (XRPD) pattern having diffractions at angles (2 theta±0.2) of 4.5, 7.3, 9.1, 11.2, 18.3, 18.9, 19.6, 21.7, 23.0, and 24.7.

35. The crystalline solid form of any one of embodiments 9-34, wherein Type C of Compound 1 is characterized by an XRPD pattern having diffractions at angles (2 theta±0.2) of 4.5, 7.3, 9.1, 11.2, 18.3, 18.9, 19.6, 21.7, 23.0, and 24.7, corresponding to d-spacing (angstroms±0.2) of 19.4, 12.0, 9.8, 7.9, 4.8, 4.7, 4.5, 4.1, 3.9, and 3.6, respectively.

36. The crystalline solid form of any one of embodiments 29-35, wherein Type C of Compound 1 is characterized by an XRPD pattern having diffractions at angles (2 theta±0.2) of:
4.5
7.3
9.1
11.2
12.3
14.5
15.7
18.3

18.9
19.6
20.4
21.7
23.0
24.7
26.4
28.3
30.1
32.3
33.9
37.2.

37. The crystalline solid form of any one of embodiments 29-36, wherein Type C of Compound 1 is characterized by an XRPD pattern having diffractions at angles (2 theta±0.2) corresponding to d-spacing (angstroms±0.2) of:

| 2 theta | d-spacing |
|---------|-----------|
| 4.5 | 19.4 |
| 7.3 | 12.0 |
| 9.1 | 9.8 |
| 11.2 | 7.9 |
| 12.3 | 7.2 |
| 14.5 | 6.1 |
| 15.7 | 5.7 |
| 18.3 | 4.8 |
| 18.9 | 4.7 |
| 19.6 | 4.5 |
| 20.4 | 4.4 |
| 21.7 | 4.1 |
| 23.0 | 3.9 |
| 24.7 | 3.6 |
| 26.4 | 3.4 |
| 28.3 | 3.2 |
| 30.1 | 3.0 |
| 32.3 | 2.8 |
| 33.9 | 2.6 |
| 37.2 | 2.4. |

38. The crystalline solid form of any one of embodiments 29-37, wherein Type C of Compound 1 is characterized by a thermogravimetric analysis (TGA) thermogram with a weight loss of about 1.0% up to 100° C.
39. The crystalline solid form of any one of embodiments 29-38, wherein Type C of Compound 1 is characterized by a thermogravimetric analysis (TGA) thermogram with a weight loss of about 2.3% up to 130° C.
40. The crystalline solid form of any one of embodiments 29-39, wherein Type C of Compound 1 is characterized by a differential scanning calorimetry (DSC) endotherm having an onset temperature of about 152.2-154.2° C.
41. The crystalline solid form of any one of embodiments 29-40, wherein Type C of Compound 1 is characterized by a dynamic vapor sorption (DVS) of about 1.8% water uptake by weight up to 60% relative humidity.
42. The crystalline solid form of any one of embodiments 29-41, wherein Type C of Compound 1 is characterized by a dynamic vapor sorption (DVS) of about 0.5% water uptake by weight from 60% to 80% relative humidity.
43. The crystalline solid form of embodiment 1, wherein the crystalline solid form is Type D of Compound 1.
44. The crystalline solid form of embodiment 43, wherein Type D of Compound 1 is characterized by an X-ray powder diffraction (XRPD) pattern having diffractions at angles (2 theta±0.2) of 9.7, 13.1, 15.7, 21.9, and 23.6.
45. The crystalline solid form of embodiment 43 or 44, wherein Type D of Compound 1 is characterized by an XRPD pattern having diffractions at angles (2 theta±0.2) of 9.7, 13.1, 15.7, 21.9, and 23.6, corresponding to d-spacing (angstroms±0.2) of 9.1, 6.8, 5.6, 4.1 and 3.8, respectively.
46. The crystalline solid form of any one of embodiments 43-45, wherein Type D of Compound 1 is characterized by an X-ray powder diffraction (XRPD) pattern having diffractions at angles (2 theta±0.2) of 6.2, 9.7, 13.1, 15.7, 21.9, and 23.6 and not having a diffraction at an angle (2 theta±0.2) of 23.3.
47. The crystalline solid form of any one of embodiments 43-46, wherein Type D of Compound 1 is characterized by an XRPD pattern having diffractions at angles (2 theta±0.2) of 6.2, 9.7, 13.1, 15.7, 21.9, and 23.6, corresponding to d-spacing (angstroms±0.2) of 14.4, 9.1, 6.8, 5.6, 4.1 and 3.8, respectively, and not having a diffraction at an angle (2 theta±0.2) of 23.3.
48. The crystalline solid form of any one of embodiments 43-47, wherein Type D of Compound 1 is characterized by an X-ray powder diffraction (XRPD) pattern having diffractions at angles (2 theta±0.2) of 4.3, 6.2, 8.7, 9.7, 12.3, 13.1, 13.8, 15.7, 18.0, 21.9, 23.6, and 26.7.
49. The crystalline solid form of any one of embodiments 43-48, wherein Type D of Compound 1 is characterized by an XRPD pattern having diffractions at angles (2 theta±0.2) of 4.3, 6.2, 8.7, 9.7, 12.3, 13.1, 13.8, 15.7, 18.0, 21.9, 23.6, and 26.7, corresponding to d-spacing (angstroms±0.2) of 20.7, 14.4, 10.2, 9.1, 7.2, 6.8, 6.4, 5.6, 4.9, 4.1, 3.8, and 3.3, respectively.
50. The crystalline solid form of any one of embodiments 43-49, wherein Type D of Compound 1 is characterized by an XRPD pattern having diffractions at angles (2 theta±0.2) of:
4.3
6.2
8.7
9.7
12.3
13.1
13.8
15.7
18.0
19.5
21.9
23.6
24.8
26.7
29.5
30.8
31.7
35.4
37.8
38.6.
51. The crystalline solid form of any one of embodiments 43-50, wherein Type D of Compound 1 is characterized by an XRPD pattern having diffractions at angles (2 theta±0.2) corresponding to d-spacing (angstroms±0.2) of:

| 2 theta | d-spacing |
|---------|-----------|
| 4.3 | 20.7 |
| 6.2 | 14.4 |
| 8.7 | 10.2 |

| 2 theta | d-spacing |
| --- | --- |
| 9.7 | 9.1 |
| 12.3 | 7.2 |
| 13.1 | 6.8 |
| 13.8 | 6.4 |
| 15.7 | 5.6 |
| 18.0 | 4.9 |
| 19.5 | 4.5 |
| 21.9 | 4.1 |
| 23.6 | 3.8 |
| 24.8 | 3.6 |
| 26.7 | 3.3 |
| 29.5 | 3.0 |
| 30.8 | 2.9 |
| 31.7 | 2.8 |
| 35.4 | 2.5 |
| 37.8 | 2.4 |
| 38.6 | 2.3. |

52. The crystalline solid form of any one of embodiments 43-51, wherein Type D of Compound 1 is characterized by a thermogravimetric analysis (TGA) thermogram with a weight loss of about 9.6% up to 130° C.

53. The crystalline solid form of any one of embodiments 43-52, wherein Type D of Compound 1 is characterized by a differential scanning calorimetry (DSC) endotherm having an onset temperature of about 91.9° C.

54. The crystalline solid form of embodiment 1, wherein the crystalline solid form is Type E of Compound 1.

55. The crystalline solid form of embodiment 54, wherein Type E of Compound 1 is characterized by an X-ray powder diffraction (XRPD) pattern having diffractions at angles (2 theta±0.2) of 15.1, 15.8, 17.5, 20.1, 21.9, and 26.7.

56. The crystalline solid form of embodiment 54 or 55, wherein Type E of Compound 1 is characterized by an XRPD pattern having diffractions at angles (2 theta±0.2) of 15.1, 15.8, 17.5, 20.1, 21.9, and 26.7, corresponding to d-spacing (angstroms±0.2) of 5.9, 5.6, 5.1, 4.4, 4.1, and 3.3, respectively.

57. The crystalline solid form of any one of embodiments 54-56, wherein Type E of Compound 1 is characterized by an X-ray powder diffraction (XRPD) pattern having diffractions at angles (2 theta±0.2) of 15.1, 15.8, 17.5, 20.1, 21.9, and 26.7.

58. The crystalline solid form of any one of embodiments 54-57, wherein Type E of Compound 1 is characterized by an XRPD pattern having diffractions at angles (2 theta±0.2) of 15.1, 15.8, 17.5, 19.0, 20.1, 21.9, and 26.7, corresponding to d-spacing (angstroms±0.2) of 5.9, 5.6, 5.1, 4.7, 4.4, 4.1, and 3.3, respectively.

59. The crystalline solid form of any one of embodiments 54-56, wherein Type E of Compound 1 is characterized by an X-ray powder diffraction (XRPD) pattern having diffractions at angles (2 theta±0.2) of 4.6, 15.1, 15.8, 17.5, 20.1, 21.9, 23.2, 23.7, and 26.7.

60. The crystalline solid form of any one of embodiments 54-56, wherein Type E of Compound 1 is characterized by an XRPD pattern having diffractions at angles (2 theta±0.2) of 4.6, 15.1, 15.8, 17.5, 20.1, 21.9, 23.2, 23.7, and 26.7, corresponding to d-spacing (angstroms±0.2) of 19.3, 5.9, 5.6, 5.1, 4.4, 4.1, 3.8, 3.8, and 3.3, respectively.

61. The crystalline solid form of any one of embodiments 54-60, wherein Type E of Compound 1 is characterized by an X-ray powder diffraction (XRPD) pattern having diffractions at angles (2 theta±0.2) of 4.6, 9.8, 12.4, 13.1, 15.1, 15.8, 16.8, 17.5, 18.1, 19.0, 20.1, 21.9, 23.2, 23.7, 26.7, and 27.8.

62. The crystalline solid form of any one of embodiments 54-61, wherein Type E of Compound 1 is characterized by an XRPD pattern having diffractions at angles (2 theta±0.2) of 4.6, 9.8, 12.4, 13.1, 15.1, 15.8, 16.8, 17.5, 18.1, 19.0, 20.1, 21.9, 23.2, 23.7, 26.7, and 27.8, corresponding to d-spacing (angstroms±0.2) of 19.3, 9.1, 7.2, 6.7, 5.9, 5.6, 5.3, 5.1, 4.9, 4.7, 4.4, 4.1, 3.8, 3.8, 3.3, and 3.2, respectively.

63. The crystalline solid form of any one of embodiments 54-62, wherein Type E of Compound 1 is characterized by an XRPD pattern having diffractions at angles (2 theta±0.2) of:
4.6
8.8
9.8
12.4
13.1
13.8
15.1
15.8
16.8
17.5
18.1
19.0
20.1
21.9
23.2
23.7
24.8
26.7
27.8
29.5
30.8
31.7
33.0
34.5
35.4
36.7
37.8
38.7.

64. The crystalline solid form of any one of embodiments 54-63, wherein Type E of Compound 1 is characterized by an XRPD pattern having diffractions at angles (2 theta±0.2) corresponding to d-spacing (angstroms±0.2) of:

| 2 theta | d-spacing |
| --- | --- |
| 4.6 | 19.3 |
| 8.8 | 10.1 |
| 9.8 | 9.1 |
| 12.4 | 7.2 |
| 13.1 | 6.7 |
| 13.8 | 6.4 |
| 15.1 | 5.9 |
| 15.8 | 5.6 |
| 16.8 | 5.3 |
| 17.5 | 5.1 |
| 18.1 | 4.9 |
| 19.0 | 4.7 |
| 20.1 | 4.4 |
| 21.9 | 4.1 |
| 23.2 | 3.8 |
| 23.7 | 3.8 |
| 24.8 | 3.6 |
| 26.7 | 3.3 |

-continued

| 2 theta | d-spacing |
|---|---|
| 27.8 | 3.2 |
| 29.5 | 3.0 |
| 30.8 | 2.9 |
| 31.7 | 2.8 |
| 33.0 | 2.7 |
| 34.5 | 2.6 |
| 35.4 | 2.5 |
| 36.7 | 2.4 |
| 37.8 | 2.4 |
| 38.7 | 2.3. |

65. The crystalline solid form of embodiment 1, wherein the crystalline solid form is Type F of Compound 1.
66. The crystalline solid form of embodiment 65, wherein Type F of Compound 1 is characterized by an X-ray powder diffraction (XRPD) pattern having diffractions at angles (2 theta±0.2) of 5.4, 14.7, 16.0, 16.8, and 21.4.
67. The crystalline solid form of embodiment 65 or 66, wherein Type F of Compound 1 is characterized by an XRPD pattern having diffractions at angles (2 theta±0.2) of 5.4, 14.7, 16.0, 16.8, and 21.4, corresponding to d-spacing (angstroms±0.2) of 16.2, 6.0, 5.5, 5.3, and 4.2, respectively.
68. The crystalline solid form of any one of embodiments 65-67, wherein Type F of Compound 1 is characterized by an X-ray powder diffraction (XRPD) pattern having diffractions at angles (2 theta±0.2) of 5.4, 14.7, 16.0, 16.8, 20.0, 21.4, and 22.5.
69. The crystalline solid form of any one of embodiments 65-68, wherein Type F of Compound 1 is characterized by an XRPD pattern having diffractions at angles (2 theta±0.2) of 5.4, 14.7, 16.0, 16.8, 20.0, 21.4, and 22.5, corresponding to d-spacing (angstroms±0.2) of 16.2, 6.0, 5.5, 5.3, 4.4, 4.2, and 4.0, respectively.
70. The crystalline solid form of any one of embodiments 65-69, wherein Type F of Compound 1 is characterized by an X-ray powder diffraction (XRPD) pattern having diffractions at angles (2 theta±0.2) of 5.4, 14.7, 16.0, 16.8, 19.0, 20.0, 21.4, 22.5, 23.2, and 25.3.
71. The crystalline solid form of any one of embodiments 65-70, wherein Type F of Compound 1 is characterized by an XRPD pattern having diffractions at angles (2 theta±0.2) of 5.4, 14.7, 16.0, 16.8, 19.0, 20.0, 21.4, 22.5, 23.2, and 25.3, corresponding to d-spacing (angstroms±0.2) of 16.2, 6.0, 5.5, 5.3, 4.7, 4.4, 4.2, 4.0, 3.8, and 3.5, respectively.
72. The crystalline solid form of any one of embodiments 65-71, wherein Type F of Compound 1 is characterized by an X-ray powder diffraction (XRPD) pattern having diffractions at angles (2 theta±0.2) of 5.4, 12.9, 14.7, 16.0, 16.8, 17.4, 19.0, 20.0, 20.6, 21.4, 22.5, 23.2, 25.3, 26.6, 27.2, 28.0, and 30.0.
73. The crystalline solid form of any one of embodiments 65-72, wherein Type F of Compound 1 is characterized by an XRPD pattern having diffractions at angles (2 theta±0.2) of 5.4, 12.9, 14.7, 16.0, 16.8, 17.4, 19.0, 20.0, 20.6, 21.4, 22.5, 23.2, 25.3, 26.6, 27.2, 28.0, and 30.0, corresponding to d-spacing (angstroms±0.2) of 16.2, 6.9, 6.0, 5.5, 5.3, 5.1, 4.7, 4.4, 4.3, 4.2, 4.0, 3.8, 3.5, 3.4, 3.3, 3.2, and 3.0, respectively.
74. The crystalline solid form of any one of embodiments 65-73, wherein Type F of Compound 1 is characterized by an XRPD pattern having diffractions at angles (2 theta±0.2) of:

5.4
10.9
12.9
14.7
16.0
16.8
17.4
19.0
20.0
20.6
21.4
22.5
23.2
25.3
26.6
27.2
28.0
30.0
32.0
32.9
38.3
39.1

75. The crystalline solid form of any one of embodiments 65-74, wherein Type F of Compound 1 is characterized by an XRPD pattern having diffractions at angles (2 theta±0.2) corresponding to d-spacing (angstroms±0.2) of:

| 2 theta | d-spacing |
|---|---|
| 5.4 | 16.23 |
| 10.9 | 8.1 |
| 12.9 | 6.9 |
| 14.7 | 6.0 |
| 16.0 | 5.5 |
| 16.8 | 5.3 |
| 17.4 | 5.1 |
| 19.0 | 4.7 |
| 20.0 | 4.4 |
| 20.6 | 4.3 |
| 21.4 | 4.2 |
| 22.5 | 4.0 |
| 23.2 | 3.8 |
| 25.3 | 3.5 |
| 26.6 | 3.4 |
| 27.2 | 3.3 |
| 28.0 | 3.2 |
| 30.0 | 3.0 |
| 32.0 | 2.8 |
| 32.9 | 2.7 |
| 38.3 | 2.4 |
| 39.1 | 2.3 |

76. The crystalline solid form of any one of embodiments 65-75, wherein Type F of Compound 1 is characterized by a thermogravimetric analysis (TGA) thermogram with a weight loss of about 6.2% up to 120° C.
77. The crystalline solid form of any one of embodiments 65-76, wherein Type F of Compound 1 is characterized by a differential scanning calorimetry (DSC) endotherm having a peak temperature of about 100.4° C. and an onset temperature of 125.9° C.
78. The crystalline solid form of embodiment 1, wherein the crystalline solid form is Type G of Compound 1.
79. The crystalline solid form of embodiment 78, wherein Type G of Compound 1 is characterized by an X-ray powder diffraction (XRPD) pattern having diffractions at angles (2 theta±0.2) of 5.4, 14.3, 16.6, and 21.3.
80. The crystalline solid form of embodiment 78 or 79, wherein Type G of Compound 1 is characterized by an XRPD pattern having diffractions at angles (2 theta±0.2) of 5.4, 14.3, 16.6, and 21.3, corresponding to d-spacing (angstroms±0.2) of 16.5, 6.2, 5.3, and 4.2, respectively.
81. The crystalline solid form of any one of embodiments 78-80, wherein Type G of Compound 1 is characterized by an X-ray powder diffraction (XRPD) pattern having diffractions at angles (2 theta±0.2) of 5.4, 14.3, 16.6, 21.3, and 22.3.
82. The crystalline solid form of any one of embodiments 78-81, wherein Type G of Compound 1 is characterized by an XRPD pattern having diffractions at angles (2 theta±0.2) of 5.4, 14.3, 16.6, 21.3, and 22.3, corresponding to d-spacing (angstroms±0.2) of 16.5, 6.2, 5.3, 4.2, and 4.0, respectively.
83. The crystalline solid form of any one of embodiments 78-82, wherein Type G of Compound 1 is characterized by an X-ray powder diffraction (XRPD) pattern having diffractions at angles (2 theta±0.2) of 5.4, 12.8, 14.3, 15.0, 16.6, 19.8, 21.3, 22.3, 25.3, and 26.4.
84. The crystalline solid form of any one of embodiments 78-83, wherein Type G of Compound 1 is characterized by an XRPD pattern having diffractions at angles (2 theta±0.2) of 5.4, 12.8, 14.3, 15.0, 16.6, 19.8, 21.3, 22.3, 25.3, and 26.4, corresponding to d-spacing (angstroms±0.2) of 16.5, 6.9, 6.2, 5.9, 5.3, 4.5, 4.2, 4.0, 3.5, and 3.4, respectively.
85. The crystalline solid form of any one of embodiments 78-84, wherein Type G of Compound 1 is characterized by an X-ray powder diffraction (XRPD) pattern having diffractions at angles (2 theta±0.2) of 5.4, 12.8, 14.3, 15.0, 15.8, 16.6, 19.8, 21.3, 22.3, 25.3, 26.4, 27.4, and 30.2.
86. The crystalline solid form of any one of embodiments 78-85, wherein Type G of Compound 1 is characterized by an XRPD pattern having diffractions at angles (2 theta±0.2) of 5.4, 12.8, 14.3, 15.0, 15.8, 16.6, 19.8, 21.3, 22.3, 25.3, 26.4, 27.4, and 30.2, corresponding to d-spacing (angstroms±0.2) of 16.5, 6.9, 6.2, 5.9, 5.6, 5.3, 4.5, 4.2, 4.0, 3.5, 3.4, 3.3, and 3.0, respectively.
87. The crystalline solid form of any one of embodiments 78-86, wherein Type G of Compound 1 is characterized by an XRPD pattern having diffractions at angles (2 theta±0.2) of:
5.4
8.7
12.8
14.3
15.0
15.8
16.6
18.5
19.8
21.3
22.3
23.4
25.3
26.4
27.4
30.2
32.3
38.0
88. The crystalline solid form of any one of embodiments 78-87, wherein Type G of Compound 1 is characterized by an XRPD pattern having diffractions at angles (2 theta±0.2) corresponding to d-spacing (angstroms±0.2) of:

| 2 theta | d-spacing |
| --- | --- |
| 5.4 | 16.5 |
| 8.7 | 10.1 |
| 12.8 | 6.9 |
| 14.3 | 6.2 |
| 15.0 | 5.9 |
| 15.8 | 5.6 |
| 16.6 | 5.3 |
| 18.5 | 4.8 |
| 19.8 | 4.5 |
| 21.3 | 4.2 |
| 22.3 | 4.0 |
| 23.4 | 3.8 |
| 25.3 | 3.5 |
| 26.4 | 3.4 |
| 27.4 | 3.3 |
| 30.2 | 3.0 |
| 32.3 | 2.8 |
| 38.0 | 2.4 |

89. The crystalline solid form of embodiment 1, wherein the crystalline solid form is Type H of Compound 1.
90. The crystalline solid form of embodiment 89, wherein Type H of Compound 1 is characterized by an X-ray powder diffraction (XRPD) pattern having diffractions at angles (2 theta±0.2) of 5.8, 14.7, 16.6, 20.0, 21.3, and 25.4.
91. The crystalline solid form of embodiment 89 or 90, wherein Type H of Compound 1 is characterized by an XRPD pattern having diffractions at angles (2 theta±0.2) of 5.8, 14.7, 16.6, 20.0, 21.3, and 25.4, corresponding to d-spacing (angstroms±0.2) of 15.3, 6.0, 5.4, 4.4, 4.2, and 3.5, respectively.
92. The crystalline solid form of any one of embodiments 89-91, wherein Type H of Compound 1 is characterized by an XRPD pattern having diffractions at angles (2 theta±0.2) of:
5.8
8.4
11.5
12.4
13.1
13.7
14.7
14.9
16.0
16.2
16.6
16.9
17.3
17.7
18.3
19.5
20.0
21.3
21.9
23.1
23.6
23.9
24.4
24.9
25.1
25.4
26.2
27.4
28.1
28.4
29.3

29.7
30.4
31.0
32.7
33.4
34.1
34.8
35.5
35.8
36.4
37.1
38.5

93. The crystalline solid form of any one of embodiments 89-92, wherein Type H of Compound 1 is characterized by an XRPD pattern having diffractions at angles (2 theta±0.2) corresponding to d-spacing (angstroms±0.2) of:

| Pos. [°2Th.] | d-spacing [Å] |
| --- | --- |
| 5.8 | 15.3 |
| 8.4 | 10.5 |
| 11.5 | 7.7 |
| 12.4 | 7.2 |
| 13.1 | 6.8 |
| 13.7 | 6.5 |
| 14.7 | 6.0 |
| 14.9 | 5.9 |
| 16.0 | 5.6 |
| 16.2 | 5.5 |
| 16.6 | 5.4 |
| 16.9 | 5.3 |
| 17.3 | 5.1 |
| 17.7 | 5.0 |
| 18.3 | 4.8 |
| 19.5 | 4.6 |
| 20.0 | 4.4 |
| 21.3 | 4.2 |
| 21.9 | 4.1 |
| 23.1 | 3.9 |
| 23.6 | 3.8 |
| 23.9 | 3.7 |
| 24.4 | 3.7 |
| 24.9 | 3.6 |
| 25.1 | 3.5 |
| 25.4 | 3.5 |
| 26.2 | 3.4 |
| 27.4 | 3.3 |
| 28.1 | 3.2 |
| 28.4 | 3.1 |
| 29.3 | 3.0 |
| 29.7 | 3.0 |
| 30.4 | 2.9 |
| 31.0 | 2.9 |
| 32.7 | 2.7 |
| 33.4 | 2.7 |
| 34.1 | 2.6 |
| 34.8 | 2.6 |
| 35.5 | 2.5 |
| 35.8 | 2.5 |
| 36.4 | 2.5 |
| 37.1 | 2.4 |
| 38.5 | 2.3 |

94. The crystalline solid form of embodiment 1, wherein the crystalline solid form is Type I of Compound 1.
95. The crystalline solid form of embodiment 94, wherein Type I of Compound 1 is characterized by an X-ray powder diffraction (XRPD) pattern having diffractions at angles (2 theta±0.2) of 5.2, 14.6, 15.5, 20.2, and 21.1.
96. The crystalline solid form of embodiment 94 or 95, wherein Type I of Compound 1 is characterized by an XRPD pattern having diffractions at angles (2 theta±0.2) of 5.2, 14.6, 15.5, 20.2, and 21.1, corresponding to d-spacing (angstroms±0.2) of 17.1, 6.1, 5.7, 4.4, and 4.2, respectively.
97. The crystalline solid form of any one of embodiments 94-96, wherein Type I of Compound 1 is characterized by an XRPD pattern having diffractions at angles (2 theta±0.2) of:

5.2
8.8
10.3
12.6
14.6
15.5
16.1
16.3
16.6
17.1
17.6
18.7
18.9
20.2
20.5
20.7
21.1
21.5
22.0
22.3
23.7
24.8
25.2
26.0
26.3
26.5
26.8
27.0
27.5
27.7
28.1
29.6
30.0
30.4
31.3
32.0
32.5
33.2
34.0
34.6
36.9
38.2
38.9
39.5

98. The crystalline solid form of any one of embodiments 94-97, wherein Type I of Compound 1 is characterized by an XRPD pattern having diffractions at angles (2 theta±0.2) corresponding to d-spacing (angstroms±0.2) of:

| Pos. [°2Th.] | d-spacing [Å] |
| --- | --- |
| 5.2 | 17.1 |
| 8.8 | 10.1 |
| 10.3 | 8.6 |
| 12.6 | 7.0 |
| 14.6 | 6.1 |
| 15.5 | 5.7 |
| 16.1 | 5.5 |
| 16.3 | 5.4 |
| 16.6 | 5.3 |

-continued

| Pos. [°2Th.] | d-spacing [Å] |
|---|---|
| 17.1 | 5.2 |
| 17.6 | 5.0 |
| 18.7 | 4.7 |
| 18.9 | 4.7 |
| 20.2 | 4.4 |
| 20.5 | 4.3 |
| 20.7 | 4.3 |
| 21.1 | 4.2 |
| 21.5 | 4.1 |
| 22.0 | 4.0 |
| 22.3 | 4.0 |
| 23.7 | 3.8 |
| 24.8 | 3.6 |
| 25.2 | 3.5 |
| 26.0 | 3.4 |
| 26.3 | 3.4 |
| 26.5 | 3.4 |
| 26.8 | 3.3 |
| 27.0 | 3.3 |
| 27.5 | 3.2 |
| 27.7 | 3.2 |
| 28.1 | 3.2 |
| 29.6 | 3.0 |
| 30.0 | 3.0 |
| 30.4 | 2.9 |
| 31.3 | 2.9 |
| 32.0 | 2.8 |
| 32.5 | 2.8 |
| 33.2 | 2.7 |
| 34.0 | 2.6 |
| 34.6 | 2.6 |
| 36.9 | 2.4 |
| 38.2 | 2.4 |
| 38.9 | 2.3 |
| 39.5 | 2.3 |

99. The crystalline solid form of embodiment 1, wherein the crystalline solid form is Type J of Compound 1.
100. The crystalline solid form of embodiment 99, wherein Type J of Compound 1 is characterized by an X-ray powder diffraction (XRPD) pattern having diffractions at angles (2 theta±0.2) of 4.5, 5.7, 22.8, 23.1, and 24.5.
101. The crystalline solid form of embodiment 99 or 100, wherein Type J of Compound 1 is characterized by an XRPD pattern having diffractions at angles (2 theta±0.2) of 4.5, 5.7, 22.8, 23.1, and 24.5, corresponding to d-spacing (angstroms±0.2) of 19.5, 15.4, 3.9, 3.8, and 3.6, respectively.
102. The crystalline solid form of any one of embodiments 99-101, wherein Type J of Compound 1 is characterized by an XRPD pattern having diffractions at angles (2 theta±0.2) of:
4.5
5.7
7.1
7.7
9.1
10.5
11.2
11.7
12.3
12.9
14.3
14.5
15.4
15.7
16.3
17.3
18.3
18.7
19.3
19.6
20.5
21.2
21.5
22.8
23.1
23.6
24.1
24.5
25.2
25.9
26.4
27.8
29.3
36.2
37.0

103. The crystalline solid form of any one of embodiments 99-102, wherein Type J of Compound 1 is characterized by an XRPD pattern having diffractions at angles (2 theta±0.2) corresponding to d-spacing (angstroms±0.2) of:

| Pos. [°2Th.] | d-spacing [Å] |
|---|---|
| 4.5 | 19.5 |
| 5.7 | 15.4 |
| 7.1 | 12.7 |
| 7.7 | 11.5 |
| 9.1 | 9.7 |
| 10.5 | 8.4 |
| 11.2 | 7.9 |
| 11.7 | 7.5 |
| 12.3 | 7.2 |
| 12.9 | 6.8 |
| 14.3 | 6.2 |
| 14.5 | 6.1 |
| 15.4 | 5.8 |
| 15.7 | 5.7 |
| 16.3 | 5.4 |
| 17.3 | 5.1 |
| 18.3 | 4.9 |
| 18.7 | 4.7 |
| 19.3 | 4.6 |
| 19.6 | 4.5 |
| 20.5 | 4.3 |
| 21.2 | 4.2 |
| 21.5 | 4.1 |
| 22.8 | 3.9 |
| 23.1 | 3.8 |
| 23.6 | 3.8 |
| 24.1 | 3.7 |
| 24.5 | 3.6 |
| 25.2 | 3.5 |
| 25.9 | 3.4 |
| 26.4 | 3.4 |
| 27.8 | 3.2 |
| 29.3 | 3.0 |
| 36.2 | 2.5 |
| 37.0 | 2.4 |

104. The crystalline solid form of embodiment 1, wherein the crystalline solid form is Type K of Compound 1.
105. The crystalline solid form of embodiment 104, wherein Type K of Compound 1 is characterized by an X-ray powder diffraction (XRPD) pattern having diffractions at angles (2 theta±0.2) of 4.6, 15.4, 15.6, 16.1, 23.2, and 27.4.
106. The crystalline solid form of embodiment 104 or 105, wherein Type K of Compound 1 is characterized by an XRPD pattern having diffractions at angles (2 theta±0.2) of 4.6, 15.4, 15.6, 16.1, 23.2, and 27.4, corresponding to d-spacing (angstroms±0.2) of 19.2, 5.7, 5.7, 5.5, 3.8, and 3.3, respectively.

107. The crystalline solid form of any one of embodiments 104-106, wherein Type K of Compound 1 is characterized by an XRPD pattern having diffractions at angles (2 theta±0.2) of:
4.6
9.3
10.1
12.9
13.9
14.7
15.4
15.6
16.1
17.8
18.3
18.6
19.3
20.0
20.7
21.6
21.9
22.9
23.2
24.4
25.0
25.5
26.0
27.4
28.8
29.2
30.7
31.1
32.7
36.3

108. The crystalline solid form of any one of embodiments 104-107, wherein Type K of Compound 1 is characterized by an XRPD pattern having diffractions at angles (2 theta±0.2) corresponding to d-spacing (angstroms±0.2) of:

| Pos. [°2Th.] | d-spacing [Å] |
|---|---|
| 4.6 | 19.2 |
| 9.3 | 9.5 |
| 10.1 | 8.7 |
| 12.9 | 6.8 |
| 13.9 | 6.4 |
| 14.7 | 6.0 |
| 15.4 | 5.7 |
| 15.6 | 5.7 |
| 16.1 | 5.5 |
| 17.8 | 5.0 |
| 18.3 | 4.9 |
| 18.6 | 4.8 |
| 19.3 | 4.6 |
| 20.0 | 4.4 |
| 20.7 | 4.3 |
| 21.6 | 4.1 |
| 21.9 | 4.1 |
| 22.9 | 3.9 |
| 23.2 | 3.8 |
| 24.4 | 3.6 |
| 25.0 | 3.6 |
| 25.5 | 3.5 |
| 26.0 | 3.4 |
| 27.4 | 3.3 |
| 28.8 | 3.1 |

-continued

| Pos. [°2Th.] | d-spacing [Å] |
|---|---|
| 29.2 | 3.1 |
| 30.7 | 2.9 |
| 31.1 | 2.9 |
| 32.7 | 2.7 |
| 36.3 | 2.5 |

109. The crystalline solid form of embodiment 1, wherein the crystalline solid form is Type L of Compound 1.

110. The crystalline solid form of embodiment 109, wherein Type L of Compound 1 is characterized by an X-ray powder diffraction (XRPD) pattern having diffractions at angles (2 theta±0.2) of 5.9, 11.9, 17.8, 21.6, 23.9, and 36.1.

111. The crystalline solid form of embodiment 109 or 110, wherein Type L of Compound 1 is characterized by an XRPD pattern having diffractions at angles (2 theta±0.2) of 5.9, 11.9, 17.8, 21.6, 23.9, and 36.1, corresponding to d-spacing (angstroms±0.2) of 14.9, 7.5, 5.0, 4.1, 3.7, and 2.5, respectively.

112. The crystalline solid form of any one of embodiments 109-111, wherein Type L of Compound 1 is characterized by an XRPD pattern having diffractions at angles (2 theta±0.2) of:
5.9
8.4
11.9
13.3
14.7
15.0
16.2
16.7
16.9
17.8
18.9
20.4
21.2
21.6
22.2
23.9
24.6
25.5
25.7
26.1
26.8
28.1
28.8
29.9
30.6
31.9
32.4
33.6
34.2
35.6
36.1
38.2

113. The crystalline solid form of any one of embodiments 109-112, wherein Type L of Compound 1 is characterized by an XRPD pattern having diffractions at angles (2 theta±0.2) corresponding to d-spacing (angstroms±0.2) of:

| Pos. [°2Th.] | d-spacing [Å] |
|---|---|
| 5.9 | 14.9 |
| 8.4 | 10.5 |
| 11.9 | 7.5 |
| 13.3 | 6.6 |
| 14.7 | 6.0 |
| 15.0 | 5.9 |
| 16.2 | 5.5 |
| 16.7 | 5.3 |
| 16.9 | 5.2 |
| 17.8 | 5.0 |
| 18.9 | 4.7 |
| 20.4 | 4.4 |
| 21.2 | 4.2 |
| 21.6 | 4.1 |
| 22.2 | 4.0 |
| 23.9 | 3.7 |
| 24.6 | 3.6 |
| 25.5 | 3.5 |
| 25.7 | 3.5 |
| 26.1 | 3.4 |
| 26.8 | 3.3 |
| 28.1 | 3.2 |
| 28.8 | 3.1 |
| 29.9 | 3.0 |
| 30.6 | 2.9 |
| 31.9 | 2.8 |
| 32.4 | 2.8 |
| 33.6 | 2.7 |
| 34.2 | 2.6 |
| 35.6 | 2.5 |
| 36.1 | 2.5 |
| 38.2 | 2.4 |

114. The crystalline solid form of embodiment 1, wherein the crystalline solid form is Type M of Compound 1.
115. The crystalline solid form of embodiment 114, wherein Type M of Compound 1 is characterized by an X-ray powder diffraction (XRPD) pattern having diffractions at angles (2 theta±0.2) of 4.5, 5.8, 9.7, 15.6, 21.9, and 26.7.
116. The crystalline solid form of embodiment 114 or 115, wherein Type M of Compound 1 is characterized by an XRPD pattern having diffractions at angles (2 theta±0.2) of 4.5, 5.8, 9.7, 15.6, 21.9, and 26.7, corresponding to d-spacing (angstroms±0.2) of 19.5, 15.3, 9.1, 5.7, 4.1, and 3.3, respectively.
117. The crystalline solid form of any one of embodiments 114-116, wherein Type M of Compound 1 is characterized by an XRPD pattern having diffractions at angles (2 theta±0.2) of:
4.5
5.8
6.1
8.7
9.0
9.7
12.3
13.1
13.7
14.5
15.1
15.6
16.8
17.4
18.0
18.5
19.5
20.0
21.4
21.9
22.3
22.9
23.3
23.5
24.1
25.0
25.8
26.3
26.7
27.8
28.1
29.4
30.8
31.7
33.0
35.3
37.8
38.6

118. The crystalline solid form of any one of embodiments 114-117, wherein Type M of Compound 1 is characterized by an XRPD pattern having diffractions at angles (2 theta±0.2) corresponding to d-spacing (angstroms±0.2) of:

| Pos. [°2Th.] | d-spacing [Å] |
|---|---|
| 4.5 | 19.5 |
| 5.8 | 15.3 |
| 6.1 | 14.4 |
| 8.7 | 10.2 |
| 9.0 | 9.9 |
| 9.7 | 9.1 |
| 12.3 | 7.2 |
| 13.1 | 6.8 |
| 13.7 | 6.4 |
| 14.5 | 6.1 |
| 15.1 | 5.9 |
| 15.6 | 5.7 |
| 16.8 | 5.3 |
| 17.4 | 5.1 |
| 18.0 | 4.9 |
| 18.5 | 4.8 |
| 19.5 | 4.5 |
| 20.0 | 4.4 |
| 21.4 | 4.1 |
| 21.9 | 4.1 |
| 22.3 | 4.0 |
| 22.9 | 3.9 |
| 23.3 | 3.8 |
| 23.5 | 3.8 |
| 24.1 | 3.7 |
| 25.0 | 3.6 |
| 25.8 | 3.5 |
| 26.3 | 3.4 |
| 26.7 | 3.3 |
| 27.8 | 3.2 |
| 28.1 | 3.2 |
| 29.4 | 3.0 |
| 30.8 | 2.9 |
| 31.7 | 2.8 |
| 33.0 | 2.7 |
| 35.3 | 2.5 |
| 37.8 | 2.4 |
| 38.6 | 2.3 |

119. The crystalline solid form of embodiment 1, wherein the crystalline solid form is selected from the group consisting of:
1) Type A of Compound 1, wherein Type A of Compound 1 is characterized by an X-ray powder diffraction (XRPD) pattern having diffractions at angles (2 theta±0.2) of 4.6, 7.2, 15.7, 21.4, 23.2, and 24.8;
2) Type B of Compound 1, wherein Type B of Compound 1 is characterized by an X-ray powder diffraction (XRPD) pattern having diffractions at angles (2 theta±0.2) of 4.5, 15.6, 22.2, 22.9, 23.3, and 25.1;
3) Type C of Compound 1, wherein Type C of Compound 1 is characterized by an X-ray powder diffraction (XRPD) pattern having diffractions at angles (2 theta±0.2) of 4.5, 7.3, 11.2, 18.9, 23.0, and 24.7;
4) Type D of Compound 1, wherein Type D of Compound 1 is characterized by an X-ray powder diffraction (XRPD) pattern having diffractions at angles (2 theta±0.2) of 6.2, 9.7, 13.1, 15.7, 21.9, and 23.6 and not having a diffraction at an angle (2 theta±0.2) of 23.3;
5) Type E of Compound 1, wherein Type E of Compound 1 is characterized by an X-ray powder diffraction (XRPD) pattern having diffractions at angles (2 theta±0.2) of 15.1, 15.8, 17.5, 20.1, 21.9, and 26.7;
6) Type F of Compound 1, wherein Type F of Compound 1 is characterized by an X-ray powder diffraction (XRPD) pattern having diffractions at angles (2 theta±0.2) of 5.5, 14.7, 16.0, 16.8, and 21.4;
7) Type G of Compound 1, wherein Type G of Compound 1 is characterized by an X-ray powder diffraction (XRPD) pattern having diffractions at angles (2 theta±0.2) of 5.4, 14.3, 16.6, 21.3, and 22.3;
8) Type H of Compound 1, wherein Type H of Compound 1 is characterized by an X-ray powder diffraction (XRPD) pattern having diffractions at angles (2 theta±0.2) of 5.8, 14.7, 16.6, 20.0, 21.3, and 25.4;
9) Type I of Compound 1, wherein Type I of Compound 1 is characterized by an X-ray powder diffraction (XRPD) pattern having diffractions at angles (2 theta±0.2) of 5.2, 14.6, 15.5, 20.2, and 21.1;
10) Type J of Compound 1, wherein Type J of Compound 1 is characterized by an X-ray powder diffraction (XRPD) pattern having diffractions at angles (2 theta±0.2) of 4.5, 5.7, 22.8, 23.1, and 24.5;
11) Type K of Compound 1, wherein Type K of Compound 1 is characterized by an X-ray powder diffraction (XRPD) pattern having diffractions at angles (2 theta±0.2) of 4.6, 15.4, 15.6, 16.1, 23.2, and 27.4;
12) Type L of Compound 1, wherein Type L of Compound 1 is characterized by an X-ray powder diffraction (XRPD) pattern having diffractions at angles (2 theta±0.2) of 5.9, 11.9, 17.8, 21.6, 23.9, and 36.1; and
13) Type M of Compound 1, wherein Type M of Compound 1 is characterized by an X-ray powder diffraction (XRPD) pattern having diffractions at angles (2 theta±0.2) of 4.5, 5.8, 9.7, 15.6, 21.9, and 26.7.
120. A pharmaceutical composition comprising a therapeutically effective amount of the crystalline solid form of any one of embodiments 1-119, and one or more pharmaceutically acceptable excipients.
121. The pharmaceutical composition of embodiment 120, wherein the pharmaceutical composition is for oral administration.
122. The pharmaceutical composition of embodiment 120 or 121, wherein the pharmaceutical composition has a water content of about 0.5-5.0 weight %.
123. The pharmaceutical composition of any one of embodiments 120-122, wherein the pharmaceutical composition has a water content of about 1.5-4.0 weight %.
124. The pharmaceutical composition of any one of embodiments 120-123, wherein the pharmaceutical composition has a water content of about 2.5-3.0 weight %.
125. An amorphous solid dispersion comprising Compound 1:

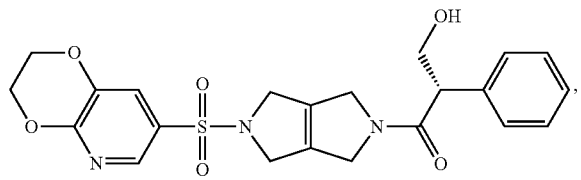

and a polymer.
126. The amorphous solid dispersion of embodiment 125, wherein the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.
127. The amorphous solid dispersion of embodiment 125 or 126, wherein the polymer is hydroxypropylmethyl cellulose (HPMC) or hydroxypropylmethyl cellulose acetate succinate (HPMC AS).
128. The amorphous solid dispersion of any one of embodiments 125-127, wherein the polymer is hydroxypropylmethyl cellulose acetate succinate (HPMC AS).
129. The amorphous solid dispersion of any one of embodiments 125-128, wherein the weight ratio of Compound 1 to the polymer is in a range of about 3:1 to about 1:3 or about 2:1 to about 1:3.
130. The amorphous solid dispersion of any one of embodiments 125-129, wherein the weight ratio of Compound 1 to the polymer is about 1:3.
131. The amorphous solid dispersion of any one of embodiments 125-129, wherein the weight ratio of Compound 1 to the polymer is about 1:1.
132. The amorphous solid dispersion of any one of embodiments 125-129, wherein the weight ratio of Compound 1 to the polymer is about 1:3, about 2:3, about 1:1, about 1.5:1, about 2:1, or about 3:1.
133. The amorphous solid dispersion of any one of embodiments 125-132, wherein crystalline diffraction peaks are not observable by XRPD analysis (Method D) of the amorphous solid dispersion.
134. The amorphous solid dispersion of any one of embodiments 125-133, wherein crystalline diffraction peaks are not observable by XRPD analysis (Method D) of the amorphous solid dispersion after storage in a container as described in Example 20 for 5 months at 2-8° C. and ambient relative humidity.
135. The amorphous solid dispersion of any one of embodiments 125-134, wherein crystalline diffraction peaks are not observable by XRPD analysis (Method D) of the amorphous solid dispersion after storage in a container as described in Example 20 for 5 months at 25° C. and 60% relative humidity.

136. The amorphous solid dispersion of any one of embodiments 125-135, wherein crystalline diffraction peaks are not observable by XRPD analysis (Method D) of the amorphous solid dispersion after storage in a container as described in Example 20 for 1 month at 2-8° C. and ambient relative humidity.

137. The amorphous solid dispersion of any one of embodiments 125-136, wherein crystalline diffraction peaks are not observable by XRPD analysis (Method D) of the amorphous solid dispersion after storage in a container as described in Example 20 for 1 month at 25° C. and 60% relative humidity.

138. The amorphous solid dispersion of any one of embodiments 125-137, wherein crystalline diffraction peaks are not observable by XRPD analysis (Method D) of the amorphous solid dispersion after storage in a container as described in Example 20 for 1 month at 40° C. and 75% relative humidity.

139. The amorphous solid dispersion of any one of embodiments 125-138, wherein a single glass transition temperature ($T_G$) and no melt endotherm is observable by DSC analysis (Method B) of the amorphous solid dispersion.

140. The amorphous solid dispersion of any one of embodiments 125-139, wherein a single glass transition temperature ($T_G$) and no melt endotherm is observable by DSC analysis (Method B) of the amorphous solid dispersion after storage in a container as described in Example 20 for 5 months at 2-8° C. and ambient relative humidity.

141. The amorphous solid dispersion of any one of embodiments 125-140, wherein a single glass transition temperature ($T_G$) and no melt endotherm is observable by DSC analysis (Method B) of the amorphous solid dispersion after storage in a container as described in Example 20 for 5 months at 25° C. and 60% relative humidity.

142. The amorphous solid dispersion of any one of embodiments 125-141, wherein a single glass transition temperature ($T_G$) and no melt endotherm is observable by DSC analysis (Method B) of the amorphous solid dispersion after storage in a container as described in Example 20 for 1 month at 2-8° C. and ambient relative humidity.

143. The amorphous solid dispersion of any one of embodiments 125-142, wherein a single glass transition temperature ($T_G$) and no melt endotherm is observable by DSC analysis (Method B) of the amorphous solid dispersion after storage in a container as described in Example 20 for 1 month at 25° C. and 60% relative humidity.

144. The amorphous solid dispersion of any one of embodiments 125-143, wherein a single glass transition temperature ($T_G$) and no melt endotherm is observable by DSC analysis (Method B) of the amorphous solid dispersion after storage in a container as described in Example 20 for 1 month at 40° C. and 75% relative humidity.

145. The amorphous solid dispersion of any one of embodiments 125-144, wherein crystalline diffraction peaks are not observable by XRPD analysis (Method D) of the amorphous solid dispersion.

146. The amorphous solid dispersion of any one of embodiments 125-145, wherein crystalline diffraction peaks are not observable by XRPD analysis (Method D) of the amorphous solid dispersion after storage in a sealed vial for 1 week at 60° C.

147. The amorphous solid dispersion of any one of embodiments 125-146, wherein crystalline diffraction peaks are not observable by XRPD analysis (Method D) of the amorphous solid dispersion after storage in a sealed vial for 2 weeks at 60° C.

148. The amorphous solid dispersion of any one of embodiments 125-147, wherein crystalline diffraction peaks are not observable by XRPD analysis (Method D) of the amorphous solid dispersion after storage in an unsealed vial for 1 week at 25° C. and 60% relative humidity.

149. The amorphous solid dispersion of any one of embodiments 125-148, wherein crystalline diffraction peaks are not observable by XRPD analysis (Method D) of the amorphous solid dispersion after storage in an unsealed vial for 2 weeks at 25° C. and 60% relative humidity.

150. The amorphous solid dispersion of any one of embodiments 125-149, wherein crystalline diffraction peaks are not observable by XRPD analysis (Method D) of the amorphous solid dispersion after storage in an unsealed vial for 1 week at 40° C. and 75% relative humidity.

151. The amorphous solid dispersion of any one of embodiments 125-150, wherein crystalline diffraction peaks are not observable by XRPD analysis (Method D) of the amorphous solid dispersion after storage in an unsealed vial for 2 weeks at 40° C. and 75% relative humidity.

152. The amorphous solid dispersion of any one of embodiments 125-151, wherein crystalline diffraction peaks are not observable by XRPD analysis (Method D) of the amorphous solid dispersion after storage in an unsealed vial for 1 week at 60° C. and 75% relative humidity.

153. The amorphous solid dispersion of any one of embodiments 125-152, wherein crystalline diffraction peaks are not observable by XRPD analysis (Method D) of the amorphous solid dispersion after storage in an unsealed vial for 2 weeks at 60° C. and 75% relative humidity.

154. The amorphous solid dispersion of any one of embodiments 125-136, wherein a single glass transition temperature ($T_G$) and no melt endotherm is observable by DSC analysis (Method B) of the amorphous solid dispersion.

155. The amorphous solid dispersion of any one of embodiments 125-154, wherein a single glass transition temperature ($T_G$) and no melt endotherm is observable by DSC analysis (Method B) of the amorphous solid dispersion after storage in a sealed vial for 1 week or 2 weeks at 60° C.

156. The amorphous solid dispersion of any one of embodiments 125-155, wherein a single glass transition temperature ($T_G$) and no melt endotherm is observable by DSC analysis (Method B) of the amorphous solid dispersion after storage in an unsealed vial for 1 week or 2 weeks at 25° C. and 60% relative humidity.

157. The amorphous solid dispersion of any one of embodiments 125-156, wherein a single glass transition temperature ($T_G$) and no melt endotherm is observable by DSC analysis (Method B) of the amorphous solid dispersion after storage in an unsealed vial for 1 week or 2 weeks at 40° C. and 75% relative humidity.

158. The amorphous solid dispersion of any one of embodiments 125-157, wherein a single glass transition temperature ($T_G$) and no melt endotherm is observable by DSC analysis (Method B) of the amorphous solid dispersion after storage in an unsealed vial for 1 week or 2 weeks at 60° C. and 75% relative humidity.

159. The amorphous solid dispersion of any one of embodiments 125-158, wherein Compound 1 has a concentration of at least 300 µg/mL after 30 minutes in the kinetic solubility experiment described in Example 23.

160. The amorphous solid dispersion of any one of embodiments 125-159, wherein Compound 1 has a Cmax of at least 600 µg/mL in the kinetic solubility experiment described in Example 23.

161. The amorphous solid dispersion of any one of embodiments 125-160, wherein Compound 1 has a concentration of at least 450 µg/mL after 4 hours in the kinetic solubility experiment described in Example 23.

162. The amorphous solid dispersion of any one of embodiments 125-158, wherein Compound 1 has a concentration of at least 200 µg/mL after 16 hours in the kinetic solubility experiment described in Example 23.

163. A pharmaceutical composition comprising a therapeutically effective amount of the amorphous solid dispersion of any one of embodiments 125-162, and one or more pharmaceutically acceptable excipients.

164. The pharmaceutical composition of embodiment 163, wherein the pharmaceutical composition is for oral administration.

165. The pharmaceutical composition of embodiment 163 or 164, wherein the pharmaceutical composition is in a tablet dosage form.

166. The pharmaceutical composition of any one of embodiments 163-165, wherein the pharmaceutical composition has a water content of about 0.5-5.0 weight %.

167. The pharmaceutical composition of any one of embodiments 163-166, wherein the pharmaceutical composition has a water content of about 1.5-4.0 weight %.

168. The pharmaceutical composition of any one of embodiments 163-167, wherein the pharmaceutical composition has a water content of about 2.5-3.0 weight %.

169. The pharmaceutical composition of any one of embodiments 163-168, wherein the pharmaceutical composition comprises about 10 mg, about 25 mg, about 50 mg, about 100 mg, about 200 mg, or about 300 mg of Compound 1.

170. The pharmaceutical composition of any one of embodiments 163-169, wherein the pharmaceutical composition comprises about 25 mg of Compound 1.

171. The pharmaceutical composition of any one of embodiments 163-169, wherein the pharmaceutical composition comprises about 100 mg of Compound 1.

172. The pharmaceutical composition of any one of embodiments 163-169, wherein the pharmaceutical composition comprises about 200 mg of Compound 1.

173. The pharmaceutical composition of any one of embodiments 163-172, wherein the one or more pharmaceutically acceptable excipients comprise one or more of a filler, a dry binder, a glidant, a lubricant, a disintegrant, and a film coating agent.

174. The pharmaceutical composition of any one of embodiments 163-173, wherein the one or more pharmaceutically acceptable excipients comprise a filler, and the filler comprises microcrystalline cellulose.

175. The pharmaceutical composition of any one of embodiments 163-174, wherein the one or more pharmaceutically acceptable excipients comprise a filler, and the filler comprises lactose monohydrate.

176. The pharmaceutical composition of any one of embodiments 163-175, wherein the one or more pharmaceutically acceptable excipients comprise a dry binder, and the dry binder comprises crospovidone.

177. The pharmaceutical composition of any one of embodiments 163-176, wherein the one or more pharmaceutically acceptable excipients comprise a glidant, and the glidant comprises colloidal silicon dioxide.

178. The pharmaceutical composition of any one of embodiments 163-177, wherein the one or more pharmaceutically acceptable excipients comprise a lubricant, and the lubricant comprises magnesium stearate.

179. The pharmaceutical composition of any one of embodiments 163-178, wherein the one or more pharmaceutically acceptable excipients comprise a disintegrant, and the disintegrant comprises croscarmellose sodium.

180. The pharmaceutical composition of any one of embodiments 163-179, comprising a tablet core, the tablet core comprising:

an intra granular portion comprising the amorphous solid dispersion; and an extra granular portion blended with the intra granular portion.

181. The pharmaceutical composition of embodiment 180, further comprising a coating disposed on the tablet core.

182. The pharmaceutical composition of embodiment 180 or 181, wherein the amorphous solid dispersion is at least about 30 weight % of the tablet core.

183. The pharmaceutical composition of any one of embodiments 180-182, wherein the amorphous solid dispersion is at least about 50 weight % of the tablet core.

184. The pharmaceutical composition of any one of embodiments 180-183, wherein the amorphous solid dispersion is at least about 60 weight % of the tablet core.

185. The pharmaceutical composition of any one of embodiments 180-184, wherein the amorphous solid dispersion is about 50 weight % of the tablet core.

186. The pharmaceutical composition of any one of embodiments 180-185, wherein the amorphous solid dispersion is about 50 to about 70 weight % of the tablet core.

187. The pharmaceutical composition of any one of embodiments 180-186, wherein the amorphous solid dispersion is about 60 to about 65 weight % of the tablet core.

188. The pharmaceutical composition of any one of embodiments 180-187, wherein the intra granular portion further comprises one or more of a filler, a dry binder, a glidant, and a lubricant.

189. The pharmaceutical composition of any one of embodiments 180-188, wherein the extra granular portion further comprises one or more of a filler, a disintegrant, and a lubricant.

190. A method for preparing an amorphous solid dispersion comprising Compound 1:

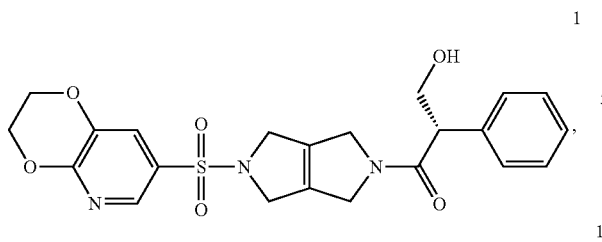

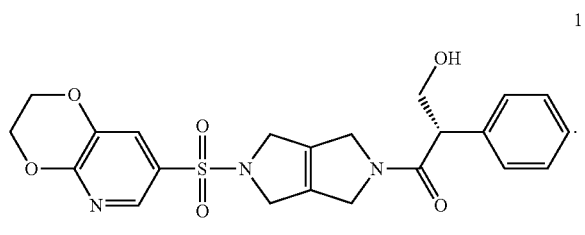 [SMILES: O=C([C@H](CO)c1ccccc1)N1CC2=C(C1)CN(S(=O)(=O)c1cnc3c(c1)OCCO3)C2]

comprising:
mixing Compound 1, a polymer, and a solvent to afford a mixture; and
spray-drying the mixture to afford an amorphous solid dispersion comprising Compound 1.

191. The method of embodiment 190, wherein the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly (methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof 192. The method of embodiment 190 or 191, wherein the polymer is hydroxypropylmethyl cellulose (HPMC) or hydroxypropylmethyl cellulose acetate succinate (HPMC AS).

193. The method of any one of embodiments 190-192, wherein the polymer is hydroxypropylmethyl cellulose acetate succinate (HPMC AS).

194. The method of any one of embodiments 190-193, wherein the weight ratio of Compound 1 to the polymer is in a range of about 3:1 to about 1:3 or about 2:1 to about 1:3.

195. The method of any one of embodiments 190-194, wherein the weight ratio of Compound 1 to the polymer is about 1:3.

196. The method of any one of embodiments 190-194, wherein the weight ratio of Compound 1 to the polymer is about 1:1.

197. The method of any one of embodiments 190-194, wherein the weight ratio of Compound 1 to the polymer is about 1:3, about 2:3, about 1:1, about 1.5:1, about 2:1, or about 3:1.

198. The method of any one of embodiments 190-197, wherein the solvent is dichloromethane and methanol.

199. A product prepared by a process comprising:
mixing Compound 1, a polymer, and a solvent to afford a mixture; and
spray-drying the mixture to afford an amorphous solid dispersion comprising Compound 1:

200. The product of embodiment 199, wherein the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly (methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.

201. The product of embodiment 199 or 200, wherein the polymer is hydroxypropylmethyl cellulose (HPMC) or hydroxypropylmethyl cellulose acetate succinate (HPMC AS).

202. The product of any one of embodiments 199-201, wherein the polymer is hydroxypropylmethyl cellulose acetate succinate (HPMC AS).

203. The product of any one of embodiments 199-202, wherein the weight ratio of Compound 1 to the polymer is in a range of about 3:1 to about 1:3 or about 2:1 to about 1:3.

204. The product of any one of embodiments 199-203, wherein the weight ratio of Compound 1 to the polymer is about 1:3.

205. The product of any one of embodiments 199-203, wherein the weight ratio of Compound 1 to the polymer is about 1:1.

206. The product of any one of embodiments 199-203, wherein the weight ratio of Compound 1 to the polymer is about 1:3, about 2:3, about 1:1, about 1.5:1, about 2:1, or about 3:1.

207. The product of any one of embodiments 199-206, wherein the solvent is dichloromethane and methanol.

208. A pharmaceutical composition comprising Compound 1:

obtained by a process comprising:
  mixing Compound 1 in a solid form, a polymer, and a solvent to afford a mixture; and
  spray-drying the mixture to afford an amorphous solid dispersion comprising Compound 1.
209. The pharmaceutical composition of embodiment 208, wherein the solid form is Type A of Compound 1.
210. The pharmaceutical composition of embodiment 208, wherein the solid form is Type B of Compound 1.
211. The pharmaceutical composition of embodiment 208, wherein the solid form is Type C of Compound 1.
212. The pharmaceutical composition of embodiment 208, wherein the solid form is Type D of Compound 1.
213. The pharmaceutical composition of embodiment 208, wherein the solid form is Type E of Compound 1.
214. The pharmaceutical composition of embodiment 208, wherein the solid form is Type F of Compound 1.
215. The pharmaceutical composition of embodiment 208, wherein the solid form is Type G of Compound 1.
216. The pharmaceutical composition of embodiment 208, wherein the solid form is Type H of Compound 1.
217. The pharmaceutical composition of embodiment 208, wherein the solid form is Type I of Compound 1.
218. The pharmaceutical composition of embodiment 208, wherein the solid form is Type J of Compound 1.
219. The pharmaceutical composition of embodiment 208, wherein the solid form is Type K of Compound 1.
220. The pharmaceutical composition of embodiment 208, wherein the solid form is Type L of Compound 1.
221. The pharmaceutical composition of embodiment 208, wherein the solid form is Type M of Compound 1.
222. The pharmaceutical composition of embodiment 208, wherein the solid form is selected from the group consisting of Type A, Type B, Type C, Type D, Type E, Type F, Type G, Type H, Type I, Type J, Type K, Type L, and Type M of Compound 1.
223. The pharmaceutical composition of embodiment 208, wherein the solid form is amorphous form of Compound 1.
224. The pharmaceutical composition of any one of embodiments 208-223, wherein the pharmaceutical composition has a water content of about 0.5-5.0 weight %.
225. The pharmaceutical composition of any one of embodiments 208-224, wherein the pharmaceutical composition has a water content of about 1.5-4.0 weight %.
226. The pharmaceutical composition of any one of embodiments 208-225, wherein the pharmaceutical composition has a water content of about 2.5-3.0 weight %.
227. The pharmaceutical composition of any one of embodiments 208-226, wherein the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.
228. The pharmaceutical composition of any one of embodiments 208-227, wherein the polymer is hydroxypropylmethyl cellulose (HPMC) or hydroxypropylmethyl cellulose acetate succinate (HPMC AS).
229. The pharmaceutical composition of any one of embodiments 208-228, wherein the polymer is hydroxypropylmethyl cellulose acetate succinate (HPMC AS).
230. The pharmaceutical composition of any one of embodiments 208-229, wherein the weight ratio of Compound 1 to the polymer is in a range of about 3:1 to about 1:3 or about 2:1 to about 1:3.
231. The pharmaceutical composition of any one of embodiments 208-230, wherein the weight ratio of Compound 1 to the polymer is about 1:3.
232. The pharmaceutical composition of any one of embodiments 208-230, wherein the weight ratio of Compound 1 to the polymer is about 1:1.
233. The pharmaceutical composition of any one of embodiments 208-230, wherein the weight ratio of Compound 1 to the polymer is about 1:3, about 2:3, about 1:1, about 1.5:1, about 2:1, or about 3:1.
234. The pharmaceutical composition of any one of embodiments 208-233, wherein the solvent is dichloromethane and methanol.
235. A tablet dosage form comprising a tablet core, the tablet core comprising at least 10 weight % of Compound 1 in amorphous form:

wherein crystalline Compound 1 (Type A) is not observable by XRPD analysis (Method D) of the tablet core.
236. The tablet dosage form of embodiment 235, wherein the tablet core comprises at least 15 weight % of Compound 1 in amorphous form.
237. The tablet dosage form of embodiment 235 or 236, wherein the tablet core comprises at least 30 weight % of Compound 1 in amorphous form.
238. The tablet dosage form of any one of embodiments 235-237, wherein the tablet core comprises about 200 mg of Compound 1 per tablet and has a total weight of no more than about 1200 mg per tablet.
239. The tablet dosage form of embodiment 238, wherein the tablet core has a total weight of no more than about 1100 mg, about 1000 mg, about 900 mg, about 800 mg, or about 700 mg per tablet.
240. A tablet dosage form comprising a tablet core, the tablet core having a total weight of no more than about 1000 mg and comprising about 200 mg of Compound 1 in amorphous form per tablet:

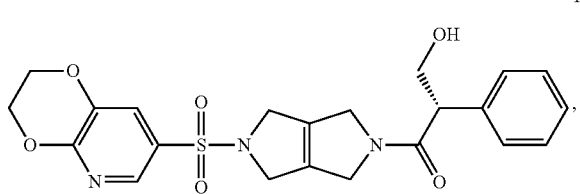

wherein crystalline Compound 1 (Type A) is not observable by XRPD analysis (Method D) of the tablet core.

241. The tablet dosage form of embodiment 240, wherein the tablet core has a total weight of no more than about 800 mg per tablet.

242. The tablet dosage form of any one of embodiments 235-241, wherein the tablet core comprises 0.05-5.0% of Compound 2:

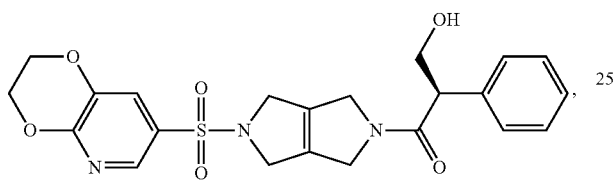

based on the total amount of Compound 1 and Compound 2.

243. The tablet dosage form of embodiment 242, wherein the tablet core comprises 0.05-3.0% of Compound 2, based on the total amount of Compound 1 and Compound 2.

244. The tablet dosage form of embodiment 242 or 243, wherein the tablet core comprises 0.05-2.0% of Compound 2, based on the total amount of Compound 1 and Compound 2.

245. The tablet dosage form of any one of embodiments 242-244, wherein the tablet core comprises 0.05-1.0% of Compound 2, based on the total amount of Compound 1 and Compound 2.

246. The tablet dosage form of any one of embodiments 235-245, wherein crystalline Compound 1 (Type A) is not observable by XRPD analysis (Method D) of the tablet core after storage in a sealed container as described in Example 29 for 1 month at 25° C. and 60% relative humidity.

247. The tablet dosage form of any one of embodiments 235-246, wherein crystalline Compound 1 (Type A) is not observable by XRPD analysis (Method D) of the tablet core after storage in a sealed container as described in Example 29 for 2 months at 25° C. and 60% relative humidity.

248. The tablet dosage form of any one of embodiments 235-247, wherein crystalline Compound 1 (Type A) is not observable by XRPD analysis (Method D) of the tablet core after storage in a sealed container as described in Example 29 for 3 months at 25° C. and 60% relative humidity.

249. The tablet dosage form of any one of embodiments 235-248, wherein crystalline Compound 1 (Type A) is not observable by XRPD analysis (Method D) of the tablet core after storage in a sealed container as described in Example 29 for 1 month at 40° C. and 75% relative humidity.

250. The tablet dosage form of any one of embodiments 235-249, wherein crystalline Compound 1 (Type A) is not observable by XRPD analysis (Method D) of the tablet core after storage in a sealed container as described in Example 29 for 2 months at 40° C. and 75% relative humidity.

251. The tablet dosage form of any one of embodiments 235-250, wherein crystalline Compound 1 (Type A) is not observable by XRPD analysis (Method D) of the tablet core after storage in a sealed container as described in Example 29 for 3 months at 40° C. and 75% relative humidity.

252. The tablet dosage form of any one of embodiments 235-251, wherein Compound 1 is present in an amorphous solid dispersion comprising Compound 1 and a polymer.

253. The tablet dosage form of embodiment 252, wherein the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.

254. The tablet dosage form of embodiment 252 or 253, wherein the polymer is hydroxypropylmethyl cellulose (HPMC) or hydroxypropylmethyl cellulose acetate succinate (HPMC AS).

255. The tablet dosage form of any one of embodiments 252-254, wherein the polymer is hydroxypropylmethyl cellulose acetate succinate (HPMC AS).

256. The tablet dosage form of any one of embodiments 252-255, wherein the weight ratio of Compound 1 to the polymer is in a range of about 3:1 to about 1:3 or about 2:1 to about 1:3.

257. The tablet dosage form of any one of embodiments 252-256, wherein the weight ratio of Compound 1 to the polymer is about 1:3.

258. The tablet dosage form of any one of embodiments 252-256, wherein the weight ratio of Compound 1 to the polymer is about 1:1.

259. The tablet dosage form of any one of embodiments 252-256, wherein the weight ratio of Compound 1 to the polymer is about 1:3, about 2:3, about 1:1, about 1.5:1, about 2:1, or about 3:1.

260. The tablet dosage form of any one of embodiments 235-259, further comprising one or more pharmaceutically acceptable excipients.

261. The tablet dosage form of embodiment 260, wherein the one or more pharmaceutically acceptable excipients comprise one or more of a filler, a dry binder, a glidant, a lubricant, a disintegrant, and a film coating agent.

262. The tablet dosage form of any one of embodiments 235-261, wherein the tablet core comprises:
an intra granular portion comprising Compound 1; and
an extra granular portion blended with the intra granular portion.

263. The tablet dosage form of embodiment 262, wherein the intragranular portion comprises an amorphous solid dispersion comprising Compound 1 and a polymer and one or more of a filler, a dry binder, a glidant, and a lubricant, and the extragranular portion comprises one or more of a filler, a disintegrant, and a lubricant.

264. The tablet dosage form of any one of embodiments 235-263, wherein the intragranular portion comprises:
an amorphous solid dispersion of Compound 1 in an amount of 30-70 weight % of the tablet core;
one or more fillers in an amount of 15-50 weight % of the tablet core;
one or more dry binders in an amount of 2.50-10 weight % of the tablet core;
one or more glidants in an amount of 0.50-1.50 weight % of the tablet core; and
one or more lubricants in an amount of 0.25-1 weight % of the tablet core; and
the extragranular portion comprises:
one or more fillers in an amount of 5-15 weight % of the tablet core;
one or more disintegrants in an amount of 1.25-5 weight % of the tablet core; and
one or more lubricants in an amount of 0.25-1 weight % of the tablet core; or
wherein the tablet dosage form comprises:
an amorphous solid dispersion of Compound 1 in an amount of 50-75 weight % of the tablet core;
one or more fillers in an amount of 15-50 weight % of the tablet core;
one or more dry binders in an amount of 2-10 weight % of the tablet core;
one or more glidants in an amount of <2 weight % of the tablet core;
one or more disintegrants in an amount of 2-10 weight % of the tablet core; and
one or more lubricants in an amount of <2 weight % of the tablet core.

265. The tablet dosage form of embodiment 264, wherein the amorphous solid dispersion comprises Compound 1 and a polymer.

266. The tablet dosage form of embodiment 265, wherein the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly (methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.

267. The tablet dosage form of embodiment 265 or 266, wherein the polymer is hydroxypropylmethyl cellulose acetate succinate (HPMC AS).

268. The tablet dosage form of any one of embodiments 265-267, wherein the weight ratio of Compound 1 to the polymer is in a range of about 3:1 to about 1:3 or about 2:1 to about 1:3.

269. The tablet dosage form of any one of embodiments 265-268, wherein the weight ratio of Compound 1 to the polymer is about 1:3.

270. The tablet dosage form of any one of embodiments 265-269, wherein the weight ratio of Compound 1 to the polymer is about 1:1.

271. The tablet dosage form of any one of embodiments 265-270, wherein the weight ratio of Compound 1 to the polymer is about 1:3, about 2:3, about 1:1, about 1.5:1, about 2:1, or about 3:1.

272. The tablet dosage form of any one of embodiments 264-271, wherein the one or more fillers comprise microcrystalline cellulose or lactose monohydrate.

273. The tablet dosage form of any one of embodiments 264-272, wherein the one or more dry binders comprise crospovidone or crosslinked polyvinylpyrrolidone.

274. The tablet dosage form of any one of embodiments 264-273, wherein the one or more glidants comprise colloidal silicon dioxide or fumed silica.

275. The tablet dosage form of any one of embodiments 264-274, wherein the one or more lubricants comprise magnesium stearate.

276. The tablet dosage form of any one of embodiments 264-275, wherein the one or more disintegrants comprise crocarmellose sodium.

277. A solid oral dosage form comprising a stabilized amorphous compound (S)-1-(5-[2H,3H-[1,4] dioxino[2,3-b]pyridine-7-sulfonyl]-1H,2H,3H,4H,5H,6H-pyrrolo[3,4-c]pyrrol-2-yl)-3-hydroxy-2-phenylpropan-1-one, wherein the stabilized amorphous compound does not show crystallinity by PXRD (Method D) after 2 weeks of storage at 60° C./75% RH (exposed).

278. The solid oral dosage form of embodiment 277, wherein the stabilized amorphous compound shows a single glass transition temperature ($T_G$) and no melt endotherm by DSC (Method B) after 2 weeks of storage at 60° C./75% RH (exposed).

279. The solid oral dosage form of embodiment 277 or 278, wherein the solid oral dosage form contains a total of 200 mg of (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one.

280. The solid oral dosage form of any one of embodiments 277-279, wherein the solid oral dosage form has a total weight of not more than 800 mg.

281. The solid oral dosage form of any one of embodiments 277-280, wherein the solid oral dosage form is a tablet or capsule.

282. The solid oral dosage form of any one of embodiments 277-281, wherein the stabilized amorphous compound is in a spray dried dispersion with a polymer.

283. The solid oral dosage form of embodiment 282, wherein the polymer is selected from the group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof, or is selected from a group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.

284. The solid oral dosage form of embodiment 283, wherein the polymer is HPMC AS.

285. The solid oral dosage form of embodiment 284, wherein the (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one is spray dried with HPMC AS in a weight ratio of 1:3 to 2:1.

286. The solid oral dosage form of embodiment 284, wherein the (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one is spray dried with HPMC AS in a weight ratio of 1:1.

287. A (S)-1-(5-[2H,3H-[1,4]dioxino[2,3-b]pyridine-7-sulfonyl]-1H,2H,3H,4H,5H,6H-pyrrolo[3,4-e]pyrrol-2-yl)-3-hydroxy-2-phenylpropan-1-one active pharmaceutical ingredient (API) composition comprising 0.05-5.0% by HPLC of (R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one.

288. A tablet comprising 200 mg of stabilized amorphous compound (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one as the active pharmaceutical ingredient (API), wherein the stabilized amorphous compound does not show crystallinity by PXRD (Method D) after 2 weeks of storage of the tablet at 60° C./75% RH (exposed).

289. The tablet of embodiment 288, wherein the API comprises less than 5.0% by HPLC of (R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one.

290. The tablet of embodiment 288 or 289, wherein the API comprises less than 0.05% by HPLC of (R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one.

291. The tablet of any one of embodiments 288-290, having a total weight of less than 800 mg.

EXAMPLES

The present teachings include descriptions provided in the Examples that are not intended to limit the scope of any claim. The following non-limiting examples are provided to further illustrate the present teachings. Those of skill in the art, in light of the present application, will appreciate that many changes can be made in the specific embodiments that are provided herein and still obtain a like or similar result without departing from the spirit and scope of the present teachings.

| Abbreviations | | | |
|---|---|---|---|
| ACN | Acetonitrile | MTBE | Methyl tert-butyl ether |
| API | Active Pharmaceutical Ingredient | n-Bu | n-butyl |
| | | ND | Not determined |
| AUC$_{last}$ | Area under the curve from zero to the last measurable point | NMP | N-methyl pyrrolidone |
| | | NMR | Nuclear magnetic resonance |
| DCM | Dichloromethane | | |
| DIEA | Diisopropylethylamine | PTFE | Polytetrafluoroethylene |
| DMAc | Dimethylacetamide | RH | Relative humidity |
| DMF | Dimethylformamide | RRT | Relative retention time |
| DMSO | Dimethyl sulfoxide | RT | Room Temperature |
| DSC | Differential scanning calorimetry | Rt | Retention time |
| | | scfh | Standard cubic feet per hour |
| DVS | Dynamic vapor sorption | | |
| EtOAc | Ethyl acetate | SDD | Spray-dried dispersion |
| EtOH | Ethanol | SEM | Scanning electron microscopy |
| FaSSIF | Fasted state simulated intestinal fluid | SGF | Simulated gastric fluid |
| FeSSIF | Fed state simulated intestinal fluid | SIF | Simulated intestinal fluid |
| h | Hour | TEA | Triethylamine |
| HATU | 1-[bis(dimethylamino) methylene]-1H-1,2,3-triazolo[4,5-b]pyridinium 3-oxide hexafluoro-phosphate | TFA | Trifluoroacetic acid |
| | | T$_G$ | Glass transition temperature |
| | | TGA | Thermogravimetric analysis |
| HPLC | High-performance liquid chromatography | THF | Tetrahydrofuran |
| HPMC | Hydroxypropyl Methylcellulose | TLC | Thin layer chromatography |
| AS-MG | Acetate Succinate MG | TRS | Total related substances |
| IPA | Isopropanol | | |
| LCMS | liquid chromatography mass spectrometry | UPLC | Ultra performance liquid chromatography |
| MeOH | Methanol | | |
| MIBK | Methyl isobutyl ketone | XRPD | X-ray powder diffraction |
| min | Minute | | |

Instrumentation and Methods

Unless otherwise indicated, the following instrumentation and methods were used in the working examples described herein.

X-Ray Powder Diffraction (XRPD or PXRD)

Method A. XRPD analysis was performed with a Panalytical X'Pert3 Powder XRPD on a Si zero-background holder. The 2θ position was calibrated against Panalytical 640 Si powder standard. Details of the XRPD method used in the experiments are listed in Table 1.

TABLE 1

| | Parameters for Reflection Mode |
|---|---|
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0262606 |
| Scan speed (°/s) | 0.066482 |

Method B. XRPD analysis was performed with a Rigaku X-Ray Powder Diffractomer MiniFlex 600 with the parameters listed in Table 2.

TABLE 2

| Parameter | Setting |
|---|---|
| Soller (inc.) | 5.0 deg |
| IHS | 10.0 mm |
| SS | 1.250 deg |
| DS | 1.250 deg |
| Soller (rec) | 5.0 deg |
| RS | 0.3 mm |
| Scan Axis | Theta/2-Theta |
| Mode | Continuous |
| Start (deg) | 2.0000 |
| Stop (deg) | 40.0000 |
| Step (deg) | 0.020 |

TABLE 2-continued

| Parameter | Setting |
| --- | --- |
| Speed (deg/min) | 2.5 |
| Spin | Yes |
| Voltage (kV) | 40 |
| Current (mA) | 15 |

Method C. XRPD analysis was performed with a Panalytical X'Pert3 powder diffractometer in reflection mode. Details of the XRPD method used in the experiments are as follows:

| | Parameters |
| --- | --- |
| X-Ray wavelength | CuKα, Kα1 (Å): 1.540598, Kα2 (Å): 1.544426 Kα2/Kα1 intensity ratio: 0.50 |
| X-Ray tube setting | 45 kV, 40 mA |
| Divergence slit (°) | 1/8 |
| Scan mode | Continuous |
| Scan range (°2TH) | 3°-40° |
| Scan step time (s) | 46.665 |
| Step size (°2TH) | 0.0263 |
| Test time | ~5 min |

Method D. XRPD analysis was performed with the following parameters:

| | Parameters |
| --- | --- |
| Start position (°2TH) | 2.00 |
| Stop position (°2TH) | 40.00 |
| DS (°) | 1.250 |
| RS (mm) | 0.3 |
| SS (°) | 1.250 |
| Step size (°) | 0.02 |
| Rate (°/minute) | 0.50 |

Thermal Analysis (TGA and DSC)

Method A. TGA was conducted using a TA Q500 TGA from TA Instruments. DSC was performed using a TA Q2000 DSC from TA Instruments. Detailed parameters used are listed in Table 3.

TABLE 3

| Parameters | TGA | DSC |
| --- | --- | --- |
| Method | Ramp | Ramp |
| Sample pan | Platinum, open | Aluminum, crimped |
| Temperature | RT-desired temperature | 25° C.-desired temperature |
| Heating rate | 10° C./min | 10° C./min |
| Purge gas | $N_2$ | $N_2$ |

Method B. DSC analysis was conducted with the following procedure: Perform DSC modulated 1.00° C. for 60 seconds with a ramp rate of 2° C./min to 250° C. Use a standby temperature range of 20° to 25° C.

Dynamic Vapor Sorption

Dynamic Vapor Sorption (DVS) was measured with a Surface Measurement System (SMS) DVS Intrinsic. Parameters for DVS analysis are listed in Table 4.

TABLE 4

| Parameters | Values |
| --- | --- |
| Temperature | 25° C. |
| Sample size | 10-20 mg |
| Gas and flow rate | $N_2$, 200 mL/min |

TABLE 4-continued

| Parameters | Values |
| --- | --- |
| dm/dt | 0.002%/min |
| Min. dm/dt stability duration | 10 min |
| Max. equilibrium time | 360 min |
| RH range | Room RH-95% RH-0% RH-95% RH |
| RH step size | 10% |

High-Pressure Liquid Chromatography (HPLC)

Method A. The HPLC parameters and gradient set forth in Tables 5 and 6, respectively, were used for sample analysis.

TABLE 5

| Parameter | Condition |
| --- | --- |
| HPLC System | Waters Alliance HPLC equipped with UV Detector |
| Column | Aglient ZORBAX StableBond-Aq, 4.6 × 150 mm, 3.5 μm, Part No. 863953-914 |
| Column Temperature | 40.0 ± 3.0° C. |
| Sample Temperature | Ambient |
| Detection Wavelength | 210 nm |
| Diluent | 25:75 Water:ACN (v/v) |
| Mobile Phase A | [90:10] 20 mM $NaH_2PO_4 \cdot H_2O$, pH 2.0:ACN (v/v) |
| Mobile Phase B | [20:80] 20 mM $NaH_2PO_4 \cdot H_2O$, pH 2.0:ACN (v/v) |
| Needle Wash | 50:50 MeOH:Water (v/v) |
| Seal Wash/Purge | 10:90 MeOH:Water (v/v) |
| Injection Volume | 20 μL |

TABLE 6

| Time (Minutes) | Flow Rate (mL/min) | % Mobile Phase A | % Mobile Phase B |
| --- | --- | --- | --- |
| 0.0 | 1.0 | 100.0 | 0.0 |
| 5.0 | 1.0 | 80.0 | 20.0 |
| 18.0 | 1.0 | 40.0 | 60.0 |
| 20.0 | 1.0 | 0.0 | 100.0 |
| 24.0 | 1.0 | 0.0 | 100.0 |
| 25.0 | 1.0 | 100.0 | 0.0 |
| 35.0 | 1.0 | 100.0 | 0.0 |

Ultra Performance Liquid Chromatography

The UPLC parameters and linear method gradients disclosed in Table 7 and Table 8, respectively, were used for sample analysis.

TABLE 7

| Parameter | Condition |
| --- | --- |
| System | Waters H-Class UPLC with TUV detector |
| Column | Acquity UPLC BEH Shield RP18, 2.1 × 50 mm, 1.7 μm |
| Column Temperature | 40.0 ± 3.0° C. |
| Sample Temperature | Ambient |
| Mobile Phase A | 0.1% Phosphoric Acid in [90:10] Water:ACN |
| Mobile Phase B/Needle Wash | 0.1% Phosphoric Acid in ACN |
| Flow Rate | 0.500 mL/min |
| Gradient | See Table 8 |
| Injection Volume | 2.0 μL |
| Run Time | 6.50 minutes |
| Detection Wavelength | 293 nm |
| Sampling Rate | 20 points/sec |

TABLE 8

| Time (Minutes) | Flow Rate (mL/min) | % Mobile Phase A | % Mobile Phase B |
|---|---|---|---|
| 0.00 | 0.500 | 100.0 | 0.0 |
| 1.00 | 0.500 | 100.0 | 0.0 |
| 3.50 | 0.500 | 0.0 | 100.0 |
| 4.00 | 0.500 | 0.0 | 100.0 |
| 4.01 | 0.500 | 100.0 | 0.0 |
| 6.50 | 0.500 | 100.0 | 0.0 |

Water Content

Water content was determined by USP <921>, Method 1c.

Dissolution

Except where otherwise indicated, dissolution of the tablets is performed with USP Apparatus 2 (paddles) by USP<711>. The determination of assay is achieved by quantitation against an external reference standard using a reversed phase gradient UPLC method. The UPLC method utilizes an Acquity UPLC BEH Shield column with two mobile phases, both consisting of acetonitrile, water, and phosphate buffer.

Example 1—Synthesis of (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (1)

Figure 2:
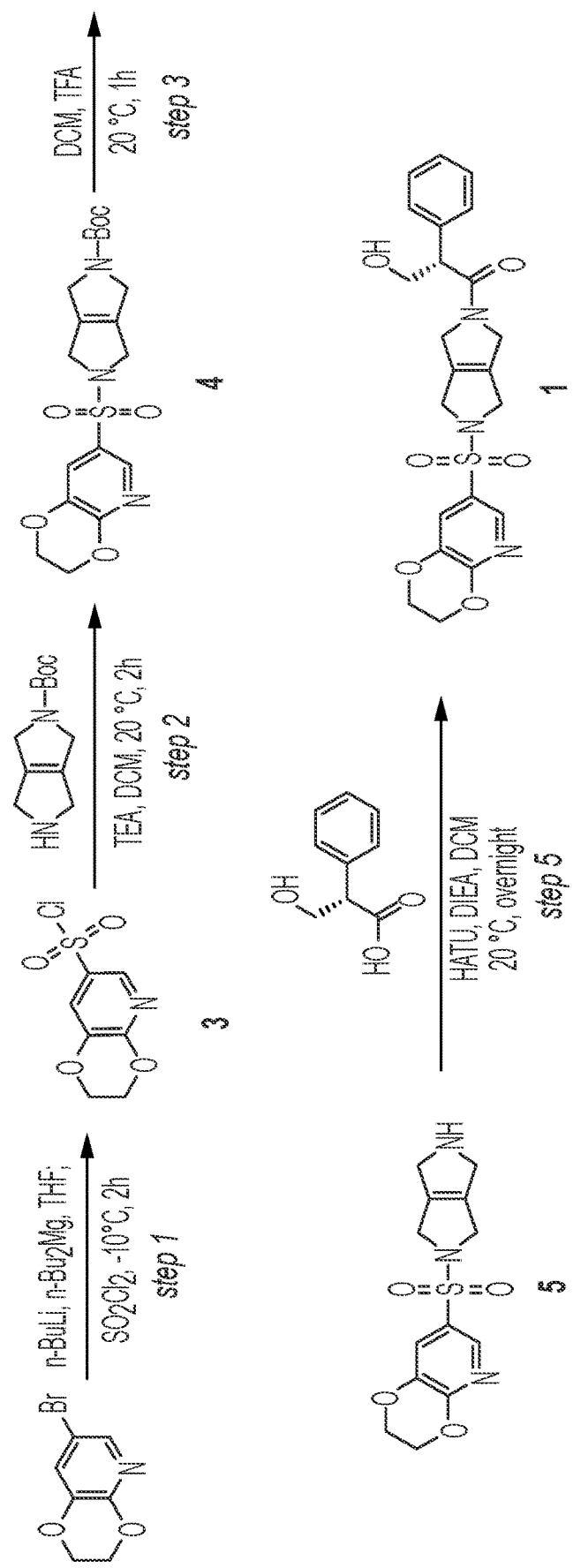
FIG. 2 depicts an alternative reaction scheme to prepare Compound 1.

The PKR Activating Compound 1 can be obtained by the method described herein and the reaction schemes shown in FIGS. 1 and 2. Compound 1 has a molecular weight of 457.50 Da.

Step 1. 2H,3H-[1,4]dioxino[2,3-b]pyridine-7-sulfonyl chloride (3)

Into a 100 mL round-bottom flask purged and maintained with an inert atmosphere of nitrogen was placed a solution of n-BuLi in hexane (2.5 M, 2 mL, 5.0 mmol, 0.54 equiv) and a solution of n-Bu$_2$Mg in heptanes (1.0 M, 4.8 mL, 4.8 mmol, 0.53 equiv). The resulting solution was stirred for 10 min at RT (20° C.). This was followed by the dropwise addition of a solution of 7-bromo-2H,3H-[1,4]dioxino[2,3-b]pyridine (2 g, 9.26 mmol, 1.00 equiv) in tetrahydrofuran (16 mL) with stirring at −10° C. in 10 min. The resulting mixture was stirred for 1 h at −10° C. The reaction mixture was slowly added to a solution of sulfuryl chloride (16 mL) at −10° C. The resulting mixture was stirred for 0.5 h at −10° C. The reaction was then quenched by the careful addition of 30 mL of saturated ammonium chloride solution at 0° C. The resulting mixture was extracted with 3×50 mL of dichloromethane. The organic layers were combined, dried over anhydrous sodium sulfate, filtered and concentrated under vacuum. The residue was purified by silica gel column chromatography, eluting with ethyl acetate/petroleum ether (1:3). This provided 1.3 g (60%) of 2H,3H-[1,4]dioxino[2,3-b]pyridine-7-sulfonyl chloride as a white solid. LCMS m/z: calculated for C$_7$H$_6$ClNO$_4$S: 235.64; found: 236 [M+H]$^+$.

Step 2. tert-Butyl 5-[2H, 3H-[1,4]dioxino[2,3-b]pyridine-7-sulfonyl]-1H, 2H, 3H, 4H, 5H, 6H-pyrrolo[3,4-c]pyrrole-2-carboxylate (4)

Into a 100-mL round-bottom flask was placed 2H,3H-[1,4]dioxino[2,3-b]pyridine-7-sulfonyl chloride (1.3 g, 5.52 mmol, 1.00 equiv), tert-butyl 1H,2H,3H,4H,5H,6H-pyrrolo[3,4-c]pyrrole-2-carboxylate (1.16 g, 5.52 mmol), dichloromethane (40 mL), and triethylamine (1.39 g, 13.74 mmol, 2.49 equiv). The solution was stirred for 2 h at 20° C., then diluted with 40 mL of water. The resulting mixture was extracted with 3×30 mL of dichloromethane. The organic layers were combined, dried over anhydrous sodium sulfate, filtered and concentrated under vacuum. The residue was purified by silica gel column chromatography, eluting with dichloromethane/methanol (10:1). This provided 1.2 g (53%) of tert-butyl 5-[2H,3H-[1,4]dioxino[2,3-b]pyridine-7-sulfonyl]-1H,2H,3H,4H,5H,6H-pyrrolo[3,4-c]pyrrol e-2-carboxylate as a yellow solid. LCMS m/z: calculated for C$_{18}$H$_{23}$N$_3$O$_6$S: 409.46; found: 410 [M+H]$^+$.

Step 3. 2-[2H,3H-[1,4]dioxino[2,3-b]pyridine-7-sulfonyl]-1H,2H,3H,4H,5H,6H-pyrrolo[3,4-c]pyrrole (5)

Into a 100-mL round-bottom flask was placed tert-butyl 5-[2H,3H-[1,4]dioxino[2,3-b]pyridine-7-sulfonyl]-1H,2H,3H,4H,5H,6H-pyrrolo[3,4-c]pyrrole-2-carboxylate (1.2 g, 2.93 mmol, 1.00 equiv), dichloromethane (30 mL), and trifluoroacetic acid (6 mL). The solution was stirred for 1 h at 20° C. The resulting mixture was concentrated under vacuum. The residue was dissolved in 10 mL of methanol and the pH was adjusted to 8 with sodium bicarbonate (2 mol/L). The resulting solution was extracted with 3×10 mL of dichloromethane. The organic layers were combined, dried over anhydrous sodium sulfate, filtered and concentrated under vacuum. The crude product was purified by silica gel column chromatography, eluting with dichloromethane/methanol (10:1). This provided 650 mg (72%) of 2-[2H,3H-[1,4]dioxino[2,3-b]pyridine-7-sulfonyl]-1H,2H,3H,4H,5H,6H-pyrrolo[3,4-c]pyrrole as a yellow solid. LCMS m/z: calculated for C$_{13}$H$_{15}$N$_3$O$_4$S: 309.34; found: 310 [M+H]$^+$.

Step 4. (S)-1-(5-[2H, 3H-[1,4]dioxino[2,3-b]pyridine-7-sulfonyl]-1H, 2H, 3H, 4H, 5H,6H-pyrrolo[3,4-c]pyrrol-2-yl)-3-hydroxy-2-phenylpropan-1-one (1) and (R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (2)

Into a 100 mL round-bottom flask was placed 2-[2H,3H-[1,4]dioxino[2,3-b]pyridine-7-sulfonyl]-1H,2H,3H,4H,5H,6H-pyrrolo[3,4-c]pyrrole (150 mg, 0.48 mmol, 1.00 equiv), 3-hydroxy-2-phenylpropanoic acid (97 mg, 0.58 mmol, 1.20 equiv), dichloromethane (10 mL), HATU (369 mg, 0.97 mmol, 2.00 equiv) and DIEA (188 mg, 1.46 mmol, 3.00 equiv). The resulting solution was stirred overnight at 20° C. The reaction mixture was diluted with 20 mL of water and was then extracted with 3×20 mL of dichloromethane. The organic layers were combined, dried over anhydrous sodium sulfate, filtered and concentrated under vacuum. The residue was purified by prep-TLC eluted with dichloromethane/methanol (20:1) and further purified by prep-HPLC (Column: XBridge C18 OBD Prep Column, 100 Å, 5-µm, 19 mm×250 mm; Mobile Phase A: water (10 mmol/L NH$_4$HCO$_3$), Mobile Phase B: MeCN; Gradient: 15% B to 45% B over 8 min; Flow rate: 20 mL/min; UV Detector: 254 nm). The two enantiomers were separated by prep-Chiral HPLC (Column, Daicel CHIRALPAK® IF, 2.0 cm×25 cm, 5-µm; mobile phase A: DCM, phase B: MeOH (hold 60% MeOH over 15 min); Flow rate: 16 mL/min; Detector, UV 254 & 220 nm). This resulted in peak 1 (2, Rt: 8.47 min) 9.0 mg (4%) of (R)-1-(5-[2H,3H-[1,4]dioxino[2,3-b]pyridine-7- sulfonyl]-1H,2H,3H,4H,5H,6H-pyrrolo[3,4-c]pyrrol-2-yl)-3-hydroxy-2-phenylpropan-1-one as a yellow solid; and peak 2 (1, Rt: 11.83 min) 10.6 mg (5%) of (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one as a yellow solid.

(1): $^1$H NMR (400 MHz, DMSO-d$_6$) δ 8.13 (d, J=2.0 Hz, 1H), 7.61 (d, J=2.0 Hz, 1H), 7.31-7.20 (m, 5H), 4.75 (t, J=5.2 Hz, 1H), 4.50-4.47 (m, 2H), 4.40-4.36 (m, 1H), 4.32-4.29 (m, 2H), 4.11-3.87 (m, 8H), 3.80-3.77 (m, 1H), 3.44-3.41 (m, 1H). LC-MS (ESI) m/z: calculated for $C_{22}H_{23}N_3O_6S$: 457.13; found: 458.0 [M+H]$^+$.

(2): $^1$H NMR (400 MHz, DMSO-d$_6$) δ 8.13 (d, J=2.0 Hz, 1H), 7.60 (d, J=2.0 Hz, 1H), 7.31-7.18 (m, 5H), 4.75 (t, J=5.2 Hz, 1H), 4.52-4.45 (m, 2H), 4.40-4.36 (m, 1H), 4.34-4.26 (m, 2H), 4.11-3.87 (m, 8H), 3.80-3.78 (m, 1H), 3.44-3.43 (m, 1H). LC-MS (ESI) m/z: calculated for $C_{22}H_{23}N_3O_6S$: 457.13; found: 458.0 [M+H]$^+$.

Step 5. (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (1)

Alternatively, Compound 1 can be synthesized using the procedure described here as Step 5.

3-Hydroxy-2-phenylpropanoic acid (1 g) was separated by Prep-SFC with the following conditions: Instrument Name: SHIMADZU LC-20AD, LC parameters: Pump Mode: Binary gradient, Start Conc. of Pump B: 100.0%, Total Flow: 170 mL/min, Phase A, Phase B: MeOH (0.1% HAC), Column Name: CHIRALPAK AD-H, Length: 100 mm, Internal Diameter: 4.6 mm, Particle Size: 5-μm, Column Temp: 20° C., PDA Model: SPD-M20A, Wavelength: from 190 nm to 500 nm. This provided peak 1: (Rt=5.76 min) 380 mg of (S)-3-hydroxy-2-phenylpropanoic acid as a white solid, and peak 2: (Rt=6.87 min) 370 mg of (R)-3-hydroxy-2-phenylpropanoic acid as a white solid. $^1$H NMR (300 MHz, DMSO-d$_6$): δ ppm 12.31 (br s, 1H), 7.40-7.20 (m, 5H), 4.94 (br s, 1H), 3.92 (t, J=9 Hz, 1H), 3.67-3.54 (m, 2H). S-enantiomer: $\alpha_D^{16.7}$=−110 (C 0.02, water); [literature: −79] R-enantiomer: $\alpha_D^{16.7}$=+125 (C 0.02, water).

A solution of 7-((3,4,5,6-tetrahydropyrrolo[3,4-c]pyrrol-2(1H)-yl)sulfonyl)-2,3-dihydro-[1,4]dioxino[2,3-b]pyridine (130.9 mg, 0.423 mmol) in DMF (2.5 ml) was cooled on an ice bath, then treated with (S)-3-hydroxy-2-phenylpropanoic acid (84.8 mg, 0.510 mmol), HATU (195.5 mg, 0.514 mmol), and DIEA (0.30 mL, 1.718 mmol) and stirred at ambient temperature overnight. The solution was diluted with EtOAc (20 mL), washed sequentially with water (20 mL) and brine (2×20 mL), dried (MgSO$_4$), filtered, treated with silica gel, and evaporated under reduced pressure. The material was chromatographed by Biotage MPLC (10 g silica gel column, 0 to 5% MeOH in DCM) to provide a white, slightly sticky solid. The sample was reabsorbed onto silica gel and chromatographed (10 g silica gel column, 0 to 100% EtOAc in hexanes) to provide (2S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (106.5 mg, 0.233 mmol, 55% yield) as a white solid.

Example 2—Preparation and Characterization of Type A of Compound 1

Preparation of Type A of Compound 1

A 1 L round-bottom flask with overhead stirring, a temperature probe, and an N$_2$ inlet was charged with 7-((3,4,5,6-tetrahydropyrrolo[3,4-c]pyrrol-2(1H)-yl)sulfonyl)-2,3-dihydro-[1,4]dioxino[2,3-b]pyridine (33.24 g, 96 mmol), (S)-3-hydroxy-2-phenylpropanoic acid (19.08 g, 115 mmol), and DMF (361 ml). The mixture was cooled to 0° C., HATU (43.7 g, 115 mmol) was added, and a mild ~5° C. exotherm was observed. DIEA (70.2 ml, 402 mmol) was added dropwise over 20 minutes, and the pot was held near 0° C. The reaction mixture was sampled after 2 h and then after 3 h. After 3 h, an additional 50 mL of DMF was added to thin the reaction mixture.

After 3.5 h at 0° C., 37 volumes of DCM was added to the reaction mixture, and the solution was transferred to a 4 L separatory funnel and washed with water (2060 mL). The organic layer was then washed 3×2060 mL of brine (26% W/W NaCl) and dried overnight with MgSO$_4$. The solution was concentrated on a rotary evaporator to afford a waxy white solid (>80 g).

The solids were triturated with 500 mL of 5:4 EtOAc/hexanes, filtered, washed with 100 mL of 1:1 EtOAc/Hexanes, and dried in a vacuum oven at ambient temperature to afford 50.3 g of a white solid.

The resulting material was ground in a mortar, charged to a 3 L round-bottom flask with overhead stirring and slurried with 1900 mL of ethanol. The slurry was heated to 76° C., and water was added dropwise. After 40 mL of water had added, the mixture was filtered with a Buchner funnel. The filtrate was charged back to the round-bottom flask, stirred overnight, and cooled slowly to room temperature.

The resulting slurry was cooled to 10° C., stirred for 1 h, and filtered. The round-bottom flask and filter cake were washed with 100 mL of ethanol. The filter cake was dried on the funnel for 1 h, and overnight in a vacuum oven at ambient temperature to afford 38.43 g of Compound 1 a white solid, which was designated as Type A of Compound 1.

Characterization of Type A of Compound 1

Type A was characterized by XRPD (Method A), TGA (Method A), DSC (Method A), and DVS analysis.

Figure 3:
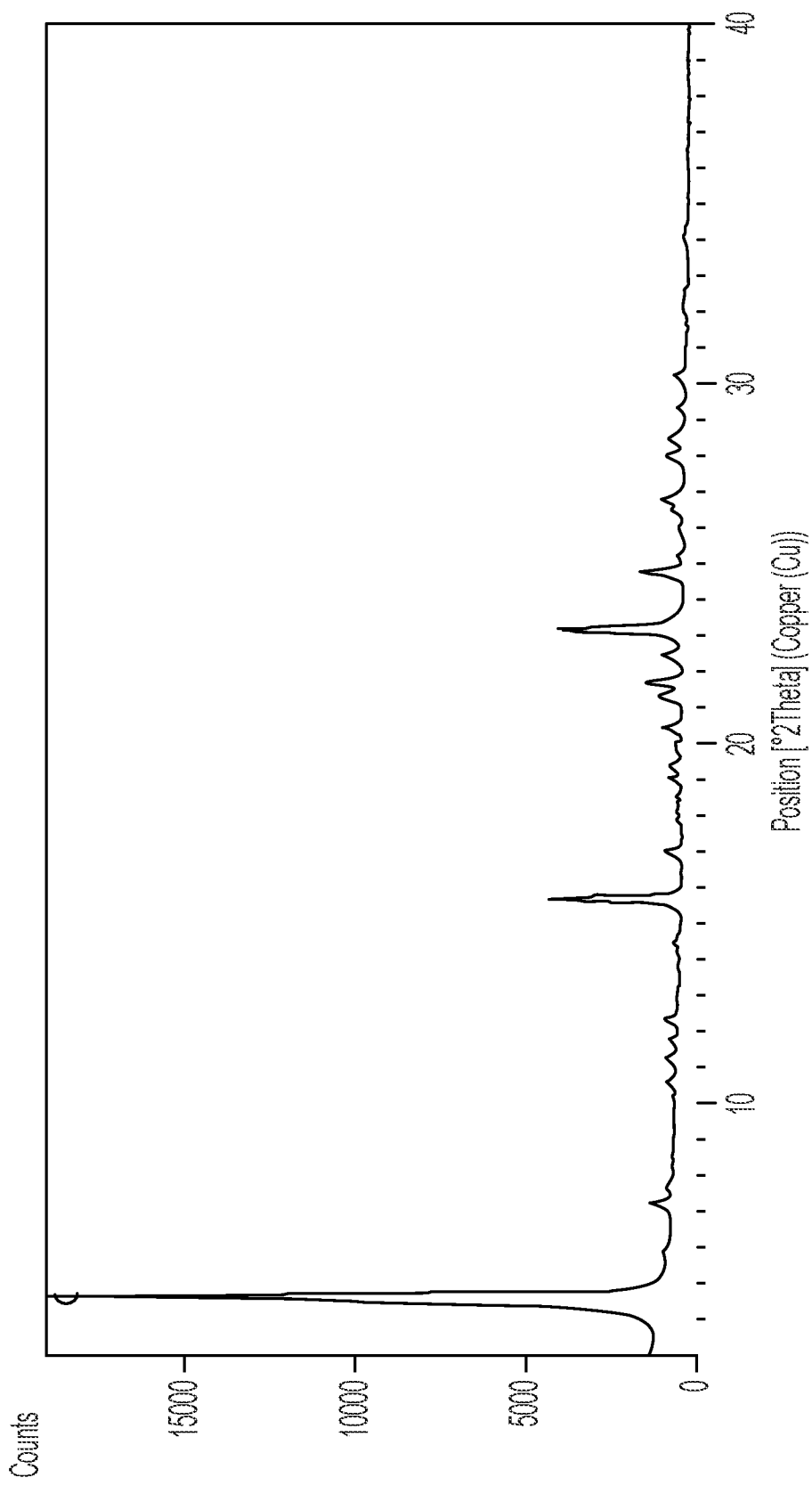
FIG. 3 depicts an XRPD pattern of Compound 1 crystalline form Type A.

The XRPD pattern for Type A is depicted in FIG. 3, and the corresponding data are summarized in the following table:

| Pos. [°2Th.] | d-spacing [Å] |
| --- | --- |
| 4.61 | 19.19 |
| 5.80 | 15.24 |
| 7.22 | 12.25 |
| 7.68 | 11.50 |
| 11.21 | 7.89 |
| 12.31 | 7.19 |
| 14.44 | 6.13 |
| 15.66 | 5.66 |
| 16.95 | 5.23 |
| 18.02 | 4.92 |
| 19.20 | 4.62 |
| 20.48 | 4.34 |
| 21.35 | 4.16 |
| 21.66 | 4.10 |
| 22.47 | 3.96 |
| 23.19 | 3.84 |
| 24.76 | 3.60 |
| 26.73 | 3.34 |
| 28.01 | 3.19 |
| 28.49 | 3.13 |
| 29.35 | 3.04 |
| 30.25 | 2.95 |
| 32.14 | 2.79 |
| 34.12 | 2.63 |
| 36.46 | 2.46 |

The foregoing XRPD data for Type A can also be rounded to a single decimal place, as summarized in the following table:

| Pos. [°2Th.] | d-spacing [Å] |
|---|---|
| 4.6 | 19.2 |
| 5.8 | 15.2 |
| 7.2 | 12.2 |
| 7.7 | 11.5 |
| 11.2 | 7.9 |
| 12.3 | 7.2 |
| 14.4 | 6.1 |
| 15.7 | 5.7 |
| 16.9 | 5.2 |
| 18.0 | 4.9 |
| 19.2 | 4.6 |
| 20.5 | 4.3 |
| 21.3 | 4.2 |
| 21.7 | 4.1 |
| 22.5 | 4.0 |
| 23.2 | 3.8 |
| 24.8 | 3.6 |
| 26.7 | 3.3 |
| 28.0 | 3.2 |
| 28.5 | 3.1 |
| 29.4 | 3.0 |
| 30.3 | 3.0 |
| 32.1 | 2.8 |
| 34.1 | 2.6 |
| 36.5 | 2.5 |

Figure 4:
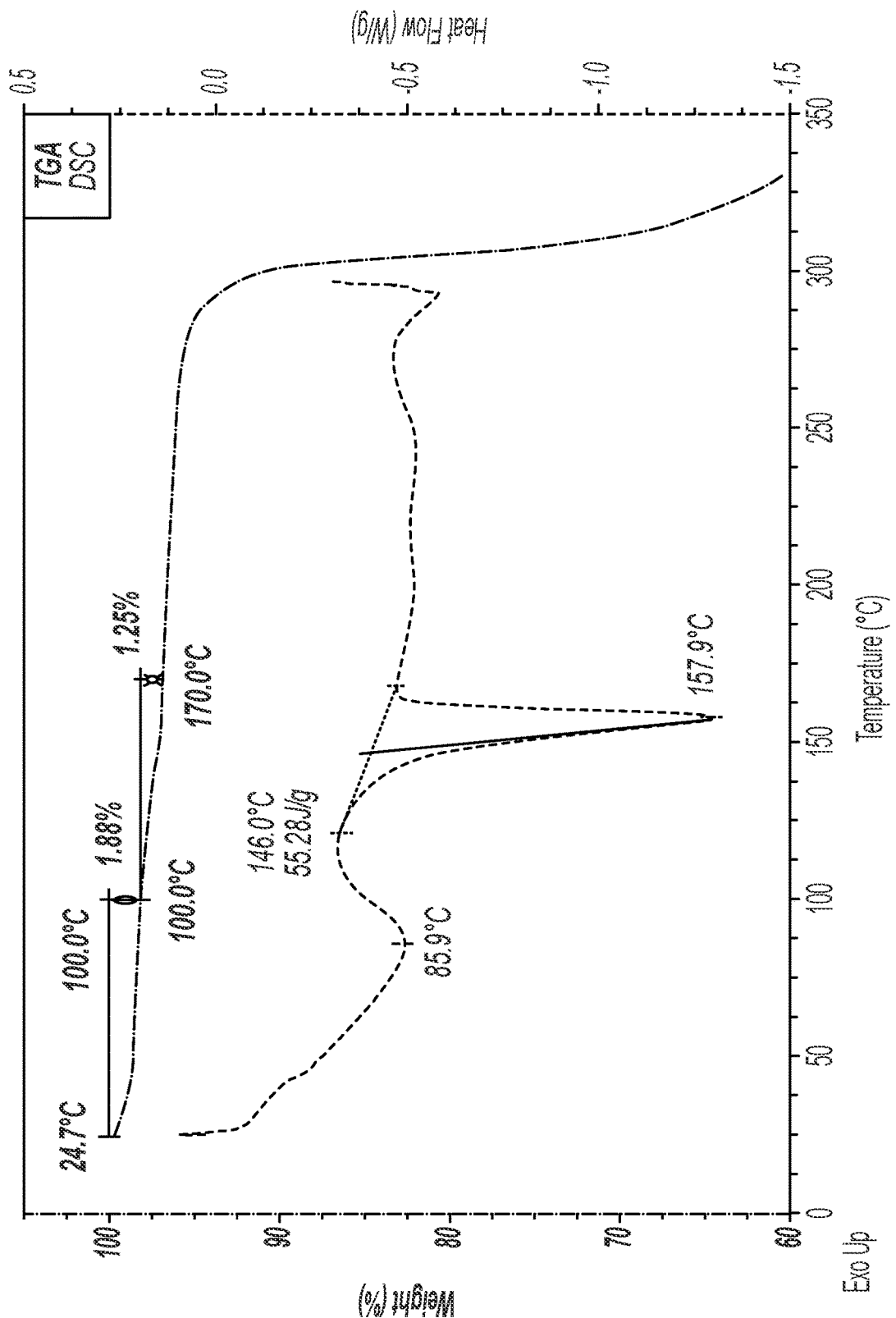
FIG. 4 depicts a thermogravimetric analysis (TGA) curve (upper curve) and a differential scanning calorimetry (DSC) thermogram (lower curve) for Compound 1 crystalline form Type A.

The TGA and DSC curves for Type A are shown in FIG. 4. As shown in FIG. 4, Type A showed 1.9% weight loss up to 100° C. by TGA and two endotherms at 85.9° C. (peak temperature) and 146.0° C. (onset temperature) by DSC.

Figure 5:
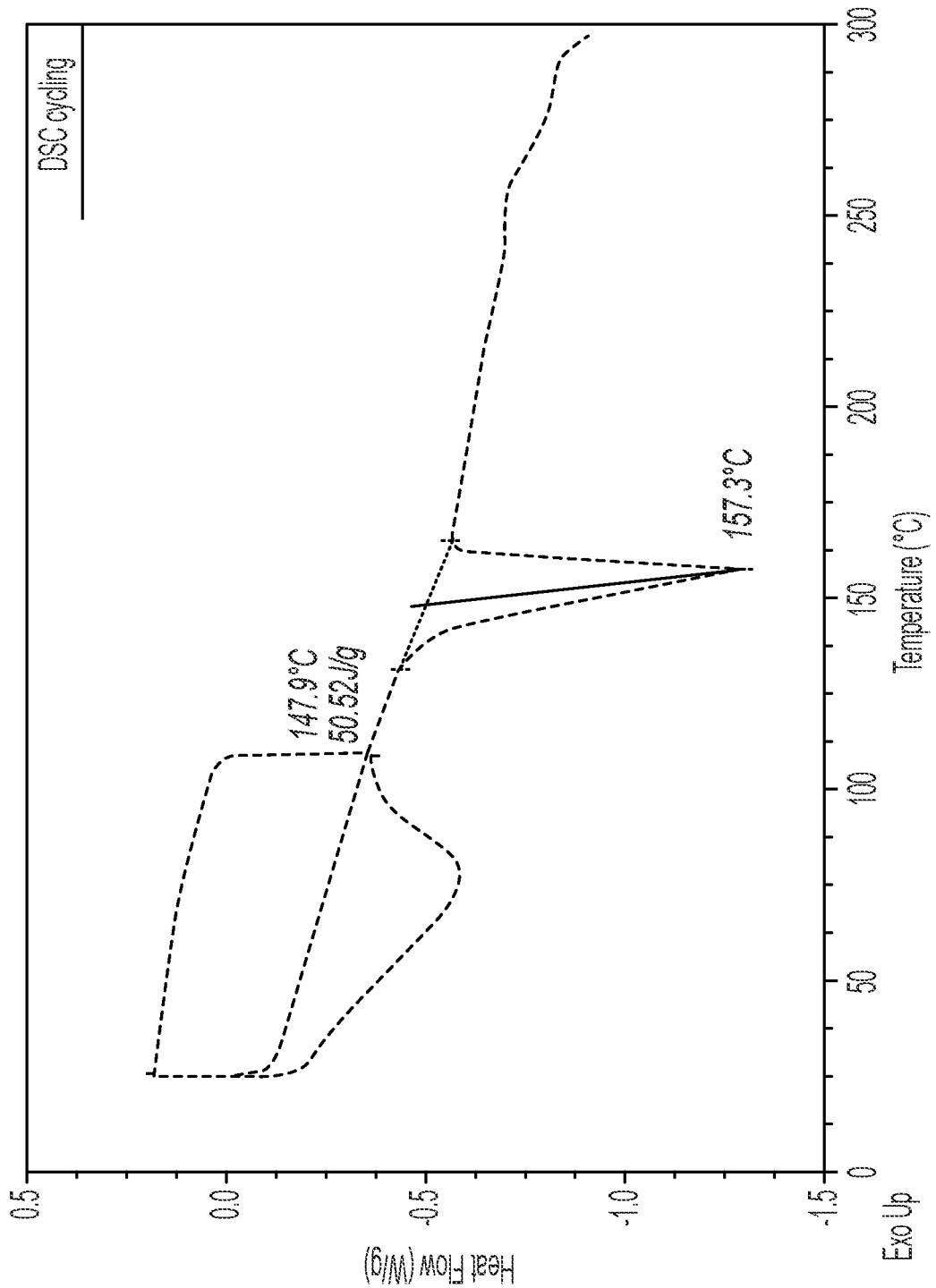
FIG. 5 depicts a DSC cycling thermogram for Compound 1 crystalline form Type A.

By DSC cycling as shown in FIG. 5, Type A was heated to 120° C. and cooled to 25° C., then heated up to 300° C. No endotherm below 100° C. was observed in the second heating cycle. XRPD analysis after DSC cycling showed no form change compared to Type A (FIG. 3).

Figure 6:
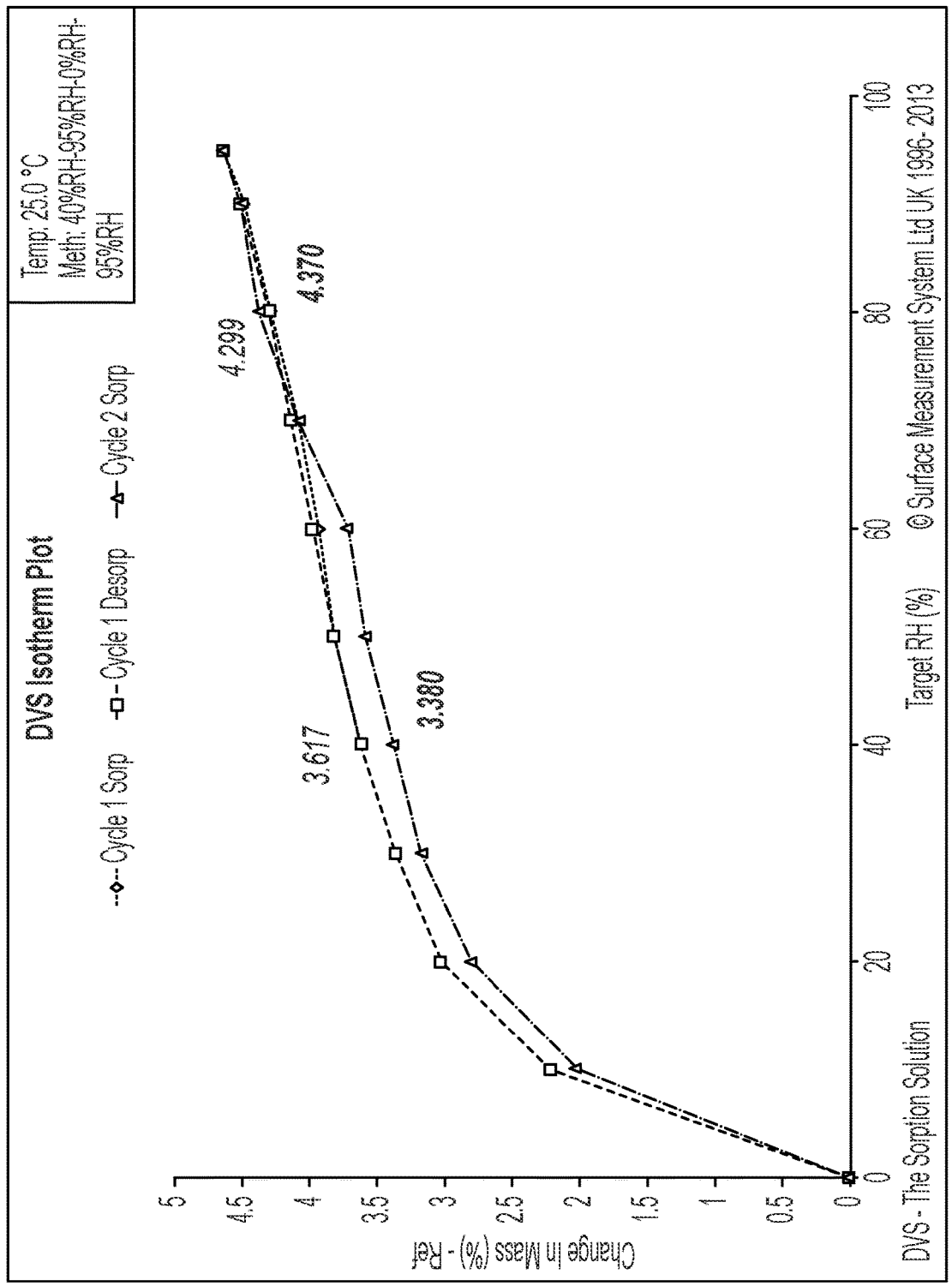
FIG. 6 depicts a dynamic vapor sorption (DVS) isotherm for Compound 1 crystalline form Type A.

DVS results showed a 3.4% water uptake up to 40% RH (ambient condition), and 1.0% water uptake from 40% RH to 80% RH at RT, indicating that Type A is hygroscopic (FIG. 6). No form change was observed for Type A before and after DVS test at RT, as determined by XRPD.

Based on the foregoing analytical data, Type A is believed to be a channel hydrate.

Example 3—Polymorph Screening of Compound 1

Polymorph screening experiments were performed using a series of crystallization and solid transition methods.

Solid Vapor Diffusion

Solid vapor diffusion experiments were conducted using 13 different solvents. Approximately 15 mg of Compound 1 (Type A) was weighed into a 4-mL vial, which was placed into a 20-mL vial with 3 mL of volatile solvent. The 20-mL vial was sealed with a cap and kept at RT for 7 days, allowing solvent vapor to interact with the sample. The solids were characterized by XRPD analysis (Method A), and the results summarized in Table 9 showed that Type A or a mixture of Types A and D were obtained.

TABLE 9

| Solvent | Solid Form |
|---|---|
| $H_2O$ | Type A |
| EtOH | Type A |
| Toluene | Type A |

TABLE 9-continued

| Solvent | Solid Form |
|---|---|
| Acetone | Type A |
| ACN | Type A |
| DCM | Type A |
| THF | Type D + Type A |
| $CHCl_3$ | Type A |
| MeOH | Type A |
| IPA | Type A |
| 1,4-Dioxane | Type A |
| DMSO | Type A |
| EtOAc | Type A |

Slurry Conversion at 4° C., RT or 50° C.

Slurry experiments were conducted at RT in different solvent systems. About 15 mg of Compound 1 (Type A) was suspended in 0.3 mL of solvent in a 2-mL glass vial. After the suspension was stirred magnetically for 7 days at 4° C., RT or 50° C., the remaining solids were isolated for XRPD analysis (Method A). Results summarized in Table 10 indicated that Type A, B, C and D, or mixtures thereof, were obtained.

TABLE 10

| Solvent (v:v) | Temperature (° C.) | Solid Form |
|---|---|---|
| $H_2O$ | 50° C. | Type B |
| MeOH | | Type B |
| EtOAc | | Type A |
| MIBK | | Type A |
| Toluene | | Type A |
| Acetone | RT | Type A |
| 1,4-Dioxane | | Type C |
| $DMSO/H_2O$ (1/9) | | Type B |
| THF | 4° C. | Type D |
| ACN | | Type A |
| $CHCl_3$/Toluene (1/3) | | Type B + Type A |
| DCM/n-Heptane (1/3) | | Type A |
| EtOH | 50° C. | Type A |
| IPA | | Type A |
| IPAc | | Type A |
| MTBE | | Type A |
| n-Heptane | | Type A |
| 2-MeTHF | | Type A |
| 1,4-Dioxane | | Type A |
| THF | | Type A |
| $CHCl_3$/MeOH (v/v, 1:3) | | Type A |
| Acetone/$H_2O$ (v/v, 1:3) | | Type B |
| $CHCl_3$/EtOAc (v/v, 1:3) | | Type A |
| ACN/IPA (v/v, 1:3) | | Type A |
| Acetone/IPAc (v/v, 1:3) | | Type A |
| DCM/EtOH (v/v, 1:3) | | Type A |
| 1,4-Dioxane/MeOH (v/v, 1:1) | | Type A |
| 1,4-Dioxane/Toluene (v/v, 1:1) | | Type A |

Liquid Vapor Diffusion

Approximately 15 mg of Compound 1 (Type A) was dissolved in an appropriate solvent to obtain a clear solution in a 4-mL vial. This solution was then placed into a 20-mL vial with 3 mL of anti-solvent. The 20-mL vial was sealed with a cap and kept at RT, allowing sufficient time for organic vapor to interact with the solution. After 7 days, solids were isolated for XRPD analysis (Method A). The results summarized in Table 11 showed that Type A and B were generated.

TABLE 11

| Solvent | Anti-solvent | Solid Form |
|---|---|---|
| THF | MeOH | Type A |
| | EtOAc | Type A |

TABLE 11-continued

| Solvent | Anti-solvent | Solid Form |
|---|---|---|
| 1,4-Dioxane | Toluene | Type A |
|  | MTBE | Type A |
| 1,4-Dioxane | MeOH | Type B |
|  | EtOAc | Type A |
|  | n-Heptane | Type F |
| Acetone | H$_2$O | Type B |
|  | IPA | Type A |
|  | MIBK | Type A |
| CHCl$_3$ | EtOH | Type A |
|  | 2-MeTHF | Type A |
|  | IPAc | Type A |

Another series of liquid vapor diffusion experiments was performed under the conditions set forth in Table 12. Compound 1 (Type A) was weighed into a 3 mL glass vial with the addition of the corresponding solvent or solvent mixture. After being vortexed and ultrasonically shaken, the suspension was filtered, and the filtrate was transferred to a clean 4 mL shell vial. A small amount of Compound 1 (Type A) was added as a seed crystal. Subsequently, the shell vial was sealed with a polyethylene plug with one pinhole and enclosed in a 20 mL glass vial containing 3 mL of the anti-solvent at room temperature for liquid vapor diffusion. The solid forms resulting from the experiments were characterized by XRPD analysis (Method C).

TABLE 12

| Amount of Compound 1 (mg) | Solvent | Solvent Volume (mL) | Anti-Solvent | Solid Form |
|---|---|---|---|---|
| 3.0 | MeOH | 0.5 | MTBE | Type B |
| 10.0 | ACN | 0.5 | MTBE | Type B |
| 10.1 | ACN | 0.5 | H$_2$O | Type B |
| 34.3 | CHCl$_3$ | 0.3 | n-pentane | Type A |
| 4.9 | Acetone | 0.5 | MTBE | Type A |
| 17.5 | 1,4-dioxane | 0.5 | H$_2$O | Clear solution |
| 17.6 | 1,4-dioxane | 0.5 | n-heptane | Type A |
| 11.5 | THF | 0.5 | MeOH | Type D |
| 12.1 | THF | 0.5 | EtOAc | Type M |
| 10.4 | THF | 0.5 | n-pentane | Type D |
| 31.9 | DMSO | 0.2 | H$_2$O | Type A |
| 10.8 | DMSO | 0.1 | IPA | Type A |
| 32.1 | DMF | 0.2 | Toluene | Type H |
| 10.9 | DMF | 0.1 | IPAc | Type I |
| 30.8 | NMP | 0.2 | MTBE | Type J |
| 10.3 | NMP | 0.1 | H$_2$O | Clear solution |

Slow Evaporation

Slow evaporation experiments were performed under 4 conditions. Briefly, about 15 mg of Compound 1 (Type A) was mixed with 1.0-2.5 mL of solvent in a 4-mL glass vial. If the solids were not dissolved completely, suspensions were filtered using a PTFE membrane (pore size of 0.2 μm) and the filtrates were used for the follow-up steps. The visually clear solutions were subjected to evaporation at RT with vials sealed by Parafilm® (3-5 pinholes). The solids were isolated for XRPD analysis (Method A), and the results summarized in Table 13 indicated that only Type A was obtained.

TABLE 13

| Solvent | Solid Form |
|---|---|
| Acetone | Type A |
| THF | Type A |

TABLE 13-continued

| Solvent | Solid Form |
|---|---|
| CHCl$_3$ | Type A |
| DCM | Type A |

Another series of slow evaporation experiments was performed under the conditions set forth in Table 14. Compound 1 (Type A) was weighed into a 3 mL glass vial with the addition of the corresponding solvent or solvent mixture. After being vortexed and ultrasonically shaken, the suspension was filtered, and the filtrate was transferred to a clean 4 mL shell vial. A small amount of Compound 1 (Type A) was added as a seed crystal. Subsequently, the shell vial was sealed with a polyethylene plug with one pinhole and placed in a fume hood at room temperature for slow evaporation. The solid forms resulting from the experiments were characterized by XRPD analysis (Method C).

TABLE 14

| Amount of Compound 1 (mg) | Solvent | Solvent Volume (mL) | Solid Form |
|---|---|---|---|
| 3.0 | MeOH | 1.0 | Type B |
| 3.2 | EtOAc | 1.0 | Type B |
| 10.0 | ACN | 0.5 | Type B |
| 4.6 | Acetone | 0.5 | Type A |
| 10.1 | THF | 0.5 | Type D |
| 5.2 | MeOH/Acetone (1:1 v/v) | 0.5 | Type B |
| 3.2 | EtOAc/2-MeTHF (1:1 v/v) | 0.5 | Type B |
| 4.5 | Acetone/EtOH (1:1 v/v) | 0.5 | Type A |
| 4.7 | Acetone/EtOAc (1:1 v/v) | 0.5 | Type A |
| 13.0 | Acetone/H$_2$O (5:1 v/v) | 0.5 | Type B |
| 13.8 | ACN/EtOH (1:1 v/v) | 0.5 | Type A |
| 17.3 | ACN/IPA (4:1 v/v) | 0.5 | Type A |
| 11.1 | ACN/EtOAc (1:1 v/v) | 0.5 | Type A |
| 5.0 | ACN/MIBK (1:1 v/v) | 0.5 | Type A |
| 14.4 | ACN/2-MeTHF (1:1 v/v) | 0.5 | Type A |
| 27.7 | ACN/n-heptane (10:1 v/v) | 0.5 | Type B |
| 9.8 | ACN/H$_2$O (5:1 v/v) | 0.5 | Type B |
| 7.3 | DCM/IPAc (1:1 v/v) | 0.5 | Type A |
| 10.8 | DCM/n-heptane (1:1 v/v) | 0.5 | Type A |
| 22.7 | CHCl$_3$/IPA (1:1 v/v) | 0.5 | Type A |
| 22.9 | CHCl$_3$/toluene (1:1 v/v) | 0.5 | Type A |
| 10.7 | THF/EtOH (1:1 v/v) | 0.5 | Type A |
| 9.6 | THF/H$_2$O (5:1 v/v) | 0.5 | Type B |
| 32.9 | 1,4-dioxane/H$_2$O (4:1 v/v) | 0.5 | Gel |

Anti-Solvent Addition

A total of 8 anti-solvent addition experiments were carried out. About 15 mg of Compound 1 (Type A) was dissolved in 0.2-4.0 mL of solvent to obtain a clear solution. The solution was magnetically stirred followed by addition of 0.2 mL anti-solvent per step until precipitate appeared or the total amount of anti-solvent reached 15.0 mL. The obtained precipitate was isolated for XRPD analysis (Method A). Results in Table 15 showed that Type A and amorphous material were generated.

TABLE 15

| Solvent/Anti-solvent | Solid Form |
|---|---|
| DMSO/H$_2$O | Type A + Amorphous |
| CHCl$_3$/Heptane | Amorphous |
| DMSO/MeOH | Amorphous |
| Acetone/H$_2$O | Amorphous |
| DMAc/IPA | Amorphous |
| ACN/EtOH | Type A + Amorphous |
| CHCl$_3$/Toluene | Amorphous |
| DCM/Heptane | Amorphous |

Reverse Anti-Solvent Addition

A total of 2 reverse anti-solvent addition experiments were carried out. About 15 mg of Compound 1 (type A) was dissolved in 0.2 mL solvent to obtain a clear solution. The solution was added into 2 mL anti-solvent. The obtained precipitate was isolated for XRPD analysis (Method A). Results summarized in Table 16 indicated Type A or a mixture of Type A and amorphous material were generated.

TABLE 16

| Solvent/Anti-solvent | Solid Form |
| --- | --- |
| DMSO/H$_2$O | Type A + Amorphous |
| CHCl$_3$/Heptane | Type A |

Slow Cooling

Slow cooling experiments were performed under the conditions set forth in Table 17. Compound 1 (Type A) was weighed into a 3 mL glass vial with the addition of the corresponding solvent or solvent mixture. After being vortexed and ultrasonically shaken to accelerate dissolution, the suspension was placed in a biochemical incubator and equilibrated at 50° C. for 30 minutes. The hot suspension was then filtered with a syringe filter (0.045 μm PTFE filter membrane, and the hot filtrate was transferred to a clean 3 mL vial (pre-heated at 50° C.). The vial was sealed and placed in an incubator for slow cooling from 50° C. to 5° C. at a rate of 0.01° C./minute. The solid forms resulting from the experiments were characterized by XRPD analysis (Method C).

TABLE 17

| Amount of Compound 1 (mg) | Solvent | Solvent Volume (mL) | Solid Form |
| --- | --- | --- | --- |
| 20.5 | MeOH | 1.5 | Type B |
| 15.7 | EtOH | 1.5 | Type A |
| 20.3 | EtOAc | 1.5 | Type B |
| 14.9 | MIBK | 1.5 | Clear solution |
| 15.4 | 2-MeTHF | 1.5 | Type K |
| 40.3 | ACN/H$_2$O (2:1 v/v) | 0.8 | Type B |
| 40.6 | Acetone/H$_2$O (2:1 v/v) | 1.0 | Type B |
| 40.3 | Acetone/n-heptane (3:1 v/v) | 1.0 | Type A |
| 40.4 | 1,4-dioxane/H$_2$O (1:1 v/v) | 1.0 | Type B |
| 39.7 | THF/H$_2$O (1:1 v/v)* | 1.0 | Type L |

*After slow cooling, only a few small crystals were observed. System was kept at 5° C. for 22 days, at which time plate crystals (Type L) were observed.

Example 4—Preparation and Characterization of Type B of Compound 1

Preparation of Type B of Compound 1

Type B was prepared on a 100 mg scale from a slurry of Type A in methanol at 50° C., via a method analogous to the method for slurry conversion described in Example 3.

Characterization of Type B of Compound 1

Type B was characterized by XRPD (Method A), TGA (Method A), DSC (Method A), and DVS analysis.

Figure 7:
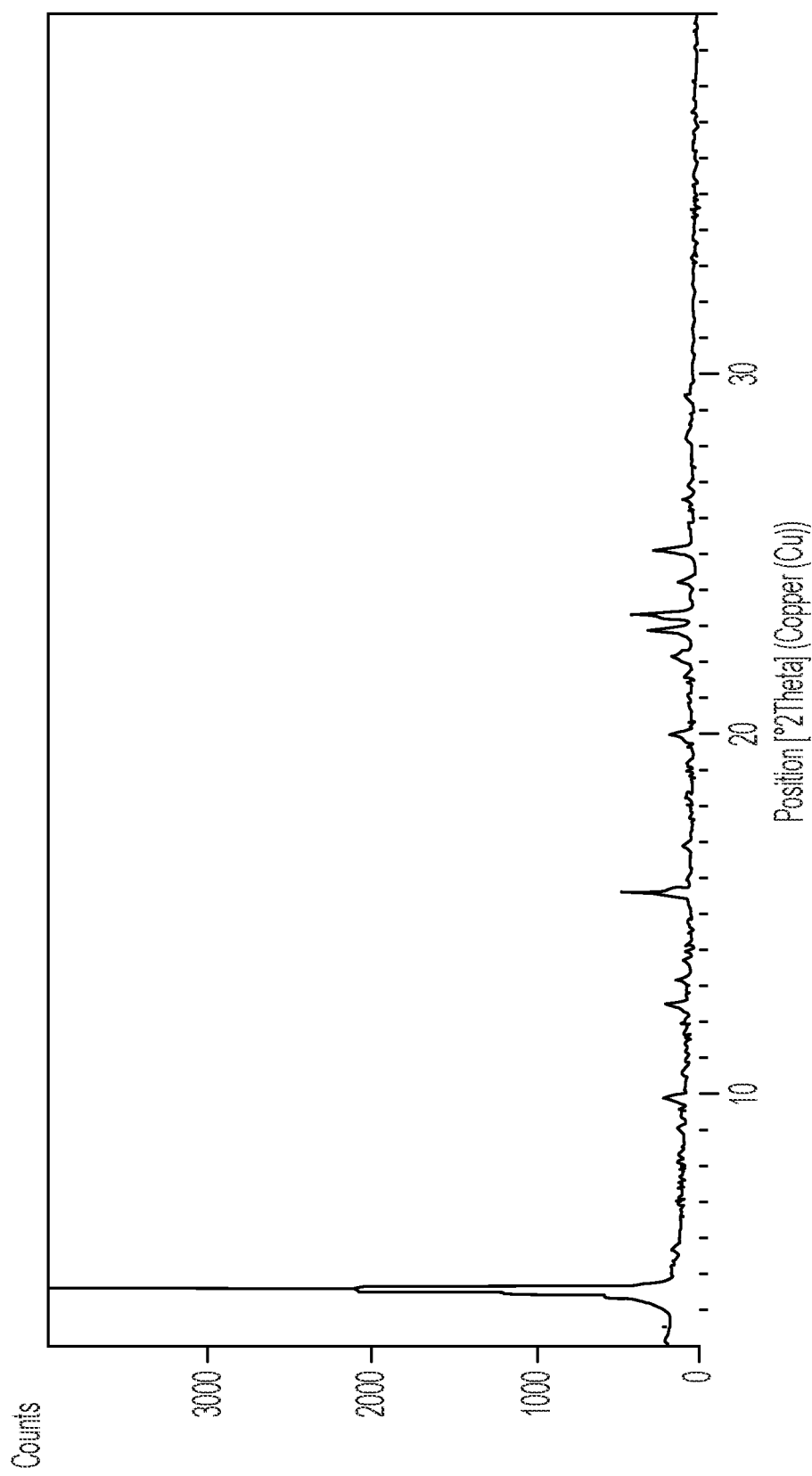
FIG. 7 depicts an XRPD pattern of Compound 1 crystalline form Type B.

The XRPD pattern for Type B is depicted in FIG. 7, and the corresponding data are summarized in the following table:

| Pos. [°2Th.] | d-spacing [Å] |
| --- | --- |
| 4.52 | 19.53 |
| 8.98 | 9.85 |
| 9.86 | 8.97 |
| 12.37 | 7.15 |
| 13.18 | 6.72 |
| 15.57 | 5.69 |
| 16.86 | 5.26 |
| 18.21 | 4.87 |
| 19.11 | 4.64 |
| 19.93 | 4.45 |
| 20.92 | 4.25 |
| 22.19 | 4.00 |
| 22.89 | 3.89 |
| 23.34 | 3.81 |
| 25.13 | 3.54 |
| 25.80 | 3.45 |
| 26.71 | 3.34 |
| 28.30 | 3.15 |
| 29.39 | 3.04 |

The foregoing XRPD data for Type B can also be rounded to a single decimal place, as summarized in the following table:

| Pos. [°2Th.] | d-spacing [Å] |
| --- | --- |
| 4.5 | 19.5 |
| 9.0 | 9.9 |
| 9.9 | 9.0 |
| 12.4 | 7.2 |
| 13.2 | 6.7 |
| 15.6 | 5.7 |
| 16.9 | 5.3 |
| 18.2 | 4.9 |
| 19.1 | 4.6 |
| 19.9 | 4.5 |
| 20.9 | 4.2 |
| 22.2 | 4.0 |
| 22.9 | 3.9 |
| 23.3 | 3.8 |
| 25.1 | 3.5 |
| 25.8 | 3.5 |
| 26.7 | 3.3 |
| 28.3 | 3.2 |
| 29.4 | 3.0 |

Figure 8:
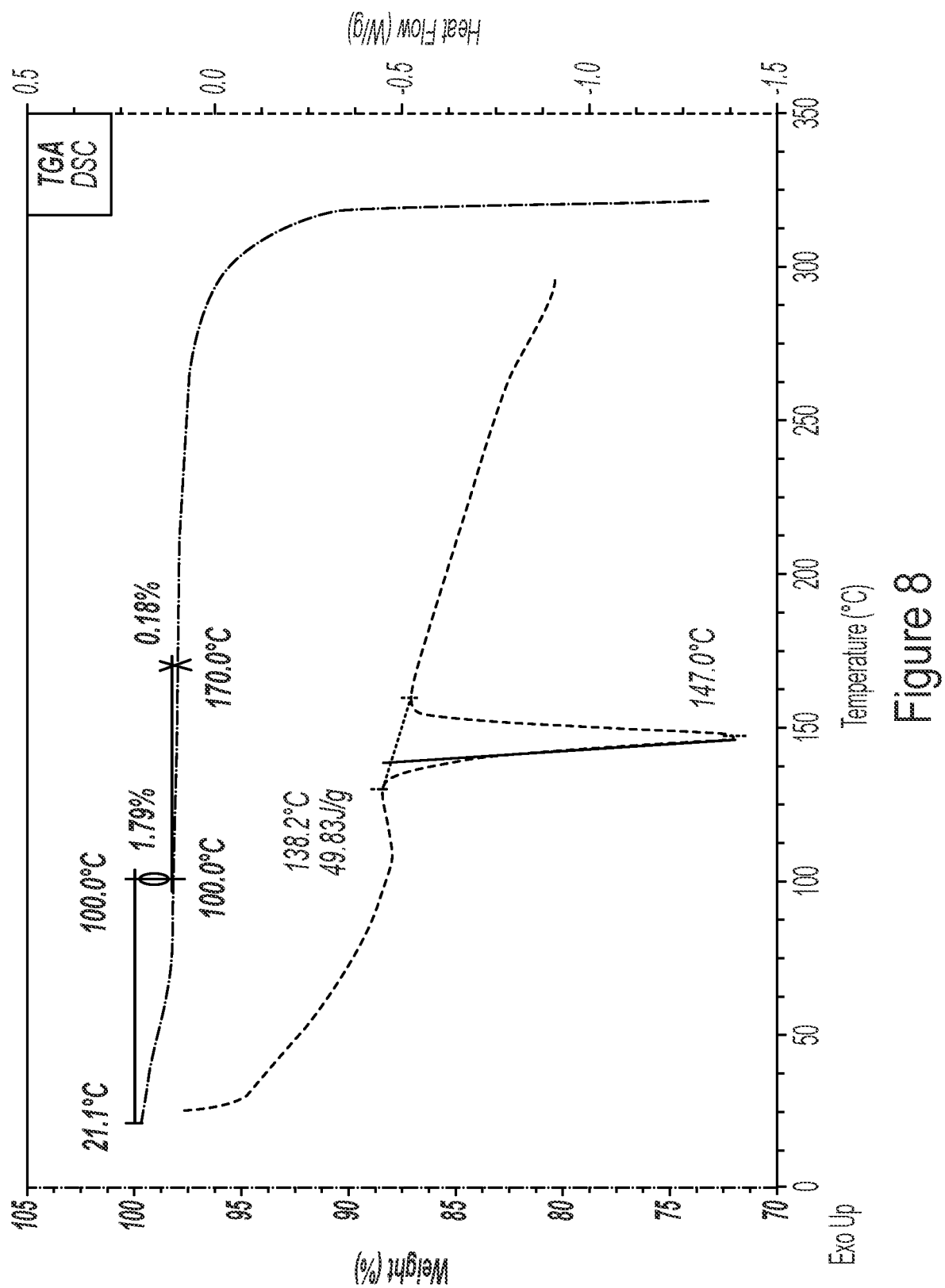
FIG. 8 depicts a thermogravimetric analysis (TGA) curve (upper curve) and a differential scanning calorimetry (DSC) thermogram (lower curve) for Compound 1 crystalline form Type B.

The TGA and DSC curves for Type B are shown in FIG. 8. As shown in FIG. 8, Type B showed 1.8% weight loss up to 100° C. and an endotherm at 138.2° C. (onset temperature) possibly due to melting.

Figure 9:
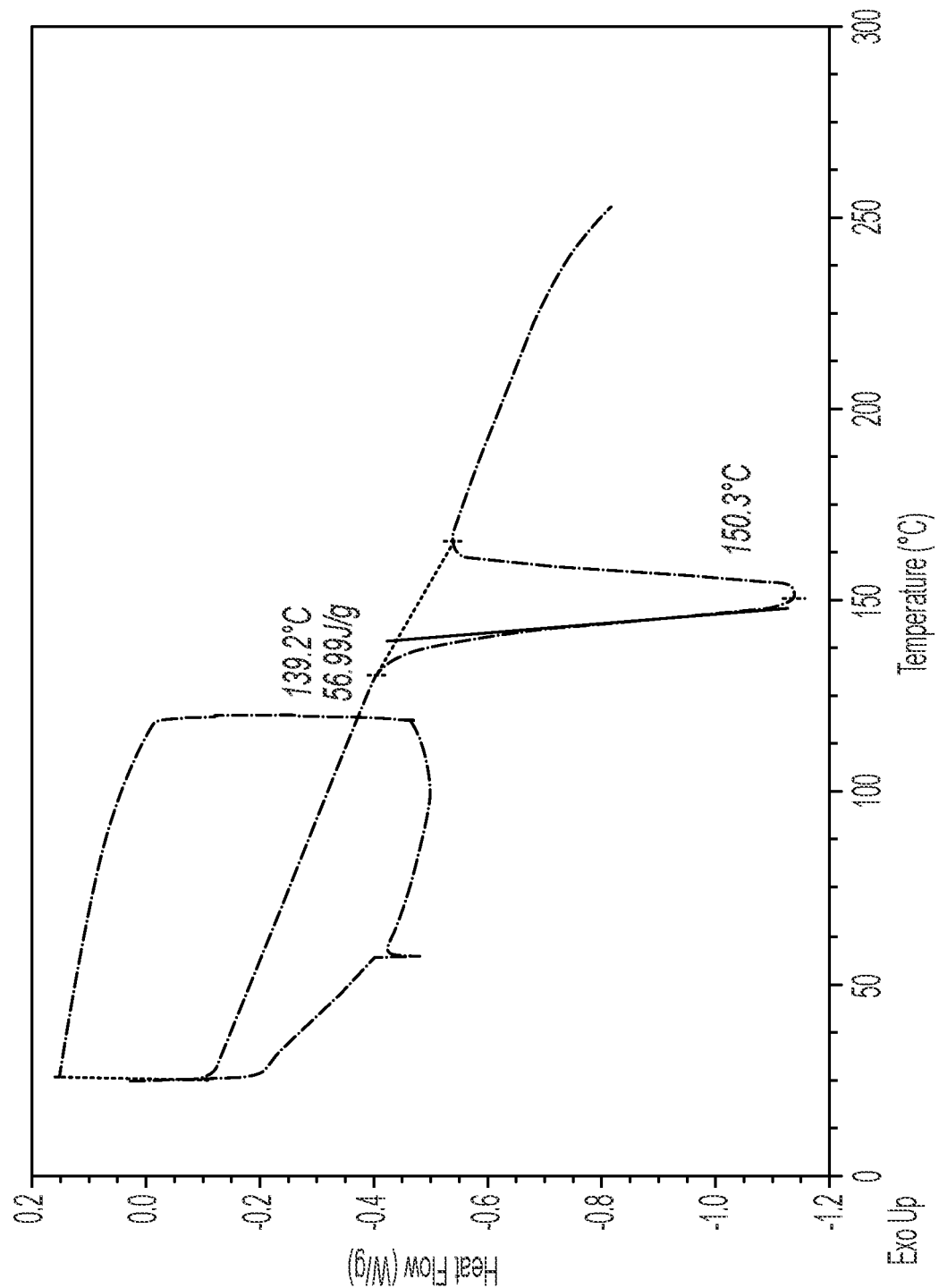
FIG. 9 depicts a DSC cycling thermogram for Compound 1 crystalline form Type B.

By DSC cycling (RT-120° C.-RT-250° C.) as shown in FIG. 9, only one melting endotherm at 139.2° C. (onset temperature) was observed, with no broad endotherm below 120° C. in the second heating cycle.

Figure 10:
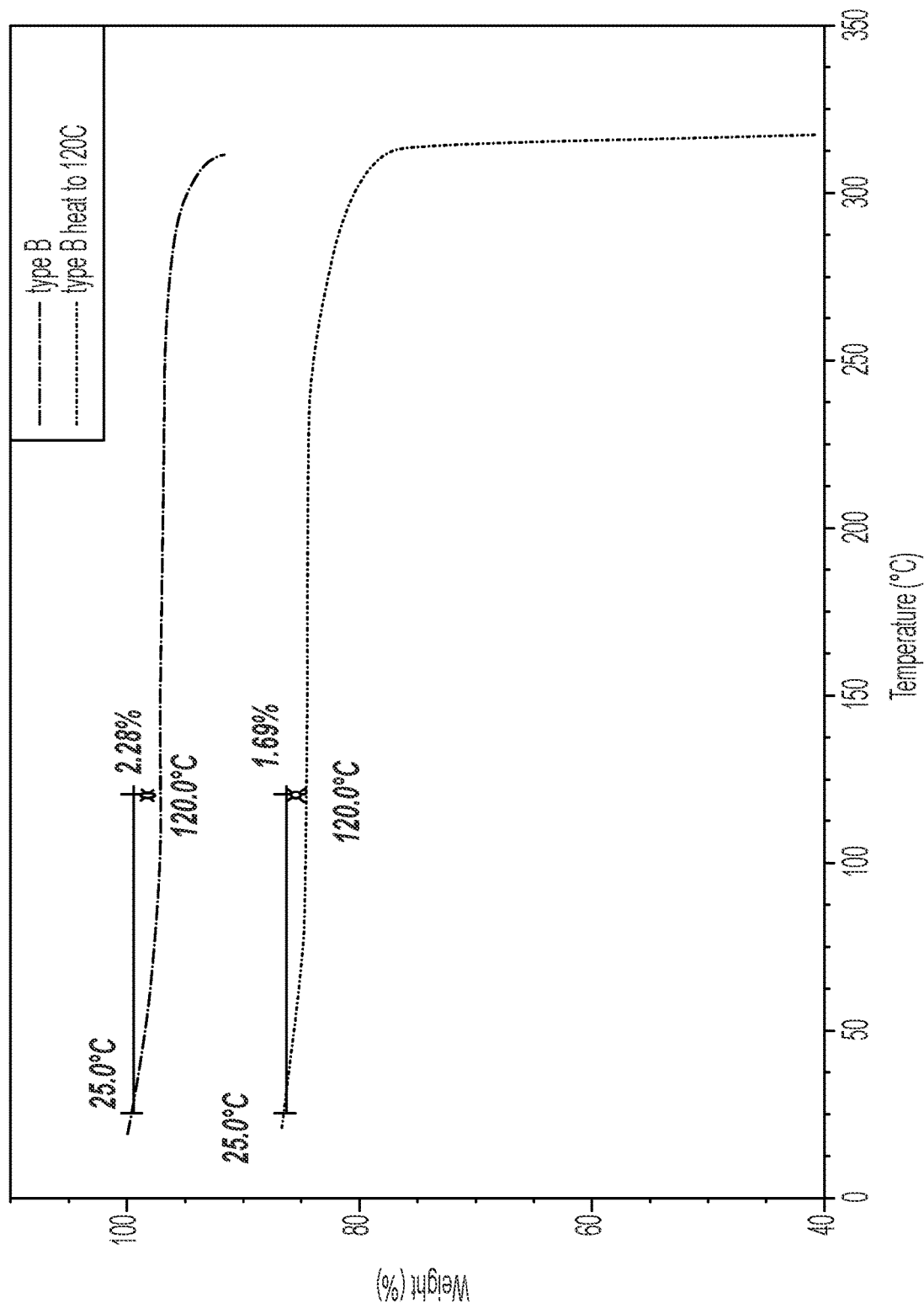
FIG. 10 depicts two thermogravimetric analysis (TGA) curves for Compound 1 crystalline form Type B.

As shown in FIG. 10, Type B showed a 1.7% weight loss up to 120° C. by instant TGA test after heating to 120° C. and exposing to ambient condition for only one minute. The normal TGA curve of Type B showed 2.3% weight loss up 120° C. without pre-heating treatment.

After heating to 120° C. and cooling to RT by DSC cycling, no form change was observed by XRPD analysis.

Figure 11:
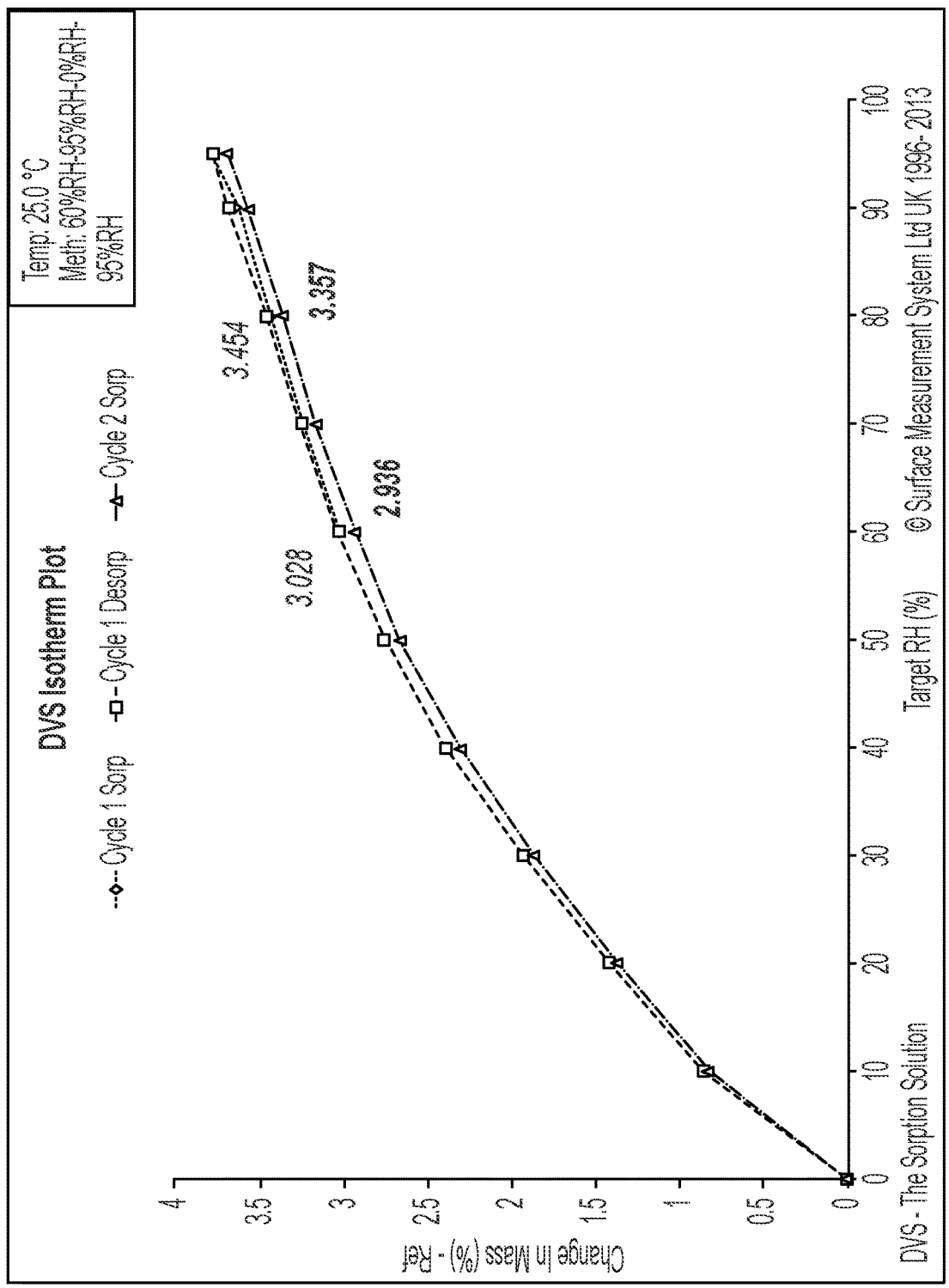
FIG. 11 depicts a dynamic vapor sorption (DVS) isotherm for Compound 1 crystalline form Type B.

By DVS analysis (FIG. 11), Type B showed a 2.9% water uptake up to 60% RH (ambient condition), and 0.4% water uptake from 60% RH to 80% RH at RT, indicating that Type B is hygroscopic. No form change was observed for Type B before and after DVS test at RT, as determined by XRPD analysis.

Based on the foregoing analytical data, Type B is believed to be a channel hydrate.

Example 5—Preparation and Characterization of Type C of Compound 1

Preparation of Type C of Compound 1

Type C was prepared on a 100 mg scale from a slurry of Type A in 1,4-Dioxane at RT, via a method analogous to the method for slurry conversion described in Example 3.

Characterization of Type C of Compound 1

Type C was characterized by XRPD (Method A), TGA (Method A), DSC (Method A), and DVS analysis.

Figure 12:
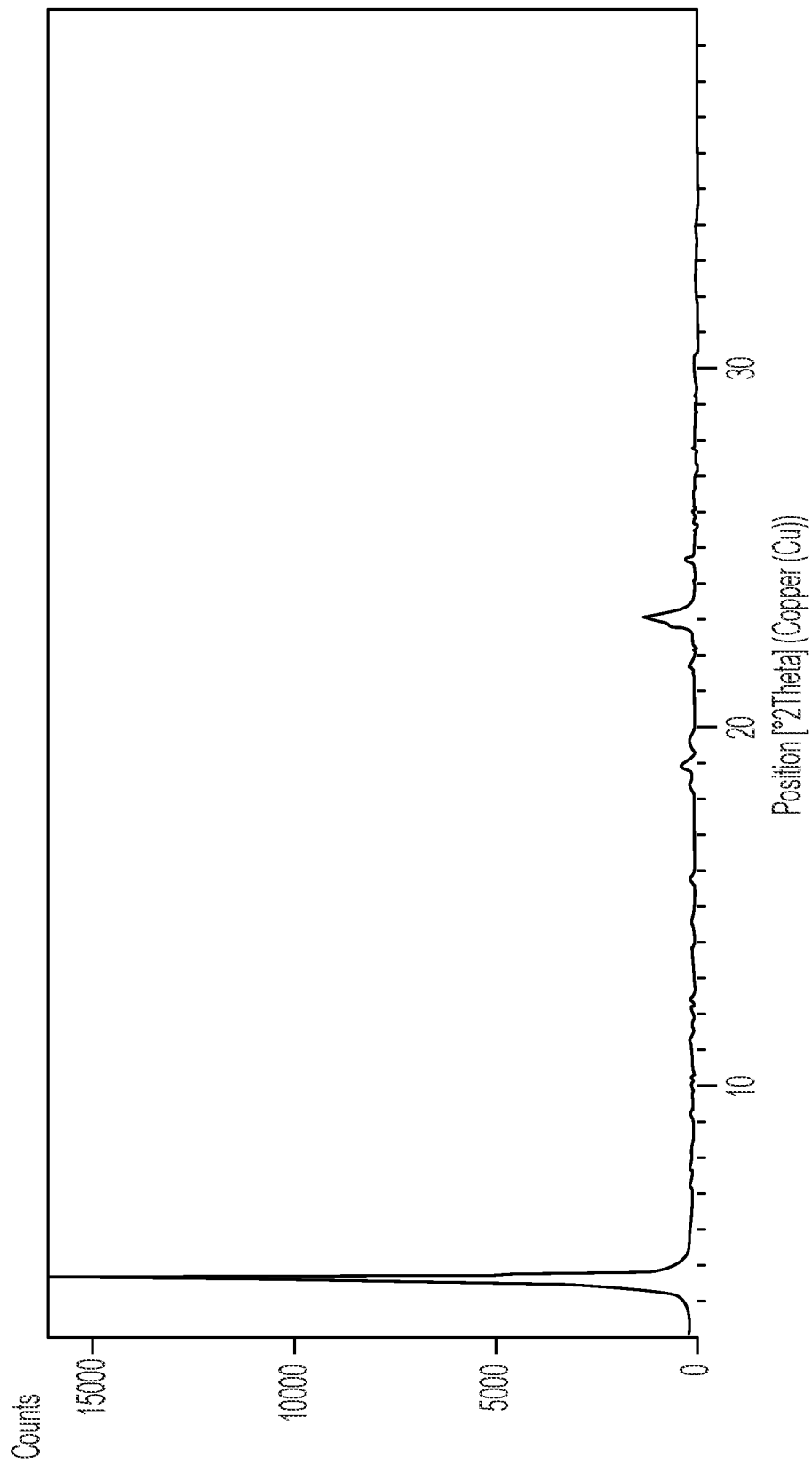
FIG. 12 depicts an XRPD pattern of Compound 1 crystalline form Type C.

The XRPD pattern for Type C is depicted in FIG. 12, and the corresponding data are summarized in the following table:

| Pos. [°2Th.] | d-spacing [Å] |
| --- | --- |
| 4.55 | 19.43 |
| 7.34 | 12.05 |
| 9.07 | 9.75 |
| 11.17 | 7.92 |
| 12.29 | 7.20 |
| 14.51 | 6.11 |
| 15.66 | 5.66 |
| 18.34 | 4.84 |
| 18.85 | 4.71 |
| 19.57 | 4.54 |
| 20.38 | 4.36 |
| 21.66 | 4.10 |
| 23.02 | 3.86 |
| 24.65 | 3.61 |
| 26.39 | 3.38 |
| 28.28 | 3.16 |
| 30.09 | 2.97 |
| 32.31 | 2.77 |
| 33.91 | 2.64 |
| 37.19 | 2.42 |

The foregoing XRPD data for Type C can also be rounded to a single decimal place, as summarized in the following table:

| Pos. [°2Th.] | d-spacing [Å] |
| --- | --- |
| 4.5 | 19.4 |
| 7.3 | 12.0 |
| 9.1 | 9.7 |
| 11.2 | 7.9 |
| 12.3 | 7.2 |
| 14.5 | 6.1 |
| 15.7 | 5.7 |
| 18.3 | 4.8 |
| 18.9 | 4.7 |
| 19.6 | 4.5 |
| 20.4 | 4.4 |
| 21.7 | 4.1 |
| 23.0 | 3.9 |
| 24.7 | 3.6 |
| 26.4 | 3.4 |
| 28.3 | 3.2 |
| 30.1 | 3.0 |
| 32.3 | 2.8 |
| 33.9 | 2.6 |
| 37.2 | 2.4 |

Figure 13:
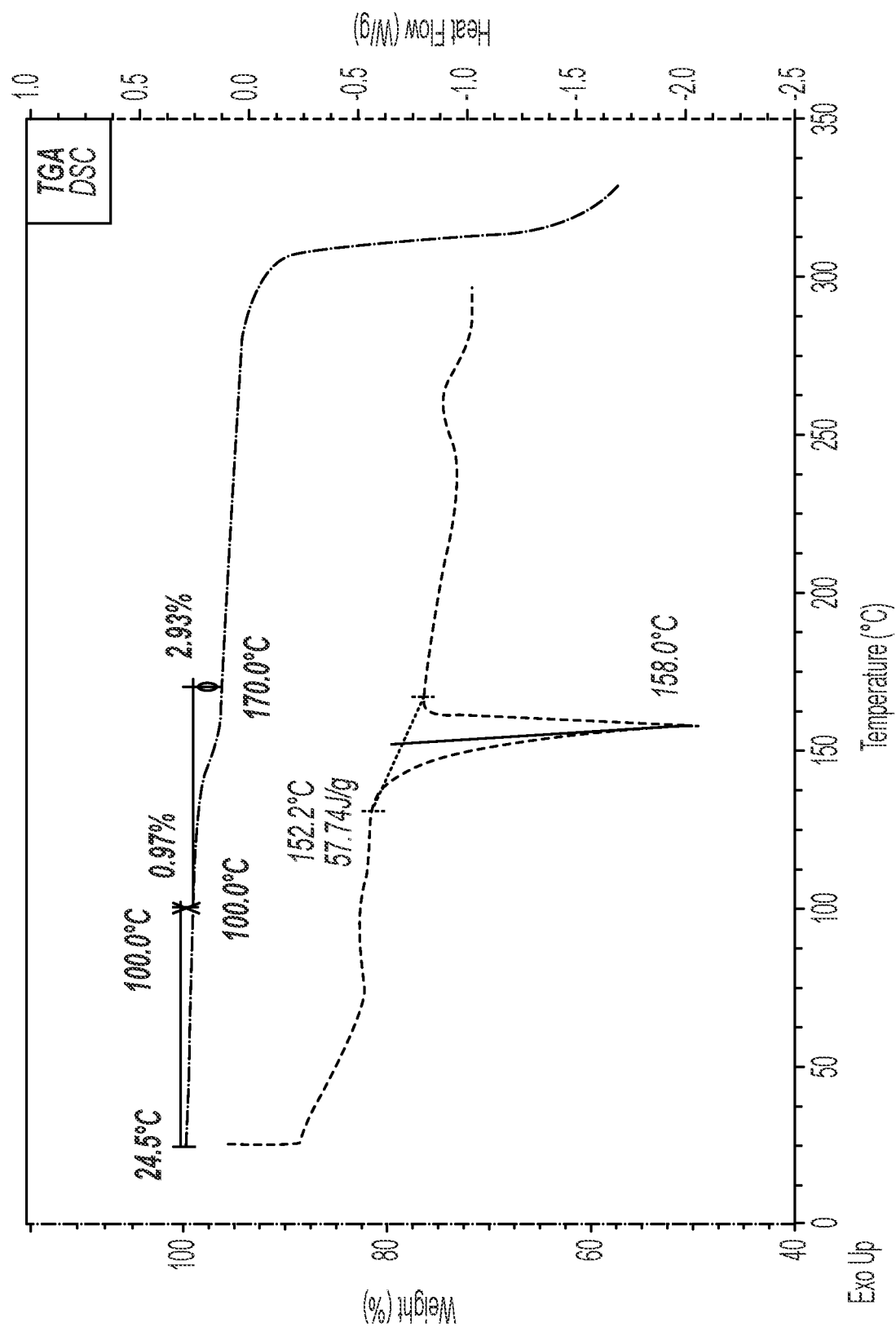
FIG. 13 depicts a thermogravimetric analysis (TGA) curve (upper curve) and a differential scanning calorimetry (DSC) thermogram (lower curve) for Compound 1 crystalline form Type C.

The TGA and DSC curves for Type C are shown in FIG. 13. As shown in FIG. 13, Type C showed 1.0% weight loss up to 100° C. and an endotherm at 152.2° C. (onset temperature) possibly due to melting.

Figure 14:
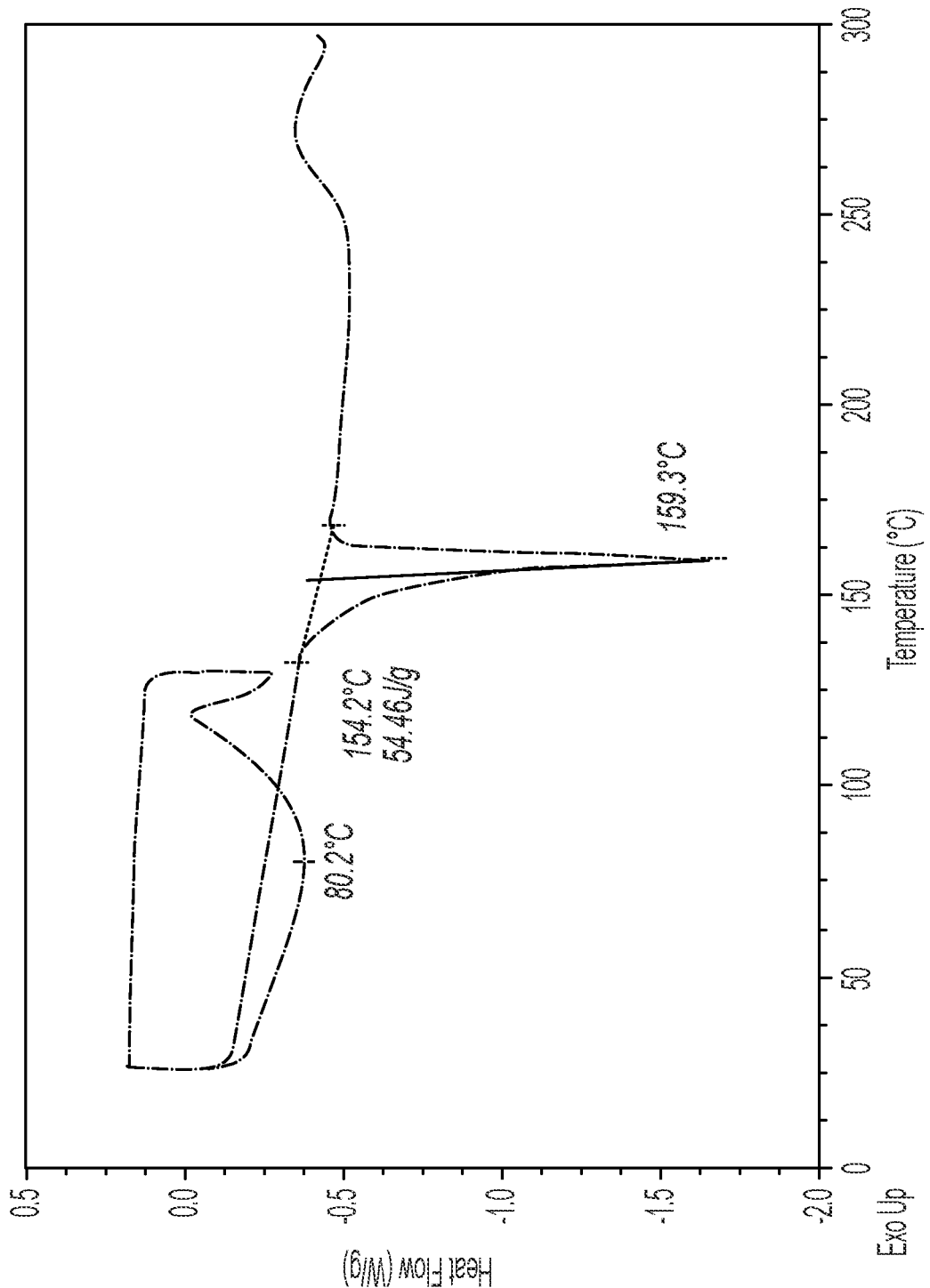
FIG. 14 depicts a DSC cycling thermogram for Compound 1 crystalline form Type C.

By using DSC cycling (RT-120° C.-RT-250° C.), only a melting endotherm at 154.2° C. (onset temperature) was observed, with no broad endotherm below 120° C. in the second heating cycle (FIG. 14).

Figure 15:
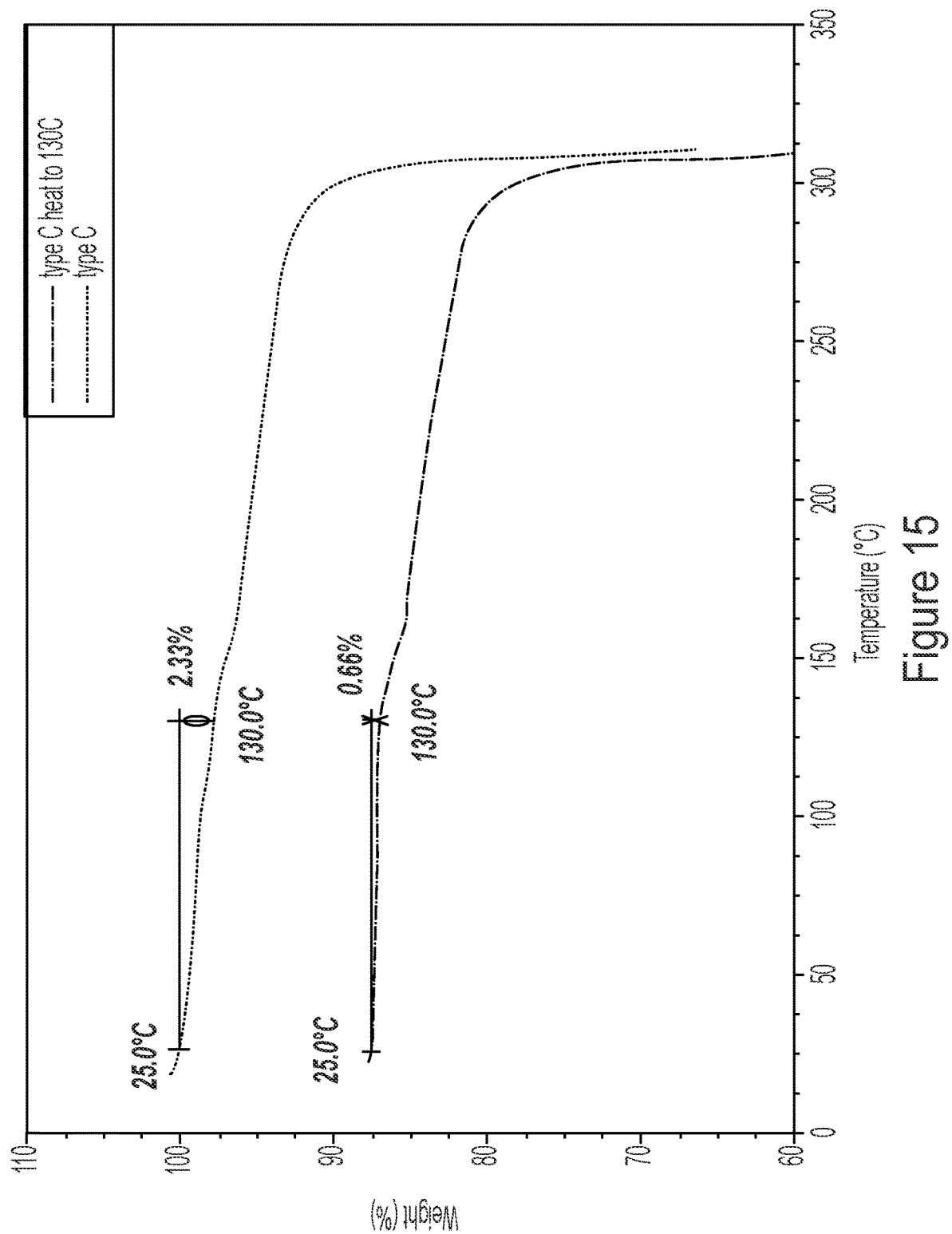
FIG. 15 depicts thermogravimetric analysis (TGA) curves for Compound 1 crystalline form Type C.

As shown in FIG. 15, Type C showed a 0.7% weight loss up to 130° C. by instant TGA test after heating to 120° C. and exposing to ambient conditions for one minute. The normal TGA curve of the Type C showed 2.3% weight loss up 130° C. without pre-heating treatment.

After heating to 120° C. and cooling to RT by DSC cycling, no form change was observed by XRPD analysis.

Figure 16:
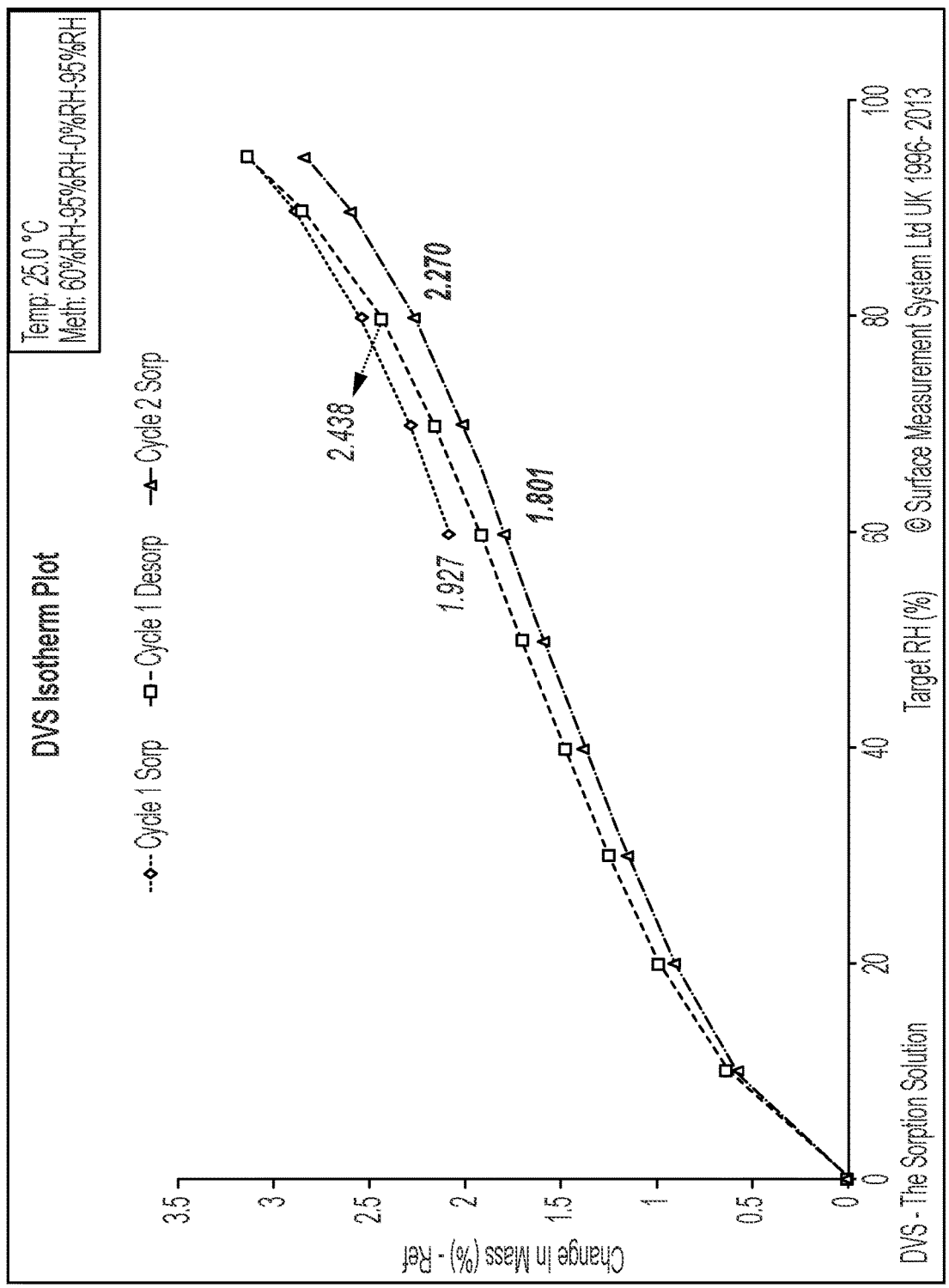
FIG. 16 depicts a dynamic vapor sorption (DVS) isotherm for Compound 1 crystalline form Type C.

By DVS analysis (FIG. 16), Type C showed a 1.8% water uptake up to 60% RH (ambient condition), and 0.5% water uptake from 60% RH to 80% RH at RT, indicating that Type C is hygroscopic. No form change was observed for Type C before and after DVS test at RT, as determined by XRPD analysis.

Based on the foregoing analytical data, Type B is believed to be a channel hydrate.

Example 6—Preparation and Characterization of Type D of Compound 1

Preparation of Type D of Compound 1

Type D was prepared from a slurry of Type A in Tetrahydrofuran (THF) at 4° C., via a method analogous to the method for slurry conversion described in Example 3.

Characterization of Type D of Compound 1

Type D was characterized by XRPD (Method A), TGA (Method A), DSC (Method A), and $^1$H NMR analysis.

Figure 17:
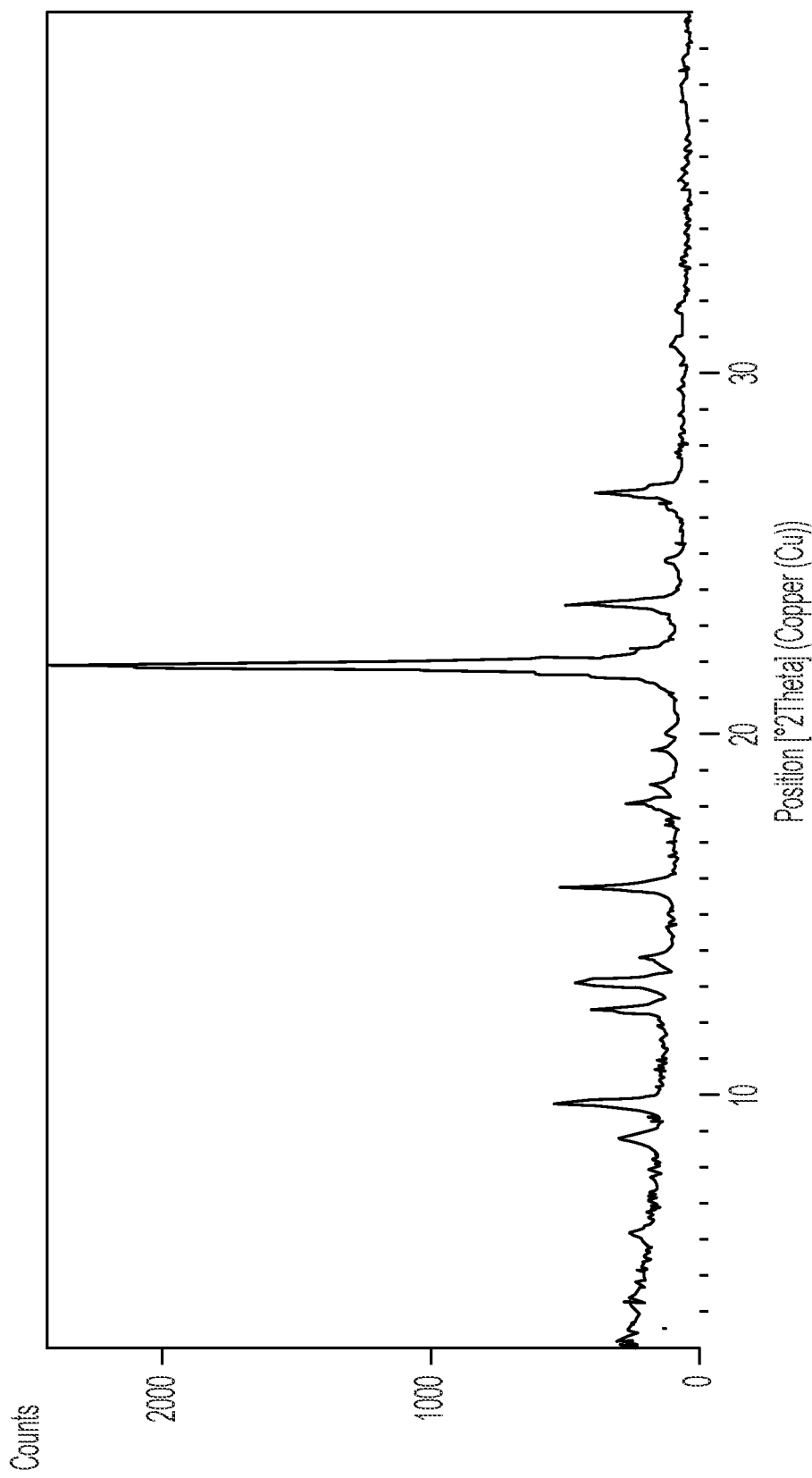
FIG. 17 depicts an XRPD pattern of Compound 1 crystalline form Type D.

The XRPD pattern for Type D is depicted in FIG. 17, and the corresponding data are summarized in the following table:

| Pos. [°2Th.] | d-spacing [Å] |
| --- | --- |
| 4.27 | 20.68 |
| 6.15 | 14.36 |
| 8.71 | 10.16 |
| 9.72 | 9.10 |
| 12.31 | 7.19 |
| 13.08 | 6.77 |
| 13.76 | 6.44 |
| 15.74 | 5.63 |
| 18.02 | 4.92 |
| 19.55 | 4.54 |
| 21.90 | 4.06 |
| 23.59 | 3.77 |
| 24.79 | 3.59 |
| 26.71 | 3.34 |
| 29.50 | 3.03 |
| 30.82 | 2.90 |
| 31.74 | 2.82 |
| 35.40 | 2.54 |
| 37.84 | 2.38 |
| 38.61 | 2.33 |

The foregoing XRPD data for Type D can also be rounded to a single decimal place, as summarized in the following table:

| Pos. [°2Th.] | d-spacing [Å] |
| --- | --- |
| 4.3 | 20.7 |
| 6.2 | 14.4 |
| 8.7 | 10.2 |
| 9.7 | 9.1 |
| 12.3 | 7.2 |
| 13.1 | 6.8 |
| 13.8 | 6.4 |
| 15.7 | 5.6 |
| 18.0 | 4.9 |
| 19.5 | 4.5 |
| 21.9 | 4.1 |

| Pos. [°2Th.] | d-spacing [Å] |
|---|---|
| 23.6 | 3.8 |
| 24.8 | 3.6 |
| 26.7 | 3.3 |
| 29.5 | 3.0 |
| 30.8 | 2.9 |
| 31.7 | 2.8 |
| 35.4 | 2.5 |
| 37.8 | 2.4 |
| 38.6 | 2.3 |

Figure 18:
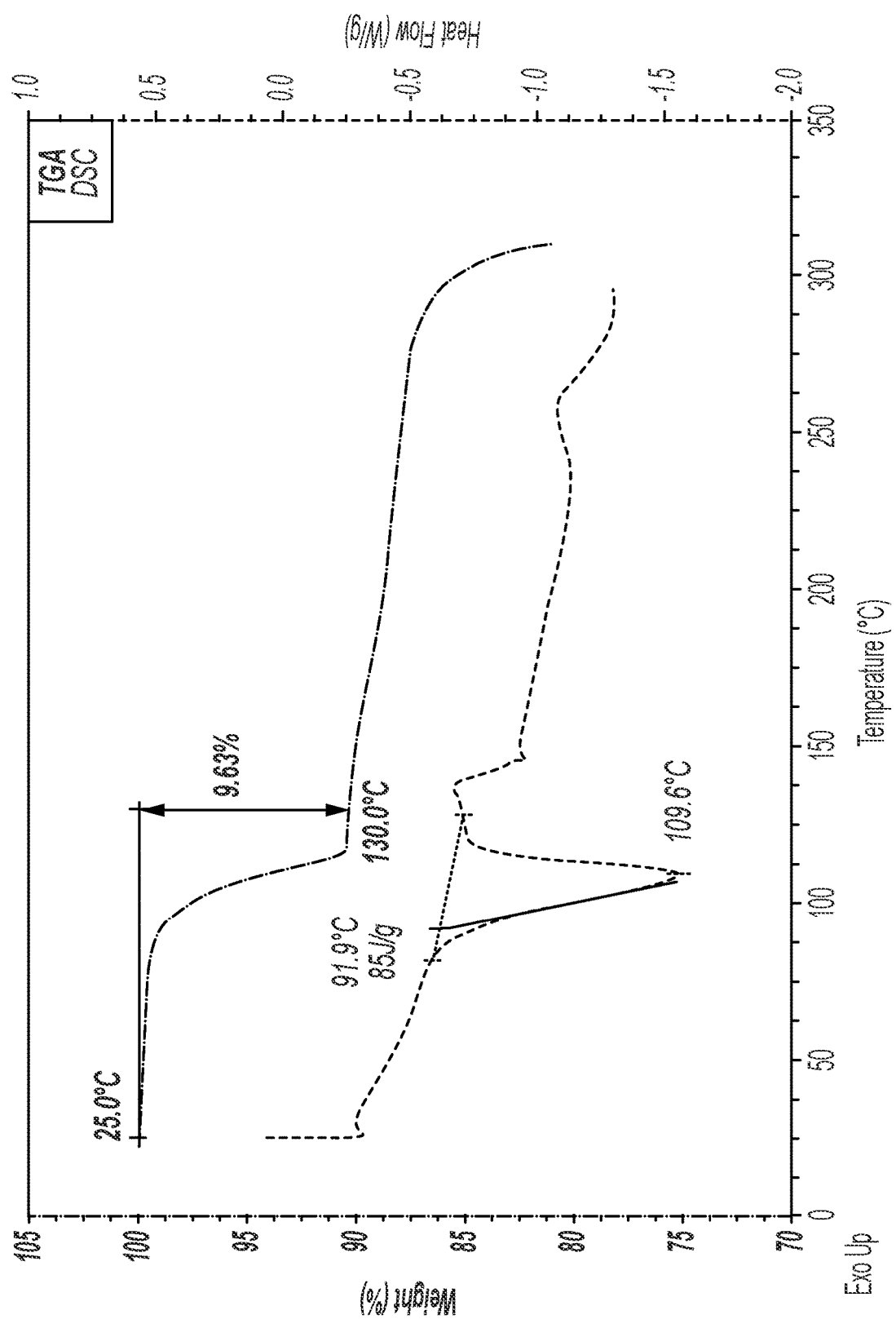
FIG. 18 depicts a thermogravimetric analysis (TGA) curve (upper curve) and a differential scanning calorimetry (DSC) thermogram (lower curve) for Compound 1 crystalline form Type D.

The TGA and DSC curves for Type D are shown in FIG. 18. As shown in FIG. 18, Type D showed 9.6% weight loss up to 130° C. by TGA and an endotherm at 91.9° C. (onset temperature) by DSC.

Figure 19:
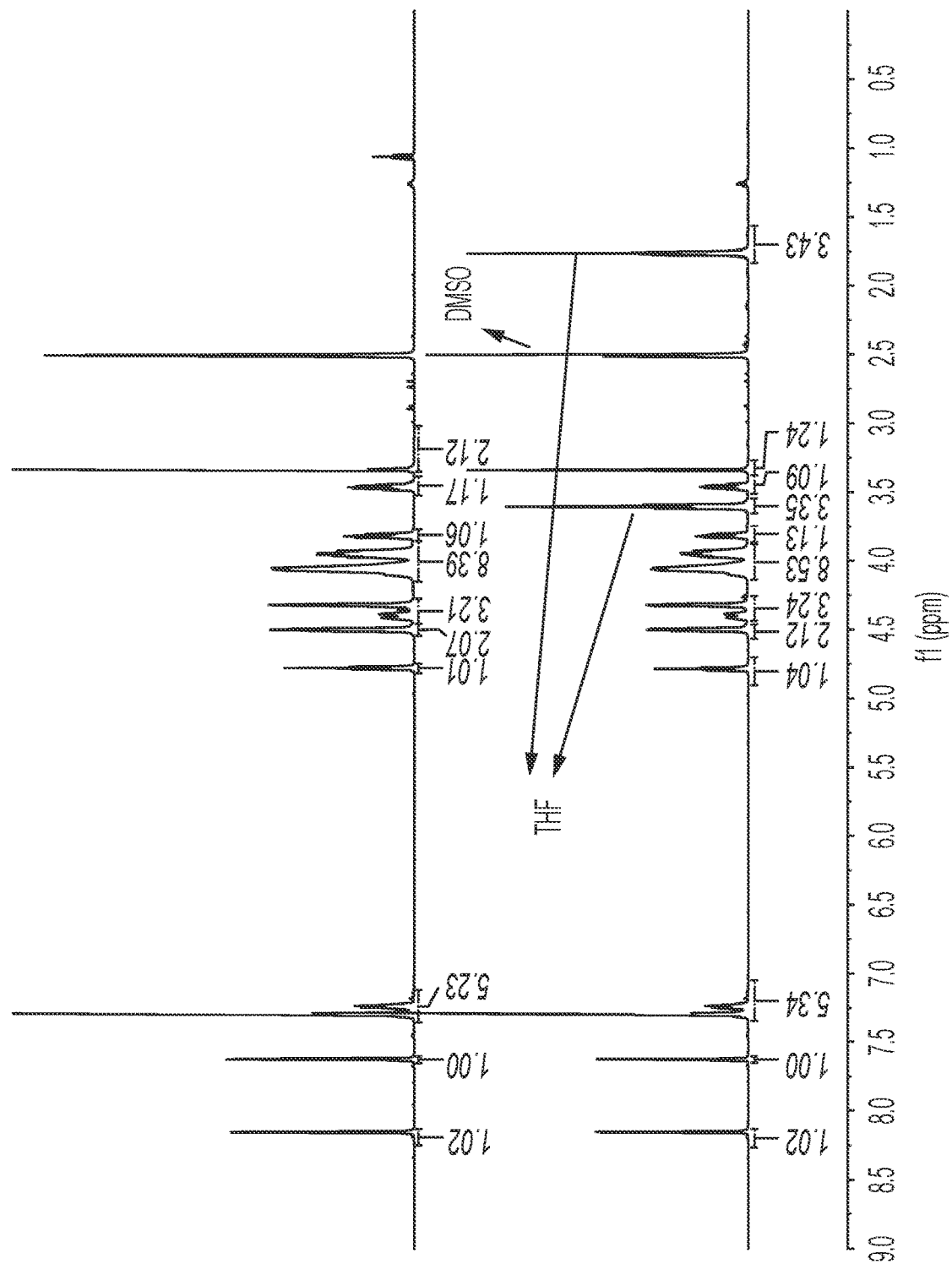
FIG. 19 depicts a $^1$H NMR spectrum of Type A (upper curve) and Type D (lower curve) crystalline forms of Compound 1.

The $^1$H NMR spectra of Type A and Type D are shown in FIG. 19. Type D appears to be a THF solvate, as indicated by the $^1$H NMR spectrum (600 MHz, DMSO-d6), which detected the presence of THF protons at ~1.76 and ~3.60 ppm.

Example 7—Preparation and Characterization of Type E of Compound 1

Characterization of Type E of Compound 1

Figure 20:
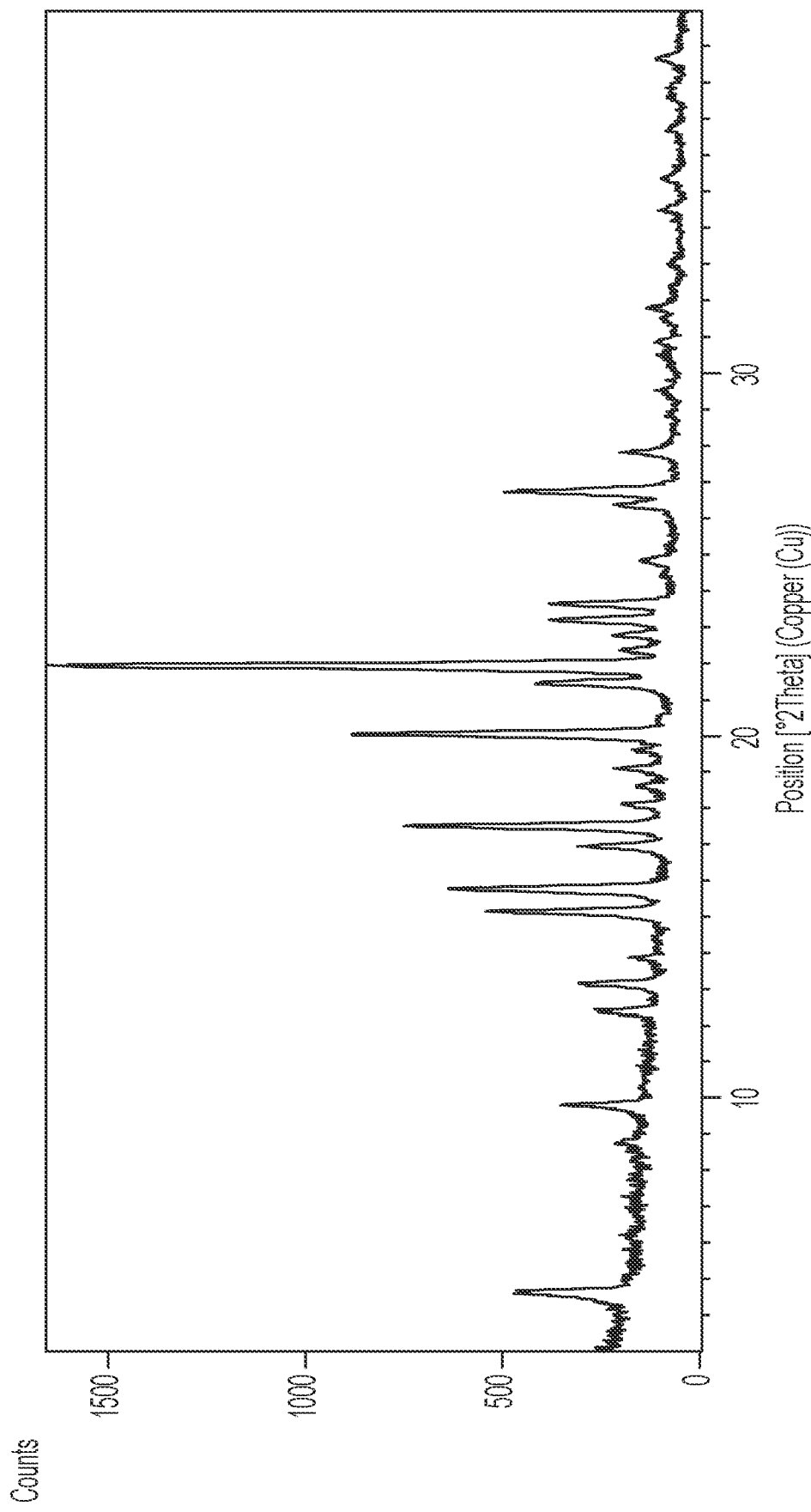
FIG. 20 depicts an XRPD pattern of Compound 1 crystalline form Type E.

Type E was characterized by XRPD (Method A) analysis.
The XRPD pattern for Type E is depicted in FIG. 20, and the corresponding data are summarized in the following table:

| Pos. [°2Th.] | d-spacing [Å] |
|---|---|
| 4.59 | 19.27 |
| 8.76 | 10.09 |
| 9.76 | 9.06 |
| 12.36 | 7.16 |
| 13.12 | 6.75 |
| 13.83 | 6.40 |
| 15.12 | 5.86 |
| 15.75 | 5.63 |
| 16.84 | 5.27 |
| 17.48 | 5.07 |
| 18.06 | 4.91 |
| 19.02 | 4.67 |
| 20.05 | 4.43 |
| 21.93 | 4.05 |
| 23.18 | 3.84 |
| 23.70 | 3.75 |
| 24.82 | 3.59 |
| 26.72 | 3.34 |
| 27.81 | 3.21 |
| 29.51 | 3.03 |
| 30.76 | 2.91 |
| 31.74 | 2.82 |
| 33.03 | 2.71 |
| 34.52 | 2.60 |
| 35.39 | 2.54 |
| 36.72 | 2.45 |
| 37.77 | 2.38 |
| 38.66 | 2.33 |

The foregoing XRPD data for Type E can also be rounded to a single decimal place, as summarized in the following table:

| Pos. [°2Th.] | d-spacing [Å] |
|---|---|
| 4.6 | 19.3 |
| 8.8 | 10.1 |
| 9.8 | 9.1 |
| 12.4 | 7.2 |
| 13.1 | 6.7 |
| 13.8 | 6.4 |
| 15.1 | 5.9 |
| 15.8 | 5.6 |
| 16.8 | 5.3 |
| 17.5 | 5.1 |
| 18.1 | 4.9 |
| 19.0 | 4.7 |
| 20.0 | 4.4 |
| 21.9 | 4.1 |
| 23.2 | 3.8 |
| 23.7 | 3.8 |
| 24.8 | 3.6 |
| 26.7 | 3.3 |
| 27.8 | 3.2 |
| 29.5 | 3.0 |
| 30.8 | 2.9 |
| 31.7 | 2.8 |
| 33.0 | 2.7 |
| 34.5 | 2.6 |
| 35.4 | 2.5 |
| 36.7 | 2.4 |
| 37.8 | 2.4 |
| 38.7 | 2.3 |

Example 8—Preparation and Characterization of Type F of Compound 1

Preparation of Type F of Compound 1

Type F of Compound 1 was produced via liquid vapor diffusion in 1,4-Dioxane/heptane at RT.

Characterization of Type F of Compound 1

Type F was characterized by XRPD (Method A), TGA, and DSC analysis (Method A).

Figure 21:
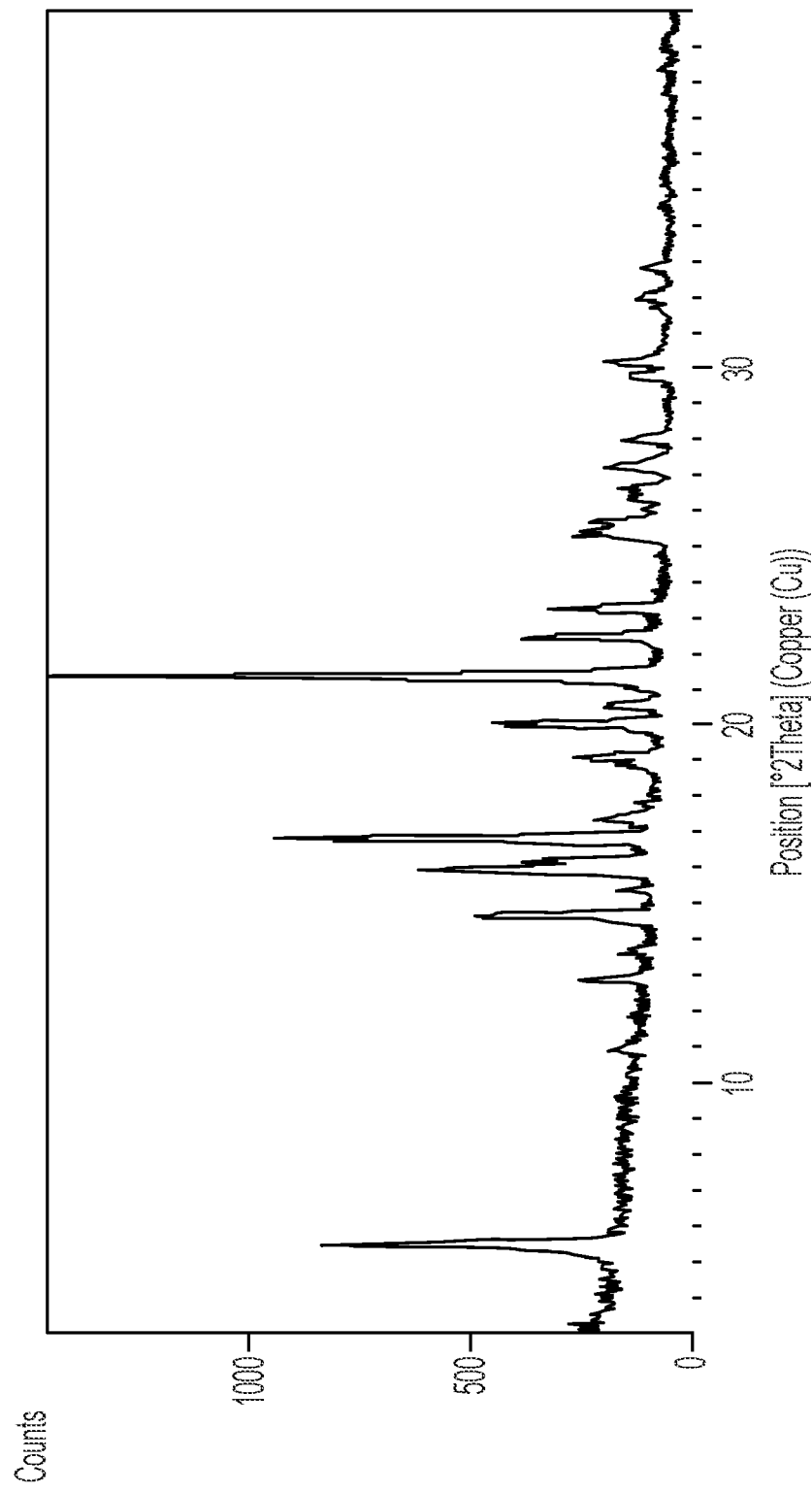
FIG. 21 depicts an XRPD pattern of Compound 1 crystalline form Type F.

The XRPD pattern for Type F is shown in FIG. 21, and the corresponding data are summarized in the following table:

| Pos. [°2Th.] | d-spacing [Å] |
|---|---|
| 5.45 | 16.23 |
| 10.92 | 8.10 |
| 12.87 | 6.88 |
| 14.66 | 6.04 |
| 16.00 | 5.54 |
| 16.79 | 5.28 |
| 17.36 | 5.11 |
| 18.99 | 4.67 |
| 20.01 | 4.44 |
| 20.57 | 4.32 |
| 21.36 | 4.16 |
| 22.45 | 3.96 |
| 23.25 | 3.83 |
| 25.32 | 3.52 |
| 26.57 | 3.35 |
| 27.25 | 3.27 |
| 27.97 | 3.19 |
| 30.02 | 2.98 |
| 31.98 | 2.80 |
| 32.89 | 2.72 |
| 38.29 | 2.35 |
| 39.09 | 2.30 |

The foregoing XRPD data for Type F can also be rounded to a single decimal place, as summarized in the following table:

| Pos. [°2Th.] | d-spacing [Å] |
|---|---|
| 5.4 | 16.2 |
| 10.9 | 8.1 |
| 12.9 | 6.9 |
| 14.7 | 6.0 |
| 16.0 | 5.5 |
| 16.8 | 5.3 |
| 17.4 | 5.1 |
| 19.0 | 4.7 |
| 20.0 | 4.4 |
| 20.6 | 4.3 |
| 21.4 | 4.2 |
| 22.5 | 4.0 |
| 23.2 | 3.8 |
| 25.3 | 3.5 |
| 26.6 | 3.4 |
| 27.2 | 3.3 |
| 28.0 | 3.2 |
| 30.0 | 3.0 |
| 32.0 | 2.8 |
| 32.9 | 2.7 |
| 38.3 | 2.4 |
| 39.1 | 2.3 |

Figure 22:
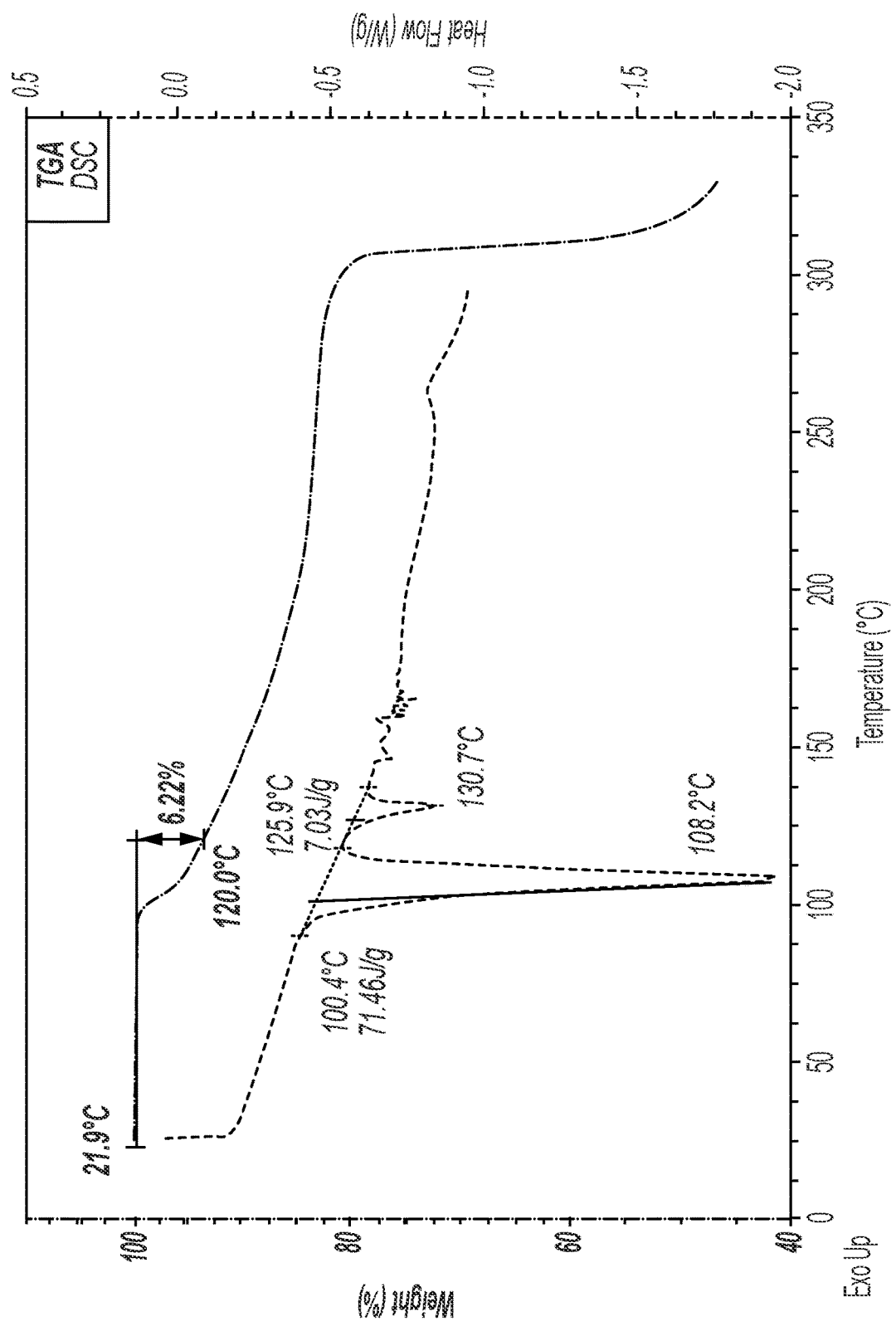
FIG. 22 is a thermogravimetric analysis (TGA) curve (upper curve) and a differential scanning calorimetry (DSC) thermogram (lower curve) for Compound 1 crystalline form Type F.

The TGA and DSC curves for Type F are shown in FIG. 22. As shown in FIG. 22, Type F showed 6.2% weight loss up to 120° C. by TGA and two endotherms at 100.4° C. and 125.9° C. (onset temperature) by DSC.

Example 9—Preparation and Characterization of Type G of Compound 1

Preparation of Type G of Compound 1

Type G was prepared from a slurry of Type A in methyl ethyl ketone at room temperature.

Characterization of Type G of Compound 1

Figure 23:
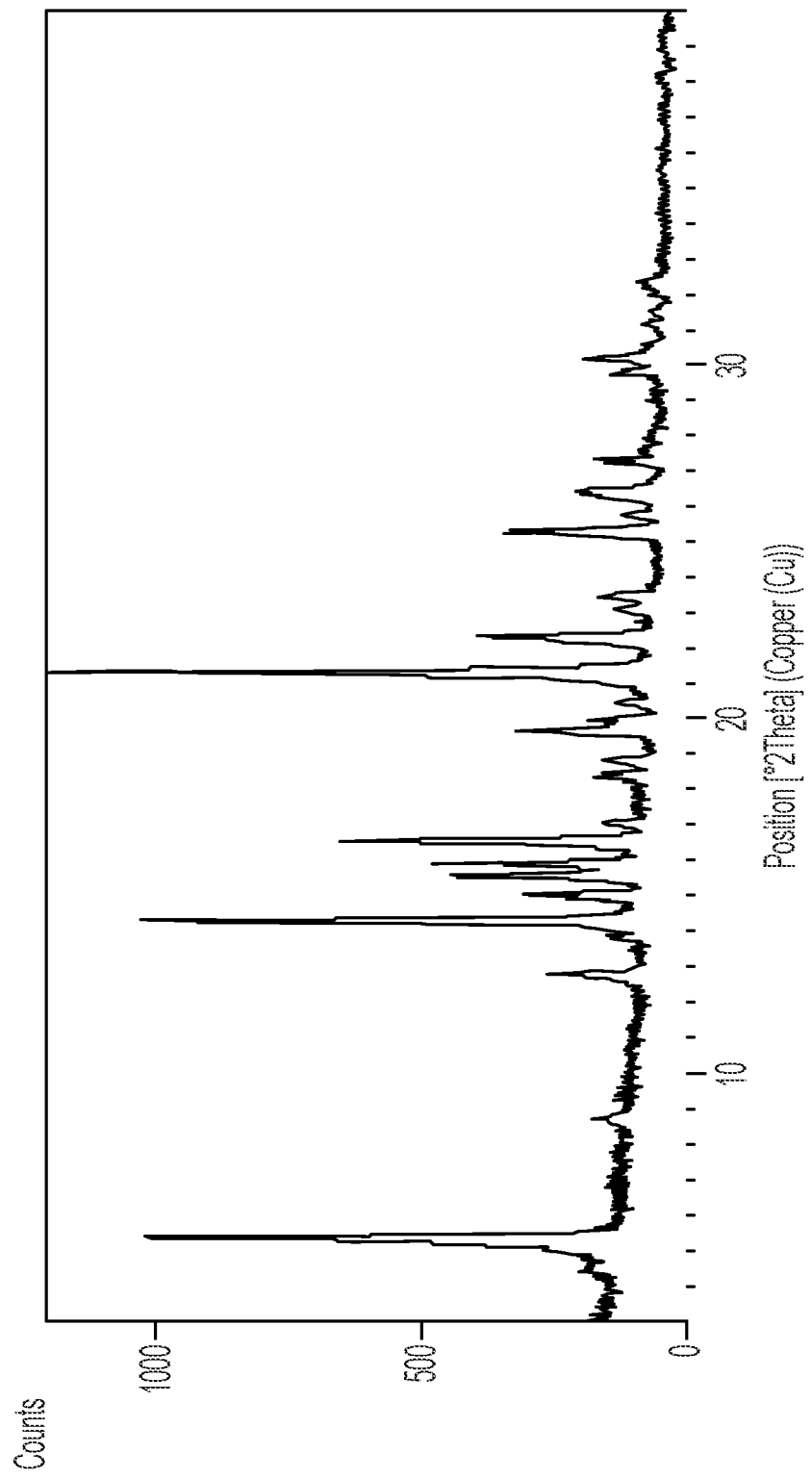
FIG. 23 depicts an XRPD pattern of Compound 1 crystalline form Type G.

Type G was characterized by XRPD (Method A) analysis.
The XRPD pattern for Type G is depicted in FIG. 23, and the corresponding data are summarized in the following table:

| Pos. [°2Th.] | d-spacing [Å] |
|---|---|
| 5.36 | 16.48 |
| 8.73 | 10.13 |
| 12.83 | 6.90 |
| 14.34 | 6.18 |
| 15.00 | 5.91 |
| 15.79 | 5.61 |
| 16.58 | 5.35 |
| 18.54 | 4.79 |
| 19.78 | 4.49 |
| 21.35 | 4.16 |
| 22.35 | 3.98 |
| 23.38 | 3.80 |
| 25.33 | 3.52 |
| 26.43 | 3.37 |
| 27.35 | 3.26 |
| 30.21 | 2.96 |
| 32.32 | 2.77 |
| 38.04 | 2.37 |

The foregoing XRPD data for Type G can also be rounded to a single decimal place, as summarized in the following table:

| Pos. [°2Th.] | d-spacing [Å] |
|---|---|
| 5.4 | 16.5 |
| 8.7 | 10.1 |
| 12.8 | 6.9 |
| 14.3 | 6.2 |
| 15.0 | 5.9 |
| 15.8 | 5.6 |
| 16.6 | 5.3 |
| 18.5 | 4.8 |
| 19.8 | 4.5 |
| 21.3 | 4.2 |
| 22.3 | 4.0 |
| 23.4 | 3.8 |
| 25.3 | 3.5 |
| 26.4 | 3.4 |
| 27.4 | 3.3 |
| 30.2 | 3.0 |
| 32.3 | 2.8 |
| 38.0 | 2.4 |

Example 10—Preparation and Characterization of Type H of Compound 1

Preparation of Type H of Compound 1

Type H was prepared by liquid vapor diffusion, as described in Example 3.

Characterization of Type H of Compound 1

Figure 24:
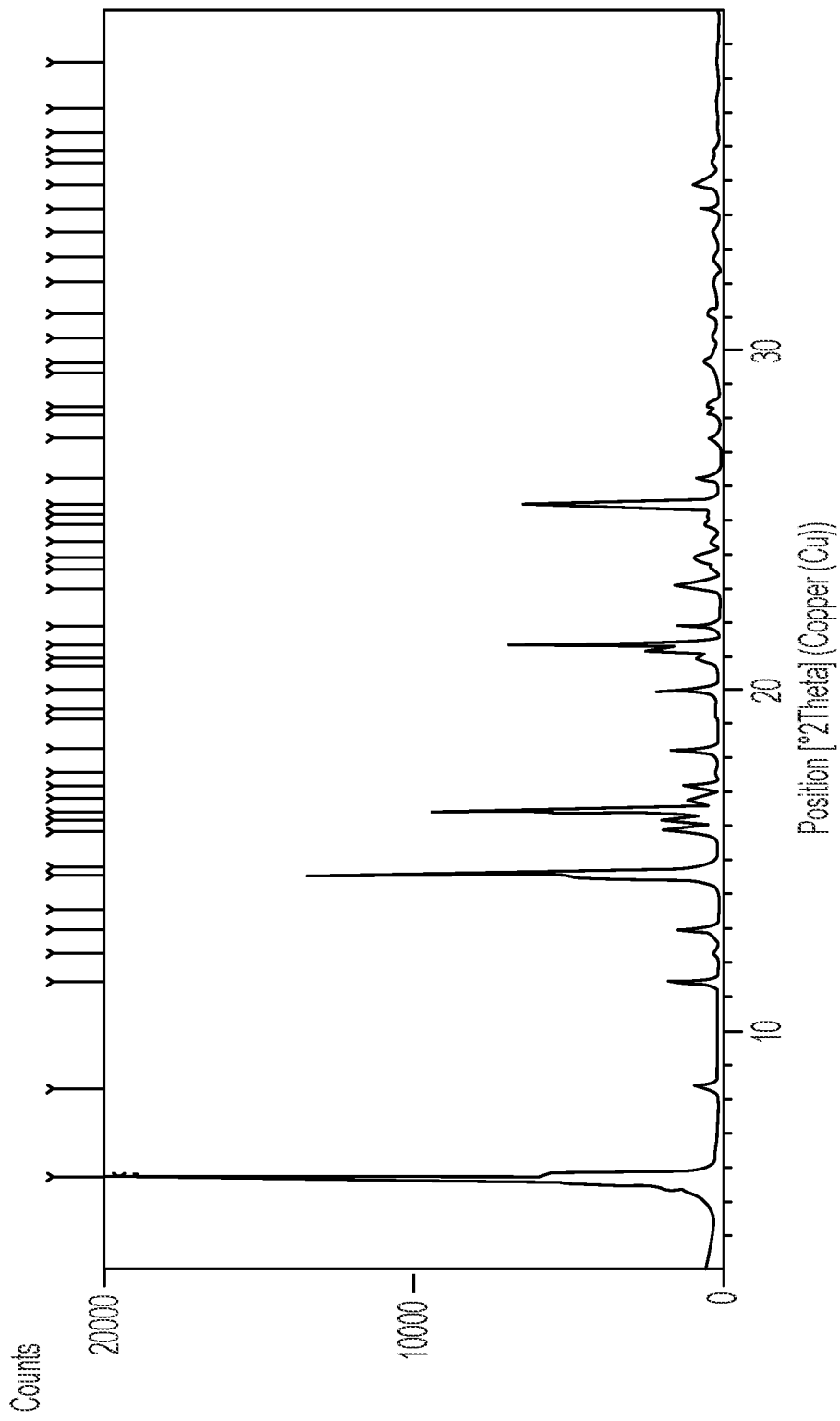
FIG. 24 depicts an XRPD pattern of Compound 1 crystalline form Type H.

Type H was characterized by XRPD (Method C) analysis.
The XRPD pattern for Type H is depicted in FIG. 24 and the corresponding data are summarized in the following table:

| Pos. [°2Th.] | d-spacing [Å] |
|---|---|
| 5.8 | 15.3 |
| 8.4 | 10.5 |
| 11.5 | 7.7 |
| 12.4 | 7.2 |
| 13.1 | 6.8 |
| 13.7 | 6.5 |
| 14.7 | 6.0 |
| 14.9 | 5.9 |
| 16.0 | 5.6 |
| 16.2 | 5.5 |
| 16.6 | 5.4 |
| 16.9 | 5.3 |
| 17.3 | 5.1 |
| 17.7 | 5.0 |
| 18.3 | 4.8 |
| 19.5 | 4.6 |
| 20.0 | 4.4 |
| 21.3 | 4.2 |
| 21.9 | 4.1 |
| 23.1 | 3.9 |
| 23.6 | 3.8 |
| 23.9 | 3.7 |
| 24.4 | 3.7 |
| 24.9 | 3.6 |
| 25.1 | 3.5 |
| 25.4 | 3.5 |
| 26.2 | 3.4 |
| 27.4 | 3.3 |
| 28.1 | 3.2 |
| 28.4 | 3.1 |
| 29.3 | 3.0 |
| 29.7 | 3.0 |
| 30.4 | 2.9 |
| 31.0 | 2.9 |
| 32.7 | 2.7 |
| 33.4 | 2.7 |
| 34.1 | 2.6 |
| 34.8 | 2.6 |
| 35.5 | 2.5 |
| 35.8 | 2.5 |
| 36.4 | 2.5 |

-continued

| Pos. [°2Th.] | d-spacing [Å] |
|---|---|
| 37.1 | 2.4 |
| 38.5 | 2.3 |

Example 11—Preparation and Characterization of Type I of Compound 1

Preparation of Type I of Compound 1

Type I was prepared by liquid vapor diffusion, as described in Example 3.

Characterization of Type I of Compound 1

Type I was characterized by XRPD (Method C) analysis.

Figure 25:
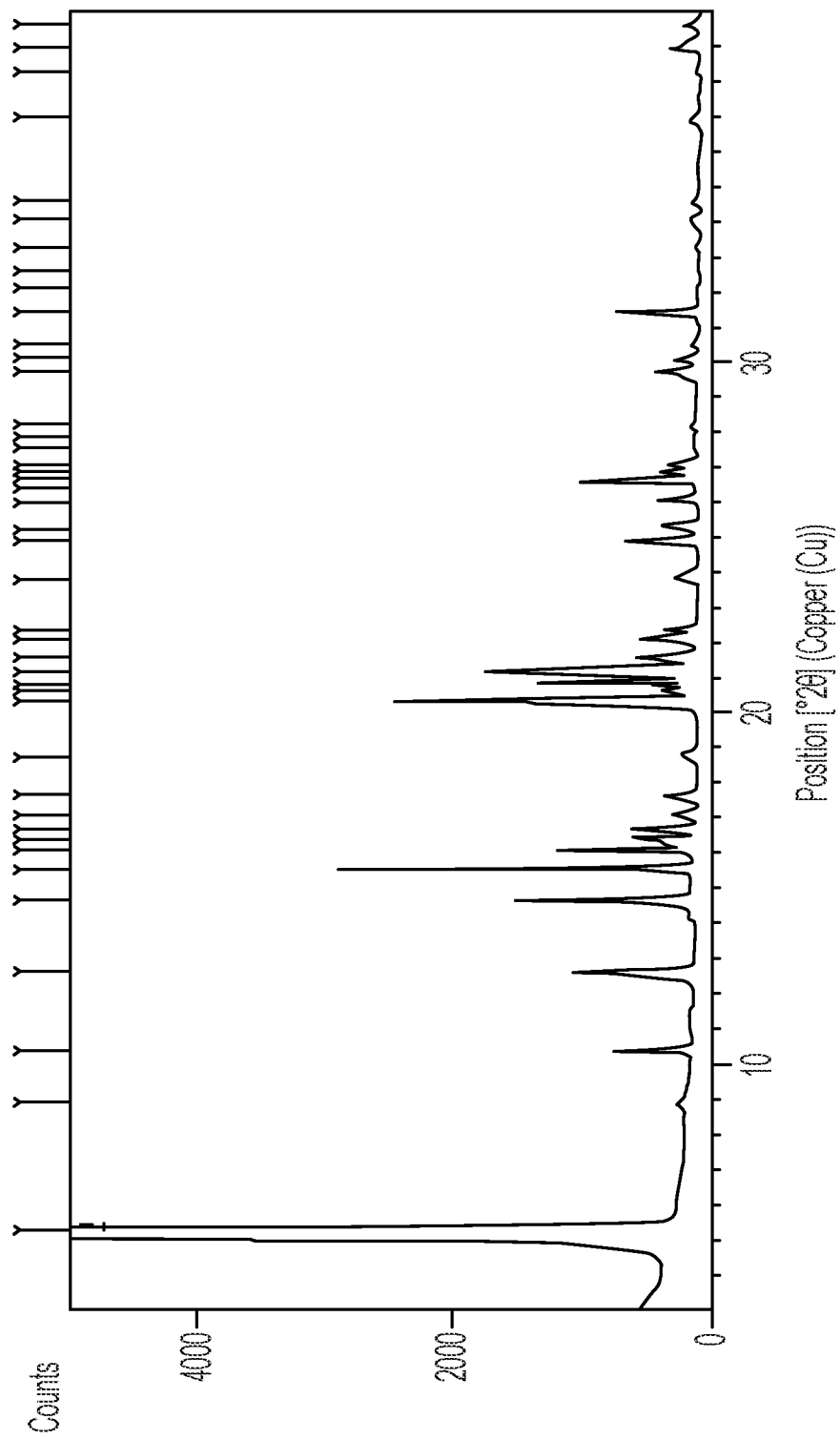
FIG. 25 depicts an XRPD pattern of Compound 1 crystalline form Type I.

The XRPD pattern for Type I is depicted in FIG. 25, and the corresponding data are summarized in the following table:

| Pos. [°2Th.] | d-spacing [Å] |
|---|---|
| 5.2 | 17.1 |
| 8.8 | 10.1 |
| 10.3 | 8.6 |
| 12.6 | 7.0 |
| 14.6 | 6.1 |
| 15.5 | 5.7 |
| 16.1 | 5.5 |
| 16.3 | 5.4 |
| 16.6 | 5.3 |
| 17.1 | 5.2 |
| 17.6 | 5.0 |
| 18.7 | 4.7 |
| 18.9 | 4.7 |
| 20.2 | 4.4 |
| 20.5 | 4.3 |
| 20.7 | 4.3 |
| 21.1 | 4.2 |
| 21.5 | 4.1 |
| 22.0 | 4.0 |
| 22.3 | 4.0 |
| 23.7 | 3.8 |
| 24.8 | 3.6 |
| 25.2 | 3.5 |
| 26.0 | 3.4 |
| 26.3 | 3.4 |
| 26.5 | 3.4 |
| 26.8 | 3.3 |
| 27.0 | 3.3 |
| 27.5 | 3.2 |
| 27.7 | 3.2 |
| 28.1 | 3.2 |
| 29.6 | 3.0 |
| 30.0 | 3.0 |
| 30.4 | 2.9 |
| 31.3 | 2.9 |
| 32.0 | 2.8 |
| 32.5 | 2.8 |
| 33.2 | 2.7 |
| 34.0 | 2.6 |
| 34.6 | 2.6 |
| 36.9 | 2.4 |
| 38.2 | 2.4 |
| 38.9 | 2.3 |
| 39.5 | 2.3 |

Example 12—Preparation and Characterization of Type J of Compound 1

Preparation of Type J of Compound 1

Type J was prepared by liquid vapor diffusion, as described in Example 3.

Characterization of Type J of Compound 1

Type J was characterized by XRPD (Method C) analysis.

Figure 26:
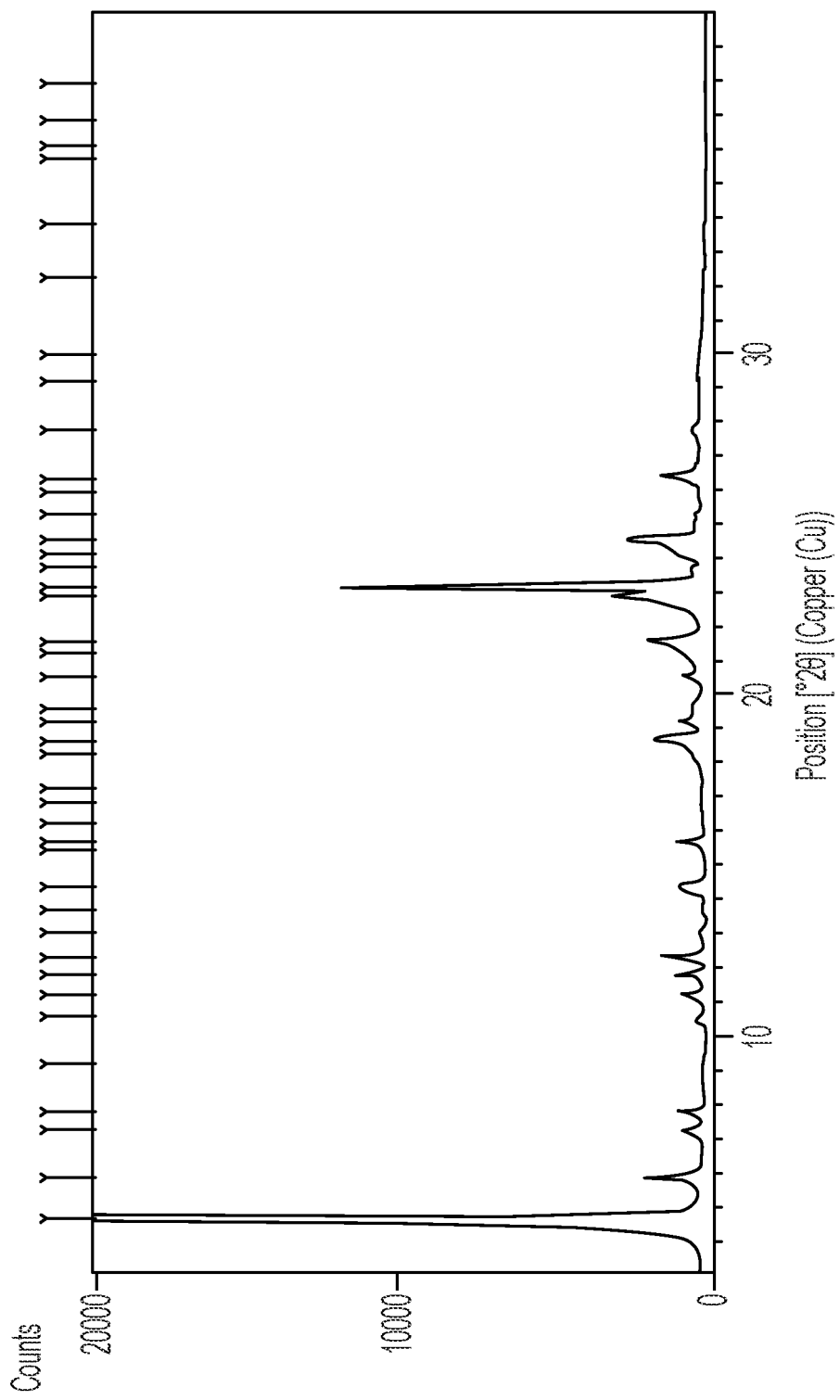
FIG. 26 depicts an XRPD pattern of Compound 1 crystalline form Type J.

The XRPD pattern for Type J is depicted in FIG. 26, and the corresponding data are summarized in the following table:

| Pos. [°2Th.] | d-spacing [Å] |
|---|---|
| 4.5 | 19.5 |
| 5.7 | 15.4 |
| 7.1 | 12.7 |
| 7.7 | 11.5 |
| 9.1 | 9.7 |
| 10.5 | 8.4 |
| 11.2 | 7.9 |
| 11.7 | 7.5 |
| 12.3 | 7.2 |
| 12.9 | 6.8 |
| 14.3 | 6.2 |
| 14.5 | 6.1 |
| 15.4 | 5.8 |
| 15.7 | 5.7 |
| 16.3 | 5.4 |
| 17.3 | 5.1 |
| 18.3 | 4.9 |
| 18.7 | 4.7 |
| 19.3 | 4.6 |
| 19.6 | 4.5 |
| 20.5 | 4.3 |
| 21.2 | 4.2 |
| 21.5 | 4.1 |
| 22.8 | 3.9 |
| 23.1 | 3.8 |
| 23.6 | 3.8 |
| 24.1 | 3.7 |
| 24.5 | 3.6 |
| 25.2 | 3.5 |
| 25.9 | 3.4 |
| 26.4 | 3.4 |
| 27.8 | 3.2 |
| 29.3 | 3.0 |
| 36.2 | 2.5 |
| 37.0 | 2.4 |

Example 13—Preparation and Characterization of Type K of Compound 1

Preparation of Type K of Compound 1

Type K was prepared by slow cooling, as described in Example 3.

Characterization of Type K of Compound 1

Type K was characterized by XRPD (Method C) analysis.

Figure 27:
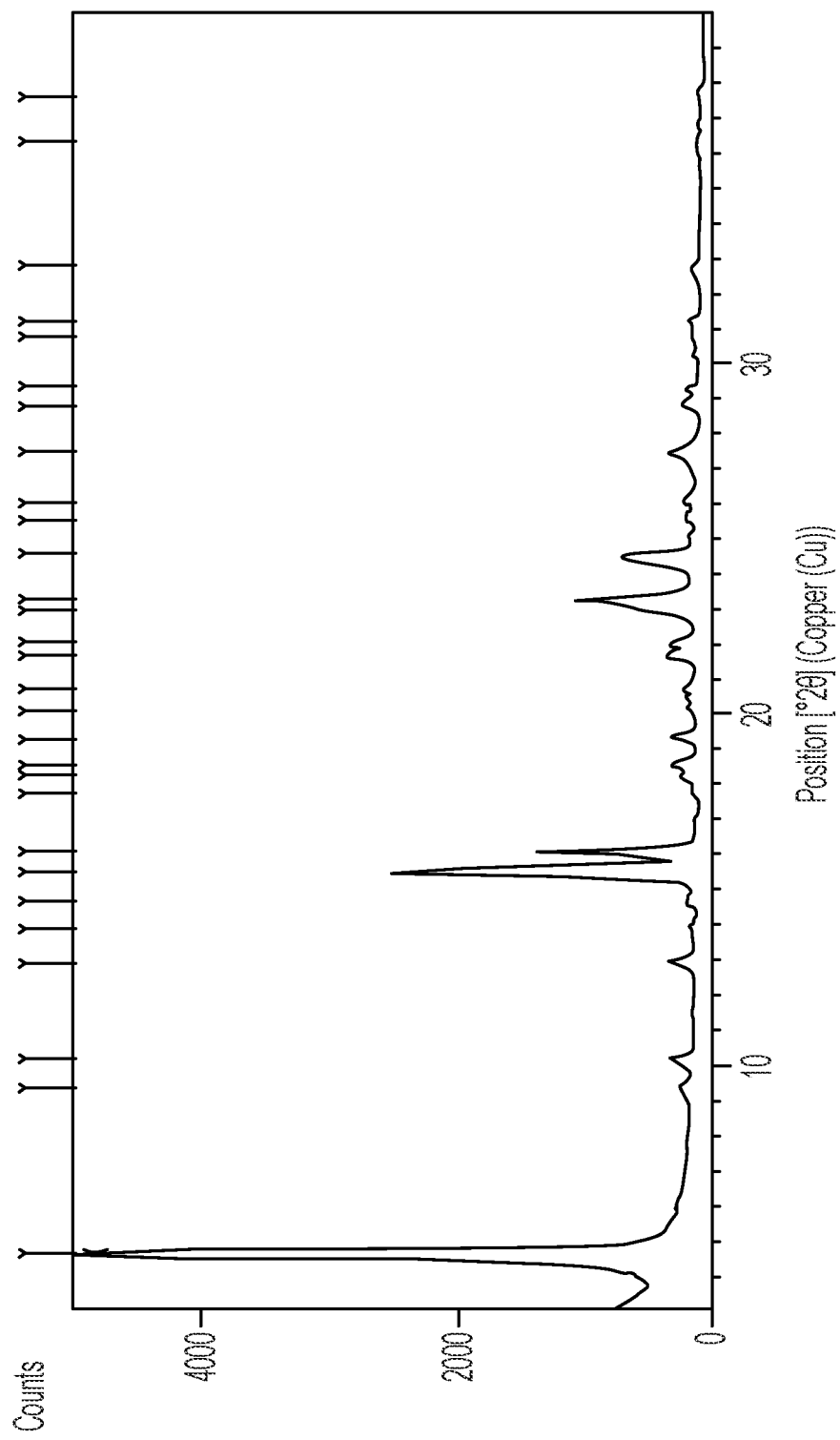
FIG. 27 depicts an XRPD pattern of Compound 1 crystalline form Type K.

The XRPD pattern for Type K is depicted in FIG. 27, and the corresponding data are summarized in the following table:

| Pos. [°2Th.] | d-spacing [Å] |
|---|---|
| 4.6 | 19.2 |
| 9.3 | 9.5 |
| 10.1 | 8.7 |
| 12.9 | 6.8 |
| 13.9 | 6.4 |
| 14.7 | 6.0 |
| 15.4 | 5.7 |
| 15.6 | 5.7 |
| 16.1 | 5.5 |
| 17.8 | 5.0 |
| 18.3 | 4.9 |
| 18.6 | 4.8 |
| 19.3 | 4.6 |
| 20.0 | 4.4 |
| 20.7 | 4.3 |
| 21.6 | 4.1 |

-continued

| Pos. [°2Th.] | d-spacing [Å] |
|---|---|
| 21.9 | 4.1 |
| 22.9 | 3.9 |
| 23.2 | 3.8 |
| 24.4 | 3.6 |
| 25.0 | 3.6 |
| 25.5 | 3.5 |
| 26.0 | 3.4 |
| 27.4 | 3.3 |
| 28.8 | 3.1 |
| 29.2 | 3.1 |
| 30.7 | 2.9 |
| 31.1 | 2.9 |
| 32.7 | 2.7 |
| 36.3 | 2.5 |

Example 14—Preparation and Characterization of Type L of Compound 1

Preparation of Type L of Compound 1

Type L was prepared by slow cooling, as described in Example 3.

Characterization of Type L of Compound 1

Type L was characterized by XRPD (Method C) analysis.

Figure 28:
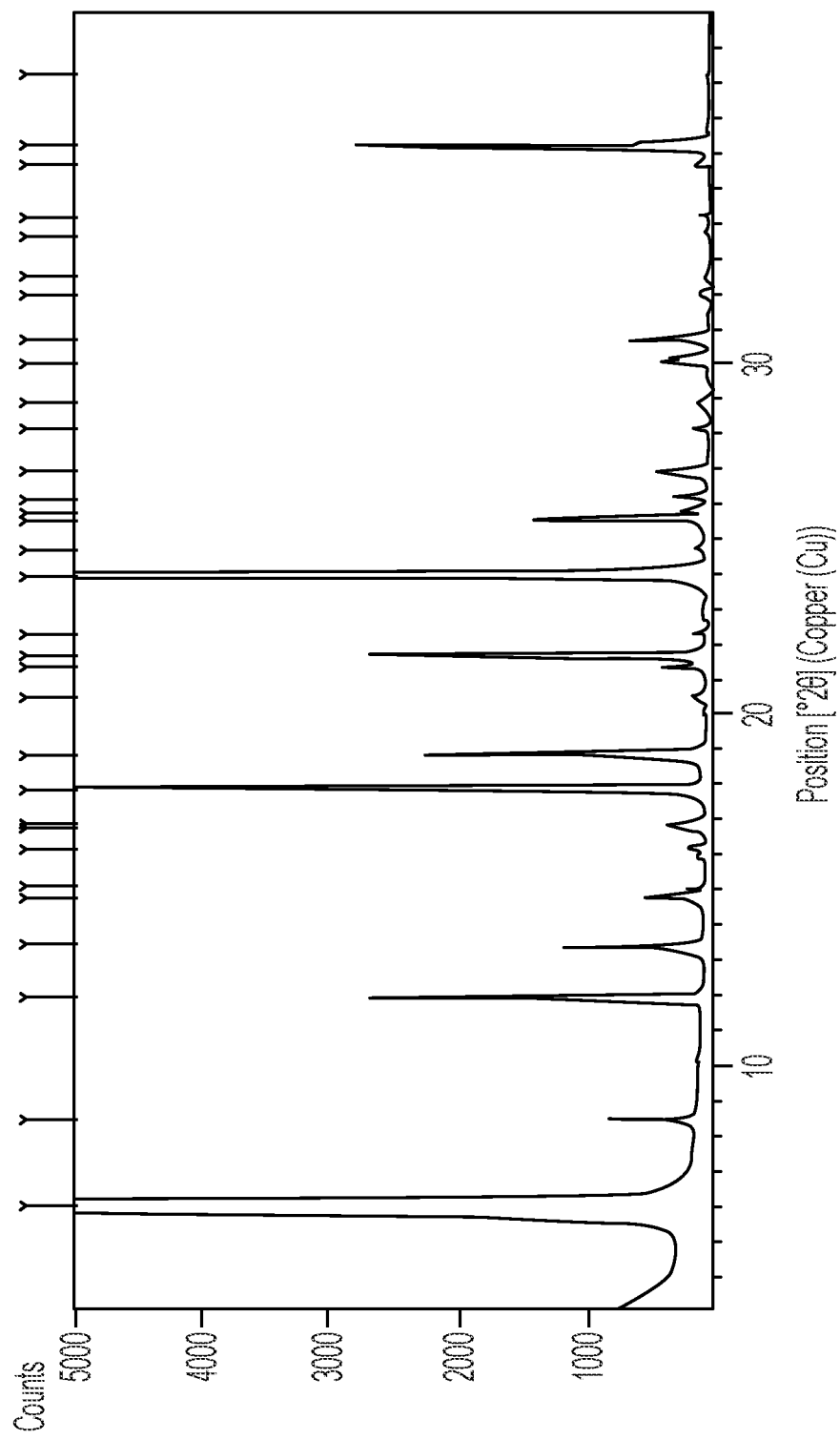
FIG. 28 depicts an XRPD pattern of Compound 1 crystalline form Type L.

The XRPD pattern for Type L is depicted in FIG. 28, and the corresponding data are summarized in the following table:

| Pos. [°2Th.] | d-spacing [Å] |
|---|---|
| 5.9 | 14.9 |
| 8.4 | 10.5 |
| 11.9 | 7.5 |
| 13.3 | 6.6 |
| 14.7 | 6.0 |
| 15.0 | 5.9 |
| 16.2 | 5.5 |
| 16.7 | 5.3 |
| 16.9 | 5.2 |
| 17.8 | 5.0 |
| 18.9 | 4.7 |
| 20.4 | 4.4 |
| 21.2 | 4.2 |
| 21.6 | 4.1 |
| 22.2 | 4.0 |
| 23.9 | 3.7 |
| 24.6 | 3.6 |
| 25.5 | 3.5 |
| 25.7 | 3.5 |
| 26.1 | 3.4 |
| 26.8 | 3.3 |
| 28.1 | 3.2 |
| 28.8 | 3.1 |
| 29.9 | 3.0 |
| 30.6 | 2.9 |
| 31.9 | 2.8 |
| 32.4 | 2.8 |
| 33.6 | 2.7 |
| 34.2 | 2.6 |
| 35.6 | 2.5 |
| 36.1 | 2.5 |
| 38.2 | 2.4 |

Single crystal X-ray analysis revealed that Type L is a THF/water co-solvate of Compound 1, with Compound 1, THF, and water present in a 1:1:1 ratio.

Example 15—Preparation and Characterization of Type M of Compound 1

Preparation of Type M of Compound 1

Type M was prepared by liquid vapor diffusion, as described in Example 3.

Characterization of Type M of Compound 1

Type M was characterized by XRPD (Method C) analysis.

Figure 29:
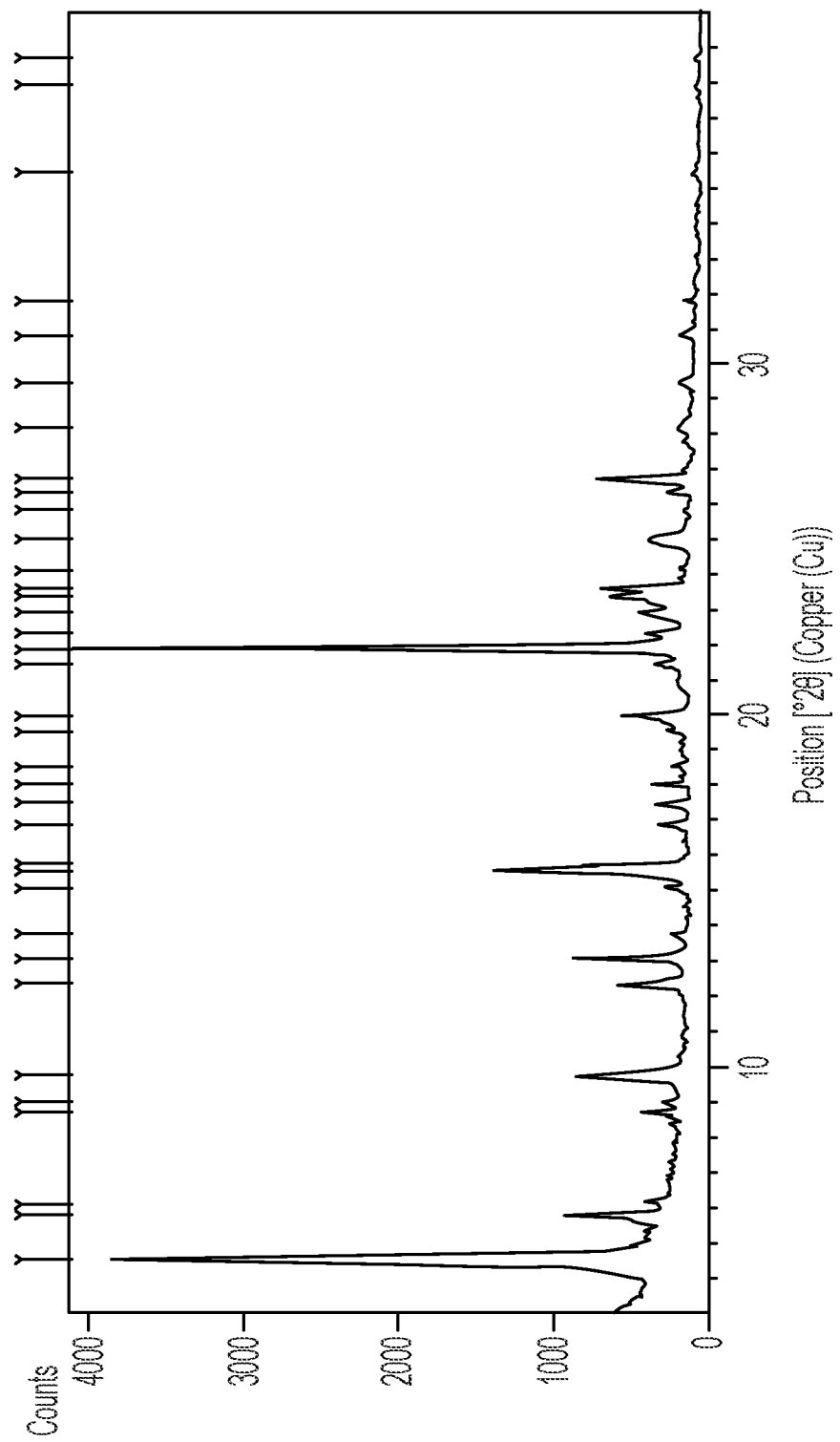
FIG. 29 depicts an XRPD pattern of Compound 1 crystalline form Type M.
Figure 30:
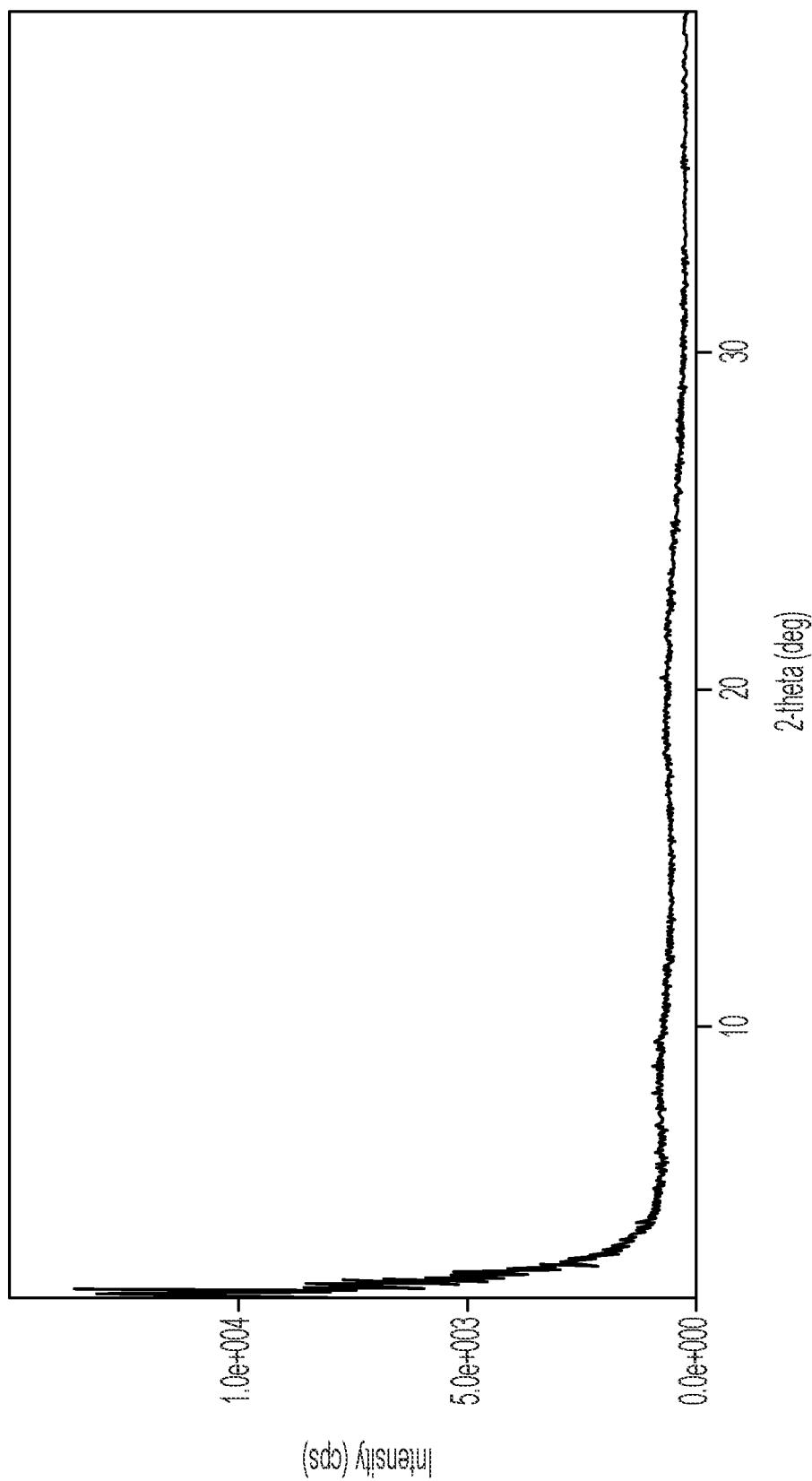
FIG. 30 depicts an XRPD pattern of a spray-dried dispersion (SDD) of Compound 1.
Figure 31:
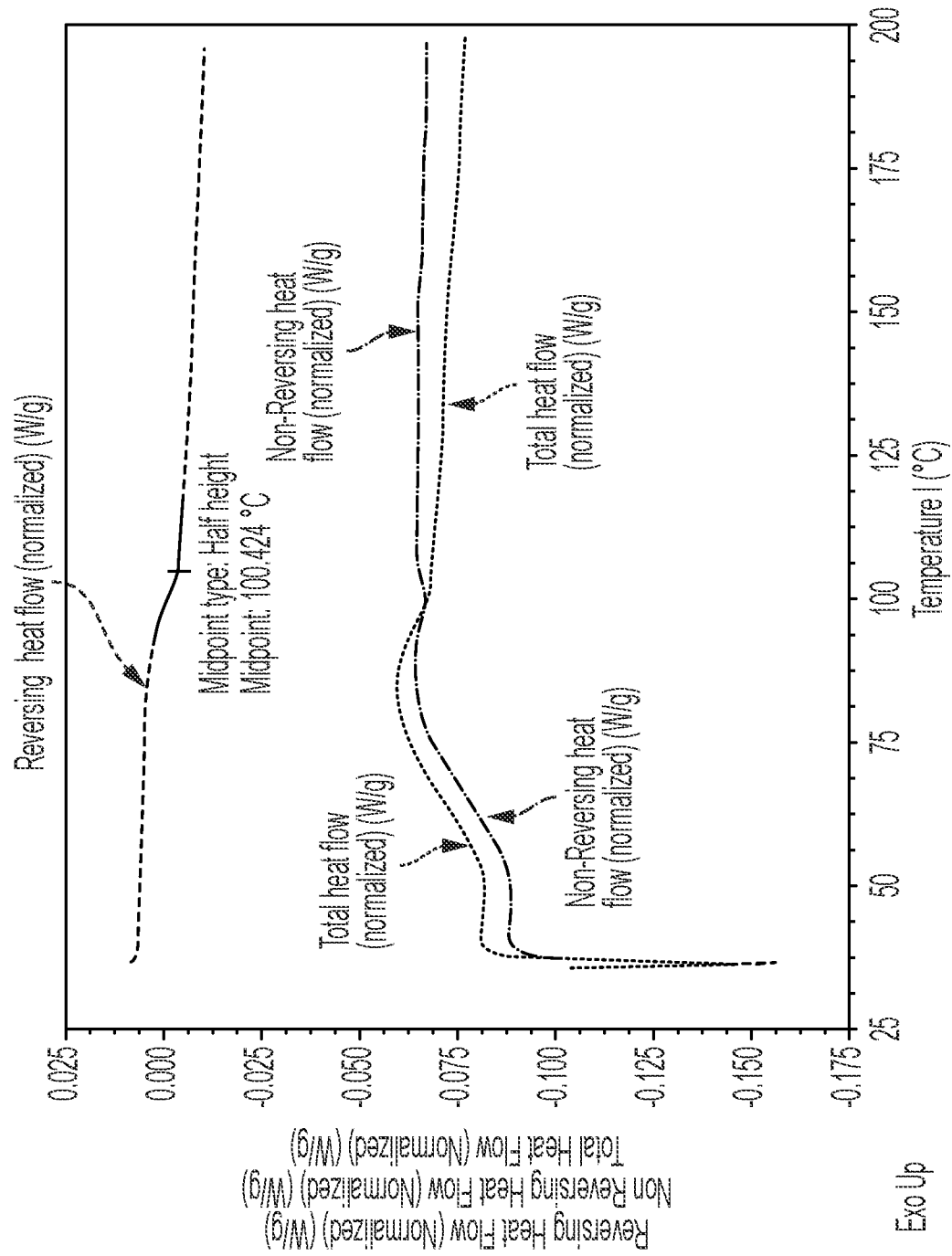
FIG. 31 depicts a differential scanning calorimetry (DSC) thermogram for a spray-dried dispersion (SDD) of Compound 1.
Figure 32:
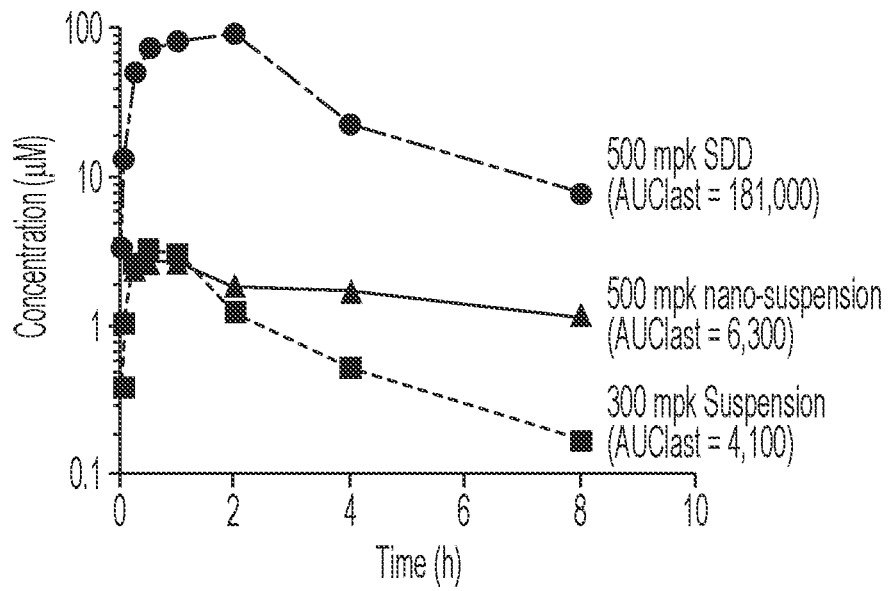
FIG. 32 depicts a graph of the plasma concentration over time following administration of three formulations of Compound 1 in rats.
Figure 33:
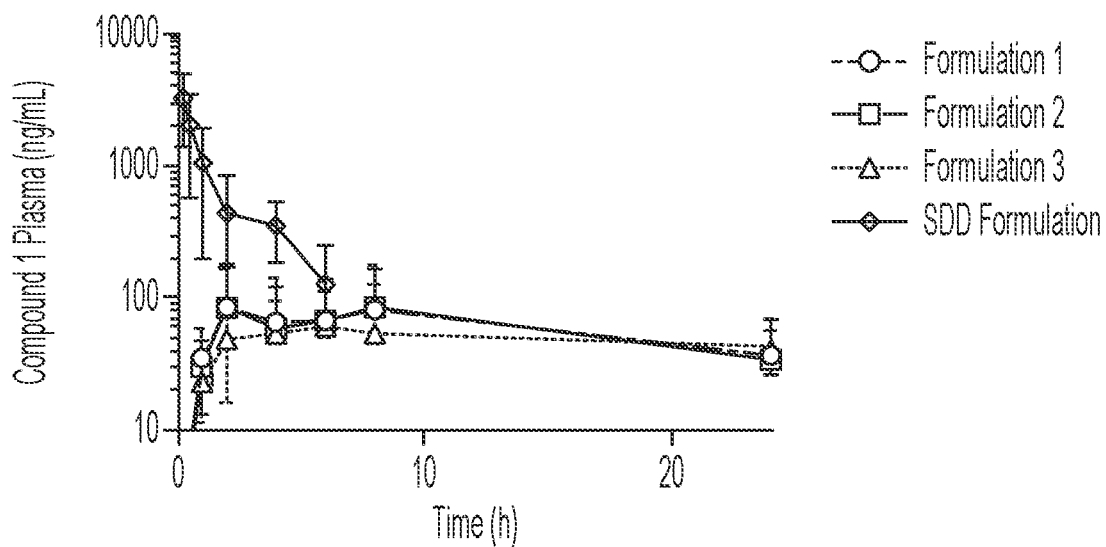
FIG. 33 depicts a graph of the plasma concentration over time following administration of four formulations of Compound 1 in monkeys.

The XRPD pattern for Type M is depicted in FIG. 29, and the corresponding data are summarized in the following table:

| Pos. [°2Th.] | d-spacing [Å] |
|---|---|
| 4.5 | 19.5 |
| 5.8 | 15.3 |
| 6.1 | 14.4 |
| 8.7 | 10.2 |
| 9.0 | 9.9 |
| 9.7 | 9.1 |
| 12.3 | 7.2 |
| 13.1 | 6.8 |
| 13.7 | 6.4 |
| 14.5 | 6.1 |
| 15.1 | 5.9 |
| 15.6 | 5.7 |
| 16.8 | 5.3 |
| 17.4 | 5.1 |
| 18.0 | 4.9 |
| 18.5 | 4.8 |
| 19.5 | 4.5 |
| 20.0 | 4.4 |
| 21.4 | 4.1 |
| 21.9 | 4.1 |
| 22.3 | 4.0 |
| 22.9 | 3.9 |
| 23.3 | 3.8 |
| 23.5 | 3.8 |
| 24.1 | 3.7 |
| 25.0 | 3.6 |
| 25.8 | 3.5 |
| 26.3 | 3.4 |
| 26.7 | 3.3 |
| 27.8 | 3.2 |
| 28.1 | 3.2 |
| 29.4 | 3.0 |
| 30.8 | 2.9 |
| 31.7 | 2.8 |
| 33.0 | 2.7 |
| 35.3 | 2.5 |
| 37.8 | 2.4 |
| 38.6 | 2.3 |

Example 16—Preparation and Characterization of the Spray-Dried Dispersion of Compound 1

A Spray Dried Dispersion (SDD) of Compound 1 was prepared. The SDD was made up of Compound 1 and a polymer (Hydroxypropylmethyl Cellulose AS-MG) at a 1:3 weight ratio. Compound 1 and the polymer were dissolved in organic solvents (Dichloromethane and Methanol) and spray dried to obtain amorphous an amorphous drug substance. The SDD comprising Compound 1 and HPMC AS (1:3) is referred to herein as SDD 0.

A spray solution was prepared at 7.8% solids content (1:3 Compound 1:HPMC AS-MG) in 80:20 DCM:Methanol per Table 18. An API correction factor of 0.966 was used to prepare the spray solution. The spray solution was prepped by adding DCM and Methanol to a 36 L stainless steel mixing vessel. HPMC AS-MG was added to the solvent system while mixing with a top down mixer at a medium vortex. Compound 1 was then added to the solution. The solution had a yellow/brown clear appearance, however white fiber particulates were seen in the solution.

TABLE 18

| Component | Formulation % | Weight, g |
|---|---|---|
| Compound 1 | 2.00% | 595.0 |
| HPMC AS-MG | 5.81% | 1724.3 |
| DCM | 73.75% | 21896.0 |
| Methanol | 18.44% | 5474.0 |
| Total | 100.0% | 29689.3 |

Correction Factor: 0.9660

A Mobile Minor spray-drying apparatus was setup per Table 19 and warmed up for approximately one hour prior to spraying. Wash solution (80:20 DCM:Methanol) was sprayed prior to the active solution to allow the nozzle to equilibrate. The Compound 1 active solution was sprayed per the settings in Table 19. The spray-dried dispersion was dried overnight (~20 hours) in a Shel Vacuum Oven at 50° C. and −25 in Hg vacuum under a nitrogen purge at 15 scfh. The resulting spray-dried dispersion was confirmed to be dry by GC analysis. This run generated approximately 2.1 kg of spray-dried dispersion.

TABLE 19

Figure 34:
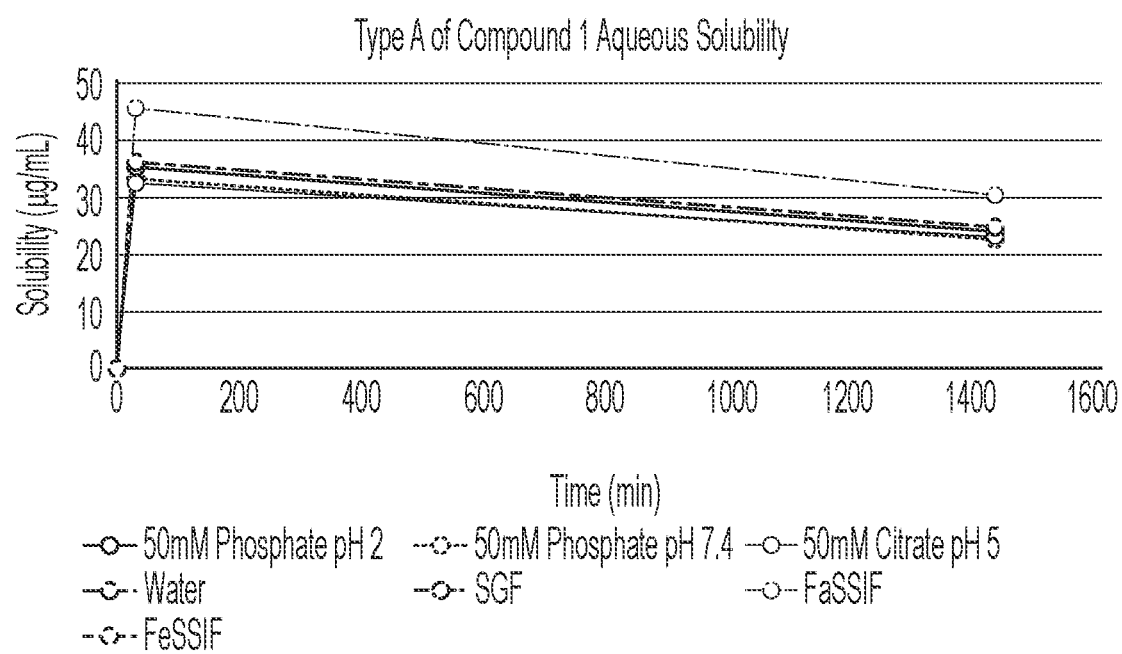
FIG. 34 depicts a graph of time-dependent solubility of Type A of Compound 1 in biorelevant media.

| Parameter | Set Point |
|---|---|
| Inline Filter | Swagelok 140 μm Stainless Steel |
| Nozzle | 0.3 mm, 60° Angle |
| Inlet Air Flow | 80 kg/hr |
| Inlet Air Temperature | 104° C. |
| Pump Stroke Length | 5.70 mm |
| Nozzle Pressure | 600 psi |
| Feed Rate (g/min) | 184 g/min |
| Outlet Temp (° C.) | 36 |
| Set Condenser Air Temp (° C.) | −10 |
| Actual Condenser Air Temp (° C.) | −3 |
| Chiller Temp (° C.) | −20 |
| Feed Temp | Ambient |

The SDD was characterized by XRPD (Method B) and DSC analysis (ambient to 200° C., 2° C./minute ramp), as shown in FIGS. 30 and 31, respectively. The SDD was determined to be homogenous and amorphous, as shown by the amorphous diffractogram, lack of a crystalline melt, and a single Tg at 100° C.

Example 17—Bioavailability of the Spray-Dried Dispersion (SDD) of Compound 1 in Rats and Mice The systemic exposure of Compound 1 in rats and mice was evaluated by dosing a SDD made up of Compound 1 and HPMC AS-MG (1:3) (SDD 0, which can be prepared as described in Example 16) dispersed in an aqueous vehicle (0.5% Hydroxypropylmethyl Cellulose in water). The SDD formulation ("500 mpk SDD") dosed at 500 mg/kg to rats showed an $AUC_{last}$ that was 40× greater than the maximum exposure obtained with the standard formulation ("300 mpk Suspension" made up of Compound 1 (Type A) in 10% Propylene Glycol, 10% Cremophore, 80% Water), as shown in Table 20 and FIG. 32. Additionally, the exposure of a 500 mpk Nano-Suspension made up of nanoparticles of Compound 1 (Type A) was evaluated, as shown in FIG. 32. Robust exposure was observed with SDD formulation in mouse as well.

TABLE 20

| Animal | $t_{1/2}$ (h) | $t_{max}$ (h) | $C_{max}$ (ng/mL) | AUClast (h*ng/mL) |
|---|---|---|---|---|
| Rat | 3.22 | 1.67 | 44400 | 180603 |
| Mouse | 2.54 | 0.5 | 75200 | 113369 |

Example 18—Bioavailability of the Spray-Dried Dispersion of Compound 1 in Monkeys Several formulations of Compound 1, including an SDD made up of Compound 1 and HPMC AS-MG (1:3) (SDD 0, which can be prepared as described in Example 16), were evaluated in monkeys. The compositions of the tested formulations are listed in Table 21.

TABLE 21

| Formulation | Dosage Form | Composition |
|---|---|---|
| Formulation #1 (with Bile Salt) | Capsule; Size 0 White Opaque Gelatin | Compound 1 (Type A), micronized 49.9%<br>Avicel PH101 23.5%<br>AcDiSol 5.0%<br>SLS 10.1%<br>Na Taurocholate 10.0%<br>Mg Stearate 0.5%<br>Silicon Dioxide 1.0% |
| Formulation #2 (Formulated Capsule) | Capsule; Size 0 White Opaque Gelatin | Compound 1 (Type A) micronized API 49.9%<br>Avicel PH101 33.3%<br>AcDiSol 5.0%<br>SLS 10.3%<br>Mg Stearate 0.5%<br>SiO2 1.0% |
| Formulation #3 (Micronized fill) | Capsule; Size 0 White Opaque Gelatin | Compound 1 (Type A) micronized API only |
| Formulation #4 (SDD) | Suspension | Compound 1 Spray Dried Dispersion 0.5% Hydroxypropylmethyl Cellulose in Water |

The formulations were evaluated for pharmacokinetic parameters in monkeys and are shown in FIG. 33. The profiles show that the SDD formulation (Formulation 4) provided a significant enhancement in overall exposure compared to the encapsulated formulations (Formulations 1, 2, and 3). The bioavailability enhancement with the SDD formulation is approximately 50-62%, which is several fold higher compared to the other formulations, at a dose equivalent to 100 mg.

Example 19—Time-Dependent Solubility of Type A of Compound 1 and the Spray-Dried Dispersion of Compound 1 in Biorelevant Media The solubility of Type A of Compound 1 was evaluated in aqueous media. Aqueous solubility samples of Type A of Compound 1 were saturated with solid content. Samples were shaken at 37° C. for 24 hours. Each aqueous media was also sampled after 30 minutes and filtered/diluted using the same procedure to be used for the t=24-hour samples. Sample pH was only measured after 24-hour equilibration.

Following 24-hour equilibration, the pH of the saturated samples was measured, and the mixtures were centrifuged through 0.22 μm nylon filters at 15,000 rpm for approximately 2 minutes. All centrifuged samples were diluted with method diluent and analyzed by HPLC (Method A). If no solids were present after overnight equilibration, the solubility was reported as "≥" to the determined value. The concentrations reported are based on a single point calibration at the method nominal and are reported as the free form. Results are shown in Table 22 and FIG. 34.

TABLE 22

| Sample | t = 30 minutes Solubility (µg/mL) | t = 24 hours Solubility (µg/mL) | Measured pH (after 24-hours) |
|---|---|---|---|
| Water | 36.29 | 24.98 | 8.69 |
| 50 mM Phosphate pH 2.0 | 35.31 | 24.16 | 1.98 |
| 50 mM Citrate pH 5.0 | 32.53 | 23.49 | 5.01 |
| 50 mM Phosphate pH 7.4 | 33.43 | 22.72 | 7.36 |
| Simulated Gastric Fluid (SGF) | 39.65 | 26.60 | 1.07 |
| Fasted-State Simulated Intestinal Fluid (FaSSIF) | 45.84 | 30.48 | 6.52 |
| Fed-State Simulated Intestinal Fluid (FeSSIF) | 67.04 | 48.18 | 5.01 |

Figure 35:
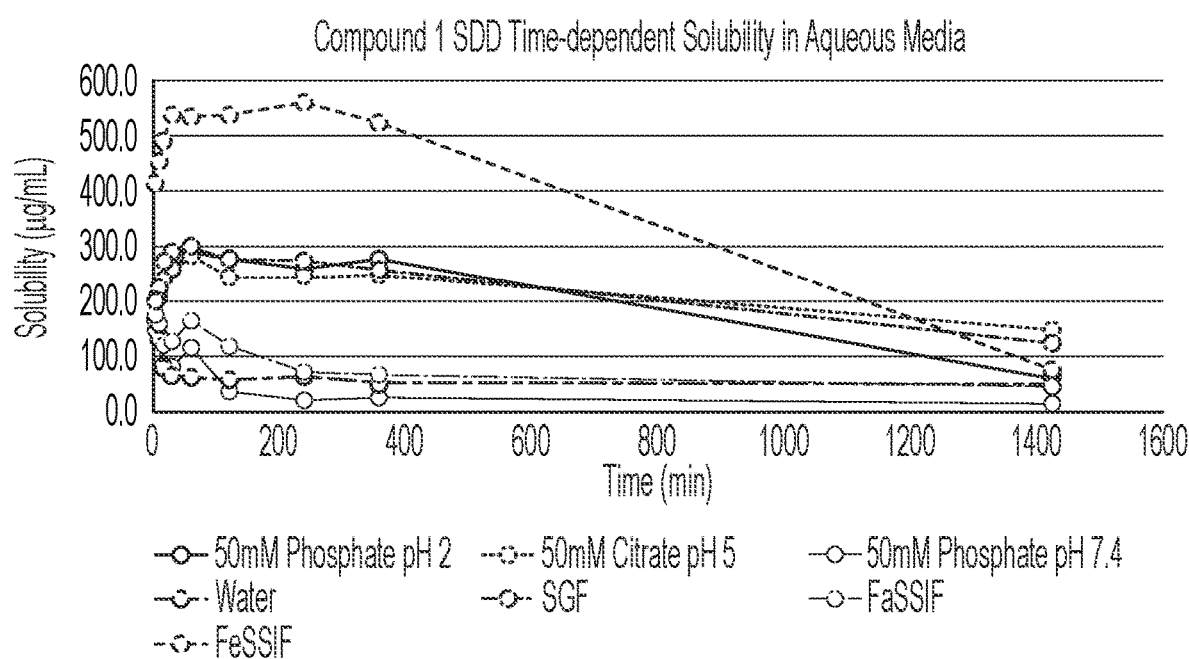
FIG. 35 depicts a graph of time-dependent solubility of a spray-dried dispersion (SDD) of Compound 1 in biorelevant media.

Solubility of the 1:3 Compound 1: HPMC-AS-MG spray-dried dispersion (SDD 0, which can be prepared as described in Example 16) was assessed in aqueous media at various timepoints over 24-hours. Individual saturated samples were prepared for each anticipated time point by adding ~10 mg of SDD material to 1.5 mL of solvent. Samples were placed at 37° C. on a thermal shaker at 600 RPM and pulled at t=2 min, 5 min, 15 min, 30 min, 1 hr, 2 hr, 4 hr, 6 hr, and 24-hours. The mixtures were centrifuged through 0.22 µm nylon filters at 15,000 rpm for approximately 5 minutes. All centrifuged samples were diluted with method diluent and analyzed by HPLC (Method A). Sample pH was measured only at 24-hours. Results are shown in Table 23 and FIG. 35.

TABLE 23

| | Solubility (µg/mL) at Actual Time (min) | | | | | | | | | |
|---|---|---|---|---|---|---|---|---|---|---|
| Media | 2 | 8 | 15 | 29 | 59 | 120 | 240 | 360 | 1435 | Final pH |
| 50 mM Phosphate pH 2 | 169.5 | 207.2 | 238.7 | 258.9 | 288.4 | 278.0 | 258.5 | 276.0 | 65.0 | 1.91 |
| 50 mM Citrate pH 5 | 163.5 | 213.2 | 239.1 | 260.5 | 281.7 | 244.9 | 245.7 | 248.1 | 149.1 | 4.96 |
| 50 mM Phosphate pH 7.4 | 148.4 | 138.6 | 86.1 | 83.1 | 117.3 | 38.1 | 22.8 | 25.6 | 15.5 | 7.19 |
| Water | 203.7 | 132.4 | 80.4 | 65.7 | 64.0 | 58.8 | 64.3 | 50.9 | 48.9 | 5.11 |
| SGF | 199.8 | 225.7 | 272.8 | 289.9 | 299.6 | 276.8 | 273.5 | 256.7 | 125.1 | 1.05 |
| FaSSIF | 175.5 | 160.0 | 120.5 | 128.5 | 164.1 | 5005.9[1] | 72.4 | 67.7 | 46.4 | 5.65 |
| FeSSIF | 413.1 | 453.5 | 490.1 | 536.0 | 532.9 | 536.0 | 558.5 | 522.2 | 76.2 | 5.02 |

[1] Solids observed in centrifuge filter, resuspended in case of supersaturation, however high value suggests faulty filter. Time point omitted from the solubility profile in FIG. 35.

The solubility of the SDD was significant, particularly at earlier time points. Solubility of the SDD after four hours was 72.4 µg/mL in FaSSIF and 558.5 µg/mL in FeSSIF. Four-hour solubility of the SDD is 273.5 µg/mL in SGF. The solubility decreased after 24-hour equilibration in all aqueous media tested.

Example 20—Stability Assessment of the Spray-Dried Dispersion of Compound 1

Stability studies were conducted on two distinct lots of the 1:3 Compound 1: HPMC-AS-MG spray-dried dispersion (SDD 0, which can be prepared as described in Example 16) under the conditions outlined in Table 24. The results of the stability study for each lot and storage condition are reported in the Tables identified in Table 24. The results for Lot 1 at the 5 month time point and Lot 2 at the 1 month time point remained consistent with the T=0 time points.

TABLE 24

| Lot No. | Container | Storage Condition | Table |
|---|---|---|---|
| Lot 1 | Double-bagged LDPE bags, Zip-tied, inside a sealed Mylar pouch with a 1 g desiccant packet | 2-8° C./Ambient RH | Table 25 |
| | | 25 ± 2° C./60 ± 5% RH | Table 26 |
| Lot 2 | Double-bagged LDPE bags, Zip-tied, inside a sealed Mylar pouch with a 1 g desiccant packet | 2-8° C./Ambient RH | Table 27 |
| | | 25 ± 2° C./60 ± 5% RH | Table 28 |
| | | 40 ± 2° C./75 ± 5% RH | Table 29 |

TABLE 25

Storage Conditions: 2-8° C./Ambient RH
Lot 1

| | Time Point (months) | |
|---|---|---|
| Test Method | 0 | 5 |
| Water Content | 2.12% | 1.07% |
| DSC (Method B) | $T_G$ at 97.707° C., absence of melt | $T_G$ at 97.555° C., absence of melt |
| XRPD (Method D) | No measurable crystalline material observed | No measurable crystalline material |

TABLE 26

Storage Conditions: 25 ± 2° C./60 ± 5% RH
Lot 1

| | Time Point (months) | |
|---|---|---|
| Test Method | 0 | 5 |
| Water Content | 2.12% | 1.03% |
| DSC (Method B) | $T_G$ at 97.707° C., absence of melt | $T_G$ at 98.630° C., absence of melt |
| XRPD (Method D) | No measurable crystalline material observed | No measurable crystalline material observed |

TABLE 27

Storage Conditions: 2-8° C./Ambient RH
Lot 2

| Test Method | Time Point (months) | |
|---|---|---|
| | 0 | 1 |
| Water Content | 1.24% | 0.95% |
| DSC (Method B) | $T_G$ at 100.345° C., absence of melt | $T_G$ at 99.456° C., absence of melt |
| XRPD (Method D) | XRPD Diffractogram showed amorphous halo without any distinct peaks | XRPD Diffractogram showed amorphous halo without any distinct peaks |

TABLE 28

Storage Conditions: 25 ± 2° C./60 ± 5% RH
Lot 2

| Test Method | Time Point (months) | |
|---|---|---|
| | 0 | 1 |
| Water Content | 1.24% | 0.77% |
| DSC (Method B) | $T_G$ at 100.345° C., absence of melt | $T_G$ at 99.343° C., absence of melt |
| XRPD (Method D) | XRPD Diffractogram showed amorphous halo without any distinct peaks | XRPD Diffractogram showed amorphous halo without any distinct peaks |

TABLE 29

Storage Conditions: 40 ± 2° C./75 ± 5% RH
Lot 2

| Test Method | Time Point (months) | |
|---|---|---|
| | 0 | 1 |
| Water Content | 1.24% | 0.74% |
| DSC (Method B) | $T_G$ at 100.345° C., absence of melt | $T_G$ at 98.367° C., absence of melt |
| XRPD (Method D) | XRPD Diffractogram showed amorphous halo without any distinct peaks | XRPD Diffractogram showed amorphous halo without any distinct peaks |

Example 21—Preparation and Characterization of Spray-Dried Dispersions of Compound 1

Figure 36:
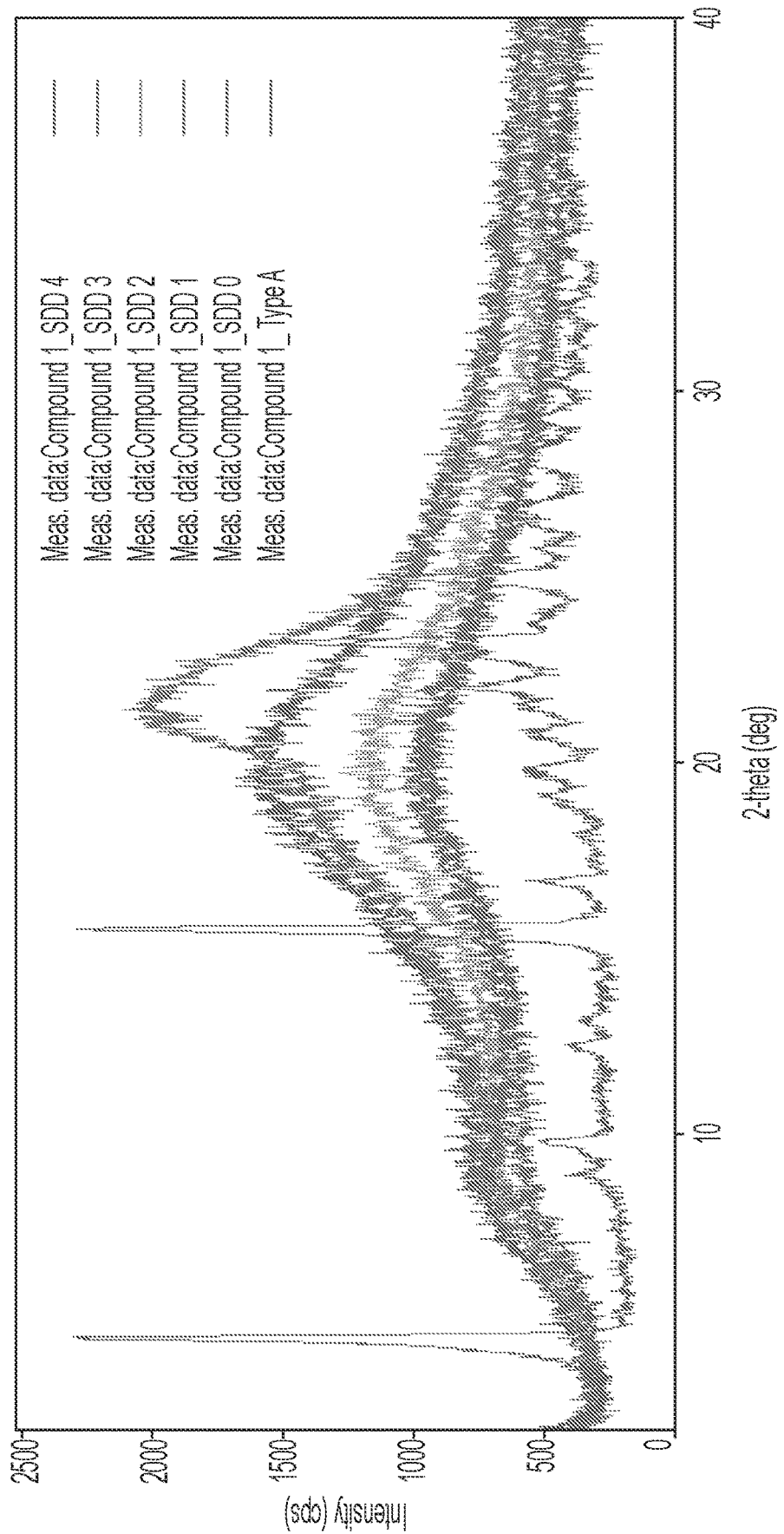
FIG. 36 depicts overlayed XRPD patterns of five spray-dried dispersions (SDDs) of Compound 1, overlayed with the XRPD pattern of crystalline Compound 1 (Type A).
Figure 37:
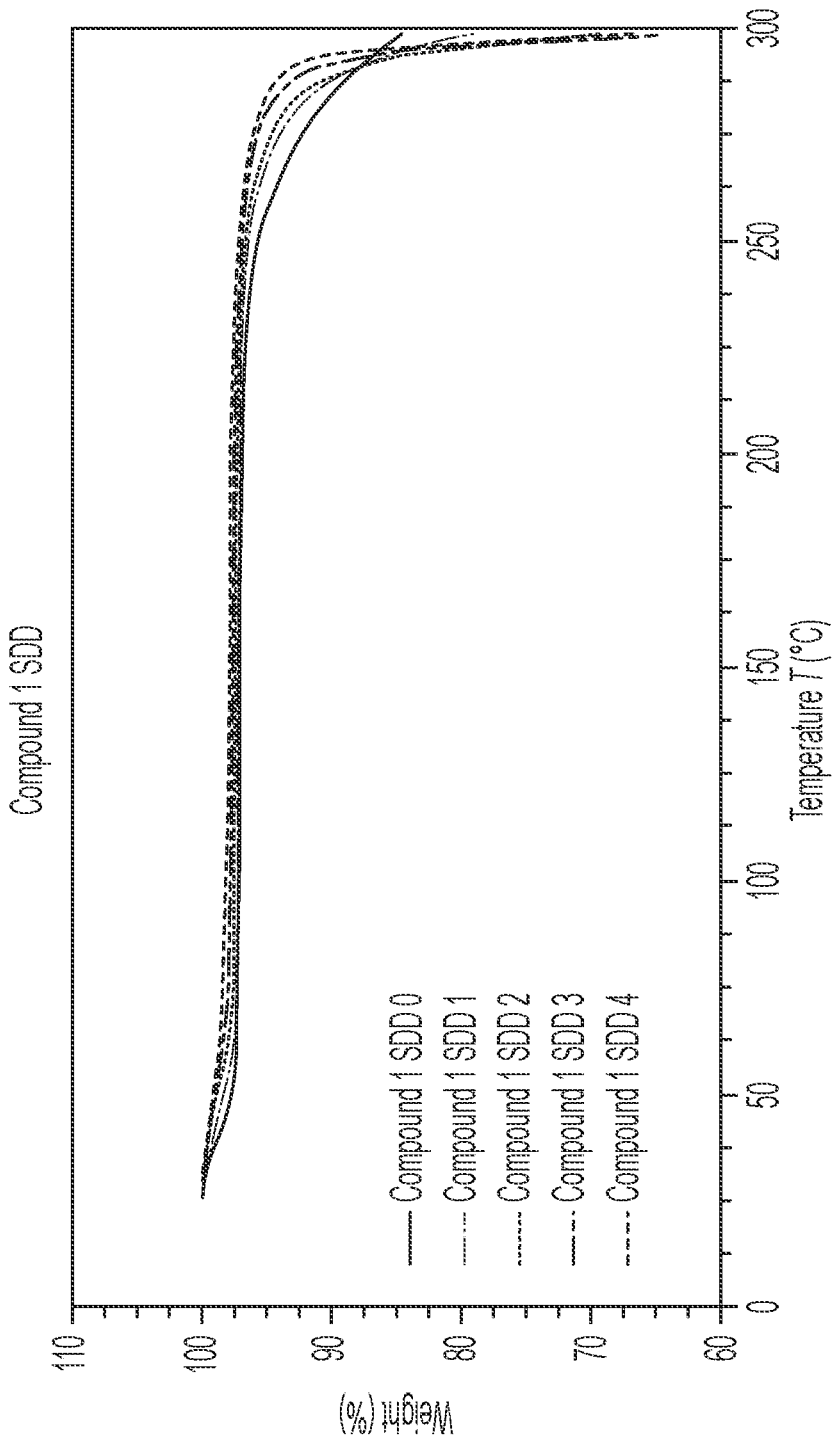
FIG. 37 depicts overlayed differential scanning calorimetry (DSC) thermograms of five spray-dried dispersions (SDDs) of Compound 1.

Spray solutions having varying ratios of Compound 1 to polymer (Hydroxypropylmethyl Cellulose AS-MG) were prepared at 8% solids content in 80:20 DCM:MeOH (Table 30). The spray solutions were spray dried using a Procept 4M8-Trix unit with the settings detailed in Table 31. The resulting spray dried dispersions (SDDs) were dried at 50° C. at −25 in. Hg in a nitrogen purged vacuum oven for 19 hours. The SDDs were evaluated by XRPD analysis (Method D; FIG. 36) and DSC analysis (Method B; FIG. 37). The SDDs appeared amorphous by PXRD analysis, with no crystalline diffraction peaks observed. A single well defined $T_G$ was seen by DSC for all dispersions. No melt endotherm was observed, further verifying the amorphous nature of all spray dried dispersions. Residual solvent analysis of the spray dried dispersions dried for 19 hours showed varying levels for dichloromethane. An observed trend is that levels of dichloromethane increase with increased ratios of Compound 1 to Polymer.

TABLE 30

| Sample | Weight Ratio (Compound 1:Polymer) | % Compound 1 | % Polymer |
|---|---|---|---|
| SDD 1 | 2:3 | 40% | 60% |
| SDD 2 | 1:1 | 50% | 50% |
| SDD 3 | 2:1 | 66.7% | 33.3% |
| SDD 4 | 3:1 | 75% | 25% |

TABLE 31

| Parameter | Setting |
|---|---|
| Nozzle Orifice | 1.0 mm |
| Inlet Air Speed | 0.35-0.39 m³/min |
| Inlet Temp | 50° C.-60° C. |
| Flow Rate | ~10 g/min |
| Pump Speed | 70-80% |
| Atom. Gas Flow | 15 L/min |
| Outlet Temp | 36° C. |

Example 22—Preparation and Characterization of Spray-Dried Dispersions of Compound 1

Spray solutions having varying ratios of Compound 1 to polymer (Hydroxypropylmethyl Cellulose AS-MG) were prepared at 12% solids content in 80:20 DCM:MeOH (Table 32). The spray solutions were sprayed on a GEA Mobile Minor spray dryer, and the SDDs were collected and dried at 50° C. and −25 in Hg under a $N_2$ purge.

TABLE 32

| Sample | Weight Ratio (Compound 1:Polymer) |
|---|---|
| SDD 5 | 1:1 |
| SDD 6 | 1.5:1 |

Example 23—Kinetic Solubility of Compound 1 SDDs

A µDISS Profiler™ instrument from Pion, Inc was used to quantify concentrations during equilibrium solubility experiments involving SDD 0 (which can be prepared as described in Example 16) and SDDs 1-4 (which can be prepared as described in Example 21). The unit consists of six photodiode array (PDA) spectrophotometers, each with its own dedicated fiber optic dip probe, center-positioned in the glass vial holding 10 mL of media. The concentration measurements are performed directly in the assay media, with processed results plotted in "real time."

Probes with 2-mm path length tips were selected for quantification of Compound 1 in SDD. The developed calibration curves were used for quantification of Compound 1 in the samples during kinetic solubility experiments at each time point. The 2-mm path length tips were selected for detecting concentrations of Compound 1 in both SGF and FaSSIF media.

Standard calibration curves were generated in the respective assay media using a serial addition protocol. A stock solution of Compound 1 was prepared in DMSO at ~20 mg/mL. Calculated aliquots of the stock were added to the respective buffers in order to prepare several standard solutions spanning specific concentration ranges. Concentrations of the standard solutions ranged from ~50 to ~300 µg/mL for channels in both SGF and FaSSIF media respectively. The area under the $2^{nd}$ derivative curves was used to calculate the concentrations. The wavelength range was selected for the compounds in such a way that sensitivity issues were avoided. Linearity of the standard curves in the selected wavelength regions were characterized by $r^2 \geq 0.999$.

Area under the 2nd derivative curve in 285-300 nm (SGF) and 305-320 nm (FaSSIF) range were used to calculate the standard curves in respective media. The corresponding standard curves were used to determine concentrations of Compound 1 in solubility assays.

Required amount of SDD materials, equivalent to 20 mg of Compound 1 were weighed into 20 mL glass vials. The vials were then transferred to the instrument for analysis. A clean stir bar was added to the vial with sample. 16 mL of SGF buffer was transferred to the vials before beginning the experiment to achieve an upper limit of ~1.25 mg/mL. The stirring was maintained at 220 RPM and the temperature of the medium at 37° C. Kinetic solubility data was collected for 30 minutes in SGF media. The data showed that all the SDD's at different loadings exhibited very similar release profile and achieved about same concentration of Compound 1 (~300 µg/mL).

At the 30-minute interval, the media was converted to FaSSIF 6.5. The final volume in the vials was increased to 20 mL from 16 mL (1.00 mg/mL). The resulting samples were then analyzed using the µDiss Profiler for ~18H in FaSSIF.

Figure 38:
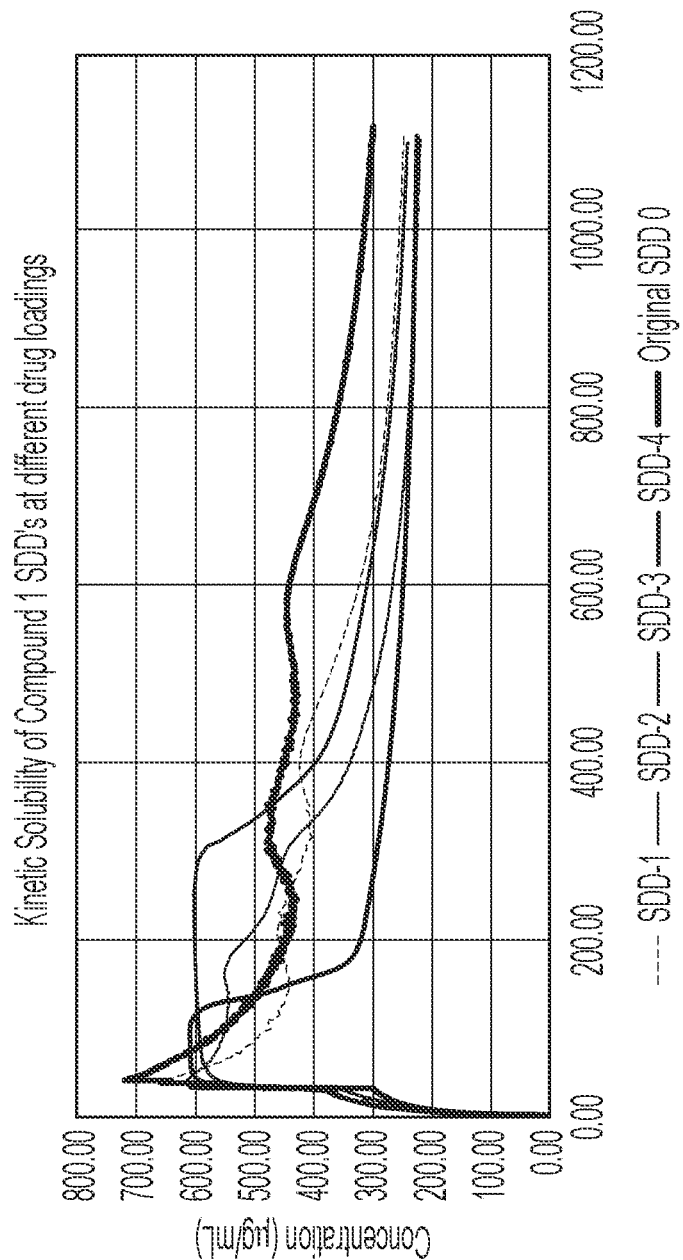
FIG. 38 depicts a graph of the kinetic solubility profiles of five SDDs of Compound 1 at different drug loadings.
Figure 39:
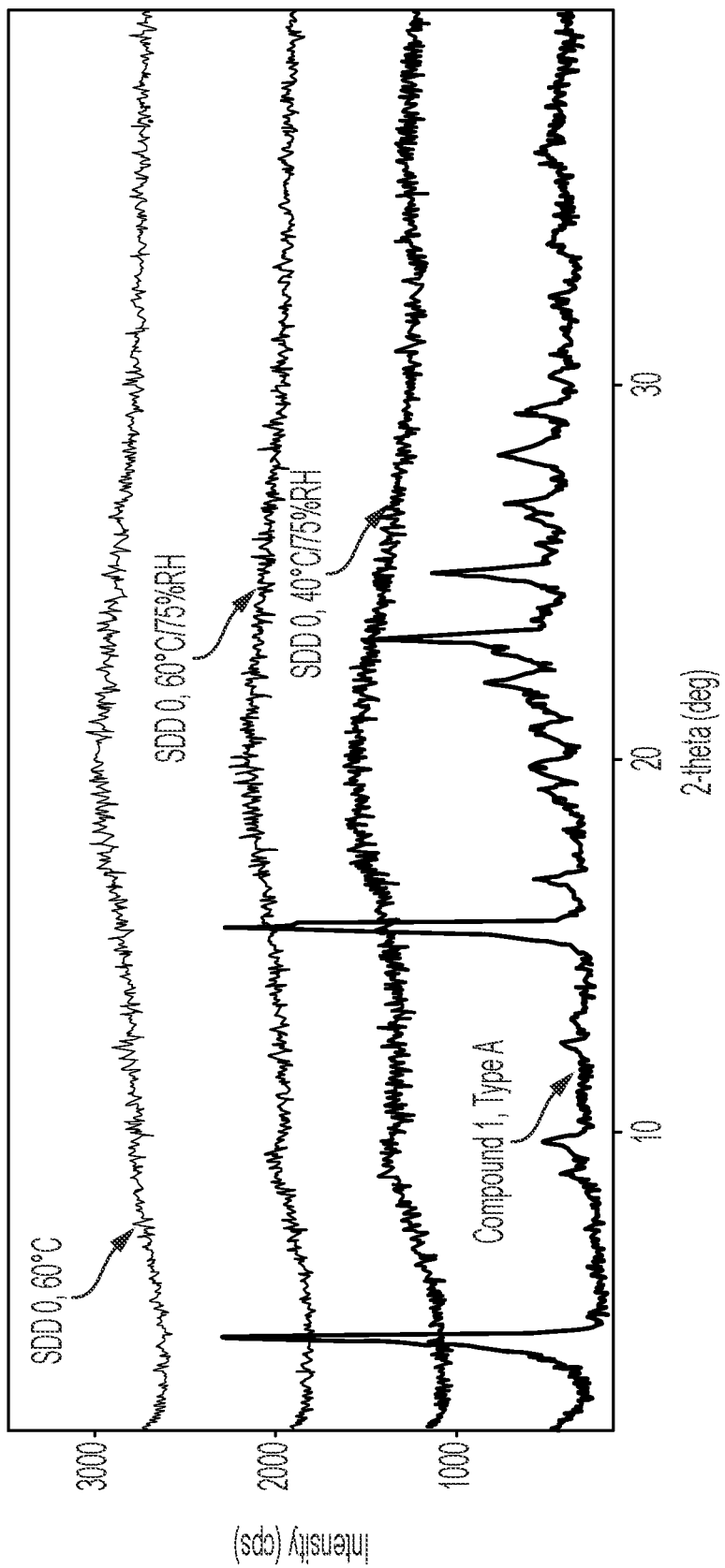
FIG. 39 depicts overlayed XRPD patterns of a spray dried dispersion of Compound 1 (SDD 0) after storage (a) in a sealed vial for 2 weeks at 60° C., (b) in an unsealed vial for 2 weeks at 40° C. and 75% relative humidity, and (c) in an unsealed vial for 2 weeks at 60° C. and 75% relative humidity, overlayed with the XRPD pattern of crystalline Compound 1 (Type A).
Figure 40:
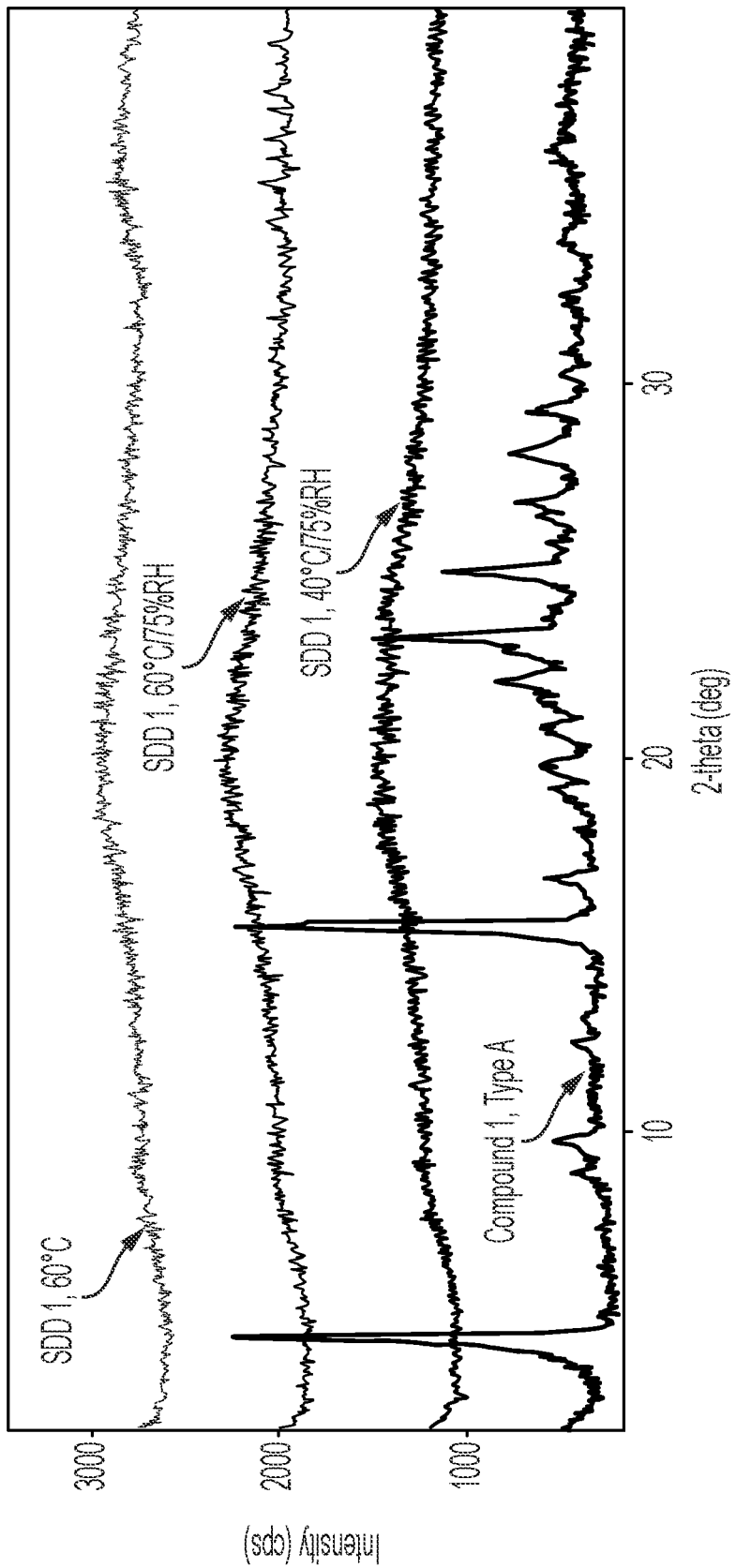
FIG. 40 depicts overlayed XRPD patterns of a spray dried dispersion of Compound 1 (SDD 1) after storage (a) in a sealed vial for 2 weeks at 60° C., (b) in an unsealed vial for 2 weeks at 40° C. and 75% relative humidity, and (c) in an unsealed vial for 2 weeks at 60° C. and 75% relative humidity, overlayed with the XRPD pattern of crystalline Compound 1 (Type A).
Figure 41:
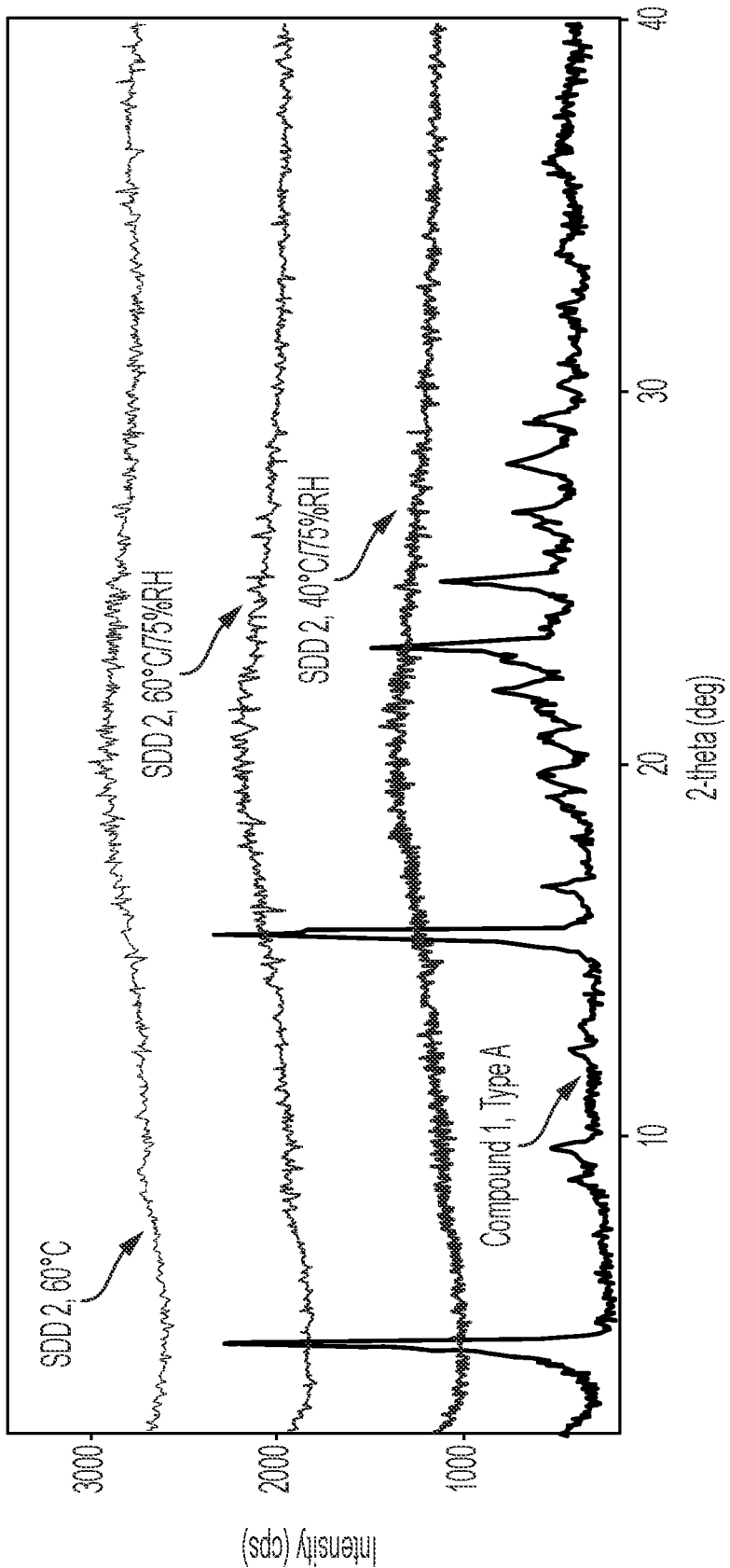
FIG. 41 depicts overlayed XRPD patterns of a spray dried dispersion of Compound 1 (SDD 2) after storage (a) in a sealed vial for 2 weeks at 60° C., (b) in an unsealed vial for 2 weeks at 40° C. and 75% relative humidity, and (c) in an unsealed vial for 2 weeks at 60° C. and 75% relative humidity, overlayed with the XRPD pattern of crystalline Compound 1 (Type A).
Figure 42:
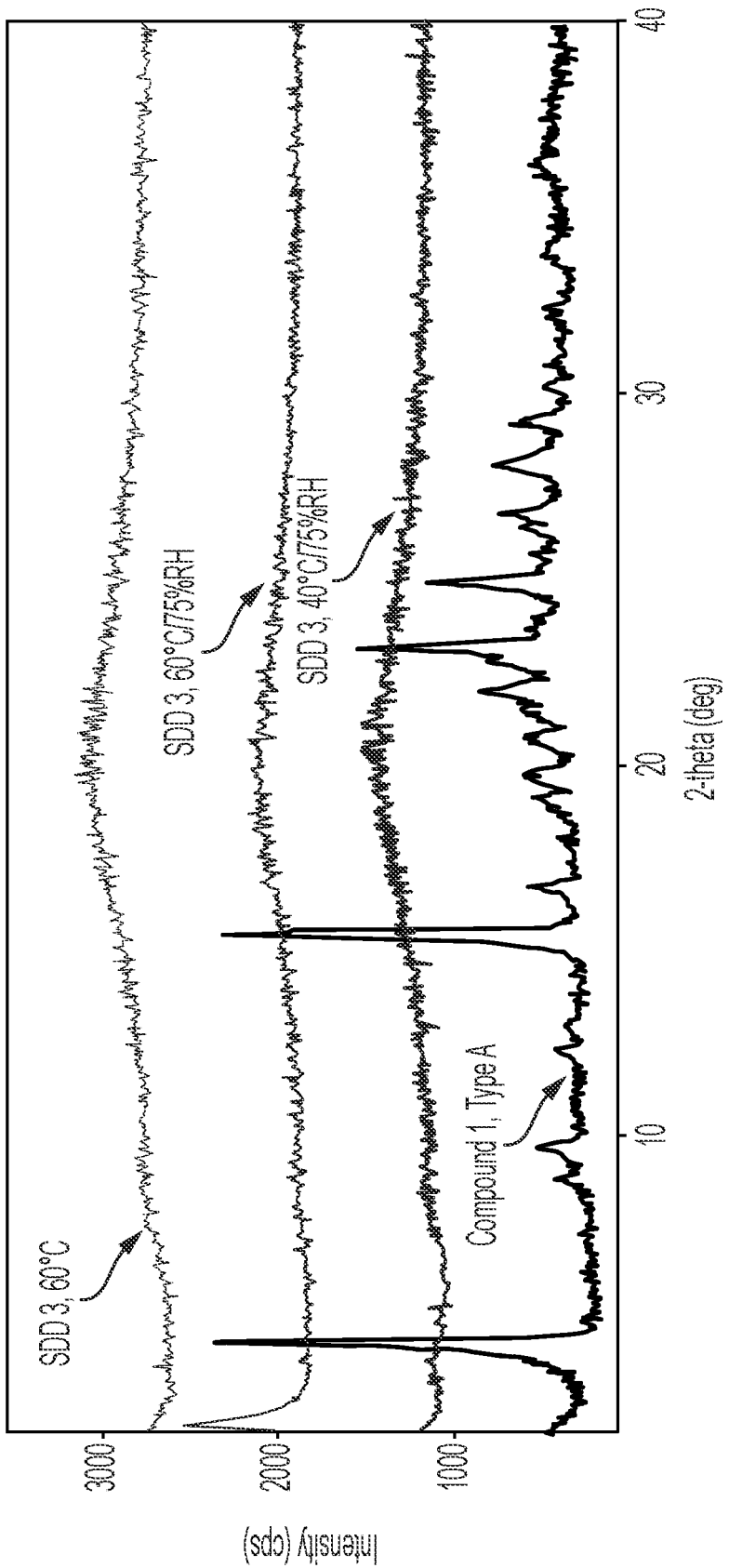
FIG. 42 depicts overlayed XRPD patterns of a spray dried dispersion of Compound 1 (SDD 3) after storage (a) in a sealed vial for 2 weeks at 60° C., (b) in an unsealed vial for 2 weeks at 40° C. and 75% relative humidity, and (c) in an unsealed vial for 2 weeks at 60° C. and 75% relative humidity, overlayed with the XRPD pattern of crystalline Compound 1 (Type A).
Figure 43:
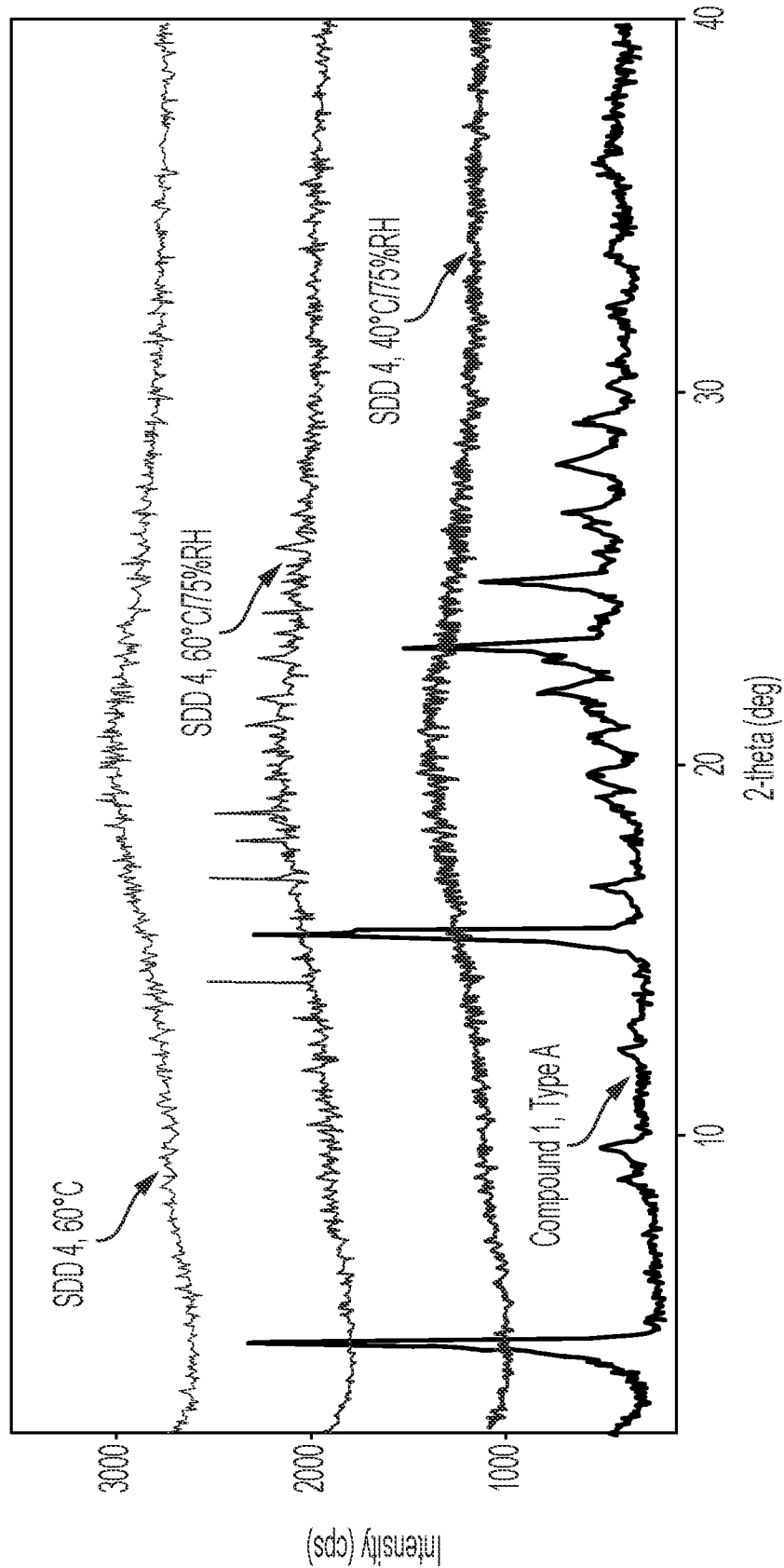
FIG. 43 depicts overlayed XRPD patterns of a spray dried dispersion of Compound 1 (SDD 4) after storage (a) in a sealed vial for 2 weeks at 60° C., (b) in an unsealed vial for 2 weeks at 40° C. and 75% relative humidity, and (c) in an unsealed vial for 2 weeks at 60° C. and 75% relative humidity, overlayed with the XRPD pattern of crystalline Compound 1 (Type A).

The SDD 0 formulation with 25% drug loading reached higher solubility of ~700 µg/mL but did not remain in the supersaturated state for longer time. Although the solubility of SDD 0 at 4H was slightly lower than the 40% API loading SDD 1, the equilibrium solubility after ~16 hours was higher than all other SDD systems. SDD 3 and SDD 4 did not reach as high of a concentration (spring effect) as SDD 0. However, SDD 3 and SDD 4 both stayed at supersaturated state for longer time when compared to all other SDD systems tested. However, the equilibrium solubility for SDD 3 and SDD 4 after 16 hours was lower than SDD 0. SDD 2 and SDD 3 show marked enhancement in the solubility and prolonged supersaturation. The Kinetic solubility profiles are shown in FIG. 38.

The results are summarized in Table 33. All the solubility Results reported in the table are an average of n=2 replicates.

TABLE 33

| Parameter | SDD 0 (1:3) | SDD 1 (2:3) | SDD 2 (1:1) | SDD 3 (2:1) | SDD 4 (3:1) |
|---|---|---|---|---|---|
| 30 min SGF (µg/mL) | 293.34 | 338.27 | 371.81 | 340.56 | 374.24 |
| Cmax (µg/mL) | 708.65 | 658.09 | 618.76 | 603.12 | 609.61 |
| 4 H (µg/mL) | 438.55 | 450.60 | 476.06 | 603.03 | 307.06 |
| Eq Sol (16 H) (µg/mL) | 301.75 | 250.53 | 221.95 | 243.60 | 226.20 |

Example 24—Stability of Spray Dried Dispersions of Compound 1

Spray dried dispersions of Compound 1 (SDD 0 (which can be prepared as described in Example 16) and SDDs 1-4 (which can be prepared as described in Example 21)) were set up on a short-term stability study in two different storage configurations at various storage conditions. Samples were set up as "Sealed" and "Exposed". Sealed samples were placed into crimp sealed vials and stored in a single storage condition; 60° C. The exposed samples were placed into a vial that was covered lightly with perforated foil to allow exposure to the humidity conditions. The exposed samples were stored at 40° C./75% RH and 60° C./75% RH. Samples were pulled after T=1 and 2 weeks for PXRD analysis (Method D).

PXRD diffractograms taken after 2 weeks for SDDs 0-4 are provided in FIGS. 39-43, respectively, and the results are summarized in Table 34. SDDs 0, 1, 2 and 3 showed amorphous character by PXRD at all tested conditions through 2 weeks. SDD 4 showed crystallinity by PXRD after 2 weeks of storage at 60° C./75% RH (exposed). SDD 4 also showed two glass transition temperatures by DSC (Method B) after 2 weeks of storage at 60° C./75% RH (exposed), suggesting phase separation.

TABLE 34

| SDD | Storage Condition | Time Point (weeks) 1 | 2 |
|---|---|---|---|
| SDD 0 (1:3) | 60° C. Sealed | No crystalline diffraction peaks observed by PXRD | No crystalline diffraction peaks observed by PXRD |
| | 40° C./75% RH Exposed | No crystalline diffraction peaks observed by PXRD | No crystalline diffraction peaks observed by PXRD |
| | 60° C./75% RH Exposed | No crystalline diffraction peaks observed by PXRD | No crystalline diffraction peaks observed by PXRD |
| SDD 1 (2:3) | 60° C. Sealed | No crystalline diffraction peaks observed by PXRD | No crystalline diffraction peaks observed by PXRD |
| | 40° C./75% RH Exposed | No crystalline diffraction peaks observed by PXRD | No crystalline diffraction peaks observed by PXRD |
| | 60° C./75% RH Exposed | No crystalline diffraction peaks observed by PXRD | No crystalline diffraction peaks observed by PXRD |
| SDD 2 (1:1) | 60° C. Sealed | No crystalline diffraction peaks observed by PXRD | No crystalline diffraction peaks observed by PXRD |
| | 40° C./75% RH Exposed | No crystalline diffraction peaks observed by PXRD | No crystalline diffraction peaks observed by PXRD |
| | 60° C./75% RH Exposed | No crystalline diffraction peaks observed by PXRD | No crystalline diffraction peaks observed by PXRD |
| SDD 3 (2:1) | 60° C. Sealed | No crystalline diffraction peaks observed by PXRD | No crystalline diffraction peaks observed by PXRD |
| | 40° C./75% RH Exposed | No crystalline diffraction peaks observed by PXRD | No crystalline diffraction peaks observed by PXRD |
| | 60° C./75% RH Exposed | No crystalline diffraction peaks observed by PXRD | No crystalline diffraction peaks observed by PXRD |
| SDD 4 (3:1) | 60° C. Sealed | No crystalline diffraction peaks observed by PXRD | No crystalline diffraction peaks observed by PXRD |
| | 40° C./75% RH Exposed | No crystalline diffraction peaks observed by PXRD | No crystalline diffraction peaks observed by PXRD |
| | 60° C./75% RH Exposed | No crystalline diffraction peaks observed by PXRD | Crystalline diffraction peaks observed by PXRD |

Example 25—Stability of Spray Dried Dispersions of Compound 1

Spray dried dispersions of Compound 1 (SDDs 5 and 6 (Example 22)) were stored in two different storage configurations at various storage conditions. Samples were set up as "Sealed" and "Exposed". Sealed samples were stored in an amber crimp sealed vial at the following conditions: 2-8° C., 25° C./60% RH, 40° C./75% RH, and 60° C. Exposed samples were stored in an amber crimp vial covered with foil, which was perforated to allow exposure to humidity, at the following conditions: 25° C./75% RH, 40° C./75% RH, and 60° C./75% RH.

Samples were analyzed by PXRD (Method D) and/or DSC (Method B) analysis at T=0, 1, and 2 weeks. Results are summarized in Table 35. No crystalline diffraction peaks were observed by PXRD in any sample. Moreover, a single $T_G$ and no melt endotherm was seen by DSC in all samples.

TABLE 35

Figure 44:
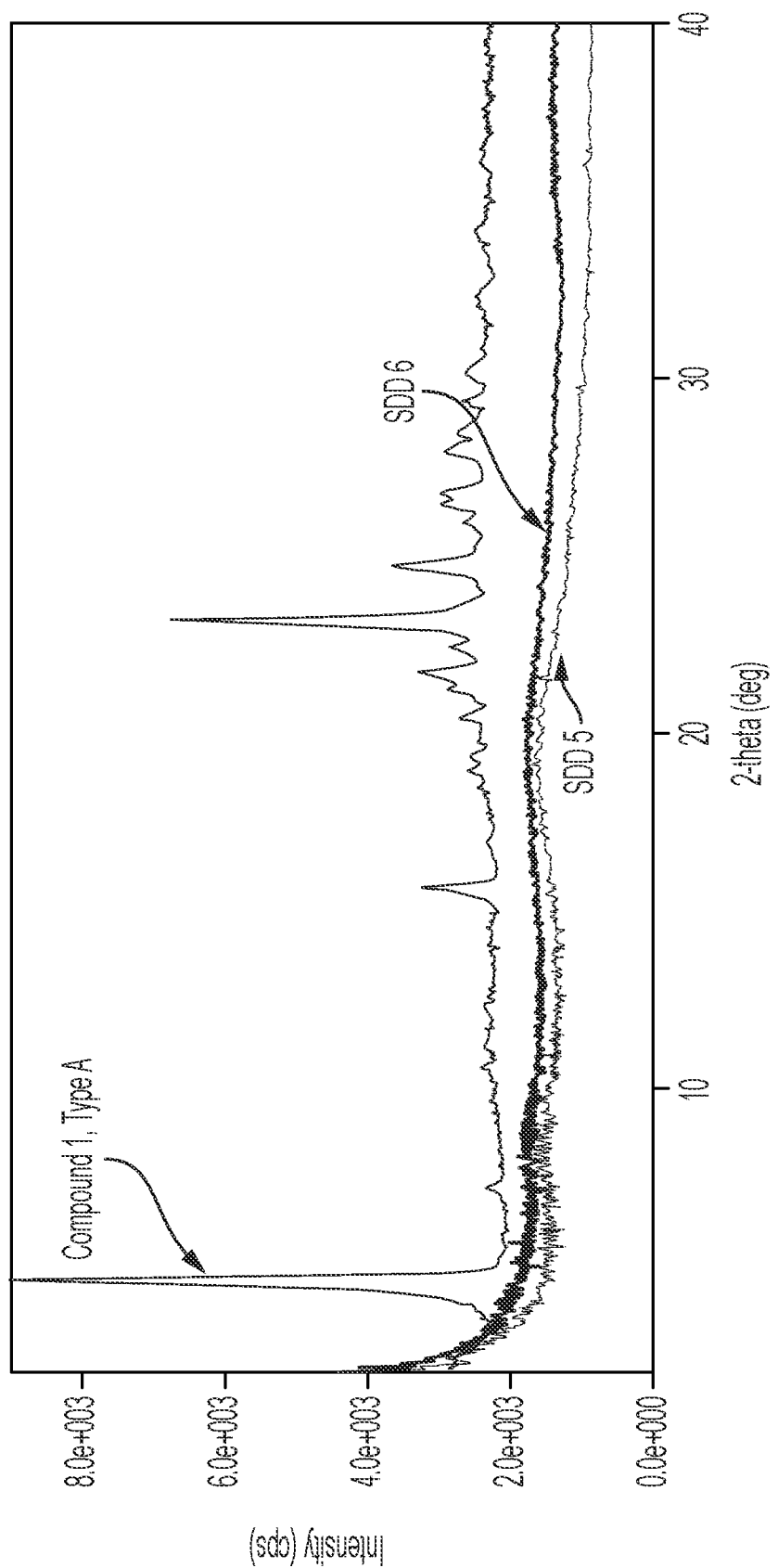
FIG. 44 depicts overlayed XRPD patterns of two spray dried dispersions of Compound 1 (SDDs 5 and 6), overlayed with the XRPD pattern of crystalline Compound 1 (Type A).
Figure 45:
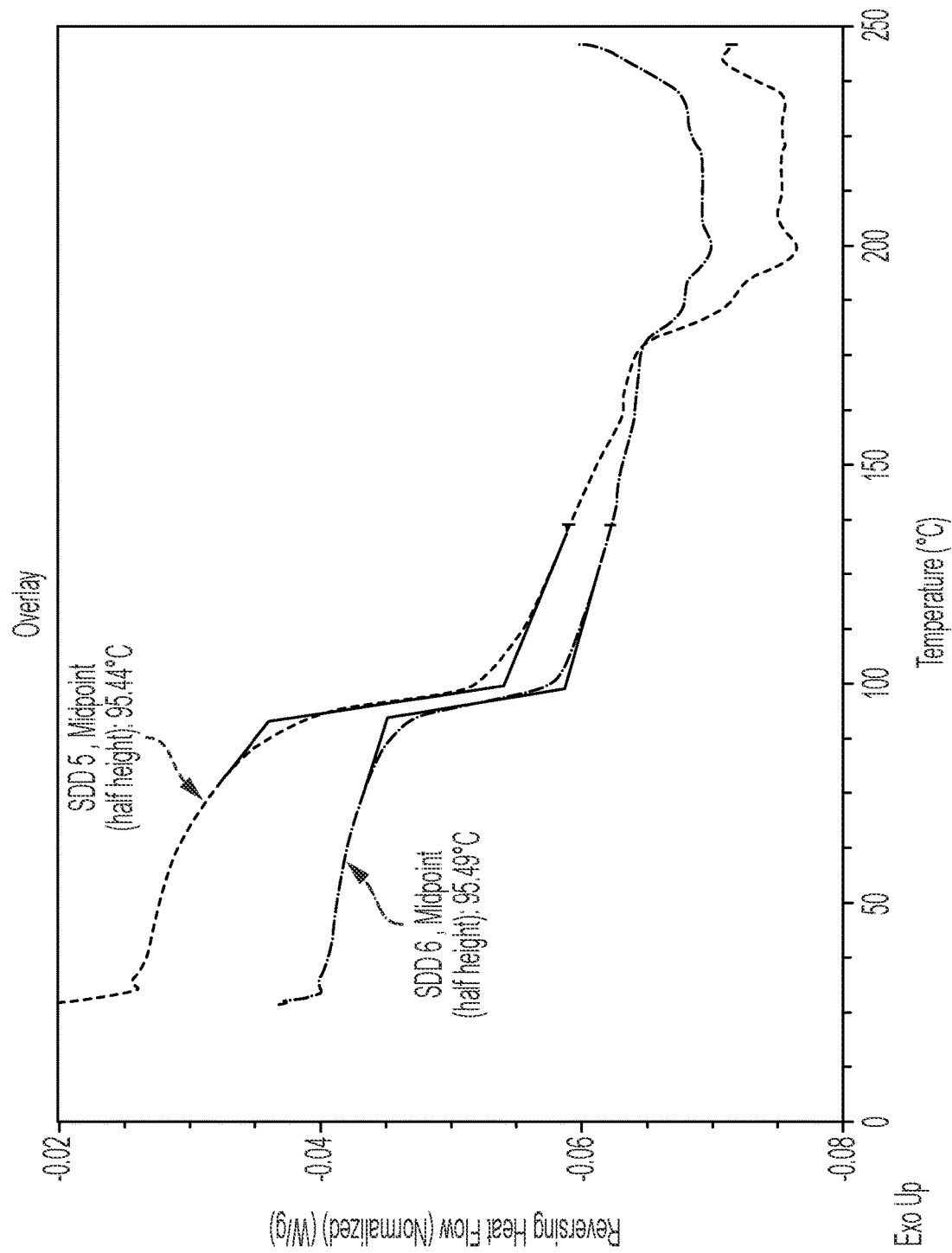
FIG. 45 depicts overlayed DSC thermograms of two spray dried dispersions of Compound 1 (SDDs 5 and 6).
Figure 46:
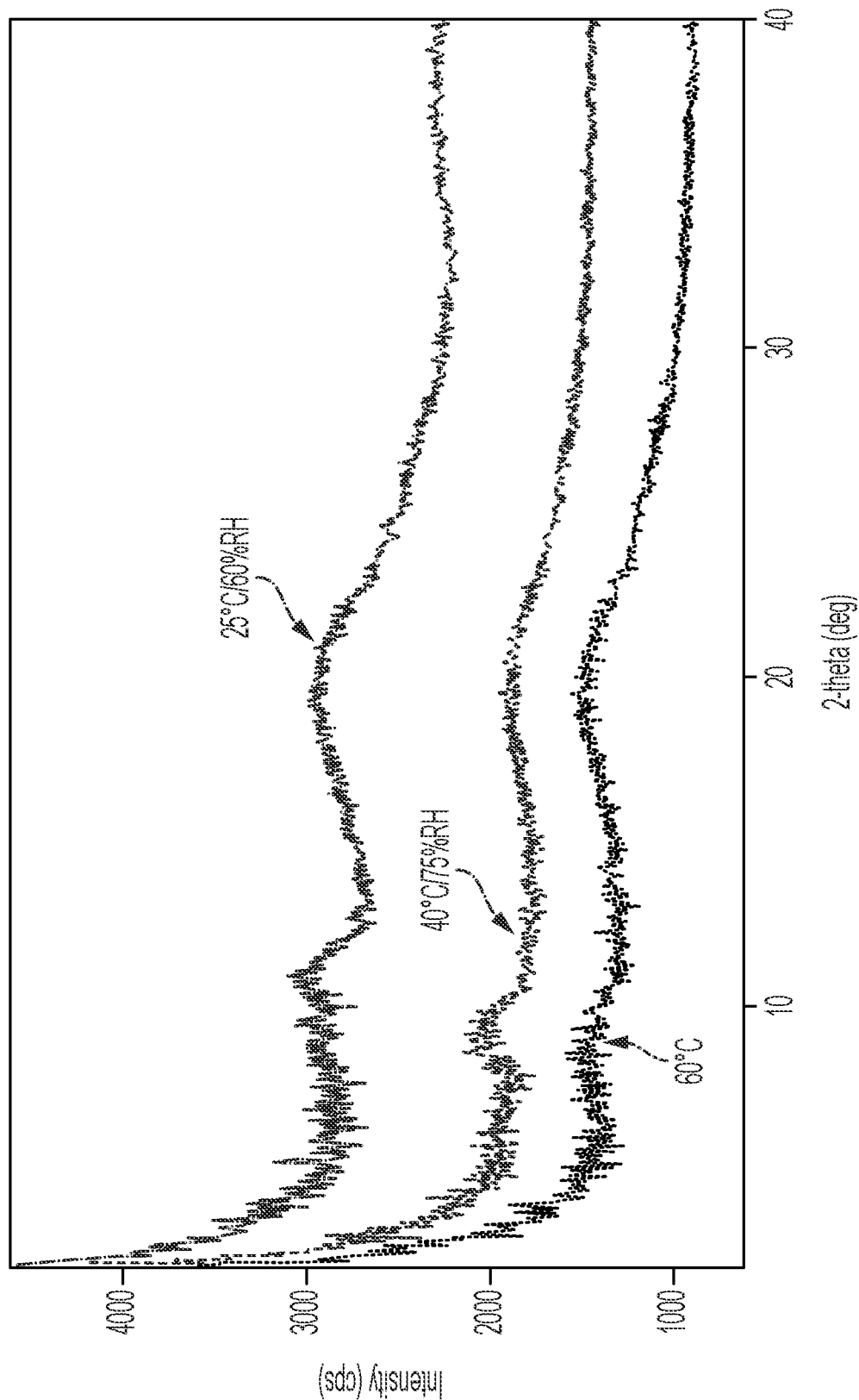
FIG. 46 depicts overlayed XRPD patterns of a spray dried dispersion of Compound 1 (SDD 5) after storage (a) in a sealed vial for 1 week at 60° C., (b) in an unsealed vial for 1 week at 25° C. and 60% relative humidity, and (c) in an unsealed vial for 1 week at 40° C. and 75% relative humidity.
Figure 47:
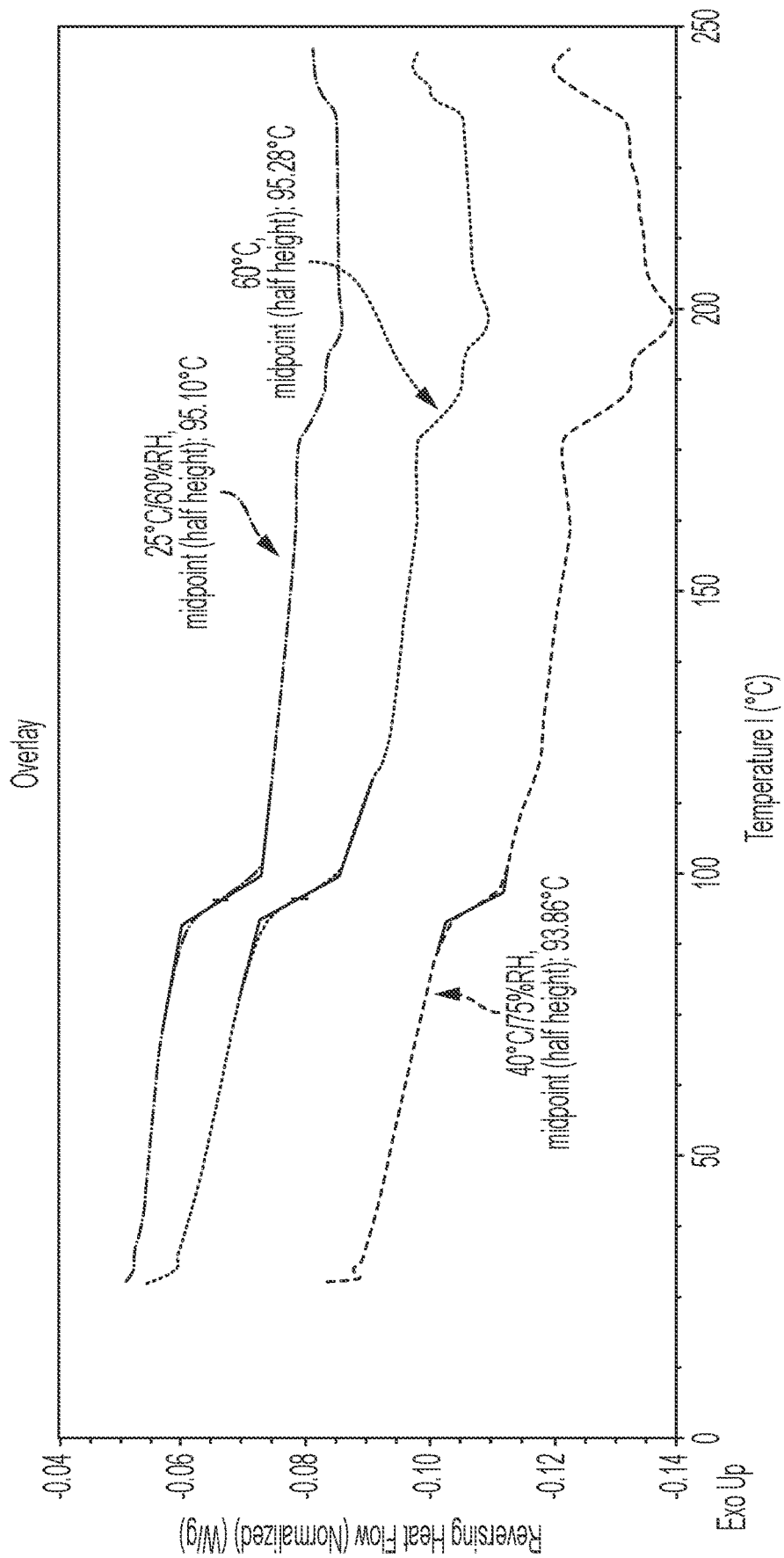
FIG. 47 depicts overlayed DSC thermograms of a spray dried dispersion of Compound 1 (SDD 5) after storage (a) in a sealed vial for 1 week at 60° C., (b) in an unsealed vial for 1 week at 25° C. and 60% relative humidity, and (c) in an unsealed vial for 1 week at 40° C. and 75% relative humidity.
Figure 48:
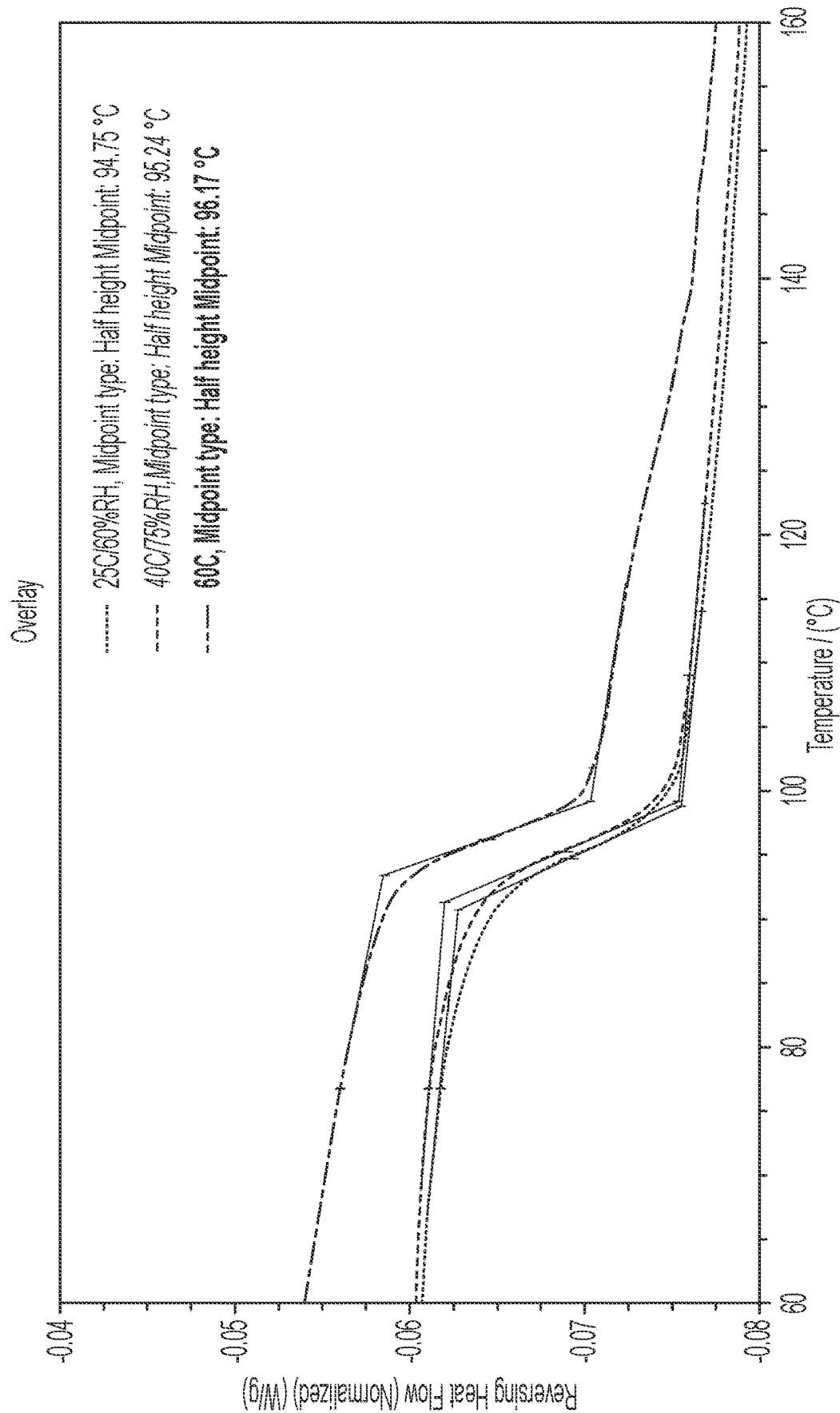
FIG. 48 depicts overlayed DSC thermograms of a spray dried dispersion of Compound 1 (SDD 5) after storage (a) in a sealed vial for 2 weeks at 60° C., (b) in an unsealed vial for 2 weeks at 25° C. and 60% relative humidity, and (c) in an unsealed vial for 2 weeks at 40° C. and 75% relative humidity.
Figure 49:
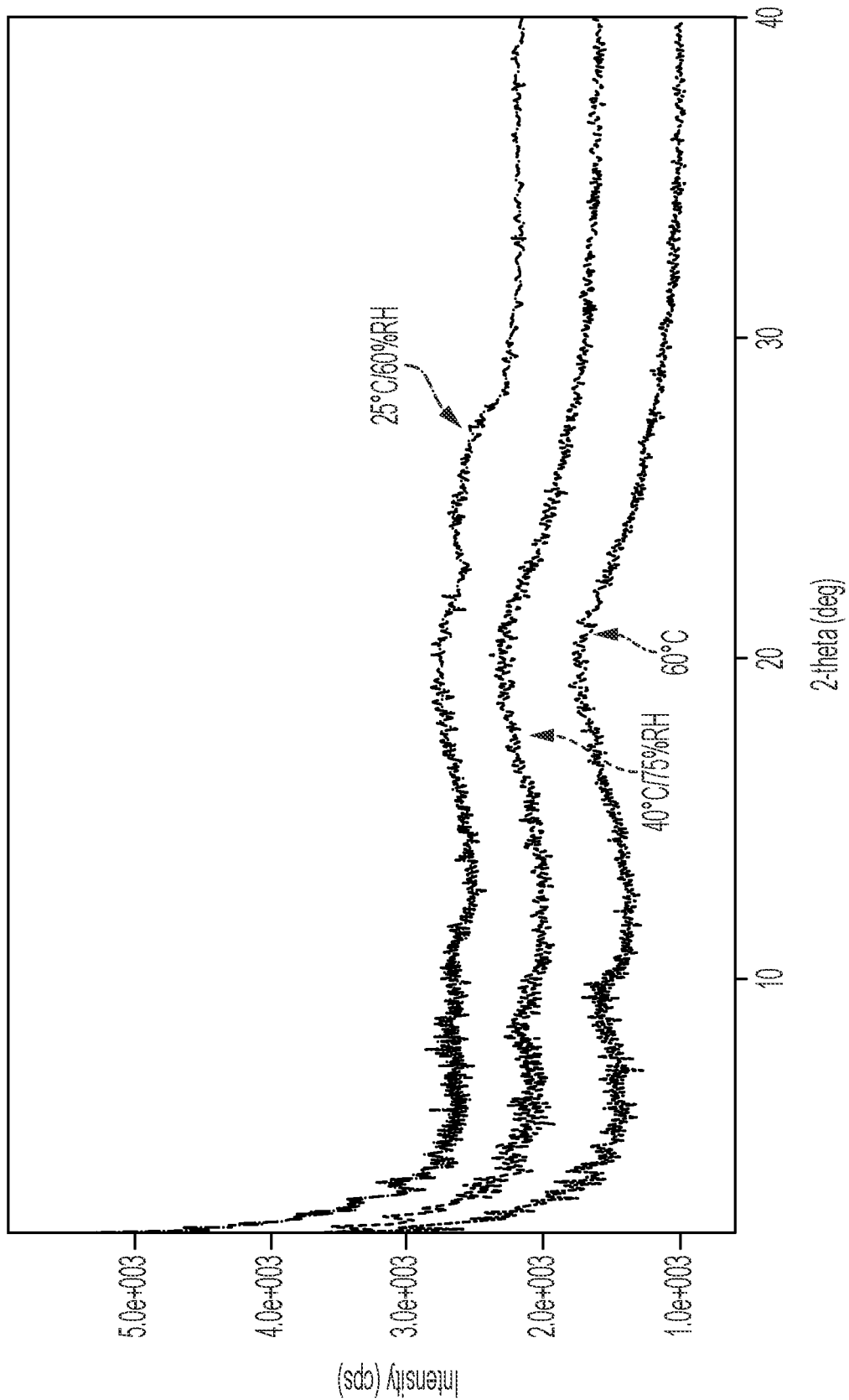
FIG. 49 depicts overlayed XRPD patterns of a spray dried dispersion of Compound 1 (SDD 6) after storage (a) in a sealed vial for 1 week at 60° C., (b) in an unsealed vial for 1 week at 25° C. and 60% relative humidity, and (c) in an unsealed vial for 1 week at 40° C. and 75% relative humidity.
Figure 50:
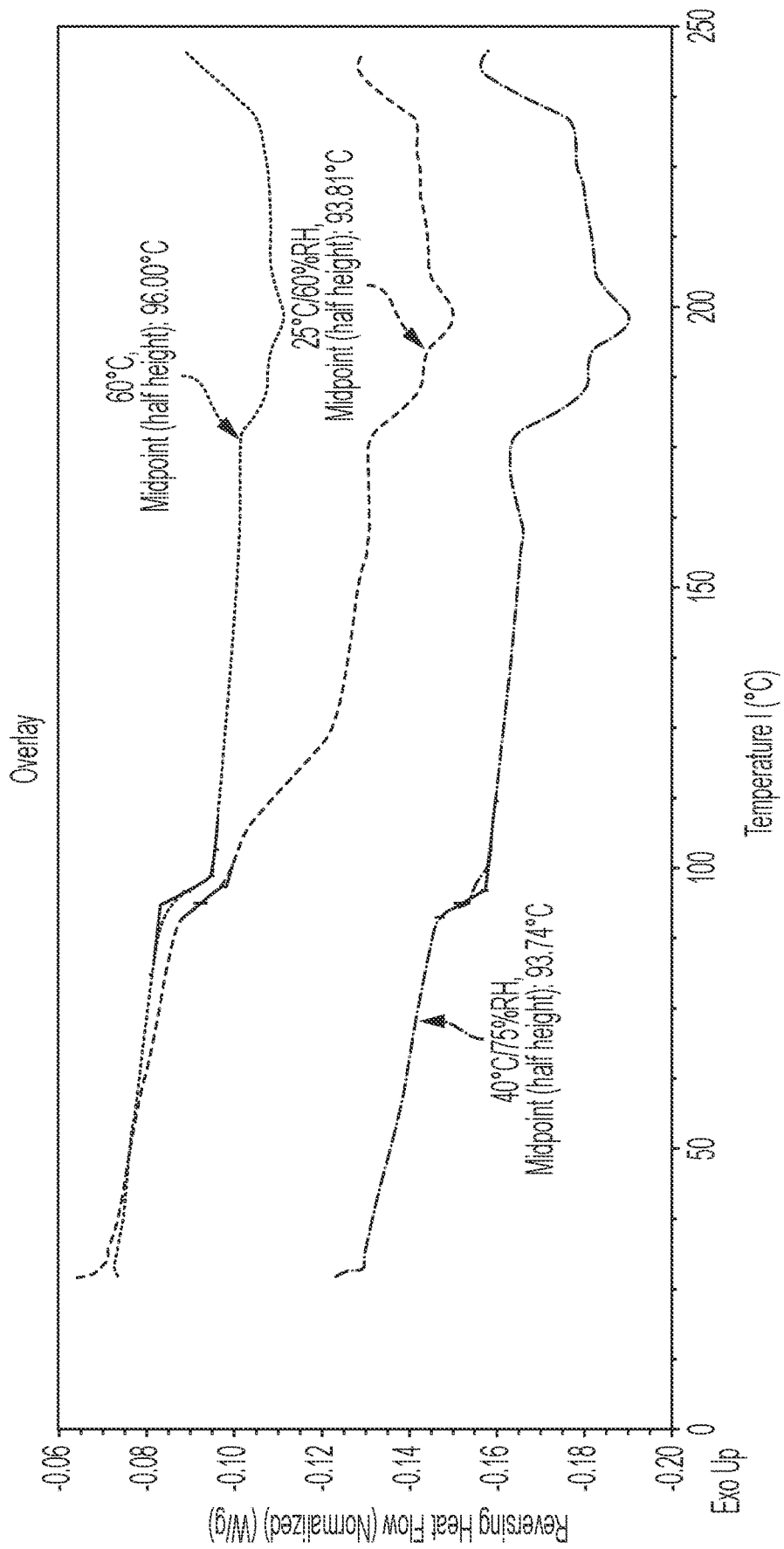
FIG. 50 depicts overlayed DSC thermograms of a spray dried dispersion of Compound 1 (SDD 6) after storage (a) in a sealed vial for 1 week at 60° C., (b) in an unsealed vial for 1 week at 25° C. and 60% relative humidity, and (c) in an unsealed vial for 1 week at 40° C. and 75% relative humidity.
Figure 51:
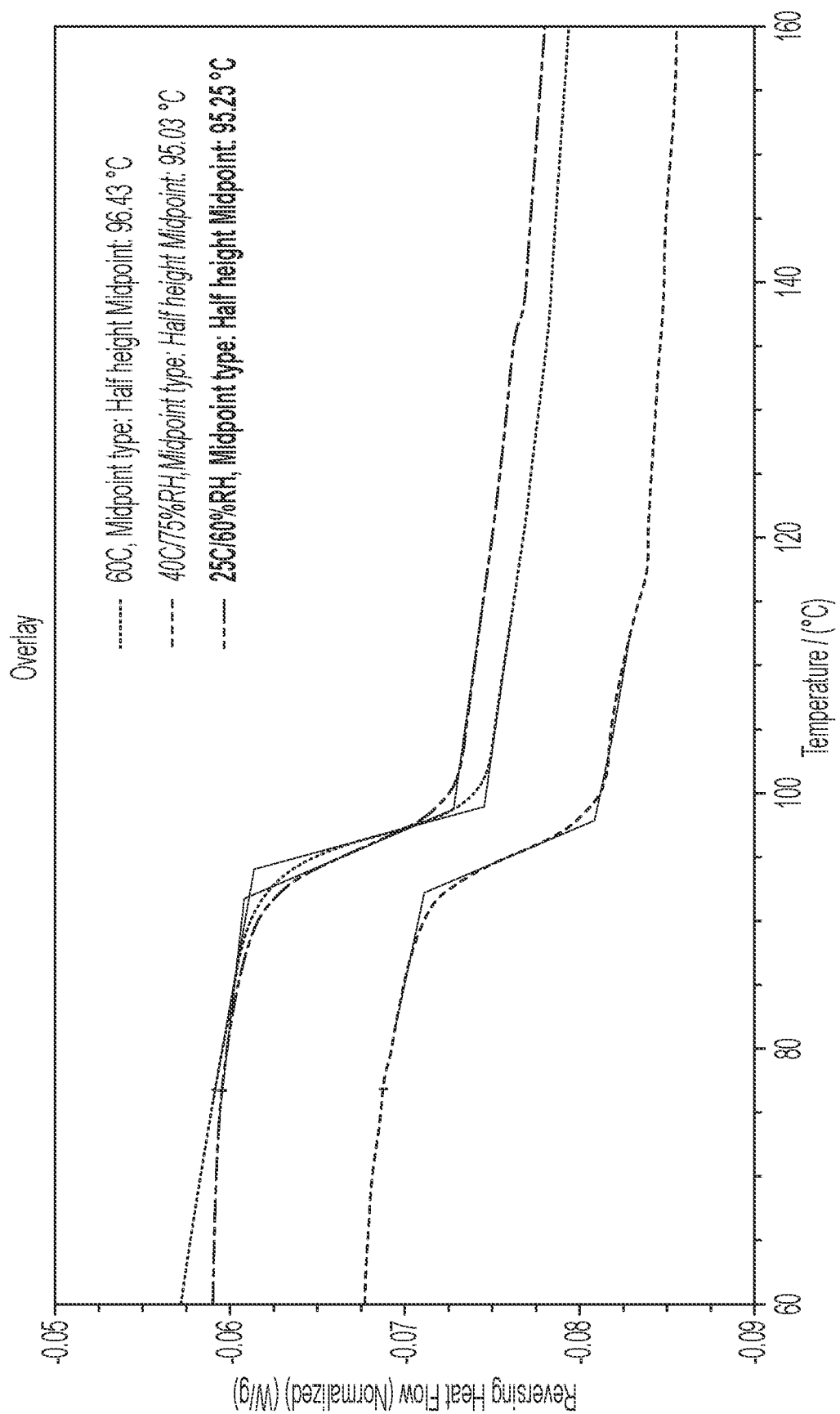
FIG. 51 depicts overlayed DSC thermograms of a spray dried dispersion of Compound 1 (SDD 6) after storage (a) in a sealed vial for 2 weeks at 60° C., (b) in an unsealed vial for 2 weeks at 25° C. and 60% relative humidity, and (c) in an unsealed vial for 2 weeks at 40° C. and 75% relative humidity.

| SDD | Storage Condition | Time Point (weeks) | | |
|---|---|---|---|---|
| | | 0 | 1 | 2 |
| SDD 5 (1:1) | N/A (T = 0 time point) | No crystalline diffraction peaks observed by PXRD (FIG. 44); A single $T_G$ and no melt endotherm was seen by DSC (FIG. 45) | N/A | N/A |
| | 60° C. Sealed | N/A | No crystalline diffraction peaks observed by PXRD (FIG. 46); A single $T_G$ and no melt endotherm was seen by DSC (FIG. 47) | A single $T_G$ and no melt endotherm was seen by DSC (FIG. 48) |
| | 25° C./60% RH Exposed | N/A | No crystalline diffraction peaks observed by PXRD (FIG. 46); A single $T_G$ and no melt endotherm was seen by DSC (FIG. 47) | A single $T_G$ and no melt endotherm was seen by DSC (FIG. 48) |
| | 40° C./75% RH Exposed | N/A | No crystalline diffraction peaks observed by PXRD (FIG. 46); A single $T_G$ and no melt endotherm was seen by DSC (FIG. 47) | A single $T_G$ and no melt endotherm was seen by DSC (FIG. 48) |
| SDD 6 (1.5:1) | N/A (T = 0 time point) | No crystalline diffraction peaks observed by PXRD (FIG. 44); A single $T_G$ and no melt endotherm was seen by DSC (FIG. 45) | N/A | N/A |
| | 60° C. Sealed | N/A | No crystalline diffraction peaks observed by PXRD (FIG. 49); A single $T_G$ and no melt endotherm was seen by DSC (FIG. 50) | A single $T_G$ and no melt endotherm was seen by DSC (FIG. 51) |
| | 25° C./60% RH Exposed | N/A | No crystalline diffraction peaks observed by PXRD (FIG. 49); A single $T_G$ and no melt endotherm was seen by DSC (FIG. 50) | A single $T_G$ and no melt endotherm was seen by DSC (FIG. 51) |
| | 40° C./75% RH Exposed | N/A | No crystalline diffraction peaks observed by PXRD (FIG. 49); A single $T_G$ and no melt endotherm was seen by DSC (FIG. 50) | A single $T_G$ and no melt endotherm was seen by DSC (FIG. 51) |

Kinetic dissolution of SDD 5 and SDD 6 samples was determined at T=0 and T=1 week (40° C./75% RH Exposed; and 40° C./75% RH Sealed) using the procedure described in Example 23. The results are summarized in Table 36.

TABLE 36

| Parameter | T = 0 | | T = 1 wk (40° C./75% RH Exposed) | | T = 1 wk (40° C./75% RH Sealed) | |
|---|---|---|---|---|---|---|
| | SDD 5 (1:1) | SDD 6 (1.5:1) | SDD 5 (1:1) | SDD 6 (1.5:1) | SDD 5 (1:1) | SDD 6 (1.5:1) |
| 30 min SGF (µg/mL) | 611.68 | 622.80 | 600.49 | 628.89 | 623.46 | 616.29 |
| Cmax (µg/mL) | 245.38 | 261.77 | 240.34 | 291.21 | 272.17 | 269.01 |
| 4 H (µg/mL) | 127.07 | 130.55 | 291.28 | 256.72 | 171.49 | 189.91 |

TABLE 36-continued

| Parameter | T = 0 | | T = 1 wk (40° C./75% RH Exposed) | | T = 1 wk (40° C./75% RH Sealed) | |
|---|---|---|---|---|---|---|
| | SDD 5 (1:1) | SDD 6 (1.5:1) | SDD 5 (1:1) | SDD 6 (1.5:1) | SDD 5 (1:1) | SDD 6 (1.5:1) |
| Eq Sol (µg/mL) | 93.37 | 92.71 | 153.88 | 162.06 | 139.64 | 150.04 |

Example 26—Composition and Preparation of a Tablet Dosage Form of Compound 1

Composition of the Tablet Dosage Form

A tablet dosage form of Compound 1 comprising an SDD made up of Compound 1 and HPMC AS-MG (1:3) compressed into tablets and film coated with compendial excipients was prepared. The tablets were presented as 25 mg (white coated round shaped tablets) and 100 mg (white coated oval shaped tablets) dose strengths. The composition of each dosage strength is summarized in Table 37.

TABLE 37

| | Component | % Formulation | Function |
|---|---|---|---|
| Intra Granular Components | Compound 1 Spray Dried Dispersion[1] | 50.00% | Drug Product Intermediate |
| | Microcrystalline Cellulose | 30.00% | Filler |
| | Crospovidone | 5.00% | Dry binder |
| | Colloidal Silicon Dioxide | 1.00% | Glidant |
| | Magnesium Stearate | 0.25% | Lubricant |
| Extra Granular Components | Microcrystalline Cellulose | 11.00% | Filler |
| | Croscarmellose Sodium | 2.50% | Disintegrant |
| | Magnesium Stearate | 0.25% | Lubricant |
| | Total Common Formulation Blend per Tablet | 100% | — |
| Coating Components | Sterile Water for Injection (SWFI) | Removed through processing | Processing aid |
| | Opadry amb II White | 6.00 | Film Coating Agent |
| | Total weight of coated tablet | | |

1 = Quantity based upon a 25.00% (w/w) potency of Compound 1 drug substance in the spray dried intermediate.

Preparation of the Tablet Dosage Form

The Compound 1 tablet formulation manufacturing process consists of four steps: 1) spray dry dispersion, 2) intragranular granulation, roller compaction/milling/blending, 3) extragranular granulation/blending, and 4) tableting and coating. The initial step of spray dry dispersion is performed by creating an organic solution containing Compound 1 drug substance, and Hypromellose Acetate Succinate (Hydroxypropyl Methylcellulose Acetate Succinate MG) (HPMCAS-MG). The solution is spray dried to produce an SDD made up of Compound 1 and HPMC AS-MG (1:3), using a method analogous to the method of Example 16. The SDD is blended with intra granular excipients followed by roller compaction/milling and blending. The resulting granulation is then mixed with the extra-granular components to create the final common granulation blend. The final blend is pressed into tablets equivalent to either 25 mg or 100 mg active followed by coating.

Example 27—Dissolution Assessment of the Tablet Dosage Form

The 100 mg tablets described in Example 26 were tested for dissolution. Dissolution testing parameters are provided in Table 38, and results are summarized in Table 39.

TABLE 38

| Parameter | Condition |
|---|---|
| Apparatus | USP Apparatus 2 (Paddles) |
| Media | SIF without enzyme |
| Vessel Size and Type | 1000 mL Amber |
| Media Volume | 900 mL |
| Temperature | 37.0 ± 0.5° C. |
| Speed | 0-60 min: 50 ± 2 RPM, 60-75 min: 200 ± 8 RPM |
| Time Points | 15, 30, 45, and 60 minutes |
| Filters | 13 mm, 0.2 µm Nylon |
| Theoretical Concentration | 111.1111 µg/mL |
| Sampling Procedure | Remove 3 mL of sample and filter through a 13 mm, 0.2 µm Nylon filter, discarding the first 2 mL to waste and collecting the remaining 1 mL in an amber UPLC vial for analysis. |

TABLE 39

| Time Point | Min % Diss. | Max % Diss. | Mean % Diss. |
|---|---|---|---|
| 15 min | 58.4 | 89.6 | 79.1 |
| 30 min | 88.0 | 92.9 | 91.2 |
| 45 min | 90.7 | 93.9 | 92.7 |
| 60 min | 90.9 | 94.2 | 93.0 |

Example 28—Release Testing of the Tablet Dosage Form

Figure 52:
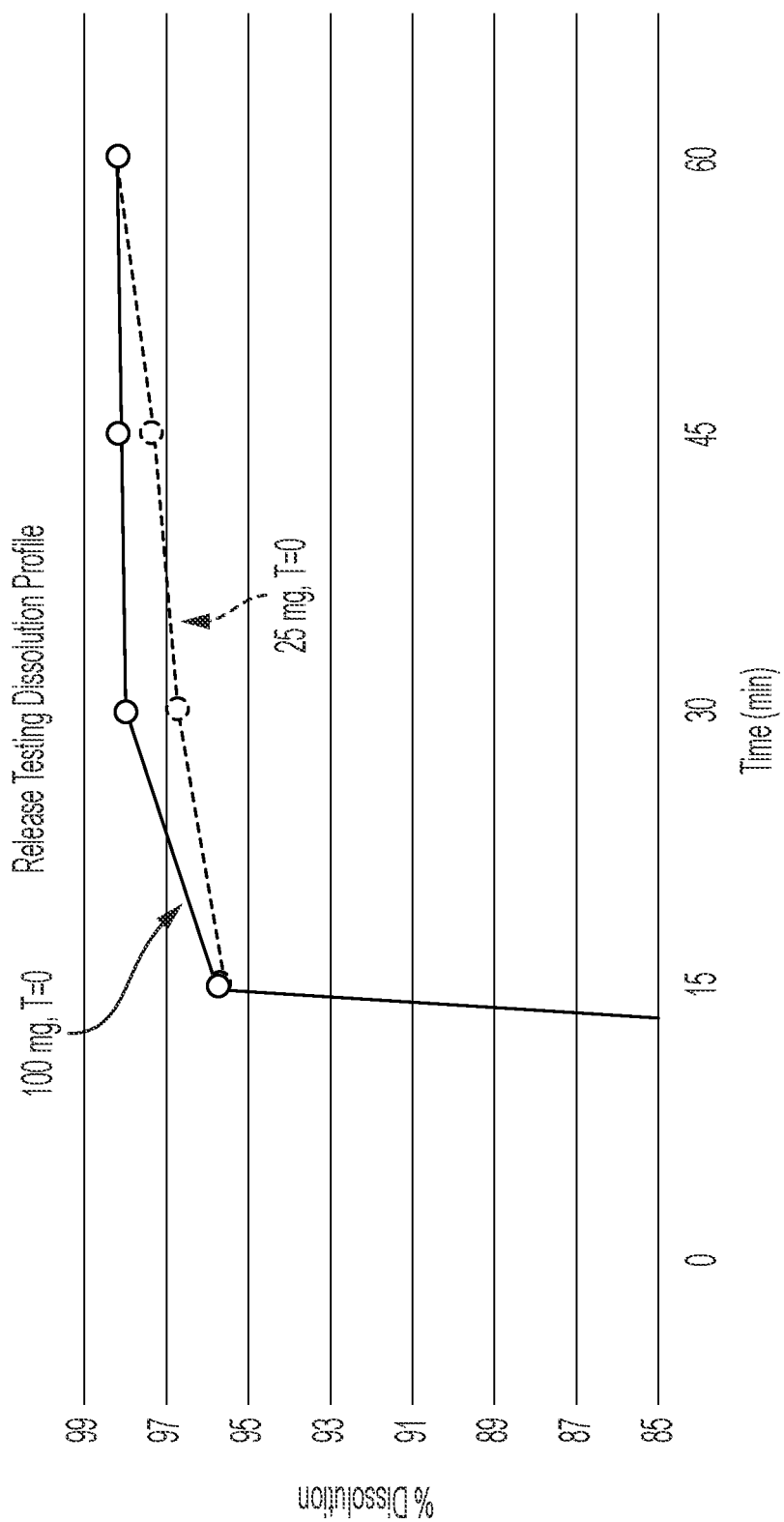
FIG. 52 depicts a graph of the dissolution profile of a tablet formulation of Compound 1.

Dissolution testing of 25 mg and 100 mg tablets having the composition specified in Example 26 was performed following the dissolution parameters listed in Table 40. Dissolution was determined by UPLC analysis. The results of the dissolution testing are reported in Table 41 and FIG. 52.

TABLE 40

| Parameter | Condition |
|---|---|
| Apparatus | USP Apparatus 2 (Paddles) |
| Media | SIF without enzyme |
| Vessel Size and Type | 1000 mL Amber |
| Media Volume | 100 mg: 900 mL |
| | 25 mg: 500 mL |
| Temperature | 37.0 ± 0.5° C. |
| Speed | 75 ± 3 RPM |
| Time Points | 15, 30, 45, and 60 minutes |
| Filters | 13 mm, 0.2 µm Nylon |
| Theoretical Concentration | 100 mg: 111.1111 µg/mL |
| | 25 mg: 50.0000 µg/mL |
| Sampling Procedure | Remove 3 mL of sample and filter through a 13 mm, 0.2 µm Nylon filter, discarding the first 2 mL to waste and collecting the remaining 1 mL in an amber UPLC vial for analysis. |

TABLE 41

| Time | 100 mg Tablet | 25 mg Tablet |
|---|---|---|
| 15 min | Min: 93.7 | Min: 89.6 |
| | Max: 98.3 | Max: 99.8 |
| | Mean: 95.8 | Mean: 95.7 |
| 30 min | Min: 97.2 | Min: 91.6 |
| | Max: 98.6 | Max: 100.4 |
| | Mean: 98.1 | Mean: 96.8 |
| 45 min | Min: 97.4 | Min: 93.1 |
| | Max: 98.8 | Max: 100.6 |
| | Mean: 98.2 | Mean: 97.4 |
| 60 min | Min: 97.4 | Min: 94.4 |
| | Max: 98.9 | Max: 101.1 |
| | Mean: 98.2 | Mean: 98.3 |

Example 29—Stability Assessment of the Tablet Dosage Form

Stability studies were conducted under the conditions outlined in Table 42 on two distinct lots of 25 mg and 100 mg tablets having the composition specified in Example 26. The results of the stability study for each lot and storage condition are reported in the Tables identified in Table 42.

The tablets were prepared for XRPD analysis (Method D) by crushing a tablet with a mortar and pestle and transferring 5-10 mg of material to a sample pan, slightly overfilling and ensuring that powder is spread evenly to cover the bottom of the plate. Weigh paper was placed atop the powder and pressed down gently to even the powder surface. The XRPD pattern of the tablet was overlaid with the XRPD pattern of a reference standard (Compound 1, Type A). A tablet was deemed to be free of the diffraction peaks that are present in the reference standard only if the peak at ~15 degrees 2-theta is absent. A small, irregular peak at ~3 degrees 2-theta is acceptable.

TABLE 42

| Dosage & Lot No. | Container | Storage Condition | Results Table |
|---|---|---|---|
| 25 mg Lot 1 | 30 cc wide mouth round white HDPE bottle, capped with 28 mm child resistant closure and induction sealed | 25 ± 2° C./ 60 ± 5% RH | Table 43 |
| | | 40 ± 2° C./ 75 ± 5% RH | Table 44 |

TABLE 42-continued

| Dosage & Lot No. | Container | Storage Condition | Results Table |
|---|---|---|---|
| 100 mg Lot 1 | 60 cc wide mouth round white HDPE bottle, capped with 33 mm child resistant closure and induction sealed | 25 ± 2° C./60 ± 5% RH<br>40 ± 2° C./75 ± 5% RH | Table 45<br><br>Table 46 |
| 25 mg Lot 2 | 30 cc wide mouth round white HDPE bottle, capped with 28 mm child resistant closure and induction sealed | 25 ± 2° C./60 ± 5% RH<br>40 ± 2° C./75 ± 5% RH | Table 47<br><br>Table 48 |
| 100 mg Lot 2 | 60 cc wide mouth round white HDPE bottle, capped with 33 mm child resistant closure and induction sealed | 25 ± 2° C./60 ± 5% RH<br>40 ± 2° C./75 ± 5% RH | Table 49<br><br>Table 450 |

TABLE 43

Lot 1 Tablets, 25 mg

Storage Conditions: 25 ± 2° C./60 ± 5% RH

| Test Method | | Time Point (months) | | | |
|---|---|---|---|---|---|
| | | 0 | 1 | 2 | 3 |
| Dissolution | 15 min | Min: 90%<br>Max: 100%<br>Mean: 96% | Min: 90%<br>Max: 98%<br>Mean: 94% | Min: 85%<br>Max: 98%<br>Mean: 93% | Min: 78%<br>Max: 86%<br>Mean: 81% |
| | 30 min | Min: 92%<br>Max: 100%<br>Mean: 97% | Min: 92%<br>Max: 99%<br>Mean: 96% | Min: 87%<br>Max: 99%<br>Mean: 94% | Min: 81%<br>Max: 89%<br>Mean: 84% |
| | 45 min | Min: 93%<br>Max: 101%<br>Mean: 97% | Min: 93%<br>Max: 99%<br>Mean: 97% | Min: 88%<br>Max: 100%<br>Mean: 95% | Min: 82%<br>Max: 89%<br>Mean: 85% |
| | 60 min | Min: 94%<br>Max: 101%<br>Mean: 98% | Min: 94%<br>Max: 100%<br>Mean: 98% | Min: 90%<br>Max: 100%<br>Mean: 95% | Min: 84%<br>Max: 91%<br>Mean: 87% |
| Water Content | | 3.52% | 2.90% | 1.92% | 1.79% |
| XPRD (Method D) | | No crystalline peaks present | No crystalline peaks present | No crystalline peaks present | No crystalline peaks present |

TABLE 44

Lot 1 Tablets, 25 mg

Storage Conditions: 40 ± 2° C./75 ± 5% RH

| Test Method | | Time Point (months) | | | |
|---|---|---|---|---|---|
| | | 0 | 1 | 2 | 3 |
| Dissolution | 15 min | Min: 90%<br>Max: 100%<br>Mean: 96% | Min: 81%<br>Max: 92%<br>Mean: 87% | Min: 78%<br>Max: 97%<br>Mean: 89% | Min: 74%<br>Max: 85%<br>Mean: 80% |
| | 30 min | Min: 92%<br>Max: 100%<br>Mean: 97% | Min: 83%<br>Max: 99%<br>Mean: 91% | Min: 81%<br>Max: 97%<br>Mean: 91% | Min: 78%<br>Max: 91%<br>Mean: 85% |
| | 45 min | Min: 93%<br>Max: 101%<br>Mean: 97% | Min: 85%<br>Max: 100%<br>Mean: 92% | Min: 83%<br>Max: 98%<br>Mean: 92% | Min: 80%<br>Max: 92%<br>Mean: 86% |
| | 60 min | Min: 94%<br>Max: 101%<br>Mean: 98% | Min: 85%<br>Max: 100%<br>Mean: 92% | Min: 84%<br>Max: 98%<br>Mean: 93% | Min: 81%<br>Max: 93%<br>Mean: 88% |
| Water Content | | 3.52% | 2.66% | 1.71% | 1.95% |
| XPRD (Method D) | | No crystalline peaks present | No crystalline peaks present | No crystalline peaks present | No crystalline peaks present |

TABLE 45

Lot 1 Tablets, 100 mg

Storage Conditions: 25 ± 2° C./60 ± 5% RH

| Test Method | | Time Point (months) | | | |
|---|---|---|---|---|---|
| | | 0 | 1 | 2 | 3 |
| Dissolution | 15 min | Min: 94% | Min: 85% | Min: 100% | Min: 96% |
| | | Max: 98% | Max: 87% | Max: 100% | Max: 98% |
| | | Mean: 96% | Mean: 86% | Mean: 100% | Mean: 97% |
| | 30 min | Min: 97% | Min: 89% | Min: 100% | Min: 97% |
| | | Max: 99% | Max: 90% | Max: 100% | Max: 99% |
| | | Mean: 98% | Mean: 90% | Mean: 100% | Mean: 98% |
| | 45 min | Min: 97% | Min: 91% | Min: 100% | Min: 98% |
| | | Max: 99% | Max: 92% | Max: 101% | Max: 99% |
| | | Mean: 98% | Mean: 91% | Mean: 100% | Mean: 99% |
| | 60 min | Min: 97% | Min: 92% | Min: 100% | Min: 98% |
| | | Max: 99% | Max: 92% | Max: 101% | Max: 99% |
| | | Mean: 98% | Mean: 92% | Mean: 100% | Mean: 99% |
| Water Content | | 3.83% | 2.57% | 2.39% | 2.72% |
| XPRD (Method D) | | No crystalline peaks present | No crystalline peaks present | No crystalline peaks present | No crystalline peaks present |

TABLE 46

Lot 1 Tablets, 100 mg

Storage Conditions: 40 ± 2° C./75 ± 5% RH

| Test Method | | Time Point (months) | | | |
|---|---|---|---|---|---|
| | | 0 | 1 | 2 | 3 |
| Dissolution | 15 min | Min: 94% | Min: 86% | Min: 99% | Min: 94% |
| | | Max: 98% | Max: 94% | Max: 99% | Max: 95% |
| | | Mean: 96% | Mean: 89% | Mean: 99% | Mean: 95% |
| | 30 min | Min: 97% | Min: 90% | Min: 99% | Min: 95% |
| | | Max: 99% | Max: 95% | Max: 99% | Max: 96% |
| | | Mean: 98% | Mean: 93% | Mean: 99% | Mean: 95% |
| | 45 min | Min: 97% | Min: 92% | Min: 99% | Min: 95% |
| | | Max: 99% | Max: 95% | Max: 99% | Max: 96% |
| | | Mean: 98% | Mean: 94% | Mean: 99% | Mean: 96% |
| | 60 min | Min: 97% | Min: 93% | Min: 99% | Min: 95% |
| | | Max: 99% | Max: 96% | Max: 99% | Max: 96% |
| | | Mean: 98% | Mean: 95% | Mean: 99% | Mean: 96% |
| Water Content | | 3.83% | 2.90% | 2.73% | 4.09% |
| XPRD (Method D) | | No crystalline peaks present | No crystalline peaks present | No crystalline peaks present | No crystalline peaks present |

TABLE 47

Lot 2 Tablets, 25 mg

Storage Conditions: 25 ± 2° C./60 ± 5% RH

| Test Method | | Time Point (months) | |
|---|---|---|---|
| | | 0 | 1 |
| Dissolution | 15 min | Min: 92% Max: 98% | Min: 81% Max: 96% |
| | | Mean: 95% | Mean: 91% |
| | 30 min | Min: 92% Max: 99% | Min: 83% Max: 98% |
| | | Mean: 96% | Mean: 93% |
| | 45 min | Min: 94% Max: 99% | Min: 85% Max: 99% |
| | | Mean: 97% | Mean: 94% |
| | 60 min | Min: 94% Max: 100% | Min: 87% Max: 100% |
| | | Mean: 98% | Mean: 96% |

TABLE 47-continued

| | Lot 2 Tablets, 25 mg | |
|---|---|---|
| | Storage Conditions: 25 ± 2° C./60 ± 5% RH | |
| | Time Point (months) | |
| Test Method | 0 | 1 |
| Water Content | 2.18% | 1.62% |
| XRPD (Method D) | Free of the diffraction peaks that are present in the reference standard | NT |

TABLE 48

| | | Lot 2 Tablets, 25 mg | |
|---|---|---|---|
| | | Storage Conditions: 40 ± 2° C./75 ± 5% RH | |
| | | Time Point (months) | |
| Test Method | | 0 | 1 |
| Dissolution | 15 min | Min: 92% Max: 98% Mean: 95% | Min: 88% Max: 98% Mean: 95% |
| | 30 min | Min: 92% Max: 99% Mean: 96% | Min: 94% Max: 100% Mean: 97% |
| | 45 min | Min: 94% Max: 99% Mean: 97% | Min: 97% Max: 101% Mean: 99% |
| | 60 min | Min: 94% Max: 100% Mean: 98% | Min: 98% Max: 101% Mean: 100% |
| Water Content | | 2.18% | 1.65% |
| XRPD (Method D) | | Free of the diffraction peaks that are present in the reference standard | NT |

TABLE 49

| | | Lot 2 Tablets, 100 mg | |
|---|---|---|---|
| | | Storage Conditions: 25 ± 2° C./60 ± 5% RH | |
| | | Time Point (months) | |
| Test Method | | 0 | 1 |
| Dissolution | 15 min | Min: 99% Max: 101% Mean: 100% | Min: 96% Max: 98% Mean: 97% |
| | 30 min | Min: 98% Max: 100% Mean: 99% | Min: 98% Max: 100% Mean: 99% |
| | 45 min | Min: 99% Max: 101% Mean: 100% | Min: 98% Max: 100% Mean: 99% |
| | 60 min | Min: 100% Max: 101% Mean: 100% | Min: 98% Max: 99% Mean: 98% |
| Water Content | | 2.74% | 2.94% |
| XRPD (Method D) | | Free of the diffraction peaks that are present in the reference standard | NT |

TABLE 50

| | | Lot 2 Tablets, 100 mg | |
|---|---|---|---|
| | | Storage Conditions: 40 ± 2° C./75 ± 5% RH | |
| | | Time Point (months) | |
| Test Method | | 0 | 1 |
| Dissolution | 15 min | Min: 99% Max: 101% Mean: 100% | Min: 96% Max: 98% Mean: 97% |

TABLE 50-continued

Lot 2 Tablets, 100 mg

Storage Conditions: 40 ± 2° C./75 ± 5% RH

| | | Time Point (months) | |
|---|---|---|---|
| Test Method | | 0 | 1 |
| | 30 min | Min: 98% Max: 100% Mean: 99% | Min: 98% Max: 99% Mean: 98% |
| | 45 min | Min: 99% Max: 101% Mean: 100% | Min: 99% Max: 100% Mean: 99% |
| | 60 min | Min: 100% Max: 101% Mean: 100% | Min: 99% Max: 100% Mean: 99% |
| Water Content | | 2.74% | 3.04% |
| XRPD (Method D) | | Free of the diffraction peaks that are present in the reference standard | NT |

The results for the tablet batches from Lot 1 at the 3 month time point and Lot 2 at the 1 month time point remained consistent with the T=0 time points.

Example 30—Composition and Preparation of a Tablet Dosage Form of Compound 1

Tablets comprising a spray dried dispersion (SDD) of Compound 1 and compendial excipients are prepared at 100 mg and 200 mg dosage strengths. The compositions of the tablets are set forth in Tables 51 and 52.

The tablets are prepared by first manufacturing the SDD (spray drying an organic solution of Compound 1 and HPMC-AS (1:1 w/w) (Table 51) or an organic solution of Compound 1 and HPMC-AS (1.5:1 w/w) (Table 52)), followed by roller compaction/milling with intragranular excipients and blending with extragranular excipients. The final blend is pressed into tablets and then film coated.

TABLE 51

| Component | Function | Range |
|---|---|---|
| SDD (1:1) | Active | 50-75% |
| Microcrystalline Cellulose | Filler | 15-30% |
| Lactose Monohydrate | Filler | 0-20% |
| Crosslinked polyvinylpyrrolidone | Dry Binder | 2-10% |
| Colloidal Silicon Dioxide | Glidant | <2% |
| Croscarmellose Sodium | Disintegrant | 2-10% |
| Magnesium Stearate | Lubricant | <2% |

TABLE 52

| Component | Function | Range |
|---|---|---|
| SDD (1.5:1) | Active | 50-75% |
| Microcrystalline Cellulose | Filler | 15-30% |
| Lactose Monohydrate | Filler | 0-20% |
| Crosslinked polyvinylpyrrolidone | Dry Binder | 2-10% |
| Colloidal Silicon Dioxide | Glidant | <2% |
| Croscarmellose Sodium | Disintegrant | 2-10% |
| Magnesium Stearate | Lubricant | <2% |

Example 31—Stability Assessment of the Tablet Dosage Form

Tablets having the compositions set forth in Tables 51 and 52 were prepared for XRPD analysis (Method D) by crushing a tablet with a mortar and pestle and transferring 5-10 mg of material to a sample pan, slightly overfilling and ensuring that powder is spread evenly to cover the bottom of the plate. Weigh paper was placed atop the powder and pressed down gently to even the powder surface. The XRPD pattern of the tablet was overlaid with the XRPD pattern of a reference standard (Compound 1, Type A). The XRPD pattern of a tablet was deemed to be free of the diffraction peaks that are present in the reference standard only if the peak at ~15 degrees 2-theta is absent. A small, irregular peak at ~3 degrees 2-theta is acceptable. The tablets were determined to be free of crystalline Type A because the XRPD patterns were free of the diffraction peaks that are present in the reference standard.

Example 32—Determination of Maximum Dose of Compound 2

Good Laboratory Practice (GLP) toxicology testing of a Compound 1 test article comprising a pre-determined amount of Compound 2 was performed in rat and cynomolgus monkeys. A no-observed-adverse-effect level (NOAEL) was determined for each species using standard toxicology techniques, and a resulting dose level for humans was calculated using the FDA Human Equivalent Dose approach based upon dose per body surface area. Based on these experiments and calculations, a maximum recommended starting dose (MRSD) for first-in-human clinical trials was determined based on results from GLP toxicology testing. API compositions of Compound 1 containing less than 5.0% (as determined by percentage area HPLC) of Compound 2 are well within the safe human equivalent dose determined for Compound 2.

What is claimed is:

1. A crystalline solid form of Compound 1:

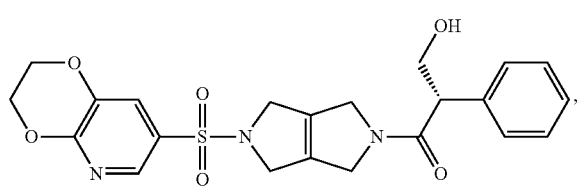 [SMILES: O=C([C@H](CO)c1ccccc1)N1CC2=C(C1)CN(S(=O)(=O)c1cnc3c(c1)OCCO3)C2]

wherein the crystalline solid form is selected from the group consisting of:
1) Type A of Compound 1, wherein Type A of Compound 1 is characterized by an X-ray powder diffraction (XRPD) pattern having diffractions at angles (2 theta ±0.2) of 4.6, 7.2, 15.7, 21.4, 23.2, and 24.8;
2) Type B of Compound 1, wherein Type B of Compound 1 is characterized by an X-ray powder diffraction (XRPD) pattern having diffractions at angles (2 theta ±0.2) of 4.5, 15.6, 22.2, 22.9, 23.3, and 25.1;
3) Type C of Compound 1, wherein Type C of Compound 1 is characterized by an X-ray powder diffraction (XRPD) pattern having diffractions at angles (2 theta ±0.2) of 4.5, 7.3, 11.2, 18.9, 23.0, and 24.7;
4) Type D of Compound 1, wherein Type D of Compound 1 is characterized by an X-ray powder diffraction (XRPD) pattern having diffractions at angles (2 theta ±0.2) of 6.2, 9.7, 13.1, 15.7, 21.9, and 23.6 and not having a diffraction at an angle (2 theta ±0.2) of 23.3;
5) Type E of Compound 1, wherein Type E of Compound 1 is characterized by an X-ray powder diffraction (XRPD) pattern having diffractions at angles (2 theta ±0.2) of 15.1, 15.8, 17.5, 20.1, 21.9, and 26.7;
6) Type F of Compound 1, wherein Type F of Compound 1 is characterized by an X-ray powder diffraction (XRPD) pattern having diffractions at angles (2 theta ±0.2) of 5.5, 14.7, 16.0, 16.8, and 21.4;
7) Type G of Compound 1, wherein Type G of Compound 1 is characterized by an X-ray powder diffraction (XRPD) pattern having diffractions at angles (2 theta ±0.2) of 5.4, 14.3, 16.6, 21.3, and 22.3;
8) Type H of Compound 1, wherein Type H of Compound 1 is characterized by an X-ray powder diffraction (XRPD) pattern having diffractions at angles (2 theta ±0.2) of 5.8, 14.7, 16.6, 20.0, 21.3, and 25.4;
9) Type I of Compound 1, wherein Type I of Compound 1 is characterized by an X-ray powder diffraction (XRPD) pattern having diffractions at angles (2 theta ±0.2) of 5.2, 14.6, 15.5, 20.2, and 21.1;
10) Type J of Compound 1, wherein Type J of Compound 1 is characterized by an X-ray powder diffraction (XRPD) pattern having diffractions at angles (2 theta ±0.2) of 4.5, 5.7, 22.8, 23.1, and 24.5;
11) Type K of Compound 1, wherein Type K of Compound 1 is characterized by an X-ray powder diffraction (XRPD) pattern having diffractions at angles (2 theta ±0.2) of 4.6, 15.4, 15.6, 16.1, 23.2, and 27.4;
12) Type L of Compound 1, wherein Type L of Compound 1 is characterized by an X-ray powder diffraction (XRPD) pattern having diffractions at angles (2 theta ±0.2) of 5.9, 11.9, 17.8, 21.6, 23.9, and 36.1; and
13) Type M of Compound 1, wherein Type M of Compound 1 is characterized by an X-ray powder diffraction (XRPD) pattern having diffractions at angles (2 theta ±0.2) of 4.5, 5.8, 9.7, 15.6, 21.9, and 26.7.

2. The crystalline solid form of claim 1, wherein the crystalline solid form is Type A of Compound 1, wherein Type A of Compound 1 is characterized by an X-ray powder diffraction (XRPD) pattern having diffractions at angles (2 theta ±0.2) of 4.6, 7.2, 15.7, 21.4, 23.2, and 24.8.

3. The crystalline solid form of claim 1, wherein the crystalline solid form is Type B of Compound 1, wherein Type B of Compound 1 is characterized by an X-ray powder diffraction (XRPD) pattern having diffractions at angles (2 theta ±0.2) of 4.5, 15.6, 22.2, 22.9, 23.3, and 25.1.

4. The crystalline solid form of claim 1, wherein the crystalline solid form is Type C of Compound 1, wherein Type C of Compound 1 is characterized by an X-ray powder diffraction (XRPD) pattern having diffractions at angles (2 theta ±0.2) of 4.5, 7.3, 11.2, 18.9, 23.0, and 24.7.

5. The crystalline solid form of claim 1, wherein the crystalline solid form is Type D of Compound 1, wherein Type D of Compound 1 is characterized by an X-ray powder diffraction (XRPD) pattern having diffractions at angles (2 theta ±0.2) of 6.2, 9.7, 13.1, 15.7, 21.9, and 23.6 and not having a diffraction at an angle (2 theta ±0.2) of 23.3.

6. The crystalline solid form of claim 1, wherein the crystalline solid form is Type E of Compound 1, wherein Type E of Compound 1 is characterized by an X-ray powder diffraction (XRPD) pattern having diffractions at angles (2 theta ±0.2) of 15.1, 15.8, 17.5, 20.1, 21.9, and 26.7.

7. The crystalline solid form of claim 1, wherein the crystalline solid form is Type F of Compound 1, wherein Type F of Compound 1 is characterized by an X-ray powder diffraction (XRPD) pattern having diffractions at angles (2 theta ±0.2) of 5.5, 14.7, 16.0, 16.8, and 21.4.

8. The crystalline solid form of claim 1, wherein the crystalline solid form is Type G of Compound 1, wherein Type G of Compound 1 is characterized by an X-ray powder diffraction (XRPD) pattern having diffractions at angles (2 theta ±0.2) of 5.4, 14.3, 16.6, 21.3, and 22.3.

9. The crystalline solid form of claim 1, wherein the crystalline solid form is Type H of Compound 1, wherein Type H of Compound 1 is characterized by an X-ray powder diffraction (XRPD) pattern having diffractions at angles (2 theta ±0.2) of 5.8, 14.7, 16.6, 20.0, 21.3, and 25.4.

10. The crystalline solid form of claim 1, wherein the crystalline solid form is Type I of Compound 1, wherein Type I of Compound 1 is characterized by an X-ray powder diffraction (XRPD) pattern having diffractions at angles (2 theta ±0.2) of 5.2, 14.6, 15.5, 20.2, and 21.1.

11. The crystalline solid form of claim 1, wherein the crystalline solid form is Type J of Compound 1, wherein Type J of Compound 1 is characterized by an X-ray powder diffraction (XRPD) pattern having diffractions at angles (2 theta ±0.2) of 4.5, 5.7, 22.8, 23.1, and 24.5.

12. The crystalline solid form of claim 1, wherein the crystalline solid form is Type K of Compound 1, wherein Type K of Compound 1 is characterized by an X-ray powder diffraction (XRPD) pattern having diffractions at angles (2 theta ±0.2) of 4.6, 15.4, 15.6, 16.1, 23.2, and 27.4.

13. The crystalline solid form of claim 1, wherein the crystalline solid form is Type L of Compound 1, wherein Type L of Compound 1 is characterized by an X-ray powder diffraction (XRPD) pattern having diffractions at angles (2 theta ±0.2) of 5.9, 11.9, 17.8, 21.6, 23.9, and 36.1.

14. The crystalline solid form of claim 1, wherein the crystalline solid form is Type M of Compound 1, wherein Type M of Compound 1 is characterized by an X-ray powder diffraction (XRPD) pattern having diffractions at angles (2 theta ±0.2) of 4.5, 5.8, 9.7, 15.6, 21.9, and 26.7.

15. A pharmaceutical composition comprising a therapeutically effective amount of the crystalline solid form of claim 1, and one or more pharmaceutically acceptable excipients.

16. The pharmaceutical composition of claim 15, wherein the pharmaceutical composition is for oral administration.

* * * * *

UNITED STATES PATENT AND TRADEMARK OFFICE
CERTIFICATE OF CORRECTION

| | | |
|---|---|---|
| PATENT NO. | : 12,161,634 B2 | Page 1 of 1 |
| APPLICATION NO. | : 17/761788 | |
| DATED | : December 10, 2024 | |
| INVENTOR(S) | : George P. Luke et al. | |

It is certified that error appears in the above-identified patent and that said Letters Patent is hereby corrected as shown below:

On the Title Page

Please insert: (60) Related U.S. Application Data at Column 1, below "US 2022/0378755 A1 Dec. 1, 2022":
--(60) Related U.S. Application Data
Provisional application No. 63/024,432, filed on May 13, 2020, provisional application No. 63/024,441, filed on May 13, 2020, provisional application No. 62/704,785, filed on May 28, 2020, provisional application No. 62/705,106, filed on Jun. 11, 2020, provisional application No. 62/902,887, filed on Sep. 19, 2019, provisional application No. 62/906,437, filed on Sep. 26, 2019.
Foreign Application Priority Data
Sep. 19, 2019 (WO). . . . . PCT/US2019/052024.--

Signed and Sealed this
First Day of July, 2025

Coke Morgan Stewart
*Acting Director of the United States Patent and Trademark Office*